(12) United States Patent
Kanda et al.

(10) Patent No.: US 7,393,683 B2
(45) Date of Patent: Jul. 1, 2008

(54) MAMMALIAN HOST CELL MODIFIED BY RNAI TO INHIBIT α 1,6-FUCOSYLTRANSFERASE

(75) Inventors: Yutaka Kanda, Machida (JP); Mitsuo Satoh, Machida (JP); Kazuyasu Nakamura, Machida (JP); Kazuhisa Uchida, Machida (JP); Toyohide Shinkawa, Machida (JP); Naoko Yamane, Machida (JP); Emi Hosaka, Machida (JP); Kazuya Yamano, Machida (JP); Motoo Yamasaki, Machida (JP); Nobuo Hanai, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 11/287,324

(22) Filed: Nov. 28, 2005

(65) Prior Publication Data

US 2006/0078990 A1  Apr. 13, 2006

Related U.S. Application Data

(62) Division of application No. 11/131,212, filed on May 18, 2005, which is a division of application No. 09/971,773, filed on Oct. 9, 2001, now Pat. No. 6,946,292.

(60) Provisional application No. 60/268,916, filed on Feb. 16, 2001.

(30) Foreign Application Priority Data

Oct. 6, 2000  (JP)  ............................. 2000-308526
Oct. 5, 2001  (JP)  ....................... PCT/JP01/08804

(51) Int. Cl.
*C12N 5/00* (2006.01)
*C12N 5/02* (2006.01)
*C12N 9/88* (2006.01)
*G01N 33/53* (2006.01)
*C12P 21/04* (2006.01)
*A01K 67/00* (2006.01)
*A01K 67/033* (2006.01)

(52) U.S. Cl. ....................... 435/325; 435/375; 435/232; 435/7.8; 435/70.1; 800/8

(58) Field of Classification Search ........................ None
See application file for complete search history.

(56) References Cited

U.S. PATENT DOCUMENTS 5,728,568 A  3/1998  Sullivan et al.

6,054,304 A  4/2000  Taniguchi

FOREIGN PATENT DOCUMENTS

| EP | 1 176 195 A | 1/2002 |
|---|---|---|
| WO | 97/27303 A1 | 7/1997 |
| WO | WO97/30087 | 8/1997 |
| WO | 97/37683 A1 | 10/1997 |
| WO | 99/54342 A1 | 10/1999 |
| WO | 99/64618 A1 | 12/1999 |
| WO | 00/61739 A1 | 10/2000 |

OTHER PUBLICATIONS

Hunter (1999) Current Biology, 9: R440-42.*
Shinoda, et al. (1998) Glycoconjugate Journal, 15: 1079-83.*
Staudacher (1999) Biochimica et Biophysica Acta, 1473: 216-236.*
Shitara et al. Journal of Immunological Methods, *167*, 271-278 (1994).
Furukawa et al Protein, Nucleic Acid and Enzyme, *43*, 2309-2317 (1998).
Oriol et al, Glycobiology, 9, No. 4, 323-334 (1999).
Breton et al, Glycobiology, 8, No. 1, 87-94 (1998).
Asano et al, The EMBO Journal, vol. 16, No. 8, pp. 1850-1857 (1997).
Maly et al, Cell , vol. 86, 643-653, Aug. 23, 1996.
Wright et al. Tibtech, 15, 26-32 (1997).
Raju, et al. (2000) Glycobiology, 10(5): 477-86.
Stryer (1988) Biochemistry, 3rd Ed., Freeman and Co., New York, NY, pp. 35-37.
Shinkawa, et al. (2003) J. Biol. Chem., 278(5):3466-73.
Jones, et al. (2001) Pharmacogenomics J., 1(2): 126-34.
Lifely, et al. (1995) Glycobiology, 5(8): 813-22.
Ripka et al, Archives of Biochemistry and Biophysics, 1986, vol. 249, No. 2, pp. 533-545.
Ohyama et al, The Journal of Biological Chemistry, 1998, vol. 273, No. 23, pp. 14582-14587.
Wang et al, The Journal of Biological Chemistry, 1998, vol. 273, No. 14, pp. 8112-8118.
Umana et al, Nature Biotechnology, 1999, vol. 17, pp. 176-180.

(Continued)

*Primary Examiner*—Joseph Woitach
*Assistant Examiner*—Robert M. Kelly
(74) *Attorney, Agent, or Firm*—Sughrue Mion, PLLC

(57) ABSTRACT

The present invention relates to a cell for the production of an antibody molecule such as an antibody useful for various diseases having high antibody-dependent cell-mediated cytotoxic activity, a fragment of the antibody and a fusion protein having the Fc region of the antibody or the like, a method for producing an antibody composition using the cell, the antibody composition and use thereof.

6 Claims, 52 Drawing Sheets

OTHER PUBLICATIONS

Supplementary European Search Report dated Jun. 1, 2005 issued in connection with EP 01974718.7.
Canadian Office Action dated Jul. 31, 2007, issued in connection with Canadian Application No. 2,424,602.
Accession No. NM 016893, NCBI (Jul. 4, 2007), Hayashi et al, DNA Seq. 11 (1-2), 91-96 (2000).
Accession No. NP 058589, NCBI (Jul. 4, 2007), Hayashi et al, DNA Seq. 11 (1-2), 91-96 (2000).
Hayashi et al, "Molecular Cloning of Mouse Alpha-1,6-Fucosyltransferase and Expression of Its mRNA in the Developing Cerebrum", DNA Sequence, 2000, vol. 11(1-2), pp. 91-96.

* cited by examiner

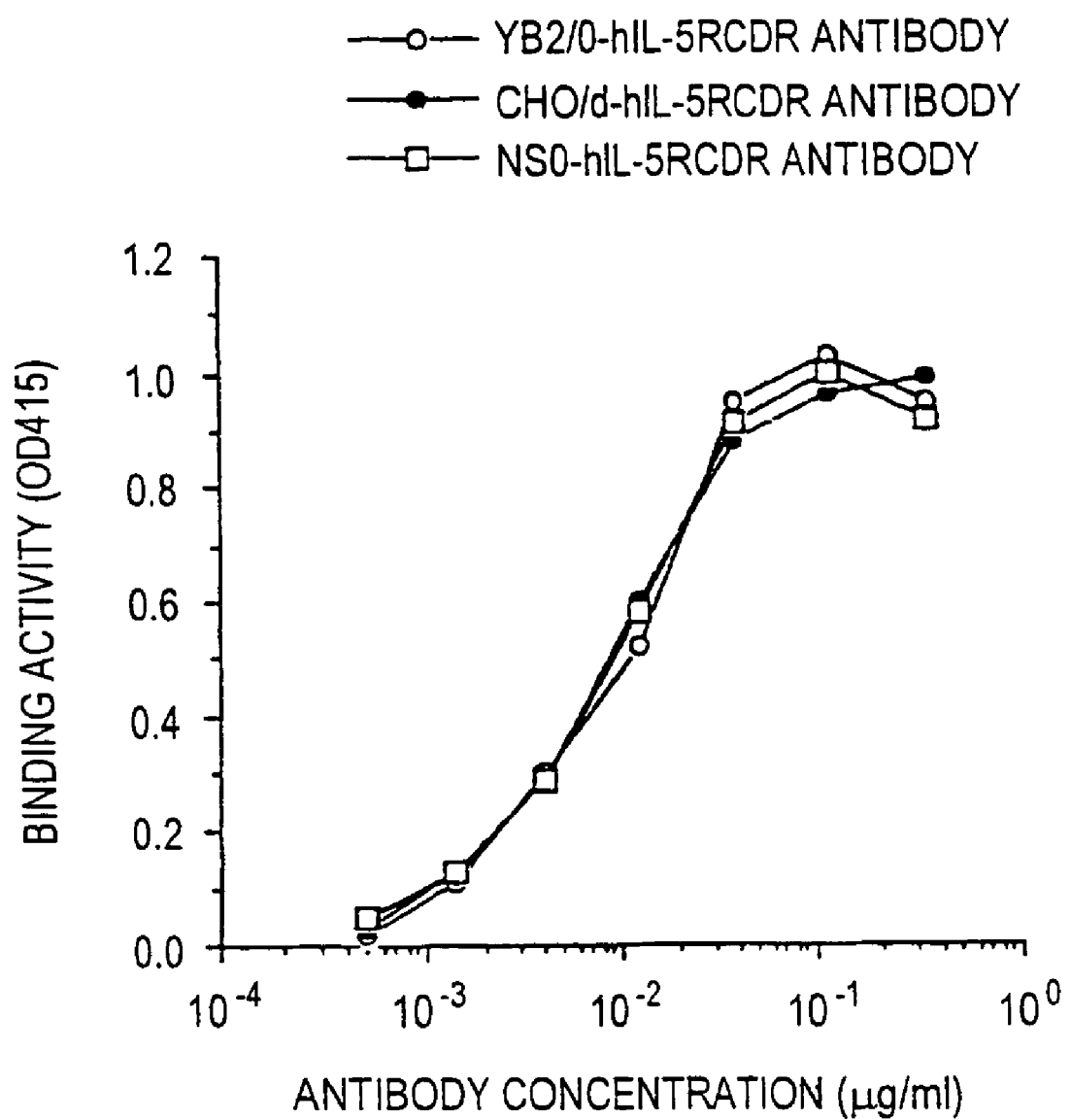

FIG. 22
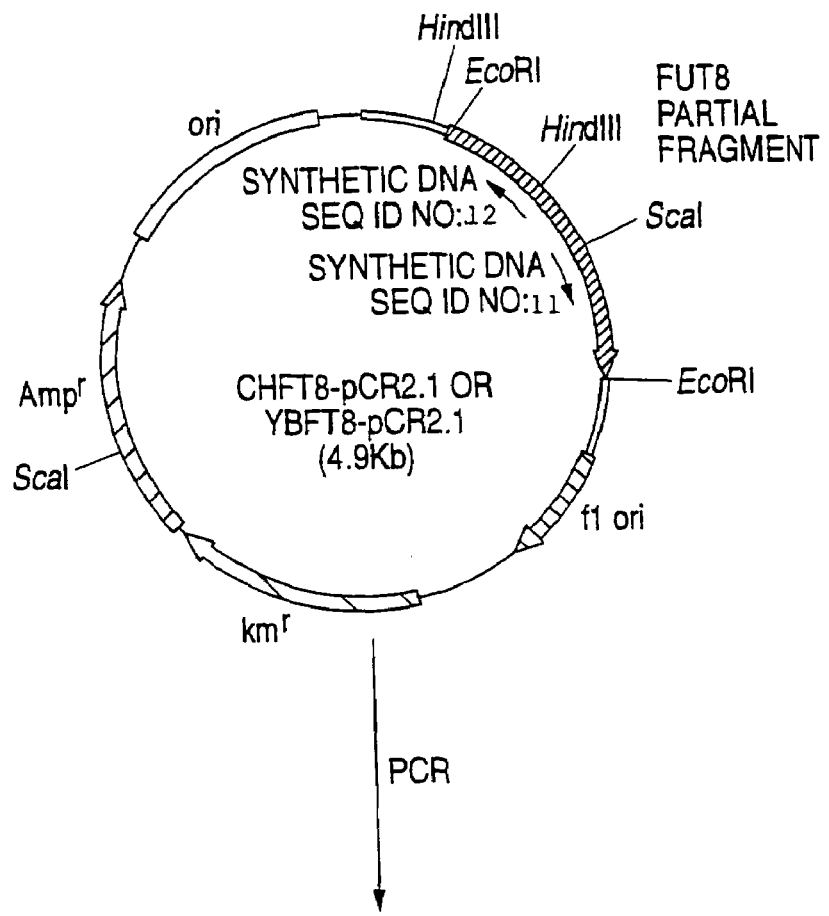
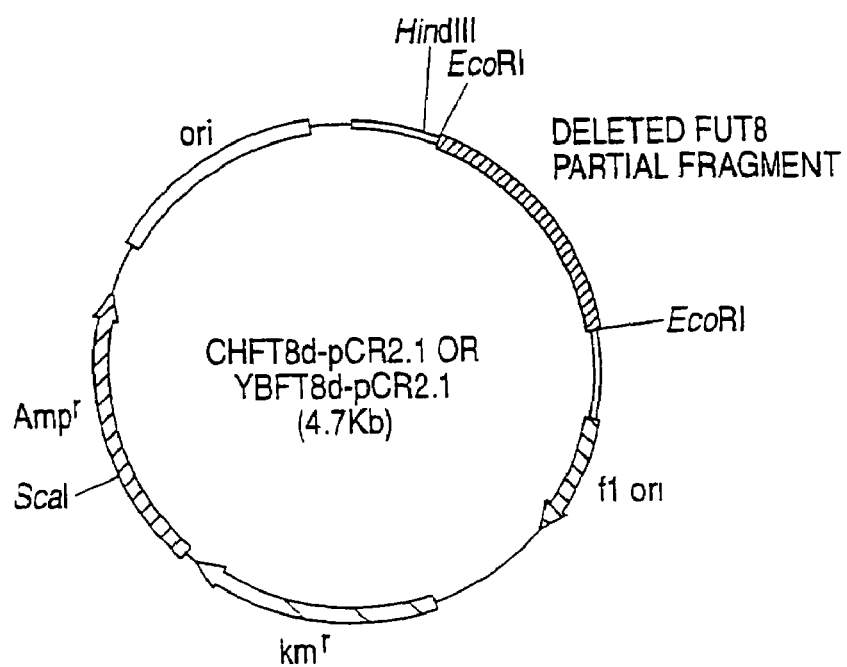

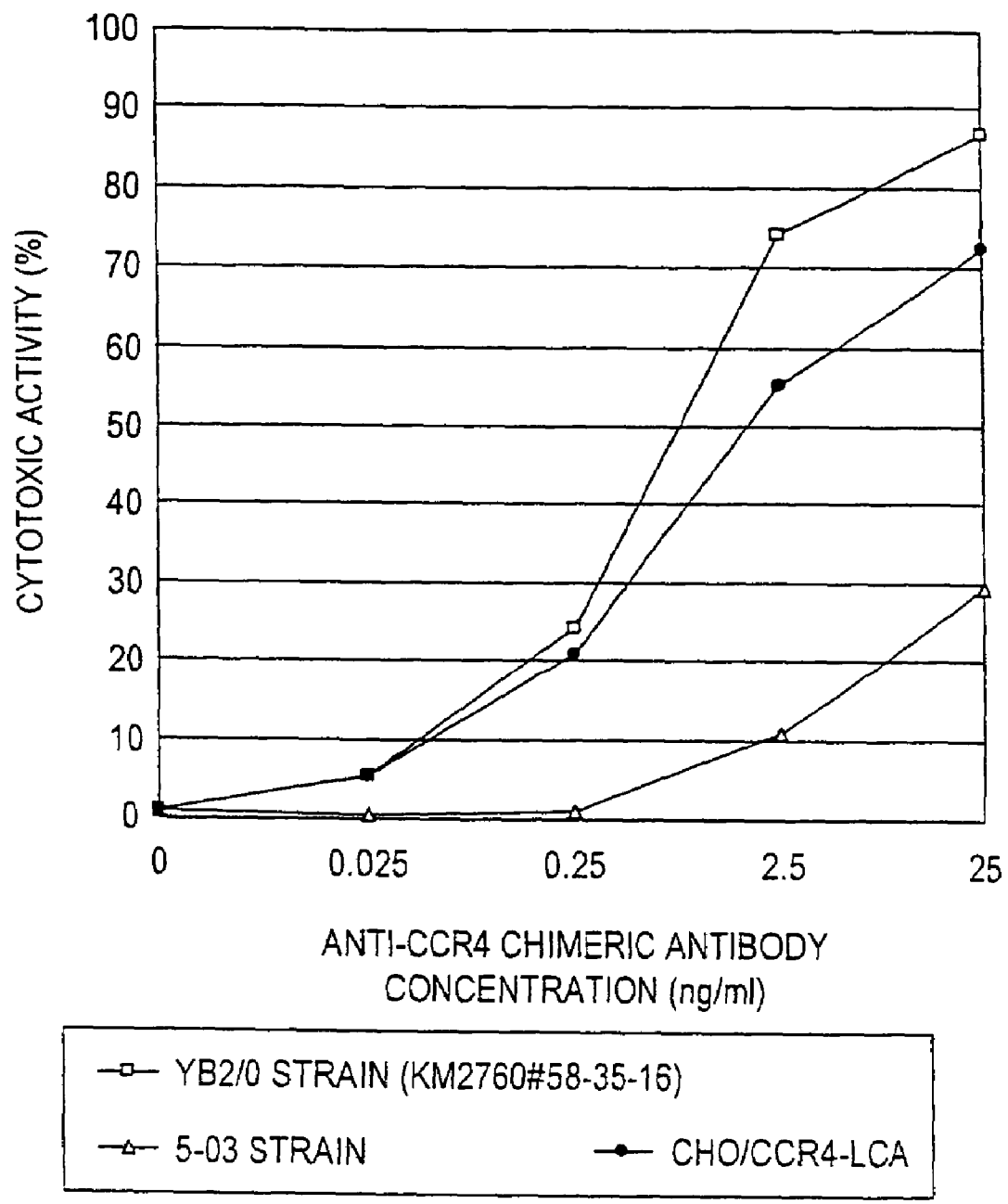

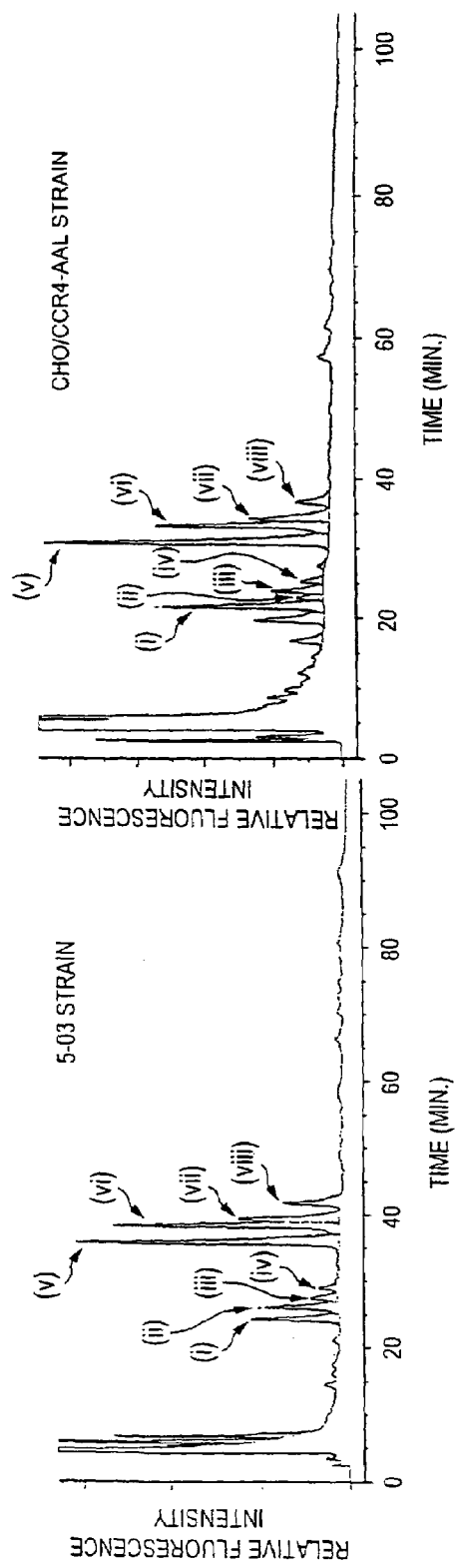
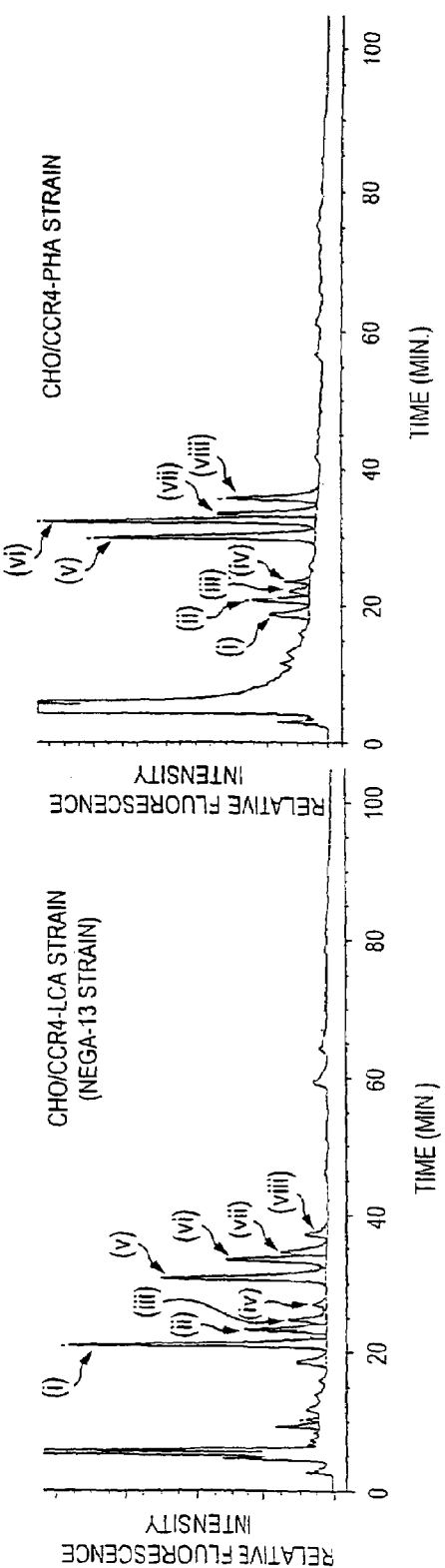
FIG. 45A  5-03 STRAIN
FIG. 45B  CHO/CCR4-LCA STRAIN (NEGA-13 STRAIN)
FIG. 45C  CHO/CCR4-AAL STRAIN
FIG. 45D  CHO/CCR4-PHA STRAIN

```
                      SEQUENCE LISTING

<160> NUMBER OF SEQ ID NOS: 73

<210> SEQ ID NO 1
<211> LENGTH: 2008
<212> TYPE: DNA
<213> ORGANISM: Cricetulus griseus

<400> SEQUENCE: 1
aacagaaact tattttcctg tgtggctaac tagaaccaga gtacaatgtt tccaattctt      60
tgagctccga gaagacagaa gggagttgaa actctgaaaa tgcgggcatg gactggttcc     120
tggcgttgga ttatgctcat tcttttttgcc tggggggacct tattgtttta tataggtggt    180
catttggttc gagataatga ccaccctgac cattctagca gagaactctc caagattctt     240
gcaaagctgg agcgcttaaa acaacaaaat gaagacttga ggagaatggc tgagtctctc     300
cgaataccag aaggccctat tgatcagggg acagctacag gaagagtccg tgttttagaa     360
gaacagcttg ttaaggccaa agaacagatt gaaaattaca agaaacaagc taggaatgat     420
ctgggaaagg atcatgaaat cttaaggagg aggattgaaa atggagctaa agagctctgg     480 tttttctac aaagtgaatt gaagaaatta aagaaattag aaggaaacga actccaaaga     540
catgcagatg aaattctttt ggatttagga catcatgaaa ggtctatcat gacagatcta     600
tactacctca gtcaaacaga tggagcaggt gagtggcggg aaaaagaagc caaagatctg     660
acagagctgg tccagcggag aataacatat ctgcagaatc ccaaggactg cagcaaagcc     720
agaaagctgg tatgtaatat caacaaaggc tgtggctatg gatgtcaact ccatcatgtg     780
gtttactgct tcatgattgc ttatggcacc cagcgaacac tcatcttgga atctcagaat     840
tggcgctatg ctactggagg atgggagact gtgtttagac ctgtaagtga gacatgcaca     900
gacaggtctg gcctctccac tggacactgg tcaggtgaag tgaaggacaa aaatgttcaa     960
gtggtcgagc tccccattgt agacagcctc catcctcgtc ctccttactt acccttggct    1020
gtaccagaag accttgcaga tcgactcctg agagtccatg gtgatcctgc agtgtggtgg    1080
gtatcccagt ttgtcaaata cttgatccgt ccacaacctt ggctggaaag ggaaatagaa    1140
gaaaccacca agaagcttgg cttcaaacat ccagttattg gagtccatgt cagacgcact    1200
gacaaagtgg gaacagaagc agccttccat cccattgagg aatacatggt acacgttgaa    1260
gaacattttc agcttctcga acgcagaatg aaagtggata aaaaaagagt gtatctggcc    1320
actgatgacc cttctttgtt aaaggaggca aagacaaagt actccaatta tgaatttatt    1380
```

```
agtgataact ctatttcttg gtcagctgga ctacacaacc gatacacaga aaattcactt  1440
cggggcgtga tcctggatat acactttctc tcccaggctg acttccttgt gtgtactttt  1500
tcatcccagg tctgtagggt tgcttatgaa atcatgcaaa cactgcatcc tgatgcctct  1560
gcaaacttcc attctttaga tgacatctac tattttggag gccaaaatgc ccacaaccag  1620
attgcagttt atcctcacca acctcgaact aaagaggaaa tccccatgga acctggagat  1680
atcattggtg tggctggaaa ccattggaat ggttactcta aaggtgtcaa cagaaaacta  1740
ggaaaaacag gcctgtaccc ttcctacaaa gtccgagaga agatagaaac agtcaaatac  1800
cctacatatc ctgaagctga aaaatagaga tggagtgtaa gagattaaca acagaattta  1860
gttcagacca tctcagccaa gcagaagacc cagactaaca tatggttcat tgacagacat  1920
gctccgcacc aagagcaagt gggaaccctc agatgctgca ctggtggaac gcctctttgt  1980
gaagggctgc tgtgccctca agcccatg  2008
```

<210> SEQ ID NO 2
<211> LENGTH: 1728
<212> TYPE: DNA
<213> ORGANISM: Mus musculus

<400> SEQUENCE: 2

```
atgcgggcat ggactggttc ctggcgttgg attatgctca ttcttttttgc ctgggggacc    60 ttgttatttt atataggtgg tcatttggtt cgagataatg accaccctga tcactccagc   120
agagaactct ccaagattct tgcaaagctt gaacgcttaa acagcaaaaa tgaagacttg   180
aggcgaatgg ctgagtctct ccgaatacca gaaggccccc attgaccaggg gacagctaca   240 ggaagagtcc gtgttttaga agaacagctt gttaaggcca agaacagat tgaaaattac   300 aagaaacaag ctagaaatgg tctggggaag atcatgaaaa tcttaagaag gaggattgaa   360 aatgagcta aagagctctg gttttttcta caaagcgaac tgaagaaatt aaagcattta   420
gaaggaaatg aactccaaag acatgcagat gaaattcttt tggatttagg acaccatgaa   480
aggtctatca tgacagatct atactacctc agtcaaacag atggagcagg ggattggcgt   540
gaaaaagagg ccaaagatct gacagagctg gtccagcgga gaataacata tctccagaat   600
cctaaggact gcagcaaagc caggaagctg gtgtgtaaca tcaataaagg ctgtggctat   660
ggttgtcaac tccatcacgt ggtctactgt ttcatgattg cttatggcac ccagcgaaca   720
ctcatcttgg aatctcagaa ttggcgctat gctactggtg gatgggagac tgtgtttaga   780
cctgtaagtg agacatgtac agacagatct ggcctctcca ctggacactg gtcaggtgaa   840
gtaaatgaca aaaacattca agtggtcgag ctccccattg tagacagcct ccatcctcgg   900
cctccttact taccactggc tgttccagaa gaccttgcag accgactcct aagagtccat   960
ggtgaccctg cagtgtggtg ggtgtcccag tttgtcaaat acttgattcg tccacaacct  1020
tggctggaaa aggaaataga agaagccacc aagaagcttg gcttcaaaca tccagttatt  1080
ggagtccatg tcagacgcac agacaaagtg ggaacagaag cagccttcca cccccatcgag  1140 gagtacatgg tacacgttga agaacatttt cagcttctcg cacgcagaat gcaagtggat  1200
aaaaaaagag tatatctggc tactgatgat cctacttttgt taaggaggc aaagacaaag  1260 tactccaatt atgaatttat tagtgataac tctatttctt ggtcagctgg actacacaat  1320
cggtacacag aaaattcact tcggggtgtg atcctggata tacactttct ctcacaggct  1380
gactttctag tgtgtacttt ttcatcccag gtctgtcggg ttgcttatga aatcatgcaa  1440
```

```
accctgcatc ctgatgcctc tgcgaacttc cattctttgg atgcatctca ctattttgga   1500
ggccaaaatg cccacaatca gattgctgtt tatcctcaca aacctcgaac tgaagaggaa   1560
attccaatgg aacctggaga tatcattggt gtggctggaa accattggga tggttattct   1620
aaaggtatca acagaaaact tggaaaaaca ggcttatatc cctcctacaa agtccgagag   1680
aagatagaaa cagtcaagta tcccacatat cctgaagctg aaaaatag                1728

<210> SEQ ID NO 3
<211> LENGTH: 9196
<212> TYPE: DNA
<213> ORGANISM: Cricetulus griseus

<400> SEQUENCE: 3
tctagaccag gctggtctcg aactcacaga gaaccacctg cctctgccac ctgagtgctg     60
ggattaaagg tgtgcaccac caccgcccgg cgtaaaatca tatttttgaa tattgtgata    120
atttacatta taattgtaag taaaaatttt cagcctattt tgttatacat ttttgcgtaa    180
attattcttt tttgaaagtt ttgttgtcca taatagtcta gggaaacata agttataat     240 ttttgtctat gtatttgcat atatatctat ttaatctcct aatgtccagg aaataaatag    300
ggtatgtaat agcttcaaca tgtggtatga tagaattttt cagtgctata aagttgtta    360 cagcaaagtg ttattaattc atatgtccat atttcaattt tttatgaatt attaaattga    420
atccttaagc tgccagaact agaattttat tttaatcagg aagccccaaa tctgttcatt    480
ctttctatat atgtggaaag gtaggcctca ctaactgatt cttcacctgt tttagaacat    540
ggtccaagaa tggagttatg taaggggaat tacaagtgtg agaaaactcc tagaaaacaa    600
gatgagtctt gtgaccttag tttctttaaa aacacaaaat tcttggaatg tgttttcatg    660
ttcctcccag gtggatagga gtgagtttat ttcagattat ttattacaac tggctgttgt    720
tacttgtttc tatgtctttta tagaaaaaca tattttttttt gccacatgca gcttgtcctt    780
atgattttat acttgtgtga ctcttaactc tcagagtata aattgtctga tgctatgaat    840
aaagttggct attgtatgag acttcagccc acttcaatta ttggcttcat tctctcagat    900
cccaccacct ccagagtggt aaacaacttg aaccattaaa cagactttag tctttatttg    960
aatgatagat ggggatatca gatttatagg cacagggttt tgagaaaggg agaaggtaaa   1020
cagtagagtt taacaacaac aaaaagtata ctttgtaaac gtaaaactat ttattaaagt   1080
agtagacaag acattaaata ttccttggga ttagtgcttt ttgaatttg ctttcaaata    1140 atagtcagtg agtatacccc tccccattc tatatttag cagaaatcag aataaatggt    1200
gtttctggta cattcttttg tagagaattt attttctttg gttttttgtg catttaaagt   1260
caataaaaat taaggttcag taatagaaaa aaaactctga ttttttggaat ccccttctt    1320 cagcttttct atttaatctc ttaatgataa tttaatttgt ggccatgtgg tcaaagtata   1380
tagccttgta tatgtaaatg ttttaaccaa cctgcctttta cagtaactat ataattttat   1440
tctataatat atgacttttc ttccatagct ttagagttgc ccagtcactt taagttacat   1500
tttcatatat gttctttgtg ggaggagata attttatttc taagagaatc ctaagcatac   1560
tgattgagaa atggcaaaca aaacacataa ttaaagctga taaagaacga acatttggag   1620
tttaaaatac atagccaccc taagggttta actgttgtta gccttctttt ggaatttta    1680 ttagttcata tagaaaaatg gattttatcg tgacatttcc atatatgtat ataatatatt   1740
tacatcatat ccacctgtaa ttattagtgt ttttaaaatat atttgaaaaa ataatggtct   1800 ggttttgatcc atttgaacct tttgatgttt ggtgtggttg ccaattggtt gatggttatg   1860
```

```
ataacctttg cttctctaag gttcaagtca gtttgagaat atgtcctcta aaaatgacag    1920
gttgcaagtt aagtagtgag atgacagcga gatggagtga tgagaatttg tagaaatgaa    1980
ttcacttata ctgagaactt gttttgcttt tagataatga acatattagc ctgaagtaca    2040
tagccgaatt gattaattat tcaaagatat aatcttttaa tccctataaa agaggtatta    2100
cacaacaatt caagaaagat agaattagac ttccagtatt ggagtgaacc atttgttatc    2160
aggtagaacc ctaacgtgtg tggttgactt aaagtgttta cttttttacct gatactgggt    2220 agctaattgt ctttcagcct cctggccaaa gataccatga aagtcaactt acgttgtatt    2280
ctatatctca aacaactcag ggtgtttctt actctttcca cagcatgtag agcccaggaa    2340
gcacaggaca agaaagctgc ctccttgtat caccaggaag atcttttttgt aagagtcatc    2400 acagtatacc agagagacta attttgtctg aagcatcatg tgttgaaaca acagaaactt    2460
attttcctgt gtggctaact agaaccgagt acaatgttt ccaattcttt gagctccgag    2520
aagacagaag ggagttgaaa ctctgaaaat gcgggcatgg actggttcct ggcgttggat    2580
tatgctcatt cttttttgcct gggggacctt attgttttat ataggtggtc atttggttcg    2640
agataatgac caccctgacc attctagcag agaactctcc aagattcttg caaagctgga    2700
gcgcttaaaa caacaaaatg aagacttgag gagaatggct gagtctctcc ggtaggtttg    2760
aaatactcaa ggatttgatg aaatactgtg cttgacctttt aggtataggg tctcagtctg    2820
ctgttgaaaa atataatttc tacaaaccgt ctttgtaaaa ttttaagtat tgtagcagac    2880 ttttttaaaag tcagtgatac atctatatag tcaatatagg tttacatagt tgcaatctta    2940
ttttgcatat gaatcagtat atagaagcag tggcatttat atgcttatgt tgcatttaca    3000
attatgttta gacgaacaca aactttatgt gatttggatt agtgctcatt aaattttttt    3060
attctatgga ctacaacaga gacataaatt ttgaaaggct tagttactct taaattctta    3120
tgatgaaaag caaaaattca ttgttaaata gaacagtgca tccggaatgt gggtaattat    3180
tgccatattt ctagtctact aaaaattgtg gcataactgt tcaaagtcat cagttgtttg    3240
gaaagccaaa gtctgattta aatggaaaac ataaacaatg atatctattt ctagatacct    3300
ttaacttgca gttactgagt ttacaagttg tctgacaact ttggattctc ttacttcata    3360
tctaagaatc atcatgtgta cagtgcttac tgtcactttta aaaaactgca gggctagaca    3420
tgcagatatg aagactttga cattagatgt ggtaattggc actaccagca agtggtatta    3480
agatacagct gaatatatta ctttttgagg aacataattc atgaatggaa agtggagcat    3540
tagagaggat gccttctggc tctcccacac cactgtttgc atccattgca tttcacactg    3600
cttttagaac tcagatgttt catatggtat attgtgtaac tcaccatcag ttttatcttt    3660
aaatgtctat ggatgataat gttgtatgtt aacacttta caaaaacaaa tgaagccata    3720
tcctcggtgt gagttgtgat ggtggtaatt gtcacaatag gattattcag caaggaacta    3780
agtcagggac aagaagtggg cgatactttg ttggattaaa tcattttact ggaagttcat    3840
cagggagggt tatgaaagtt gtggtctttg aactgaaatt atatgtgatt cattattctt    3900
gatttaggcc ttgctaatag taactatcat ttattgggaa tttgtcatat gtgccaattt    3960
gtcatgggcc agacagcgtg ttttactgaa tttctagata tctttatgag attctagtac    4020
tgttttcagc catttttacag atgaagaatc ttaaaaaatg ttaaataatt tagtttgccc    4080
aagattatac gttaacaaat ggtagaacct tctttgaatt ctggcagtat ggctacacag    4140
tccgaactct tatcttccta agctgaaaac agaaaaagca atgacccaga aaattttatt    4200
```

```
taaaagtctc aggagagact tcccatcctg agaagatctc ttttcccttt tataatttag    4260
gctcctgaat aatcactgaa ttttctccat gttccatcta tagtactgtt atttctgttt    4320
tccttttttc ttaccacaaa gtatcttgtt tttgctgtat gaaagaaaat gtgttattgt    4380
aatgtgaaat tctctgtccc tgcagggtcc cacatccgcc tcaatcccaa ataaacacac    4440
agaggctgta ttaattatga aactgttggt cagttggcta gggcttctta ttggctagct    4500
ctgtcttaat tattaaacca taactactat tgtaagtatt tccatgtggt cttatcttac    4560
caaggaaagg gtccagggac ctcttactcc tctggcgtgt tggcagtgaa gaggagagag    4620
cgatttccta tttgtctctg cttatttcct gattctgctc agctatgtca cttcctgcct    4680
ggccaatcag ccaatcagtg ttttattcat tagccaataa agaaacatt tacacagaag     4740 gacttccccc atcatgttat ttgtatgagt tcttcagaaa atcatagtat cttttaatac    4800
taatttttat aaaaaattaa ttgtattgaa aattatgtgt atatgtgtct gtgtgtcgat    4860
ttgtgctcat aagtagcatg gagtgcagaa gagggaatca gatcttttt taagggacaa     4920 agagtttatt cagattacat tttaaggtga taatgtatga ttgcaaggtt atcaacatgg    4980
cagaaatgtg aagaagctgg tcacattaca tccagagtca agagtagaga gcaatgaatt    5040
gatgcatgca ttcctgtgct cagctcactt ttcctggagc tgagctgatt gtaagccatc    5100
tgatgtcttt gctgggaact aactcaaagg caagttcaaa acctgttctt aagtataagc    5160
catctctcca gtccctcata tggtctctta agacactttc tttatattct tgtacataga    5220
aattgaattc ctaacaactg cattcaaatt acaaaatagt ttttaaaagc tgatataata    5280
aatgtaaata caatctagaa cattttata aataagcata ttaactcagt aaaaataaat     5340
gcatggttat tttccttcat tagggaagta tgtctcccca ggctgttctc tagattctac    5400
tagtaatgct gtttgtacac catccacagg ggttttattt taaagctaag acatgaatga    5460
tggacatgct tgttagcatt tagactttt tccttactat aattgagcta gtattttgt      5520 gctcagtttg atatctgtta attcagataa atgtaatagt aggtaatttc tttgtgataa    5580
aggcatataa attgaagttg gaaaacaaaa gcctgaaatg acagttttta agattcagaa    5640
caataatttt caaaagcagt tacccaactt tccaaataca atctgcagtt ttcttgatat    5700
gtgataaatt tagacaaaga aatagcacat tttaaaatag ctatttactc ttgattttt     5760 tttcaaattt aggctagttc actagttgtg tgtaaggtta tggctgcaaa catctttgac    5820
tcttggttag ggaatccagg atgatttacg tgtttggcca aaatcttgtt ccattctggg    5880
tttcttctct atctaggtag ctagcacaag ttaaggtgt ggtagtattg gaaggctctc      5940
aggtatatat ttctatattc tgtatttttt tcctctgtca tatatttgct ttctgtttta    6000
ttgatttcta ctgttagttt gatacttact ttcttacact ttctttggga tttattttgc    6060
tgttctaaga tttcttagca agttcatatc actgatttta acagttgctt cttttgtaat    6120
atagactgaa tgcccttat ttgaaatgct tgggatcaga aactcagatt tgaacttttc      6180
ttttttaata tttccatcaa gtttaccagc tgaatgtcct gatccaagaa tatgaaatct    6240
gaaatgcttt gaaatctgaa acttttagag tgataaagct tccctttaaa ttaatttgtg    6300
ttctatattt tttgacaatg tcaacctttc attgttatcc aatgagtgaa catattttca    6360 attttttgt ttgatctgtt atattttgat ctgaccatat ttataaaatt ttatttaatt     6420
tgaatgttgt gctgttactt atctttatta ttatttttgc ttattttcta gccaaatgaa    6480
attatattct gtattatttt agtttgaatt ttacttgtg gcttagtaac tgcctttgt       6540 tggtgaatgc ttaagaaaaa cgtgtggtct actgatattg gttctaatct tatatagcat    6600
```

```
gttgtttgtt aggtagttga ttatgctggt cagattgtct tgagtttatg caaatgtaaa   6660
atatttagat gcttgttttg ttgtctaaga acaaagtatg cttgctgtct cctatcggtt   6720
ctggtttttc cattcatctc ttcaagctgt tttgtgtgtt gaatactaac tccgtactat   6780
cttgttttct gtgaattaac cccttttcaa aggtttcttt tctttttttt tttaagggac   6840
aacaagttta ttcagattac attttaagct gataatgtat gattgcaagg ttatcaacat   6900
ggcagaaatg tgaagaagct aggcacatta catccacatg gagtcaagag cagagagcag   6960
tgaattaatg catgcattcc tgtggtcagc tcacttttcc tattcttaga tagtctagga   7020
tcataaacct ggggaatagt gctaccacaa tgggcatatc cacttacttc agttcatgca   7080
atcaaccaag gcacatccac aggaaaaact gatttagaca acctctcatt gagactcttc   7140
ccagatgatt agactgtgtc aagttgacaa ttaaaactat cacacctgaa gccatcacta   7200
gtaaatataa tgaaaatgtt gattatcacc ataattcatc tgtatccctt tgttattgta   7260
gattttgtga agttcctatt caagtccctg ttccttcctt aaaaacctgt tttttagtta   7320
aataggtttt ttagtgttcc tgtctgtaaa tactttttta aagttagata ttattttcaa   7380
gtatgttctc ccagtctttg gcttgtattt tcatcccttc aatacatata tttttgtaat   7440 ttatttttt tatttaaatt agaaacaaag ctgcttttac atgtcagtct cagttccctc   7500
tccctcccct cctccctgc tccccaccta agccccaatt ccaactcctt tcttctcccc   7560
aggaagggtg aggccctcca tgggggaaat cttcaatgtc tgtcatatca tttggagcag   7620
ggcctagacc ctccccagtg tgtctaggct gagagagtat ccctctatgt ggagagggct   7680
cccaaagttc atttgtgtac taggggtaaa tactgatcca ctatcagtgg ccccatagat   7740
tgtccggacc tccaaactga cttcctcctt cagggagtct ggaacagttc tatgctggtt   7800
tcccagatat cagtctgggg tccatgagca acccttgtt caggtcagtt gtttctgtag   7860
gtttccccag cccggtcttg accccctttgc tcatcacttc tccctctctg caactggatt   7920
ccagagttca gctcagtgtt tagctgtggg tgtctgcatc tgcttccatc agctactgga   7980
tgagggctct aggatggcat ataaggtagt catcagtctc attatcagag aagggctttt   8040
aaggtagcct cttgattatt gcttagattg ttagttgggg tcaaccttgt aggtctctgg   8100
acagtgacag aattctcttt aaacctataa tggctccctc tgtggtggta tccctttct   8160 tgctctcatc cgttcctccc ctgactagat cttcctgctc cctcatgtcc tcctctcccc   8220
tccccttctc cccttctctt tcttctaact ccctctcccc tccacccacg atccccatta   8280
gcttatgaga tcttgtcctt attttagcaa aaccttttg gctataaaat taattaattt   8340
aatatgctta tatcaggttt attttggcta gtatttgtat gtgttggtt agtgttttta   8400 accttaattg acatgtatcc ttatatttag acacagattt aaatatttga agtttttttt   8460
tttttttttt ttaaagattt atttatttt tatgtcttct gcctgcatgc cagaagaggg   8520
caccagatct cattcaaggt ggttgtgagc caccatgtgg ttgctgggaa ttgaactcag   8580
gacctctgga agaacagtca gtgctcttaa ccgctgagcc atctctccag cccctgaagt   8640
gtttctttta aagaggatag cagtgcatca ttttccctt tgaccaatga ctcctacctt   8700
actgaattgt tttagccatt tatatgtaat gctgttacca ggtttacatt ttcttttatc   8760
ttgctaaatt tcttccctgt ttgtctcatc tcttatttt gtctgttgga ttatataggc   8820
ttttattttt ctgttttac agtaagttat atcaaattaa aattatttta tggaatgggt   8880
gtgttgacta catgtatgtc tgtgcaccat gtgctgacct ggtcttggcc agaagaaggt   8940
```

```
gtcatattct ctgaaactgg tattgtggat gttacgaact gccataggt gctaggaatc      9000 aaaccccagc tcctctggaa aagcagccac tgctctgagc cactgagtcc tctcttcaag      9060
caggtgatgc caacttttaa tggttaccag tggataagag tgcttgtatc tctagcaccc      9120
atgaaaattt atgcattgct atatgggctt gtcacttcag cattgtgtga cagagacagg      9180
aggatcccaa gagctc                                                     9196

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 4
actcatcttg gaatctcaga attgg                                             25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 5
cttgaccgtt tctatcttct ctcg                                              24

<210> SEQ ID NO 6
<211> LENGTH: 979
<212> TYPE: DNA
<213> ORGANISM: Cricetulus griseus

<400> SEQUENCE: 6
actcatcttg gaatctcaga attggcgcta tgctactgga ggatgggaga ctgtgtttag        60
acctgtaagt gagacatgca cagacaggtc tggcctctcc actggacact ggtcaggtga       120
agtgaaggac aaaaatgttc aagtggtcga gctccccatt gtagacagcc tccatcctcg       180
tcctccttac ttacccttgg ctgtaccaga agaccttgca gatcgactcc tgagagtcca       240
tggtgatcct gcagtgtggt gggtatccca gtttgtcaaa tacttgatcc gtccacaacc       300
ttggctggaa agggaaatag aagaaaccac caagaagctt ggcttcaaac atccagttat       360
tggagtccat gtcagacgca ctgacaaagt gggaacagaa gcagccttcc atcccattga       420
ggaatacatg gtacacgttg aagaacattt tcagcttctc gaacgcagaa tgaaagtgga       480
taaaaaaaga gtgtatctgg ccactgatga cccttctttg ttaaaggagg caaagacaaa       540
gtactccaat tatgaattta ttagtgataa ctctatttct tggtcagctg gactacacaa       600
ccgatacaca gaaaattcac ttcggggcgt gatcctggat atacactttc tctcccaggc       660
tgacttcctt gtgtgtactt tttcatccca ggtctgtagg gttgcttatg aaatcatgca       720
aacactgcat cctgatgcct ctgcaaactt ccattcttta gatgacatct actattttgg       780
aggccaaaat gcccacaacc agattgcagt ttatcctcac caacctcgaa ctaaagagga       840
aatccccatg gaacctggag atatcattgg tgtggctgga accattgga atggttactc       900 taaaggtgtc aacagaaaac taggaaaaac aggcctgtac ccttcctaca aagtccgaga       960
gaagatagaa acggtcaag                                                   979
```

<210> SEQ ID NO 7
<211> LENGTH: 979
<212> TYPE: DNA
<213> ORGANISM: Rattus norvegicus

<400> SEQUENCE: 7

```
actcatcttg gaatctcaga attggcgcta tgctactggt ggatgggaga ctgtgtttag      60
acctgtaagt gagacatgca cagacagatc tggcctctcc actggacact ggtcaggtga     120
agtgaatgac aaaaatattc aagtggtgga gctccccatt gtagacagcc ttcatcctcg     180
gcctccttac ttaccactgg ctgttccaga agaccttgca gatcgactcg taagagtcca     240
tggtgatcct gcagtgtggt gggtgtccca gttcgtcaaa tatttgattc gtccacaacc     300
ttggctagaa aaggaaatag aagaagccac caagaagctt ggcttcaaac atccagtcat     360
tggagtccat gtcagacgca cagacaaagt gggaacagag gcagccttcc atcccatcga     420
agagtacatg gtacatgttg aagaacattt tcagcttctc gcacgcagaa tgcaagtgga     480
taaaaaaga gtatatctgg ctaccgatga ccctgctttg ttaaaggagg caaagacaaa     540
gtactccaat tatgaattta ttagtgataa ctctatttct tggtcagctg gactacacaa     600
tcggtacaca gaaaattcac ttcggggcgt gatcctggat atacactttc tctctcaggc     660
tgacttccta gtgtgtactt tttcatccca ggtctgtcgg gttgcttatg aaatcatgca     720
aaccctgcat cctgatgcct ctgcaaactt ccactcttta gatgacatct actattttgg     780
aggccaaaat gcccacaacc agattgccgt ttatcctcac aaacctcgaa ctgatgagga     840
aattccaatg gaacctggag atatcattgg tgtggctgga aaccattggg atggttattc     900
taaaggtgtc aacagaaaac ttggaaaaac aggcttatat ccctcctaca aagtccgaga     960
gaagatagaa acggtcaag                                                  979
```

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 8

```
aagtataagc ttacatggat gacgatatcg ctgcgctcgt                            40
```

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 9

```
atttaactgc aggaagcatt tgcggtggac gatggagggg                            40
```

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 10

```
atttaaggta ccgaagcatt tgcggtgcac gatggagggg                            40
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequense: Synthetic DNA

<400> SEQUENCE: 11
ctccaattat gaatttatta gtg                                      23

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequense: Synthetic DNA

<400> SEQUENCE: 12
ggatgtttga agccaagctt cttgg                                    25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequense: Synthetic DNA

<400> SEQUENCE: 13
gtccatggtg atcctgcagt gtgg                                     24

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequense: Synthetic DNA

<400> SEQUENCE: 14
caccaatgat atctccaggt tcc                                      23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequense: Synthetic DNA

<400> SEQUENCE: 15
gatatcgctg cgctcgttgt cgac                                     24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequense: Synthetic DNA

<400> SEQUENCE: 16
caggaaggaa ggctggaaaa gagc                                     24

```
<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 17
gatatcgctg cgctcgtcgt cgac                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 18
caggaaggaa ggctggaaga gagc                                          24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 19
atgcgggcat ggactggttc ctgg                                          24

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 20
ctatttttca gcttcaggat atgtggg                                       27

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 21
gtctgaagca ttatgtgttg aagc                                          24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 22
gtgagtacat tcattgtact gtg                                           23
```

-continued

```
<210> SEQ ID NO 23
<211> LENGTH: 575
<212> TYPE: PRT
<213> ORGANISM: Cricetulus griseus

<400> SEQUENCE: 23

Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Asp Leu Gly Lys Asp His
            100                 105                 110

Glu Ile Leu Arg Arg Arg Ile Glu Asn Gly Ala Lys Glu Leu Trp Phe
        115                 120                 125

Phe Leu Gln Ser Glu Leu Lys Lys Leu Lys Lys Leu Glu Gly Asn Glu
    130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Glu Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Lys Asp Lys Asn Val Gln Val
        275                 280                 285

Val Glu Leu Pro Ile Val Asp Ser Leu His Pro Arg Pro Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Arg Glu Ile Glu Thr Thr Lys Lys
            340                 345                 350

Leu Gly Phe Lys His Pro Val Ile Gly Val His Val Arg Arg Thr Asp
        355                 360                 365

Lys Val Gly Thr Glu Ala Ala Phe His Pro Ile Glu Glu Tyr Met Val
    370                 375                 380
```

```
His Val Glu Glu His Phe Gln Leu Leu Glu Arg Arg Met Lys Val Asp
385                 390                 395                 400

Lys Lys Arg Val Tyr Leu Ala Thr Asp Asp Pro Ser Leu Leu Lys Glu
            405                 410                 415

Ala Lys Thr Lys Tyr Ser Asn Tyr Glu Phe Ile Ser Asp Asn Ser Ile
        420                 425                 430

Ser Trp Ser Ala Gly Leu His Asn Arg Tyr Thr Glu Asn Ser Leu Arg
    435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
            500                 505                 510

His Gln Pro Arg Thr Lys Glu Glu Ile Pro Met Glu Pro Gly Asp Ile
        515                 520                 525

Ile Gly Val Ala Gly Asn His Trp Asn Gly Tyr Ser Lys Gly Val Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 24
<211> LENGTH: 575
<212> TYPE: PRT
<213> ORGANISM: Mus musculus

<400> SEQUENCE: 24

Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
            85                  90                  95

Ile Glu Asn Tyr Lys Lys Gln Ala Arg Asn Gly Leu Gly Lys Asp His
        100                 105                 110

Glu Ile Leu Arg Arg Arg Ile Glu Asn Gly Ala Lys Glu Leu Trp Phe
    115                 120                 125

Phe Leu Gln Ser Glu Leu Lys Lys Leu Lys His Leu Glu Gly Asn Glu
130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190
```

-continued

```
Arg Arg Ile Thr Tyr Leu Gln Asn Pro Lys Asp Cys Ser Lys Ala Arg
            195                 200                 205

Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Asn Asp Lys Asn Ile Gln Val
    275                 280                 285

Val Glu Leu Pro Ile Val Asp Ser Leu His Pro Arg Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Ala Thr Lys Lys
            340                 345                 350

Leu Gly Phe Lys His Pro Val Ile Gly Val His Val Arg Arg Thr Asp
                355                 360                 365

Lys Val Gly Thr Glu Ala Ala Phe His Pro Ile Glu Glu Tyr Met Val
    370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Thr Leu Leu Lys Glu
                405                 410                 415

Ala Lys Thr Lys Tyr Ser Asn Tyr Glu Phe Ile Ser Asp Asn Ser Ile
                420                 425                 430

Ser Trp Ser Ala Gly Leu His Asn Arg Tyr Thr Glu Asn Ser Leu Arg
    435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Val Tyr Pro
                500                 505                 510

His Lys Pro Arg Thr Glu Glu Ile Pro Met Glu Pro Gly Asp Ile
    515                 520                 525

Ile Gly Val Ala Gly Asn His Trp Asp Gly Tyr Ser Lys Gly Ile Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 25
<211> LENGTH: 18
<212> TYPE: PRT
<213> ORGANISM: Homo sapiens
```

-continued

```
<400> SEQUENCE: 25

Asp Glu Ser Ile Tyr Ser Asn Tyr Tyr Leu Tyr Glu Ser Ile Pro Lys
 1               5                  10                  15

Pro Cys

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 26
cttgtgtgac tcttaactct cagag                                          25

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 27
ccctcgagat aacttcgtat agc                                            23

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 28
ggtaggcctc actaactg                                                  18

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 29
catagaaaca agtaacaaca gccag                                          25

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequense: Synthetic
      DNA

<400> SEQUENCE: 30
gagacttcag cccacttcaa ttattggc                                       28

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequense: Synthetic
```

```
                        DNA

<400> SEQUENCE: 31
gaggccactt gtgtagcgcc aagtg                                          25

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
aggaaggtgg cgctcatcac gggc                                           24

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
taaggccaca gtcttaatt gcatcc                                          26

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34 cagggggtgtt cccttgagga ggtggaa                                       27

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35 ccccctcacgc atgaagcctg gag                                           23

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
ggcaggagac caccttgcga gtgcccac                                       28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA
```

```
<400> SEQUENCE: 37
ggcgctggct tacccggaga ggaatggg                                              28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
aaaaggcctc agttagtgaa ctgtatgg                                              28

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
cgcggatcct caagcgttgg ggttggtcc                                             29

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
cccaagcttg ccaccatggc tcacgctccc gctagctgcc cgagc                           45

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
ccggaattct gccaagtatg agccatcctg g                                          31

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
gccatccaga aggtggt                                                          17

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA
```

-continued

```
<400> SEQUENCE: 43
gtcttgtcag ggaagat                                                   17

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
ggcaggagac caccttgcga gtgcccac                                       28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
gggtgggctg taccttctgg aacagggc                                       28

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
ggcgctggct tacccggaga ggaatggg                                       28

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
ggaatgggtg tttgtctcct ccaaagatgc                                     30

<210> SEQ ID NO 48
<211> LENGTH: 1316
<212> TYPE: DNA
<213> ORGANISM: Cricetulus griseus

<400> SEQUENCE: 48
gccccgcccc ctccacctgg accgagagta gctggagaat tgtgcaccgg aagtagctct    60
tggactggtg gaaccctgcg caggtgcagc aacaatgggt gagccccagg gatccaggag   120
gatcctagtg acaggggggct ctggactggt gggcagagct atccagaagg tggtcgcaga   180
tggcgctggc ttacccggag aggaatgggt gtttgtctcc tccaaagatg cagatctgac   240
ggatgcagca caaaccccaag ccctgttcca gaaggtacag cccacccatg tcatccatct   300
tgctgcaatg gtaggaggcc ttttccggaa tatcaaatac aacttggatt tctggaggaa   360
gaatgtgcac atcaatgaca acgtcctgca ctcagctttc gaggtgggca ctcgcaaggt   420
ggtctcctgc ctgtccacct gtatcttccc tgacaagacc acctatccta ttgatgaaac   480
```

```
aatgatccac aatggtccac cccacagcag caattttggg tactcgtatg ccaagaggat      540
gattgacgtg cagaacaggg cctacttcca gcagcatggc tgcaccttca ctgctgtcat      600
ccctaccaat gtctttggac ctcatgacaa cttcaacatt gaagatggcc atgtgctgcc      660
tggcctcatc cataaggtgc atctggccaa gagtaatggt tcagccttga ctgtttgggg      720
tacagggaaa ccacggaggc agttcatcta ctcactggac ctagcccggc tcttcatctg      780
ggtcctgcgg gagtacaatg aagttgagcc catcatcctc tcagtgggcg aggaagatga      840
agtctccatt aaggaggcag ctgaggctgt agtggaggcc atggacttct gtggggaagt      900
cacttttgat tcaacaaagt cagatgggca gtataagaag acagccagca atggcaagct      960
tcgggcctac ttgcctgatt ccgtttcac accccttcaag caggctgtga aggagacctg     1020
tgcctggttc accgacaact atgagcaggc ccggaagtga agcatgggac aagcgggtgc     1080
tcagctggca atgcccagtc agtaggctgc agtctcatca tttgcttgtc aagaactgag     1140
gacagtatcc agcaacctga ccacatgct ggtctctctg ccaggggct tcatgcagcc      1200 atccagtagg gcccatgttt gtccatcctc gggggaaggc cagaccaaca ccttgtttgt     1260
ctgcttctgc cccaacctca gtgcatccat gctggtcctg ctgtcccttg tctaga        1316
```

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 49

```
gatcctgctg ggaccaaaat tgg                                               23
```

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50

```
cttaacatcc caagggatgc tg                                                22
```

<210> SEQ ID NO 51
<211> LENGTH: 1965
<212> TYPE: DNA
<213> ORGANISM: Cricetulus griseus

<400> SEQUENCE: 51

```
acgggggget cccggaagcg gggaccatgg cgtctctgcg cgaagcgagc ctgcggaagc       60
tgcggcgctt ttccgagatg agaggcaaac ctgtggcaac tgggaaattc tgggatgtag      120
ttgtaataac agcagctgac gaaaagcagg agcttgctta caagcaacag ttgtcggaga      180
agctgaagag aaaggaattg ccccttggag ttaactacca tgttttcact gatcctcctg      240
gaaccaaaat tggaaatgga ggatcaacac tttgttctct tcagtgcctg aaagcctct       300 atggagacaa gtggaattcc ttcacagtcc tgttaattca ctctggtggc tacagtcaac      360
gacttcccaa tgcaagcgct ttaggaaaaa tcttcacggc tttaccactt ggtgagccca      420
tttatcagat gttggactta aaactagcca tgtacatgga tttcccctca cgcatgaagc      480
```

-continued

```
ctggagtttt ggtcacctgt gcagatgata ttgaactata cagcattggg gactctgagt      540
ccattgcatt tgagcagcct ggctttactg ccctagccca tccatctagt ctggctgtag      600
gcaccacaca tggagtattt gtattggact ctgccggttc tttgcaacat ggtgacctag      660
agtacaggca atgccaccgt ttcctccata agcccagcat tgaaaacatg caccacttta      720
atgccgtgca tagactagga agctttggtc aacaggactt gagtgggggt gacaccacct      780
gtcatccatt gcactctgag tatgtctaca cagatagcct attttacatg gatcataaat      840
cagccaaaaa gctacttgat ttctatgaaa gtgtaggccc actgaactgt gaaatagatg      900
cctatggtga ctttctgcag gcactgggac ctggagcaac tgcagagtac accaagaaca      960
cctcacacgt cactaaagag gaatcacact tgttggacat gaggcagaaa atattccacc     1020
tcctcaaggg aacacccctg aatgttgttg tccttaataa ctccaggttt tatcacattg     1080
gaacaacgga ggagtatctg ctacatttca cttccaatgg ttcgttacag gcagagctgg     1140
gcttgcaatc catagctttc agtgtctttc caaatgtgcc tgaagactcc catgagaaac     1200
cctgtgtcat tcacagcatc ctgaattcag gatgctgtgt ggcccctggc tcagtggtag     1260
aatattccag attaggacct gaggtgtcca tctcggaaaa ctgcattatc agcggttctg     1320
tcatagaaaa agctgttctg cccccatgtt ctttcgtgtg ctctttaagt gtggagataa     1380
atggacactt agaatattca actatggtgt tggcatgga agacaacttg aagaacagtg     1440
ttaaaaccat atcagatata aagatgcttc agttctttgg agtctgtttc ctgacttgtt     1500
tagatatttg gaaccttaaa gctatggaag aactattttc aggaagtaag acgcagctga     1560
gcctgtggac tgctcgaatt ttccctgtct gttcttctct gagtgagtcg gttgcagcat     1620
cccttgggat gttaaatgcc attcgaaacc attcgccatt cagcctgagc aacttcaagc     1680
tgctgtccat ccaggaaatg cttctctgca agatgtagg agacatgctt gcttacaggg     1740
agcaactctt tctagaaatc agttcaaaga gaaaacagtc tgattcggag aaatcttaaa     1800
tacaatggat tttgcctgga aacaggattg caaatgcagg catattctat agatctctgg     1860
gttcttcttt ctttctcccc tctctccttt cctttccctt tgatgtaatg acaaaggtaa     1920
aaatggccac ttctgatgga aaaaaaaaaa aaaaaaaaa aaaaa                       1965
```

```
<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 52 cagggggtgtt cccttgagga ggtggaa                                          27

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 53
cactgagcca ggggccacac agcatcc                                           27

<210> SEQ ID NO 54
<211> LENGTH: 23
```

-continued

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54
cccctcacgc atgaagcctg gag                                              23

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 55
tgccaccgtt tcctccataa gcccagc                                          27

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56
atggctcaag ctcccgctaa gtgcccga                                         28

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57
tcaagcgttt gggttggtcc tcatgag                                          27

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 58
tccggggatg gcgagatggg caagc                                            25

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
cttgacatgg ctctgggctc caag                                             24

<210> SEQ ID NO 60
<211> LENGTH: 25
<212> TYPE: DNA
```

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic DNA

<400> SEQUENCE: 60
ccacttcagt cggtcggtag tattt                                    25

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic DNA

<400> SEQUENCE: 61
cgctcacccg cctgaggcga catg                                     24

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic DNA

<400> SEQUENCE: 62
ggcaggtgct gtcggtgagg tcaccatagt gc                            32

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic DNA

<400> SEQUENCE: 63
ggggccatgc caaggactat gtcg                                     24

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic DNA

<400> SEQUENCE: 64
atgtggctga tgttacaaaa tgatg                                    25

<210> SEQ ID NO 65
<211> LENGTH: 1504
<212> TYPE: DNA
<213> ORGANISM: Cricetulus griseus
<220> FEATURE:
<221> NAME/KEY: CDS
<222> LOCATION: (1)..(1119)

<400> SEQUENCE: 65 atg gct cac gct ccc gct agc tgc ccg agc tcc agg aac tct ggg gac    48
Met Ala His Ala Pro Ala Ser Cys Pro Ser Ser Arg Asn Ser Gly Asp
 1               5                   10                  15 ggc gat aag ggc aag ccc agg aag gtg gcg ctc atc acg ggc atc acc    96
Gly Asp Lys Gly Lys Pro Arg Lys Val Ala Leu Ile Thr Gly Ile Thr
            20                  25                  30

```
ggc cag gat ggc tca tac ttg gca gaa ttc ctg ctg gag aaa gga tac        144
Gly Gln Asp Gly Ser Tyr Leu Ala Glu Phe Leu Leu Glu Lys Gly Tyr
         35                  40                  45 gag gtt cat gga att gta cgg cga tcc agt tca ttt aat aca ggt cga        192
Glu Val His Gly Ile Val Arg Arg Ser Ser Ser Phe Asn Thr Gly Arg
 50                  55                  60 att gaa cat tta tat aag aat cca cag gct cat att gaa gga aac atg        240
Ile Glu His Leu Tyr Lys Asn Pro Gln Ala His Ile Glu Gly Asn Met
 65                  70                  75                  80 aag ttg cac tat ggt gac ctc acc gac agc acc tgc cta gta aaa atc        288
Lys Leu His Tyr Gly Asp Leu Thr Asp Ser Thr Cys Leu Val Lys Ile
                 85                  90                  95 atc aat gaa gtc aaa cct aca gag atc tac aat ctt ggt gcc cag agc        336
Ile Asn Glu Val Lys Pro Thr Glu Ile Tyr Asn Leu Gly Ala Gln Ser
            100                 105                 110 cat gtc aag att tcc ttt gac tta gca gag tac act gca gat gtt gat        384
His Val Lys Ile Ser Phe Asp Leu Ala Glu Tyr Thr Ala Asp Val Asp
        115                 120                 125 gga gtt ggc acc ttg cgg ctt ctg gat gca att aag act tgt ggc ctt        432
Gly Val Gly Thr Leu Arg Leu Leu Asp Ala Ile Lys Thr Cys Gly Leu
130                 135                 140 ata aat tct gtg aag ttc tac cag gcc tca act agt gaa ctg tat gga        480
Ile Asn Ser Val Lys Phe Tyr Gln Ala Ser Thr Ser Glu Leu Tyr Gly
145                 150                 155                 160 aaa gtg caa gaa ata ccc cag aaa gag acc acc cct ttc tat cca agg        528
Lys Val Gln Glu Ile Pro Gln Lys Glu Thr Thr Pro Phe Tyr Pro Arg
                165                 170                 175 tcg ccc tat gga gca gcc aaa ctt tat gcc tat tgg att gta gtg aac        576
Ser Pro Tyr Gly Ala Ala Lys Leu Tyr Ala Tyr Trp Ile Val Val Asn
            180                 185                 190 ttt cga gag gct tat aat ctc ttt gcg gtg aac ggc att ctc ttc aat        624
Phe Arg Glu Ala Tyr Asn Leu Phe Ala Val Asn Gly Ile Leu Phe Asn
        195                 200                 205 cat gag agt cct aga aga gga gct aat ttt gtt act cga aaa att agc        672
His Glu Ser Pro Arg Arg Gly Ala Asn Phe Val Thr Arg Lys Ile Ser
    210                 215                 220 cgg tca gta gct aag att tac ctt gga caa ctg gaa tgt ttc agt ttg        720
Arg Ser Val Ala Lys Ile Tyr Leu Gly Gln Leu Glu Cys Phe Ser Leu
225                 230                 235                 240 gga aat ctg gac gcc aaa cga gac tgg ggc cat gcc aag gac tat gtc        768
Gly Asn Leu Asp Ala Lys Arg Asp Trp Gly His Ala Lys Asp Tyr Val
                245                 250                 255 gag gct atg tgg ctg atg tta caa aat gat gaa cca gag gac ttt gtc        816
Glu Ala Met Trp Leu Met Leu Gln Asn Asp Glu Pro Glu Asp Phe Val
            260                 265                 270 ata gct act ggg gaa gtt cat agt gtc cgt gaa ttt gtt gag aaa tca        864
Ile Ala Thr Gly Glu Val His Ser Val Arg Glu Phe Val Glu Lys Ser
        275                 280                 285 ttc atg cac att gga aag acc att gtg tgg gaa gga aag aat gaa aat        912
Phe Met His Ile Gly Lys Thr Ile Val Trp Glu Gly Lys Asn Glu Asn
    290                 295                 300 gaa gtg ggc aga tgt aaa gag acc ggc aaa att cat gtg act gtg gat        960
Glu Val Gly Arg Cys Lys Glu Thr Gly Lys Ile His Val Thr Val Asp
305                 310                 315                 320 ctg aaa tac tac cga cca act gaa gtg gac ttc ctg cag gga gac tgc       1008
Leu Lys Tyr Tyr Arg Pro Thr Glu Val Asp Phe Leu Gln Gly Asp Cys
                325                 330                 335 tcc aag gcg cag cag aaa ctg aac tgg aag ccc cgc gtt gcc ttt gac       1056
Ser Lys Ala Gln Gln Lys Leu Asn Trp Lys Pro Arg Val Ala Phe Asp
```

-continued

```
              340                 345                 350
gag ctg gtg agg gag atg gtg caa gcc gat gtg gag ctc atg aga acc    1104
Glu Leu Val Arg Glu Met Val Gln Ala Asp Val Glu Leu Met Arg Thr
        355                 360                 365 aac ccc aac gcc tga gcacctctac aaaaaaattc gcgagacatg gactatggtg    1159
Asn Pro Asn Ala
    370 cagagccagc caaccagagt ccagccactc ctgagaccat cgaccataaa ccctcgactg    1219 cctgtgtcgt ccccacagct aagagctggg ccacaggttt gtgggcacca ggacggggac    1279 actccagagc taaggccact tcgcttttgt caaaggctcc tctcaatgat tttgggaaat    1339 caagaagttt aaaatcacat actcatttta cttgaaatta tgtcactaga caacttaaat    1399 ttttgagtct tgagattgtt tttctctttt cttattaaat gatctttcta tgacccagca    1459 aaaaaaaaaa aaaaaaggga tataaaaaaa aaaaaaaaa aaaaa                     1504
```

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
atgaagttgc actatggtga cctca                                          25

<210> SEQ ID NO 67
<211> LENGTH: 59
<212> TYPE: DNA
<213> ORGANISM: Cricetulus griseus

<400> SEQUENCE: 67
ccgacagcac ctgcctagta aaatcatca atgaagtcaa acctacagag atctacaat      59

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
gacttagcag agtacactgc agatg                                          25

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
accttggata gaaagggtg gtctc                                           25

<210> SEQ ID NO 70
<211> LENGTH: 125
<212> TYPE: DNA
<213> ORGANISM: Cricetulus griseus

<400> SEQUENCE: 70

```
ttgatggagt tggcacccttg cggcttctgg atgcaattaa gacttgtggc cttataaatt    60
ctgtgaagtt ctaccaggcc tcaactagtg aactgtatgg aaaagtgcaa gaaatacccc   120
agaaa                                                                125
```

<210> SEQ ID NO 71
<211> LENGTH: 372
<212> TYPE: PRT
<213> ORGANISM: Cricetulus griseus

<400> SEQUENCE: 71

```
Met Ala His Ala Pro Ala Ser Cys Pro Ser Ser Arg Asn Ser Gly Asp
  1               5                  10                  15

Gly Asp Lys Gly Lys Pro Arg Lys Val Ala Leu Ile Thr Gly Ile Thr
             20                  25                  30

Gly Gln Asp Gly Ser Tyr Leu Ala Glu Phe Leu Leu Glu Lys Gly Tyr
         35                  40                  45

Glu Val His Gly Ile Val Arg Arg Ser Ser Phe Asn Thr Gly Arg
     50                  55                  60

Ile Glu His Leu Tyr Lys Asn Pro Gln Ala His Ile Glu Gly Asn Met
 65                  70                  75                  80

Lys Leu His Tyr Gly Asp Leu Thr Asp Ser Thr Cys Leu Val Lys Ile
                 85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
        115                 120                 125

Gly Val Gly Thr Leu Arg Leu Leu Asp Ala Ile Lys Thr Cys Gly Leu
    130                 135                 140

Ile Asn Ser Val Lys Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                165                 170                 175

Ser Pro Tyr Gly Ala Ala Lys Leu Tyr Ala Tyr Trp Ile Val Val Asn
            180                 185                 190

Phe Arg Glu Ala Tyr Asn Leu Phe Ala Val Asn Gly Ile Leu Phe Asn
        195                 200                 205

His Glu Ser Pro Arg Arg Gly Ala Asn Phe Val Thr Arg Lys Ile Ser
    210                 215                 220

Arg Ser Val Ala Lys Ile Tyr Leu Gly Gln Leu Glu Cys Phe Ser Leu
225                 230                 235                 240

Gly Asn Leu Asp Ala Lys Arg Asp Trp Gly His Ala Lys Asp Tyr Val
                245                 250                 255

Glu Ala Met Trp Leu Met Leu Gln Asn Asp Glu Pro Glu Asp Phe Val
            260                 265                 270

Ile Ala Thr Gly Glu Val His Ser Val Arg Glu Phe Val Glu Lys Ser
        275                 280                 285

Phe Met His Ile Gly Lys Thr Ile Val Trp Glu Gly Lys Asn Glu Asn
    290                 295                 300

Glu Val Gly Arg Cys Lys Glu Thr Gly Lys Ile His Val Thr Val Asp
305                 310                 315                 320

Leu Lys Tyr Tyr Arg Pro Thr Glu Val Asp Phe Leu Gln Gly Asp Cys
                325                 330                 335

Ser Lys Ala Gln Gln Lys Leu Asn Trp Lys Pro Arg Val Ala Phe Asp
            340                 345                 350
```

```
Glu Leu Val Arg Glu Met Val Gln Ala Asp Val Glu Leu Met Arg Thr
        355                 360                 365
Asn Pro Asn Ala
        370

<210> SEQ ID NO 72
<211> LENGTH: 321
<212> TYPE: PRT
<213> ORGANISM: Cricetulus griseus

<400> SEQUENCE: 72

Met Gly Glu Pro Gln Gly Ser Arg Arg Ile Leu Val Thr Gly Gly Ser
  1               5                  10                  15

Gly Leu Val Gly Arg Ala Ile Gln Lys Val Val Ala Asp Gly Ala Gly
             20                  25                  30

Leu Pro Gly Glu Glu Trp Val Phe Val Ser Ser Lys Asp Ala Asp Leu
         35                  40                  45

Thr Asp Ala Ala Gln Thr Gln Ala Leu Phe Gln Lys Val Gln Pro Thr
 50                  55                  60

His Val Ile His Leu Ala Ala Met Val Gly Gly Leu Phe Arg Asn Ile
 65                  70                  75                  80

Lys Tyr Asn Leu Asp Phe Trp Arg Lys Asn Val His Ile Asn Asp Asn
                 85                  90                  95

Val Leu His Ser Ala Phe Glu Val Gly Thr Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala
210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe Cys Gly Glu Val Thr Phe Asp
            260                 265                 270

Ser Thr Lys Ser Asp Gly Gln Tyr Lys Lys Thr Ala Ser Asn Gly Lys
        275                 280                 285

Leu Arg Ala Tyr Leu Pro Asp Phe Arg Phe Thr Pro Phe Lys Gln Ala
    290                 295                 300

Val Lys Glu Thr Cys Ala Trp Phe Thr Asp Asn Tyr Glu Gln Ala Arg
305                 310                 315                 320

Lys

<210> SEQ ID NO 73
```

```
<211> LENGTH: 590
<212> TYPE: PRT
<213> ORGANISM: Cricetulus griseus

<400> SEQUENCE: 73
```

| | | | | | | | | | | | | | | |
|---|---|---|---|---|---|---|---|---|---|---|---|---|---|---|
| Met | Ala | Ser | Leu | Arg | Glu | Ala | Ser | Leu | Arg | Lys | Leu | Arg | Arg | Phe | Ser |
| 1 | | | | 5 | | | | | 10 | | | | | 15 | |
| Glu | Met | Arg | Gly | Lys | Pro | Val | Ala | Thr | Gly | Lys | Phe | Trp | Asp | Val | Val |
| | | | 20 | | | | | 25 | | | | | 30 | | |
| Val | Ile | Thr | Ala | Ala | Asp | Glu | Lys | Gln | Glu | Leu | Ala | Tyr | Lys | Gln | Gln |
| | | 35 | | | | | 40 | | | | | 45 | | | |
| Leu | Ser | Glu | Lys | Leu | Lys | Arg | Lys | Glu | Leu | Pro | Leu | Gly | Val | Asn | Tyr |
| | 50 | | | | | 55 | | | | | 60 | | | | |
| His | Val | Phe | Thr | Asp | Pro | Pro | Gly | Thr | Lys | Ile | Gly | Asn | Gly | Gly | Ser |
| 65 | | | | | 70 | | | | | 75 | | | | | 80 |
| Thr | Leu | Cys | Ser | Leu | Gln | Cys | Leu | Glu | Ser | Leu | Tyr | Gly | Asp | Lys | Trp |
| | | | | 85 | | | | | 90 | | | | | 95 | |
| Asn | Ser | Phe | Thr | Val | Leu | Leu | Ile | His | Ser | Gly | Gly | Tyr | Ser | Gln | Arg |
| | | | 100 | | | | | 105 | | | | | 110 | | |
| Leu | Pro | Asn | Ala | Ser | Ala | Leu | Gly | Lys | Ile | Phe | Thr | Ala | Leu | Pro | Leu |
| | | | | 115 | | | | | 120 | | | | | 125 | |
| Gly | Glu | Pro | Ile | Tyr | Gln | Met | Leu | Asp | Leu | Lys | Leu | Ala | Met | Tyr | Met |
| | 130 | | | | | 135 | | | | | 140 | | | | |
| Asp | Phe | Pro | Ser | Arg | Met | Lys | Pro | Gly | Val | Leu | Val | Thr | Cys | Ala | Asp |
| 145 | | | | | 150 | | | | | 155 | | | | | 160 |
| Asp | Ile | Glu | Leu | Tyr | Ser | Ile | Gly | Asp | Ser | Glu | Ser | Ile | Ala | Phe | Glu |
| | | | | 165 | | | | | 170 | | | | | 175 | |
| Gln | Pro | Gly | Phe | Thr | Ala | Leu | Ala | His | Pro | Ser | Ser | Leu | Ala | Val | Gly |
| | | | 180 | | | | | 185 | | | | | 190 | | |
| Thr | Thr | His | Gly | Val | Phe | Val | Leu | Asp | Ser | Ala | Gly | Ser | Leu | Gln | His |
| | | 195 | | | | | 200 | | | | | 205 | | | |
| Gly | Asp | Leu | Glu | Tyr | Arg | Gln | Cys | His | Arg | Phe | Leu | His | Lys | Pro | Ser |
| | 210 | | | | | 215 | | | | | 220 | | | | |
| Ile | Glu | Asn | Met | His | His | Phe | Asn | Ala | Val | His | Arg | Leu | Gly | Ser | Phe |
| 225 | | | | | 230 | | | | | 235 | | | | | 240 |
| Gly | Gln | Gln | Asp | Leu | Ser | Gly | Gly | Asp | Thr | Thr | Cys | His | Pro | Leu | His |
| | | | | 245 | | | | | 250 | | | | | 255 | |
| Ser | Glu | Tyr | Val | Tyr | Thr | Asp | Ser | Leu | Phe | Tyr | Met | Asp | His | Lys | Ser |
| | | | 260 | | | | | 265 | | | | | 270 | | |
| Ala | Lys | Lys | Leu | Leu | Asp | Phe | Tyr | Glu | Ser | Val | Gly | Pro | Leu | Asn | Cys |
| | | 275 | | | | | 280 | | | | | 285 | | | |
| Glu | Ile | Asp | Ala | Tyr | Gly | Asp | Phe | Leu | Gln | Ala | Leu | Gly | Pro | Gly | Ala |
| | 290 | | | | | 295 | | | | | 300 | | | | |
| Thr | Ala | Glu | Tyr | Thr | Lys | Asn | Thr | Ser | His | Val | Thr | Lys | Glu | Ser | |
| 305 | | | | | 310 | | | | | 315 | | | | | 320 |
| His | Leu | Leu | Asp | Met | Arg | Gln | Lys | Ile | Phe | His | Leu | Leu | Lys | Gly | Thr |
| | | | | 325 | | | | | 330 | | | | | 335 | |
| Pro | Leu | Asn | Val | Val | Leu | Asn | Asn | Ser | Arg | Phe | Tyr | His | Ile | Gly | |
| | | | 340 | | | | | 345 | | | | | 350 | | |
| Thr | Thr | Glu | Glu | Tyr | Leu | Leu | His | Phe | Thr | Ser | Asn | Gly | Ser | Leu | Gln |
| | | 355 | | | | | 360 | | | | | 365 | | | |
| Ala | Glu | Leu | Gly | Leu | Gln | Ser | Ile | Ala | Phe | Ser | Val | Phe | Pro | Asn | Val |
| | 370 | | | | | 375 | | | | | 380 | | | | |
| Pro | Glu | Asp | Ser | His | Glu | Lys | Pro | Cys | Val | Ile | His | Ser | Ile | Leu | Asn |

```
                                -continued
385                 390                 395                 400
Ser Gly Cys Cys Val Ala Pro Gly Ser Val Val Glu Tyr Ser Arg Leu
                405                 410                 415

Gly Pro Glu Val Ser Ile Ser Glu Asn Cys Ile Ile Ser Gly Ser Val
                420                 425                 430

Ile Glu Lys Ala Val Leu Pro Pro Cys Ser Phe Val Cys Ser Leu Ser
                435                 440                 445

Val Glu Ile Asn Gly His Leu Glu Tyr Ser Thr Met Val Phe Gly Met
            450                 455                 460

Glu Asp Asn Leu Lys Asn Ser Val Lys Thr Ile Ser Asp Ile Lys Met
465                 470                 475                 480

Leu Gln Phe Phe Gly Val Cys Phe Leu Thr Cys Leu Asp Ile Trp Asn
                485                 490                 495

Leu Lys Ala Met Glu Glu Leu Phe Ser Gly Ser Lys Thr Gln Leu Ser
                500                 505                 510

Leu Trp Thr Ala Arg Ile Phe Pro Val Cys Ser Ser Leu Ser Glu Ser
            515                 520                 525

Val Ala Ala Ser Leu Gly Met Leu Asn Ala Ile Arg Asn His Ser Pro
            530                 535                 540

Phe Ser Leu Ser Asn Phe Lys Leu Leu Ser Ile Gln Glu Met Leu Leu
545                 550                 555                 560

Cys Lys Asp Val Gly Asp Met Leu Ala Tyr Arg Glu Gln Leu Phe Leu
                565                 570                 575

Glu Ile Ser Ser Lys Arg Lys Gln Ser Asp Ser Glu Lys Ser
            580                 585                 590
```

MAMMALIAN HOST CELL MODIFIED BY RNAI TO INHIBIT α 1,6-FUCOSYLTRANSFERASE

The present application is a divisional of U.S. application Ser. No. 11/131,212, filed May 18, 2005, which is a divisional of U.S. application Ser. No. 09/971,773, filed Oct. 9, 2001 (issued as U.S. Pat. No. 6,946,292), which claims benefit of U.S. Provisional Application Ser. No. 60/268,916, filed Feb. 16, 2001, and Japanese applications P 2000-308526, filed Oct. 6, 2000 and PCT/JP01/08804, filed Oct. 5, 2001, the entire contents of each of which is incorporated herein by reference.

BACKGROUND OF THE INVENTION

1. Field of the Invention

The present invention relates to a cell for the production of an antibody molecule such as an antibody useful for various diseases, a fragment of the antibody and a fusion protein having the Fc region of the antibody or the like, a method for producing an antibody composition using the cell, the antibody composition and use thereof.

2. Brief Description of the Background Art

Since antibodies have high binding activity, binding specificity and high stability in blood, their applications to diagnosis, prevention and treatment of various human diseases have been attempted [*Monoclonal Antibodies: Principles and Applications*, Wiley-Liss, Inc., Chapter 2.1 (1995)]. Also, production of a humanized antibody such as a human chimeric antibody or a human complementarity determining region (hereinafter referred to as "CDR")-grafted antibody from an antibody derived from an animal other than human have been attempted by using genetic recombination techniques. The human chimeric antibody is an antibody in which its antibody variable region (hereinafter referred to as "V region") is an antibody derived from an animal other than human and its constant region (hereinafter referred to as "C region") is derived from a human antibody. The human CDR-grafted antibody is an antibody in which the CDR of a human antibody is replaced by CDR of an antibody derived from an animal other than human.

It has been revealed that five classes, namely IgM, IgD, IgG, IgA and IgE, are present in antibodies derived from mammals. Antibodies of human IgG class are mainly used for the diagnosis, prevention and treatment of various human diseases because they have functional characteristics such as long half-life in blood, various effector functions and the like [*Monoclonal Antibodies: Principles and Applications*, Wiley-Liss, Inc., Chapter 1 (1995)]. The human IgG class antibody is further classified into the following 4 subclasses: IgG1, IgG2, IgG3 and IgG4. A large number of studies have so far been conducted for antibody-dependent cell-mediated cytotoxic activity (hereinafter referred to as "ADCC activity") and complement-dependent cytotoxic activity (hereinafter referred to as "CDC activity") as effector functions of the IgG class antibody, and it has been reported that among antibodies of the human IgG class, the IgG1 subclass has the highest ADCC activity and CDC activity [*Chemical Immunology*, 6, 88 (1997)]. In view of the above, most of the anti-tumor humanized antibodies, including commercially available Rituxan and Herceptin, which require high effector functions for the expression of their effects, are antibodies of the human IgG1 subclass.

Expression of ADCC activity and CDC activity of the human IgG1 subclass antibodies requires binding of the Fc region of the antibody to an antibody receptor existing on the surface of an effector cell, such as a killer cell, a natural killer cell, an activated macrophage or the like (hereinafter referred to as "FcγR") and various complement components are bound. Regarding the binding, it has been suggested that several amino acid residues in the hinge region and the second domain of C region (hereinafter referred to as "Cγ2 domain") of the antibody are important [*Eur. J. Immunol.*, 23, 1098 (1993), *Immunology*, 86, 319 (1995), *Chemical Immunology*, 65, 88 (1997)] and that a sugar chain binding to the Cγ2 domain [*Chemical Immunology*, 65, 88 (1997)] is also important.

Regarding the sugar chain, Boyd et al. have examined effects of a sugar chain on the ADCC activity and CDC activity by treating a human CDR-grafted antibody CAMPATH-1H (human IgG1 subclass) produced by a Chinese hamster ovary cell (CHO cell) or a mouse myeloma NSO cell (NSO cell) with various sugar hydrolyzing enzymes, and reported that elimination of the non-reducing end sialic acid did rot have influence upon bosh activities, but the CDC activity alone was affected by further removal of galactose residue and about 50% of the activity was decreased, and that complete removal of the sugar chain caused disappearance of both activities [*Molecular Immunol.*, 32, 1311 (1995)]. Also, Lifely et al. have analyzed the sugar chain bound to a human CDR-grafted antibody CAMPATH-1H (human IgG1 subclass) which was produced by CHO cell, NSO cell or rat myeloma YO cell, measured its ADCC activity, and reported that the CAMPATH-1H derived from YO cell showed the highest ADCC activity, suggesting that N-acetylglucosamine (hereinafter referred also to as "GlcNAc") at the bisecting position is important for the activity [*Glycobiology*, 5, 813 (1995); WO 99/54342]. These reports indicate that the structure of the sugar chain plays an important role in the effector functions of human antibodies of IgG1 subclass and that it is possible to prepare an antibody having more higher effector function by changing the structure of the sugar chain. However, actually, structures of sugar chains are various and complex, and it cannot be said that an actual important structure for the effector unction was identified.

Sugar chains of glycoproteins are roughly divided into two types, namely a sugar chain which binds to asparagine (N-glycoside-linked sugar chain) and a sugar chain which binds to other amino acid such as serine, threonine (O-glycoside-linked sugar chain), based on the binding form to the protein moiety. The N-glycoside-linked sugar chains have various structures [*Biochemical Experimentation Method 23—Method for Studying Glycoprotein Sugar Chain* (Gakujutsu Shuppan Center), edited by Reiko Takahashi (1989)], but it is known that they have a basic common core structure shown by the following structural formula (I).

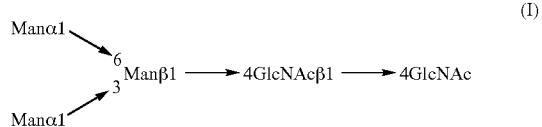

(I)

The sugar chain terminus which binds to asparagine is called a reducing end, and the opposite side is called a non-reducing end. It is known that the N-glycoside-linked sugar chain includes a high mannose type in which mannose alone binds to the non-reducing end of the core structure; a complex type in which the non-reducing end side of the core structure has at least one parallel branches of galactose-N-acetylglucosamine (hereinafter referred to as "Gal-GlcNAc") and the non-reducing end side of Gal-GlcNAc has a structure of sialic acid, bisecting N-acetylglucosamine or the like; a hybrid type in which the non-reducing end side of the core structure has branches of both of the high mannose type and complex type; and the like.

In the Fc region of an antibody of an IgG type, two N-glycoside-linked sugar chain binding sites are present. In serum IgG, to the sugar chain binding site, generally, binds a complex type sugar chain having plural branches and in which addition of sialic acid or bisecting N-acetylglucosamine is low. It is known that there is variety in the manner and form in which addition of galactose is made to the non-reducing end of the complex type sugar chain and the addition of fucose to the N-acetylglucosamine in the reducing end [Leppanen, A, et al., *Biochemistry* (1997) 36, 7026-7036, "in vitro Biosynthesis of a Decasaccharide Prototype of Multiply Branched Polylactoaminoglycan Backbones"].

It has been considered that such a structure of a sugar chain is determined by sugar chain genes, namely a gene for a glycosyltransferase which synhesizes a sugar chain and a gene for a glycolytic enzyme which hydrolyzes the sugar chain.

Synthesis of an N-glycoside-linked sugar chain is described below.

Glycoproteins are modified with a sugar chain in the endoplasmic reticulum (hereinafter referred to as "ER") lumen. During the biosynthesis step of the N-glycoside-linked sugar chain, a relatively large sugar chain is transferred to the polypeptide chain which is elongating in the ER lumen. In the transformation, the sugar chain is firstly added in succession to phosphate groups of a long chain lipid carrier comprising about 20 α-isoprene units, which is called dolichol phosphate (hereinafter referred also to as "P-Dol"). That is, N-acetylglucosamine is transferred to dolichol phosphate to thereby form GlcNAc-P-P-Dol and then one more GlcNAc is transferred to form GlcNAc-GlcNAc-P-P-Dol. Next, five mannoses (hereinafter mannose is also referred to as "Man") are transferred to thereby form $(Man)_5$-$(GlcNAc)_2$-P-P-Dol and then four Man's and three glucoses (hereinafter glucose is also referred to as "Glc") are transferred. Thus, a sugar chain precursor, $(Glc)_3$-$(Man)_9$-$(GlcNAc)_2$-P-P-Dol, called core oligosaccharide is formed. The sugar chain precursor comprising 14 sugars is transferred as a mass to a polypeptide having an asparagine-X-serine or asparagine-X-threonine sequence in the ER lumen. In the reaction, dolichol pyrophosphate (P-P-Dol) bound to the core oligosaccharide is released but again becomes dolichol phosphate by hydrolysis with pyrophosphatase and is recycled. Trimming of the sugar chain immediately starts after the sugar chain binds to the polypeptide. That is, 3 Glc's and 1 or 2 Man's are eliminated on the ER, and it is known that α-1,2-glucosidase I, α-1,3-glucosidase II and α-1,2-mannosidase relates to the elimination.

The glycoprotein which was subjected to trimming on the ER is transferred to the Golgi body and are variously modified. In the cis part of the Golgi body, N-acetylglucosamine phosphotransferase which relates to addition of mannose phosphate, N-acetylglucosamine 1-phosphodiester α-N-acetylglucosaminidase and α-mannosidase I are present and reduce the Man residues to 5. In the medium part of the Golgi body, N-acetylglucosamine transferase I (GnTI) which relates to addition of the first outside GlcNAc of the complex type N-glycoside-linked sugar chain, α-mannosidase II which relates to elimination of 2 Man's, N-acetylglucosamine transferase II (GnTII) which relates to addition of the second GlcNAc From the outside and α-1,6-fucosyltransferase which relates to addition of fucose to the reducing end N-acetylglucosamine are present. In the trans part of the Golgi body, galactose transferase which relates to addition of galactose and sialyltransferase which relates to addition of sialic acid such as N-acetylneuraminic acid or the like are present. It is known that N-glycoside-linked sugar chain is formed by activities of these various enzymes.

In general, most of the humanized antibodies of which application to medicaments is in consideration are prepared using genetic recombination techniques and produced using Chinese hamster ovary tissue-derived CHO cell as the host cell. But as described above, since the sugar chain structure plays a remarkably important role in the effector function of antibodies and differences are observed in the sugar chain structure of glycoproteins expressed by host cells, development of a host cell which can be used for the production of an antibody having higher effector function is desired.

In order to modify the sugar chain structure of the produced glycoprotein, various methods have been attempted, such as 1) application of an inhibitor against an enzyme relating to the modification of a sugar chain, 2) selection of a mutant, 3) introduction of a gene encoding an enzyme relating to the modification of a sugar chain, and the like. Specific examples are described below.

Examples of an inhibitor against an enzyme relating to the modification of a sugar chain include tunicamycin which selectively inhibits formation of GlcNAc-P-P-Dol which is the first step of the formation of a core oligosaccharide which is a precursor of an N-glycoside-linked sugar chain, castanospermin and N-methyl-1-deoxynojirimycin which are inhibitors of glycosidase I, bromocondulitol which is an inhibitor of glycosidase II, 1-deoxynojirimycin and 1,4-dioxy-1,4-imino-D-mannitol which are inhibitors of mannosidase I, swainsonine which is an inhibitor of mannosidase II and the like. Examples of an inhibitor specific for a glycosyltransferase include deoxy derivatives of substrates against N-acetylglucosamine transferase V (GnTV) and the like [*Glycobiology Series* 2—*Destiny of Sugar Chain in Cell* (Kodan-sha Scientific), edited by Katsutaka Nagai, Senichiro Hakomori and Akira Kobata (1993)]. Also, it is known that 1-deoxynojirimycin inhibits synthesis of a complex type sugar chain and increases the ratio of high mannose type and hybrid type sugar chains. Actually, it has been reported that sugar chain structure of IgG was changed and properties such as antigen binding activity and the like was changed when the inhibitors were added to a medium [*Molecular Immunol.*, 26, 1113 (1989)].

Mutants regarding the activity of an enzyme relating to the modification of a sugar chain are mainly selected and obtained as a lectin-resistant cell line. For example, CHO cell mutants having various sugar chain structures have been obtained as a lectin-resistant cell line using a lectin such as WGA (wheat-germ agglutinin derived from *T. vulgaris*), ConA (cocanavalin A derived from *C. ensiformis*), RIC (a toxin derived from *R. communis*), L-PHA (leucoagglutinin derived from *P. vulgaris*), LCA (lentil agglutinin derived from *L. culinaris*), PSA (pea lectin derived from *P. sativum*) or the like [*Somatic Cell Mol. Genet.*, 12, 51 (1986)].

As an example of the modification of the sugar chain structure of a product obtained by introducing the gene of an enzyme relating to the modification of a sugar chain into a host cell, it has been reported that a protein in which a number of sialic acid is added to the non-reducing end of the sugar chain can be produced by introducing rat β-galactoside-α-2,6-sialyltransferase into CHO cell [*J. Biol. Chem.*, 261, 13848 (1989)].

Also, it was confirmed that an H antigen (Fucα1-2Galβ1-) in which fucose (hereinafter also referred to as "Fuc") was added to the non-reducing end of the sugar chain was expressed by introducing human β-galactoside-2-α-fucosyltransferase into mouse L cell [*Science,* 252, 1668 (1991)]. In addition, based on knowledge that addition of the bisecting-positioned N-acetylglucosamine of N-glycoside-linked sugar chain is important for the ADCC activity of antibody, Umana et al. have prepared CHO cell which expresses β-1,4-N-acetylglucosamine transferase III (GnTIII) and compared it with the parent cell line on the expresion of GnTIII. It was confirmed that express of GnTIII was not observed in the parent cell line of CHO cell [*J. Biol. Chem.,* 6, 13370 (1984)], and that the antibody expressed using the produced GnTIII expressing CHO cell had ADCC activity 16 times higher than the antibody expressed using the parent cell line [*Glycobiology,* 5, 813 (1995): WO 99/54342]. At this time, Umana et al. have also produced CHO cell into which β-1,4-N-acetylglucosamine transferase V (GnTV) was introduced and reported that excess expression of GnTIII or GnTV shows toxicity for CHO cell.

Thus, in order to modify the sugar chain structure of the glycoprotein to be produced, control of the activity of the enzyme relating to the modification of a sugar chain in the host cell has been attempted, but actually, the structures of sugar chains are various and complex, and solution of the physiological roles of sugar chains would be insufficient, so that trial and error are repeated. Particularly, although it has been revealed little by little that the effector function of antibodies is greatly influenced by the sugar chain structure, a truly important sugar chain structure has not been specified yet. Accordingly, identification of a sugar chain which has influence upon the effector function of antibodies and development of a host cell to which such a sugar chain structure can be added are expected for developing medicaments.

SUMMARY OF THE INVENTION

An object of the present invention is to provide a host cell which produces an antibody composition and can control a sugar chain structure bound to an antibody molecule, a cell which can produce an antibody composition having high ADCC activity, a production method of an antibody composition using the cell and an antibody composition produced by the production method.

The present invention relates to the following (1) to (61).

(1) A Chinese hamster ovary tissue-derived CHO cell into which a gene encoding an antibody molecule is introduced, which produces an antibody composition comprising an antibody molecule having complex N-glycoside-linked sugar chains bound to the Fc region, wherein among the total complex N-glycoside-linked sugar chains bound to the Fc region in the composition, the ratio of a sugar chain in which fucose is not bound to N-acetylglucosamine in the reducing end in the sugar chain is 20% or more.

(2) The CHO cell according to (1), wherein the sugar chain to which fucose is not bound is a complex N-glycoside-linked sugar chain in which 1-position of fucose is not bound to 6-position of N-acetylglucosamine in the reducing end through α-bond.

(3) The CHO cell according to (1) or (2), wherein the antibody molecule belongs to an IgG class.

(4) The CHO cell according to any one of (1) to (3), wherein the activity of an enzyme relating to the synthesis of an intracellular sugar nucleotide, GDP-fucose and/or the activity of an enzyme relating to the modification of a sugar chain in which 1-position of fucose is bound to 6-position of N-acetylglucosamine in the reducing end through α-bond in the complex N-glycoside-linked sugar chain is decreased or deleted.

(5) The CHO cell according to (4), wherein the enzyme relating to the synthesis of an intracellular sugar nucleotide, GDP-fucose is an enzyme selected from the group consisting of the following (a), (b) and (c):
(a) GMD (GDP-mannose 4,6-dehydratase);
(b) Fx (GDP-keto-6-deoxymannose 3,5-epimerase, 4-reductase);
(c) GFPP (GDP-beta-L-fucose pyrophosphorylase).

(6) The CHO cell according to (5), wherein the GMD is a protein encoded by a DNA of the following (a) or (b):
(a) a DNA comprising the nucleotide sequence represented by SEQ ID NO:65;
(b) a DNA which hybridizes with the DNA comprising the nucleotide sequence represented by SEQ ID NO:65 under stringent conditions and encodes a protein having GMD activity.

(7) The CHO cell according to (5), wherein the GMD is a protein selected from the group consisting of the following (a), (b) and (c):
(a) a protein comprising the amino acid sequence represented by SEQ ID NO:71;
(b) a protein which comprises an amino acid sequence in which at least one amino acid is deleted, substituted, inserted and/or added in the amino acid sequence represented by SEQ ID NO:71 and has GMD activity;
(c) a protein which comprises an amino acid sequence having a homology of at least 80% with the amino acid sequence represented by SEQ ID NO:71 and has GMD activity.

(8) The CHO cell according to (5), wherein the Fx is a protein encoded by a DNA of the following (a) or (b):
(a) a DNA comprising the nucleotide sequence represented by SEQ ID NO:48;
(b) a DORA which hybridizes with the DNA comprising the nucleotide sequence represented by SEQ ID NO:48 under stringent conditions and encodes a protein having Fx activity.

(9) The CHO cell according to (5), wherein the Fx is a protein selected from the group consisting of the following (a), (b) and (c):
(a) a protein comprising the amino acid sequence represented by SEQ ID NO:72;
(b) a protein which comprises an amino acid sequence in which at least one amino acid is deleted, substituted, inserted and/or added in the amino acid sequence represented by SEQ ID NO:72 and has Fx activity;
(c) a protein which comprises an amino acid sequence having a homology of at least 80% with the amino acid sequence represented by SEQ ID NO:72 and has Fx activity.

(10) The CHO cell according to (5), wherein the GFPP is a protein encoded by a DNA of the following (a) or (b):
(a) a DNA comprising the nucleotide sequence represented by SEQ ID NO:51;
(b) a DNA which hybridizes with the DNA comprising the nucleotide sequence represented by SEQ ID NO:51 under stringent conditions and encodes a protein having GFPP activity.

(11) The CHO cell according to (5), wherein the GFPP is a protein selected from the group consisting of the following (a), (b) and (c):
(a) a protein comprising the amino acid sequence represented by SEQ ID NO:73;

(b) a protein which comprises an amino acid sequence in which at least one amino acid is deleted, substituted, inserted and/or added in the amino acid sequence represented by SEQ ID NO:73 and has GFPP activity;

(c) a protein which comprises an amino acid sequence having a homology of at least 80% with the amino acid sequence represented by SEQ ID NO:73 and has GFPP activity.

(12) The CHO cell according to (4), wherein the enzyme relating to the modification of a sugar chain in which 1-position of fucose is bound to 6-position of the N-acetylglucosamine in the reducing end through α-bond in the complex N-glycoside-linked sugar chain is α-1,6-fucosyltransferase.

(13) The CHO cell according to (12), wherein the α-1,6-fucosyltransferase is a protein encoded by a DNA of the following (a) or (b):

(a) a DNA comprising the nucleotide sequence represented by SEQ ID NO:1;

(b) a DNA which hybridizes with the DNA comprising the nucleotide sequence represented by SEQ ID NO:1 under stringent conditions and encodes a protein having α-1,6-fucosyltransferase activity.

(14) The CHO cell according to (12), wherein the α-1,6-fucosyltransferase is a protein selected from the group consisting of the following (a), (b) and (c):

(a) a protein comprising the amino acid sequence represented by SEQ ID NO:23;

(b) a protein which comprises an amino acid sequence in which at least one amino acid is deleted, substituted, inserted and/or added in the amino acid sequence represented by SEQ ID NO:23 and has α-1,6-fucosyltransferase activity;

(c) a protein which comprises an amino acid sequence having a homology of at least 80% with the amino acid sequence represented by SEQ ID NO:23 and has α-1,6-fucosyltransferase activity.

(15) The CHO cell according to any one of (4) to (14), wherein the enzyme activity is decreased or deleted by a technique selected from the group consisting of the following (a), (b), (c), (d) and (e):

(a) a gene disruption technique targeting a gene encoding the enzyme;

(b) a technique for introducing a dominant negative mutant of a gene encoding the enzyme;

(c) a technique for introducing mutation into the enzyme;

(d) a technique for inhibiting transcription or translation of a gene encoding the enzyme;

(e) a technique for selecting a cell line resistant to a lectin which recognizes a sugar chain in which 1-position of fucose is bound to 6-position of N-acetylglucosamine in the reducing end through α-bond in the complex N-glycoside-linked sugar chain.

(16) The CHO cell according to any one of (4) to (15), which is resistant to at least a lectin which recognizes a sugar chain in which 1-position of fucose is bound to 6-position of N-acetylglucosamine in the reducing end through α-bond in the complex N-glycoside-linked sugar chain.

(17) The CHO cell according to any one of (4) to (16), which produces an antibody composition having higher antibody-dependent cell-mediated cytotoxic activity than an antibody composition produced by its parent CHO cell.

(18) The CHO cell according to (17), which produces an antibody composition having higher antibody-dependent cell-mediated cytotoxic activity than an antibody composition in which among the total complex N-glycoside-linked sugar chains bound to the Fc region contained in the antibody composition, the ratio of a sugar chain in which fucose is not bound to N-acetylglucosamine in the reducing end in the sugar chain is less than 20%.

(19) The CHO cell according to (18), wherein the sugar chain to which fucose is not bound is a complex N-glycoside-linked sugar chain in which 1-position of fucose is not bound to 6-position of N-acetylglucosamine in the reducing end through α-bond.

(20) A method for producing an antibody composition, which comprises culturing the CHO cell according to any one of (1) to (19) in a medium to produce and accumulate an antibody composition in the culture; and recovering the antibody composition from the culture.

(21) An antibody composition which is produced using the method according to (20).

(22) An antibody composition which comprises an antibody molecule having complex N-glycoside-linked sugar chains bound to the Fc region which is produced by a CHO cell, wherein among the total complex N-glycoside-linked sugar chains bound to the Fc region in the composition, the ratio of a sugar chain in which fucose is not bound to N-acetylglucosamine in the reducing end in the sugar chain is 20% or more.

(23) A cell in which the activity of an enzyme relating to the synthesis of an intracellular sugar nucleotide, GDP-fucose and/or the activity of an enzyme relating to the modification of a sugar chain wherein 1-position of fucose is bound to 6-position of N-acetylglucosamine in the reducing end through α-bond in the complex N-glycoside-linked sugar chain is decreased or deleted by a genetic engineering technique.

(24) The cell according to (23), wherein the enzyme relating to the synthesis of an intracellular sugar nucleotide, GDP-fucose is an enzyme selected from the group consisting of the following (a), (b) and (c):

(a) GMD (GDP-mannose 4,6-dehydratase);

(b) Fx (GDP-keto-6-deoxymannose 3,5-epimerase, 4-reductase);

(c) GFPP (GDP-beta-L-fucose pyrophosphorylase).

(25) The cell according to (24), wherein the GMD is a protein encoded by a DNA of the following (a) or (b):

(a) a DNA comprising the nucleotide sequence represented by SEQ ID NO:65;

(b) a DNA which hybridizes with the DNA comprising the nucleotide sequence represented by SEQ ID NO:65 under stringent conditions and encodes a protein having GMD activity.

(26) The cell according to (24), wherein the GMD is a protein selected from the group consisting of the following (a), (b) and (c):

(a) a protein comprising the amino acid sequence represented by SEQ ID NO:71;

(b) a protein which comprises an amino acid sequence in which at least one amino acid is deleted, substituted, inserted and/or added in the amino acid sequence represented by SEQ ID NO:71 and has GMD activity;

(c) a protein which comprises an amino acid sequence having a homology of at least 80% with the amino acid sequence represented by SEQ ID NO:71 and has GMD activity.

(27) The cell according to (24), wherein the Fx is a protein encoded by a DNA of the following (a) or (b):

(a) a DNA comprising the nucleotide sequence represented by SEQ ID NO:48;

(b) a DNA which hybridizes with the DNA comprising the nucleotide sequence represented by SEQ ID NO:48 under stringent conditions and encodes a protein having Fx activity.

(28) The cell according to (24), wherein the Fx is a protein selected from the group consisting of the following (a), (b) and (c):
- (a) a protein comprising the amino acid sequence represented by SEQ ID NO:72;
- (b) a protein which comprises an amino acid sequence in which at least one amino acid is deleted, substituted, inserted and/or added in the amino acid sequence represented by SEQ ID NO:72 and has Fx activity;
- (c) a protein which comprises an amino acid sequence having a homology of at least 80% with the amino acid sequence represented by SEQ ID NO:72 and has Fx activity.

(29) The cell according to (24), wherein the GFPP is a protein encoded by a DNA of the following (a) or (b):
- (a) a DNA comprising the nucleotide sequence represented by SEQ ID NO:51;
- (b) a DNA which hybridizes with the DNA comprising the nucleotide sequence represented by SEQ ID NO:51 under stringent conditions and encodes a protein having GFPP activity.

(30) The cell according to (24), wherein the GFPP is a protein selected from the group consisting of the following (a), (b) and (c):
- (a) a protein comprising the amino acid sequence represented by SEQ ID NO:73;
- (b) a protein which comprises an amino acid sequence in which at least one amino acid is deleted, substituted, inserted and/or added in the amino acid sequence represented by SEQ ID NO:73 and has GFPP activity;
- (c) a protein which comprises an amino acid sequence having a homology of at least 80% with the amino acid sequence represented by SEQ ID NO:73 and has GFPP activity.

(31) The cell according to (23), wherein the enzyme relating to the modification of a sugar chain in which 1-position of fucose is bound to 6-position of N-acetylglucosamine in the reducing end through α-bond in the N-glycoside-linked sugar chain is α-1,6-fucosyltransferase.

(32) The cell according to (31), wherein the α-1,6-fucosyltransferase is a protein encoded by a DNA selected from the group consisting of the following (a), (b), (c) and (d):
- (a) a DNA comprising the nucleotide sequence represented by SEQ ID NO:1;
- (b) a DNA comprising the nucleotide sequence represented by SEQ ID NO:2;
- (c) a DNA which hybridizes with the DNA comprising the nucleotide sequence represented by SEQ ID NO:1 under stringent conditions and encodes a protein having α-1,6-fucosyltransferase activity;
- (d) a DNA which hybridizes with the DNA comprising the nucleotide sequence represented by SEQ ID NO:2 under stringent conditions and encodes a protein having α-1,6-fucosyltransferase activity.

(33) The cell according to (31), wherein the α-1,6-fucosyltransferase is a protein selected from the group consisting of the following (a), (b), (c), (d), (e) and (f):
- (a) a protein comprising the amino acid sequence represented by SEQ ID NO:23;
- (b) a protein comprising the amino acid sequence represented by SEQ ID NO:24;
- (c) a protein which comprises an amino acid sequence in which at least one amino acid is deleted, substituted, inserted and/or added in the amino acid sequence represented by SEQ ID NO:23 and has α-1,6-fucosyltransferase activity;
- (d) a protein which comprises an amino acid sequence in which at least one amino acid is deleted, substituted, inserted and/or added in the amino acid sequence represented by SEQ ID NO:24 and has α-1,6-fucosyltransferase activity;
- (e) a protein which comprises an amino acid sequence having a homology of at least 80% with the amino acid sequence represented by SEQ ID NO:23 and has α-1,6-fucosyltransferase activity;
- (f) a protein which comprises an amino acid sequence having a homology of at least 80% with the amino acid sequence represented by SEQ ID NO:24 and has α-1,6-fucosyltransferase activity.

(34) The cell according to any one of (23) to (33), wherein the genetic engineering technique is a technique selected from the group consisting of the following (a), (b), (c) and (d):
- (a) a gene disruption technique targeting a gene encoding the enzyme;
- (b) a technique for introducing a dominant negative mutant of a gene encoding the enzyme;
- (c) a technique for introducing mutation into the enzyme;
- (d) a technique for inhibiting transcription and/or translation of a gene encoding the enzyme.

(35) The cell according to any one of (23) to (34), which is resistant to at least a lectin which recognizes a sugar chain in which 1-position of fucose is bound to 6-position of N-acetylglucosamine in the reducing end through α-bond in the N-glycoside-linked sugar chain.

(36) The cell according to any one of (23) to (35), which is a cell selected from the group consisting of the following (a) to (i):
- (a) a CHO cell derived from a Chinese hamster ovary tissue;
- (b) a rat myeloma cell line, YB2/3HL.P2.G11.16Ag.20 cell;
- (c) a mouse myeloma cell line, NS0 cell;
- (d) a mouse myeloma cell line, SP2/0-Ag14 cell;
- (e) a BHY cell derived from a syrian hamster kidney tissue;
- (f) an antibody-producing hybridoma cell;
- (g) a human leukemia cell line, Namalwa cell;
- (h) an embryonic stem cell;
- (i) a fertilized egg cell.

(37) The cell according to any one of (23) to (36) into which a gene encoding an antibody molecule is introduced.

(38) The cell according to (37), wherein the antibody molecule belongs to an IgG class.

(39) A method for producing an antibody composition, which comprises culturing the cell according to (37) or (38) in a medium to produce and accumulate the antibody composition in the culture; and recovering the antibody composition from the culture.

(40) The method according to (39), which produces an antibody composition having higher antibody-dependent cell-mediated cytotoxic activity than an antibody composition obtained from its parent cell line.

(41) An antibody composition which is produced using the method according to (39) or (40).

(42) A transgenic non-human animal or plant or the progenies thereof, comprising a genome which is modified such that the activity of an enzyme relating to the synthesis of an intracellular sugar nucleotide, GDP-fucose and/or the activity of an enzyme relating to the modification of a sugar chain in which 1-position of fucose is bound to 6-position of N-acetylglucosamine in the reducing end through α-bond in the N-glycoside-linked sugar chain is decreased.

(43) The transgenic non-human animal or plant or the progenies thereof according to (42), wherein a gene encoding the enzyme relating to the synthesis of an intracellular sugar nucleotide, GDP-fucose or a gene encoding the enzyme relating to the modification of a sugar chain in which 1-position of fucose is bound to 6-position of N-acetylglucosamine in the reducing end through α-bond in the N-glycoside-linked sugar chain is knocked out.

(44) The transgenic non-human animal or plant or the progenies thereof according to (42) or (43), wherein the enzyme relating to the synthesis of an intracellular sugar nucleotide, GDP-fucose is an enzyme selected from the group consisting of the following (a), (b) and (c):
  (a) GMD (GDP-mannose 4,6-dehydratase);
  (b) Fx (GDP-keto-6-deoxymannose 3,5-epimerase, 4-reductase);
  (c) GFPP (GDP-beta-L-fucose pyrophosphorylase).

(45) The transgenic non-human animal or plant or the progenies thereof according to (44), wherein the GMD is a protein encoded by a DNA of the following (a) or (b):
  (a) a DNA comprising the nucleotide sequence represented by SEQ ID NO:65;
  (b) a DNA which hybridizes with the DNA comprising the nucleotide sequence represented by SEQ ID NO:65 under stringent conditions and encodes a protein having GMD activity.

(46) The transgenic non-human animal or plant or the progenies thereof according to (44), wherein the Fx is a protein encoded by a DNA of the following (a) or (b):
  (a) a DNA comprising the nucleotide sequence represented by SEQ ID NO:48;
  (b) a DNA which hybridizes with the DNA comprising the nucleotide sequence represented by SEQ ID NO:48 under stringent conditions and encodes a protein having Fx activity.

(47) The transgenic non-human animal or plant or the progenies thereof according to (44), wherein the GFPP is a protein encoded by a DNA of the following (a) or (b):
  (a) a DNA comprising the nucleotide sequence represented by SEQ ID NO:51;
  (b) a DNA which hybridizes wish the DNA comprising the nucleotide sequence represented by SEQ ID NO:51 under stringent conditions and encodes a protein having GFPP activity.

(48) The transgenic non-human animal or plant or the progenies thereof according to (42) or (43), wherein the enzyme relating to the modification of a sugar chain in which 1-position of fucose is bound to 6-position of N-acetylglucosamine in the reducing end through α-bond in the N-glycoside-linked sugar chain is α-1,6-fucosyltransferase.

(49) The transgenic non-human animal or plant or the progenies thereof according to (48), wherein the α-1,6-fucosyltransferase is a protein encoded by a DNA selected from the group consisting of the following (a), (b), (c) and (d):
  (a) a DNA comprising the nucleotide sequence represented by SEQ ID NO:1;
  (b) a DNA comprising the nucleotide sequence represented by SEQ ID NO:2;
  (c) a DNA which hybridizes with the DNA comprising the nucleotide sequence represented by SEQ ID NO:1 under stringent conditions and encodes a protein having α-1, 6-fucosyltransferase activity;
  (d) a DNA which hybridizes with the DNA comprising the nucleotide sequence represented by SEQ ID NO:2 under stringent conditions and encodes a protein having α-1, 6-fucosyltransferase activity.

(50) The transgenic non-human animal or plant or the progenies thereof according to any one of (42) to (49), wherein the transgenic non-human animal is an animal selected from the group consisting of cattle, sheep, goat, pig, horse, mouse, rat, fowl, monkey and rabbit.

(51) A method for producing an antibody composition, which comprises introducing a gene ecoding an antibody molecule into the transgenic non-human animal or plant or the progenies thereof according to any one of (42) to (50); rearing the animal or plant; isolating tissue or body fluid comprising the introduced antibody from the reared animal or plant; and recovering the antibody composition from the isolated tissue or body fluid.

(52) The method according to (51), wherein the antibody molecule belongs to an IgG class.

(53) The method according to (51) or (52), which produces an antibody composition having higher antibody-dependent cell-mediated cytotoxic activity than an antibody composition obtained from a non-human animal or plant or the progenies thereof whose genome is not modified.

(54) An antibody composition which is produced using the method according to any one of (51) to (53).

(55) A medicament comprising the antibody composition according to any one of (21), (22), (41) and (54) as an active ingredient.

(56) The medicament according to (55), wherein the medicament is a diagnostic drug, a preventive drug or a therapeutic drug for diseases accompanied by tumors, diseases accompanied by allergies, diseases accompanied by inflammations, autoimmune diseases, circulatory organ diseases, diseases accompanied by viral infections or diseases accompanied by bacterial infections.

(57) A protein selected from the group consisting of the following (a), (b), (c), (d), (e), (f), (g), (h), (i) and (j):
  (a) a protein comprising the amino acid sequence represented by SEQ ID NO:71;
  (b) a protein which comprises an amino acid sequence in which at least one amino aced is deleted, substituted, inserted and/or added in the amino acid sequence represented by SEQ ID NO:71 and has GMD activity;
  (c) a protein comprising the amino acid sequence represented by SEQ ID NO:72;
  (d) a protein which comprises an amino acid sequence in which at least one amino acid is deleted, substituted, inserted and/or added in the amino acid sequence represented by SEQ D NO:72 and has Fx activity;
  (e) a protein comprising the amino acid sequence represented by SEQ ID NO:73;
  (f) a protein which comprises an amino acid sequence in which at least one amino acid is deleted, substituted, inserted and/or added in the amino acid sequence represented by SEQ ID NO:73 and has GFPP activity;
  (g) a protein comprising the amino acid sequence represented by SEQ ID NO:23;
  (h) a protein which comprises an amino acid sequence in which at least one amino acid is deleted, substituted, inserted and/or added in the amino acid sequence represented by SEQ ID NO:23 and has α-1,6-fucosyltransferase activity;
  (i) a protein comprising the amino acid sequence represented by SEQ ID NO:24;
  (j) a protein which comprises an amino acid sequence in which at least one amino acid is deleted, substituted, inserted and/or added in the amino acid sequence represented by SEQ ID NO:24 and the α-1,6-fucosyltransferase activity.

(58) A DNA which encodes the protein according to (57).

(59) A DNA selected from the group consisting of the following (a), (b), (c), (d) and (e):
  (a) a DNA comprising the nucleotide sequence represented by SEQ ID NO:1;
  (b) a DNA comprising the nucleotide sequence represented by SEQ ID NO:2;
  (c) a DNA comprising the nucleotide sequence represented by SEQ ID NO:65;
  (d) a DNA comprising the nucleotide sequence represented by SEQ ID NO:48;
  (e) a DNA comprising the nucleotide sequence represented by SEQ ID NO:51.

(60) A genome DNA selected from the group consisting of the following (a), (b) and (c):
  (a) a genome DNA comprising the nucleotide sequence represented by SEQ ID NO:3;
  (b) a genome DNA comprising the nucleotide sequence represented by SEQ ID NO:67;
  (c) a genome DNA comprising the nucleotide sequence represented by SEQ ID NO:70.

(61) A target vector for homologous recombination, comprising a full length of the DNA according to any one of (58) to (60), or a part thereof.

BRIEF EXPLANATION OF THE DRAWINGS

FIG. 1 shows electrophoresis patterns of SDS-PAGE of five purified anti-GD3 chimeric antibodies (using gradient gel from 4 to 15%).

FIG. 4 shows electrophoresis patterns of SDS-PAGE of three purified anti-hIL-5Rα CDR-grafted antibodies (using gradient gel from 4 to 15%).

FIG. 5 shows activities of three purified anti-hIL-5Rα CDR-grafted antibodies to bind to hIL-5Rα, measured by changing the antibody concentration. The ordinate and the abscissa show the binding activity with hIL-5Rα and the antibody concentration, respectively. "○", "●" and "□" show the activities of YB2/0-hIL-5R CDR antibody, CHO/d-hIL-5R CDR antibody and NS0-hIL-5R CDR antibody, respectively.

In FIG. 10.

FIG. 11 shows elution patterns obtained by analyzing PA-treated sugar chains prepared from a non-adsorbed fraction and a part of an adsorbed fraction by a reverse HPLC.

FIG. 18A and FIG. 18B show results obtained using effector cells of the donor A and the donor B, respectively.

FIG. 22 shows construction of plasmids CHFT8d-pCR2.1 and YBFT8d-pCR2.1.

FIG. 30 shows elution patterns of PA-treated sugar chains prepared from antibodies produced by mfFUT8-6 and pAGE249-introduced cell lines, obtained by analyzing them by reverse phase HPLC.

FIG. 44 shows ADCC activities of anti-CCR4 human chimeric antibodies produced by lectin-resistant cell lines. The ordinate and the abscissa show the cytotoxic activity and the antibody concentration, respectively. "□", "Δ" and "●" show activities of antibodies produced by YB2/0 (KM2760 # 58-35-16), 5-03 and CHO/CCR4-LCA, respectively.

FIG. 45 shows elution patterns of PA-treated sugar chains prepared from purified anti-CCR4 human chimeric antibodies, obtained by analyzing them by reverse phase HPLC. The ordinate and the abscissa show the relative fluorescence intensity and the elution time, respectively. FIG. 45A, FIG. 45B, FIG. 45C and FIG. 45D show results of analyses of an antibody produced by the strain 5-03, an antibody produced by CHO/CCR4-LCA, an antibody produced by CHO/CCR4-AAL and an antibody produced by CHO/CCR4-PHA, respectively.

DETAILED DESCRIPTION OF THE INVENTION

Figure 1A:
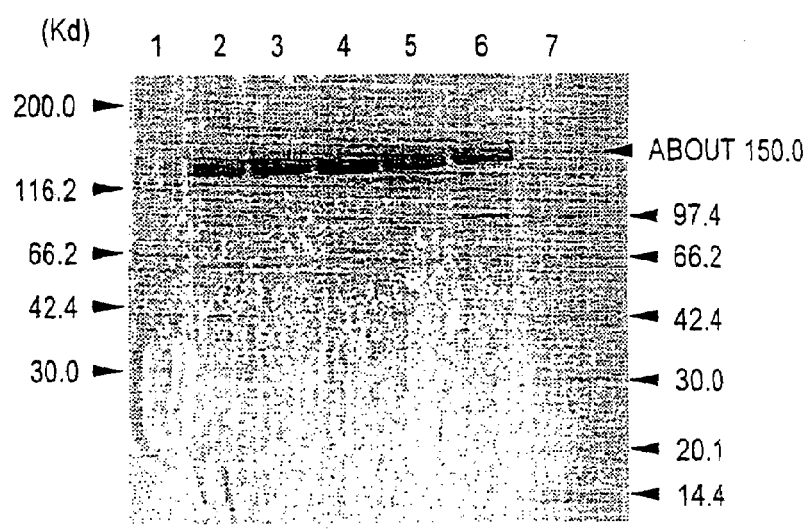
FIG. 1A and FIG. 1B show a result of the electrophoresis under non-reducing conditions and that under reducing conditions, respectively. Lanes 1 to 7 show electrophoresis patterns of high molecular weight markers, YB2/0-GD3 chimeric antibody, CHO/DG44-GD3 chimeric antibody, SP2/0-GD3 chimeric antibody, NS0-GD3 chimeric antibody (302), NS0-GD3 chimeric antibody (GIT) and low molecular weight markers, respectively.

The Chinese hamster ovary tissue-derived CHO cell into which a gene encoding an antibody molecule is introduced according to the present invention may be any CHO cell, so long as it is a Chinese hamster ovary tissue-derived CHO cell into which a gene encoding an antibody molecule is introduced, which produces an antibody composition comprising complex N-glycoside-linked sugar chains bound to the Fc region of an antibody molecule, wherein among the total complex N-glycoside-linked sugar chains bound to the Fc region in the composition, the ratio of a sugar chain in which fucose is not bound to N-acetylglucosamine in the reducing end in the sugar chain is 20% or more.

In the present invention, the antibody molecule includes any molecule, so long as it comprises the Fc region of an antibody. Examples include an antibody, an antibody fragment, a fusion protein comprising an Fc region, and the like.

The antibody is a protein which is produced in the living body by immune reaction as a result of exogenous antigen stimulation and has an activity to specifically bind to the antigen. Examples of the antibody include an antibody secreted by a hybridoma cell prepared from a spleen cell of an animal immunized with an antigen; an antibody prepared by a genetic recombination technique, namely an antibody obtained by introducing an antibody gene-inserted antibody expression vector into a host cell; and the like. Specific examples include an antibody produced by a hybridoma, a humanized antibody, a human antibody and the like.

A hybridoma is a cell which is obtained by cell fusion between a B cell obtained by immunizing a mammal other than human with an antigen and a myeloma cell derived from mouse or the like and can produce a monoclonal antibody having the desired antigen specificity.

Examples of the humanized antibody include a human chimeric antibody, a human CDR-grafted antibody and the like.

A human chimeric antibody is an antibody which comprises an antibody heavy chain variable region (hereinafter referred to as "HV" or "VH", the heavy chain being "H chain") and an antibody light chain variable region (hereinafter referred to as "LV" or "VL", the light chain being "L chain"), both of an animal other than human, a human antibody heavy chain constant region (hereinafter also referred to as "CH") and a human antibody light chain constant region (hereinafter also referred to as "CL"). As the animal other than human, any animal such as mouse, rat, hamster, rabbit or the like can be used, so long as a hybridoma can be prepared therefrom.

The human chimeric antibody can be produced by obtaining cDNA's encoding VH and VL from a monoclonal antibody-producing hybridoma, inserting them into an expression vector for host cell having genes encoding human antibody CH and human antibody CL to thereby construct a human chimeric antibody expression vector, and then introducing the vector into a host cell to express the antibody.

As the CH of human chimeric antibody, any CH can be used, so long as it belongs to human immunoglobulin (hereinafter referred to as "hIg") can be used. But those belonging to the hIgG class are preferable and any one of the subclasses belonging to the hIgG class, such as hIgG1, hIgG2, hIgG3 and hIgG4, can be used. Also, as the CL of human chimeric antibody, any CL can be used, so long as it belongs to the hIg class, and those belonging to the κ class or λ class can also be used.

A human CDR-grafted antibody is an antibody in which amino acid sequences of CDR's of VH and VL of an antibody derived from an animal other than human are grafted into appropriate positions of VH and VT of a human antibody.

The human CDR-grafted antibody can be produced by constructing cDNA's encoding V regions in which CDR's of VH and VL of an antibody derived from an animal other than human are grafted into CDR's of VH and VL of a human antibody, inserting them into an expression vector for host cell having genes encoding human antibody CH and human antibody CL to thereby construct a human CDR-grafted antibody expression vector, and then introducing the expression vector into a host cell to express the human CDR-grafted antibody.

As the CH of human CDR-grafted antibody, any CH can be used, so long as it belongs to the hIg, but those of the hIgG class are preferable and any one of the subclasses belonging to the hIgG class, such as hIgG1, hIgG2, hIgG3 and hIgG4, can be used. Also, as the CL of human CDR-grafted antibody, any CL can be used, so long as it belongs to the hIg class, and those belonging to the κ class or λ class can also be used.

A human antibody is originally an antibody naturally existing in the human body, but it also includes antibodies obtained from a human antibody phage library, a human antibody-producing transgenic animal and a human antibody-producing transgenic plant, which are prepared based on the recent advance in genetic engineering, cell engineering and developmental engineering techniques.

Regarding the antibody existing in the human body, a lymphocyte capable of producing the antibody can be cultured by isolating a human peripheral blood lymphocyte, immortalizing it by its infection with EB virus or the like and then cloning it, and the antibody can be purified from the culture.

The human antibody phage library is a library in which antibody fragments such as Fab, single chain antibody and the like are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the marker. The antibody fragment can be converted further into a human antibody molecule comprising two full H chains and two full L chains by genetic engineering techniques.

A human antibody-producing transgenic non-human animal is an animal in which a human antibody gene is introduced into cells. Specifically, a human antibody-producing transgenic animal can be prepared by introducing a human antibody gene into ES cell of a mouse, transplanting the ES cell into an early stage embryo of other mouse and then developing it. By introducing a human chimeric antibody gene into a fertilized egg and developing it, the transgenic animal can be also prepared. Regarding the preparation method of a human antibody from the human antibody-producing transgenic animal, the human antibody can be produced and accumulated in a culture by obtaining a human antibody-producing hybridoma by a hybridoma preparation method usually carried out in mammals other than human and then culturing it.

Examples of the transgenic non-human animal include cattle, sheep, goat, pig, horse, mouse, rat, fowl, monkey, rabbit and the like.

Also, in the present invention, it is preferable that the antibody is an antibody which recognizes a tumor-related antigen, an antibody which recognizes an allergy- or inflammation-related antigen, an antibody which recognizes circulatory organ disease-related antigen, an antibody which recognizes an autoimmune disease-related antigen or an antibody which recognizes a viral or bacterial infection-related antigen, and a human antibody which belongs to the IgG class is preferable.

An antibody fragment is a fragment which comprises the Fc region of an antibody. Examples of the antibody fragment include an H chain monomer, an H chain dimer and the like.

A fusion protein comprising an Fc region is a composition in which an antibody comprising the Fc region of an antibody or the antibody fragment is fused with a protein such as an enzyme, a cytokine or the like.

In the present invention, examples of the sugar chain which binds to the Fc region of an antibody molecule includes an N-glycoside-linked sugar chain. Examples of the N-glycoside-linked sugar chain include a complex type in which the non-reducing end side of the core structure has one or plural parallel branches of galactose-N-acetylglucosamine (hereinafter referred to as "Gal-GlcNAc") and the non-reducing end side of Gal-GlcNAc has a structure such as sialic acid, bisecting N-acetylglucosamine or the like.

In one antibody, the Fc region has positions to which an N-glycoside-linked sugar chain is sound which will be described later. Accordingly, two sugar chains are bound per one antibody molecule. Since the N-glycoside-linked sugar chain which binds to an antibody includes any sugar chain having the core structure represented by the structural formula (I), a number of combinations of sugar chains may possible for the two N-glycoside-linked sugar chains which bind to the antibody. Accordingly, identity of substances can be judged from the viewpoint of the sugar structure bound to the Fc region.

In the present invention, the composition which comprises an antibody molecule having complex N-glycoside-linked sugar chains in the Fc region (hereinafter referred to as "the antibody composition of the present invention") may comprise an antibody having the same sugar chain structure or an antibody having different sugar chain structures, so long as the effect of the present invention is obtained from the composition.

In the present invention, the ratio of a sugar chain in which fucose is not bound to N-acetylglucosamine in the reducing end in the sugar chain among the total complex N-glycoside-linked sugar chains bound to the Fc region contained in the antibody composition is a ratio of the number of a sugar chain in which fucose is not bound to N-acetylglucosamine in the reducing end in the sugar chain to the total number of the complex N-glycoside-linked sugar chains bound to the Fc region contained in the composition.

In the present invention, the sugar chain in which fucose is not bound to N-acetylglucosamine in the reducing end in the complex N-glycoside-linked sugar chain is a sugar chain in which the fucose is not bound to N-acetylglucosamine in the reducing end through α-bond in the complex N-glycoside-linked sugar chain. Examples include a complex N-glycoside-linked sugar chain in which 1-position of fucose is not bound to 6-position of N-acetylglucosamine through α-bond.

The antibody composition shows high ADCC activity when the ratio of a sugar chain in which fucose is not bound to N-acetylglucosamine in the reducing end in the sugar chain among the total complex N-glycoside-linked sugar chains binding to the Fc region contained in the antibody composition of the present invention is preferably 20% or more, more preferably 25% or more, still more preferably 30% or more, far preferably 40% or more, and most preferably 50% or more. As the antibody concentration is decreased, the ADCC activity is decreased, but high ADCC activity can be obtained even when the antibody concentration is low, so long as the ratio of a sugar chain in which fucose is not bound to N-acetylglucosamine in the reducing end in the sugar chain is 20% or more.

The ratio of a sugar chain in which fucose is not bound to N-acetylglucosamine in the reducing end in the sugar chain contained in the composition which comprises an antibody molecule having complex N-glycoside-linked sugar chains in she Fc region can be determined by releasing the sugar chain from the antibody molecule using a known method such as hydrazinolysis, enzyme digestion or the like [*Biochemical Experimentation Methods* 23—*Method for Studying Glycoprotein Sugar Chain* (Japan Scientific Societies Press), edited by Reiko Takahashi (1989)], carrying out fluorescence labeling or radioisotope labeling of the released sugar chain and then separating the labeled sugar chain by chromatography. Also, the released sugar chain can also be determined by analyzing it with the HPAED-PAD method [*J. Liq. Chromatogr.*, 6, 1557 (1983)].

In the present invention, the Chinese hamster ovary tissue-derived CHO cell includes any cell which is a cell line established from an ovary tissue of Chinese hamster (*Cricetulus griseus*). Examples include CHO cells described in documents such as *Journal of Experimental Medicine*, 108, 945 (1958); *Proc. Natl. Acad. Sci. USA*, 60, 1275 (1968); *Genetics*, 55, 513 (1968); *Chromosoma*, 41, 129 (1973); *Methods in Cell Science*, 18, 115 (1996); *Radiation Research*, 148, 260 (1997); *Proc. Natl. Acad. Sci. USA*, 77, 4216 (1980); *Proc. Natl. Acad. Sci.*, 60, 1275 (1968); *Cell*, 6, 121 (1975); *Molecular Cell Genetics*, Appendix I, II (pp. 883-900); and the like. In addition, CHO-K1 (ATCC CCL-61), DUXB11 (ATCC CCL-9096) and Pro-5 (ATCC CCL-1781) registered in ATCC (The American Type Culture Collection) and a commercially available CHO-S (Life Technologies, Cat # 11619) or sub-cell lines obtained by adapting the cell lines using various media can also be exemplified.

In the present invention, the enzyme relating to the synthesis of an intracellular sugar nucleotide, GDP-fucose ray be any enzyme, so long as it is an enzyme relating to the synthesis of the intracellular sugar nucleotide, GDP-fucose as a supply source of fucose to a sugar chain. The enzyme relating to the synthesis of an intracellular sugar nucleotide, GDP-fucose is an enzyme which has influence on the synthesis of the intracellular sugar nucleotide, GDP-fucose.

The intracellular sugar nucleotide, GDP-fucose is supplied by a de novo synthesis pathway or a salvage synthesis pathway. Thus, all enzymes relating to the synthesis pathways are included in the enzyme relating to the syntheses of an intracellular sugar nucleotide, GDP-fucose.

Examples of the enzyme relating to the de novo synthesis pathway of the intracellular sugar nucleotide, GDP-fucose include GDP-mannose 4,6-dehydratase (hereinafter referred to as "GMD"), GDP-keto-6-deoxymannose 3,5-epimerase 4,6-reductase (hereinafter referred to as "Fx") and the like.

Examples of the enzyme relating to the salvage synthesis pathway of the intracellular sugar nucleotide, GDP-fucose include GDP-beta-L-fucose pyrophosphorylase (hereinafter referred to as "GFPP"), fucokinase and the like.

As the enzyme which has influence on the synthesis of an intracellular sugar nucleotide, GDP-fucose, an enzyme which has influence on the activity of the enzyme relating to the synthesis of the intracellular sugar nucleotide, GDP-fucose and an enzyme which has influence on the structure of substances as the substrate of the enzyme are also included.

In the present invention, examples of the GMD include:
a protein encoded by a DNA of the following (a) or (b):
(a) a DNA comprising the nucleotide sequence represented by SEQ ID NO:65;
(b) a DNA which hybridizes with the DNA comprising the nucleotide sequence represented by SEQ ID NO:65 under stringent conditions and encodes a protein having GMD activity,
(c) a protein comprising the amino acid sequence represented by SEQ ID NO:71,
(d) a protein which comprises an amino acid sequence in which at least one amino acid is deleted, substituted, inserted and/or added in the amino acid sequence represented by SEQ ID NO:71 and has GMD activity,
(e) a protein which comprises an amino acid sequence having a homology of at least 80% with the amino acid sequence represented by SEQ ID NO:71 and has GMD activity, and the like.

Also, examples of the DNA encoding the amino acid sequence of GMD include a DNA comprising the nucleotide sequence represented by SEQ ID NO:65 and a DNA which hybridizes with the DNA comprising the nucleotide sequence represented by SEQ ID NO:65 under stringent conditions and encodes an amino acid sequence having GMD activity.

In the present invention, examples of the Fx include:
a protein encoded by a DNA of the following (a) or (b):
(a) a DNA comprising the nucleotide sequence represented by SEQ ID NO:48;
(b) a DNA which hybridizes with the DNA comprising the nucleotide sequence represented by SEQ ID NO:48 under stringent conditions and encodes a protein having Fx activity,
(c) a protein comprising the amino acid sequence represented by SEQ ID NO:72,
(d) a protein which comprises an amino acid sequence in which at least one amino acid is deleted, substituted, inserted and/or added in the amino acid sequence represented by SEQ ID NO:72 and has Fx activity,
(e) a protein which comprises an amino acid sequence having a homology of at least 80% with the amino acid sequence represented by SEQ ID NO:72 and has Fx activity, and the like.

Also, examples of the DNA encoding the amino acid sequence of Fx include a DNA comprising the nucleotide sequence represented by SEQ ID NO:48 and a DNA which hybridizes with the DNA comprising the nucleotide sequence represented by SEQ ID NO:48 under stringent conditions and encodes an amino acid sequence having Fx activity.

In the present invention, examples of the GFPP include:
a protein encoded by a DNA of the following (a) or (b):
(a) a DNA comprising the nucleotide sequence represented by SEQ ID-NO:51;
(b) a DNA which hybridizes with the DNA comprising the nucleotide sequence represented by SEQ ID NO:51 under stringent conditions and encodes a protein having GFPP activity,
(c) a protein comprising the amino acid sequence represented by SEQ ID NO:73,
(d) a protein which comprises an amino acid sequence in which at least one amino acid is deleted, substituted, inserted and/or added in the amino acid sequence represented by SEQ ID NO:73 and has GFPP activity,
(e) a protein which comprises an amino acid sequence having a homology of at least 80% with the amino acid sequence represented by SEQ ID NO:73 and has GFPP activity, and the like.

Also, examples of the DNA encoding the amino acid sequence of GFPP include a DNA comprising the nucleotide sequence represented by SEQ ID NO:51 and a DNA which hybridizes with the DNA comprising the nucleotide sequence represented by SEQ ID NO:51 under stringent conditions and encodes an amino acid sequence having Fx activity.

In the present invention, the enzyme relating to the modification of a sugar chain in which 1-position of fucose is bound to 6-position of N-acetylglucosamine in the reducing end through α-bond in the complex N-glycoside-linked sugar chain includes any enzyme, so long as it is an enzyme relating to the reaction of binding of 1-position of fucose to 6-position of N-acetylglucosamine in the reducing end through α-bond in the complex N-glycoside-linked sugar chain.

Examples of the enzyme relating to the reaction of binding of 1-position of fucose to 6-position of N-acetylglucosamine in the reducing end through α-bond in the complex N-glycoside-linked sugar chain include α-1,6-fucosyltransferase, α-L-fucosidase and the like.

Also, examples include an enzyme which has influence on the activity the enzyme relating to the reaction of binding of 1-position of fucose to 6-position of N-acetylglucosamine in the reducing end through α-bond in the complex N-glycoside-linked sugar chain and an enzyme which has influence on the structure of substances as the substrate of the enzyme.

In the present invention, examples of the α-1,6-fucosyltransferase include:

a protein encoded by a DNA of the following (a), (b), (c) or (d):

(a) a DNA comprising the nucleotide sequence represented by SEQ ID NO:1;

(b) a DNA comprising the nucleotide sequence represented by SEQ ID NO:2;

(c) a DNA which hybridizes with the DNA comprising the nucleotide sequence represented by SEQ ID NO:1 under stringent conditions and encodes a protein having α-1,6-fucosyltransferase activity;

(d) a DNA which hybridizes with the DNA comprising the nucleotide sequence represented by SEQ ID NO:2 under stringent conditions and encodes a protein having α-1,6-fucosyltransferase activity;

(e) a protein comprising the amino acid sequence represented by SEQ ID NO:23, (f) a protein comprising the amino acid sequence represented by SEQ ID NO:24, (g) a protein which comprises an amino acid sequence in which at least one amino acid is deleted, substituted, inserted and/or added in the amino acid sequence represented by SEQ ID NO:23 and has α-1,6-fucosyltransferase activity, (h) a protein which comprises an amino acid sequence in which at least one amino acid is deleted, substituted, inserted and/or added in the amino acid sequence represented by SEQ ID NO:24 and has α-1,6-fucosyltransferase activity, (i) a protein which comprises an amino acid sequence having a homology of at least 80% with the amino acid sequence represented by SEQ ID NO:23 and has α-1,6-fucosyltransferase activity, (j) a protein which comprises an amino acid sequence having a homology of at least 80% with the amino acid sequence represented by SEQ ID NO:24 and has α-1,6-fucosyltransferase activity, and the like.

Also, examples of the DNA encoding the amino acid sequence of α-1,6-fucosyltransferase include a DNA having the nucleotide sequence represented by SEQ ID NO:1 or 2 and a DNA which hybridizes with the DNA having the nucleotide sequence represented by SEQ ID NO:1 or 2 under stringent conditions and encodes an amino acid sequence having α-1,6-fucosyltransferase activity.

In the present invention, a DNA which hybridizes under stringent conditions is a DNA obtained, e.g., by a method such as colony hybridization, plaque hybridization or Southern blot hybridization using a DNA such as the DNA having the nucleotide sequence represented by SEQ ID NO:1, 2, 48, 51 or 65 or a partial fragment thereof as the probe, and specifically includes a DNA which can be identified by carrying out hybridization at 65° C. in the presence of 0.7 to 1.0 M sodium chloride using a filter to which colony- or plaque-derived DNA fragments are immobilized, and then washing the filter at 65° C. using 0.1 to 2×SSC solution (composition of the 1×SSC solution comprising 150 mM sodium chloride and 15 mm sodium citrate). The hybridization can be carried out in accordance with the methods described, e.g., in *Molecular Cloning, A Laboratory Manual,* 2nd Ed., Cold Spring Harbor Laboratory Press (1989) (hereinafter referred to as "*Molecular Cloning,* Second Edition"), *Current Protocols in Molecular Biology,* John Wiley & Sons, 1987-1997 (hereinafter referred to as "*Current Protocols in Molecular Biology*"); *DNA Cloning* 1: *Core Techniques, A Practical Approach,* Second Edition, Oxford University (1995); and the like. Examples of the hybridizable DNA include a DNA having at least 60% or more, preferably 70% or more, more preferably 80% or more, still more preferably 90% or more, far more preferably 95% or more, and most preferably 98% or more, of homology with the nucleotide sequence represented by SEQ ID NO:1, 2, 48, 51 or 65.

In the present invention, the protein which comprises an amino acid sequence in which at least one amino acid is deleted, substituted, inserted and/or added in the amino acid sequence represented by SEQ ID NO:23, 24, 71, 72 or 73 and has α-1,6-fucosyltransferase activity, GMD activity, FX activity or GFPP activity can be obtained, e.g., by introducing a site-directed mutation into a DNA encoding a protein having the amino acid sequence represented by SEQ ID NO:1, 2, 65, 48 or 51, respectively, using the site-directed mutagenesis described, e.g., in *Molecular Cloning,* Second Edition; *Current Protocols in Molecular Biology; Nucleic Acids Research,* 10, 6487 (1982); *Proc. Natl. Acad. Sci. USA,* 79, 6409 (1982); *Gene,* 34, 315 (1985); *Nucleic Acids Research,* 13, 4431 (1985); *Proc. Natl. Acad. Sci. USA,* 82, 488 (1985); and the like. The number of amino acids to be deleted, substituted, inserted and/or added is one or more, and the number is not particularly limited, but is a number which can be deleted, substituted or added by a known technique such as the site-directed mutagenesis, e.g., it is 1 to several tens, preferably 1 to 20, more preferably 1 to 10, and most preferably 1 to 5.

Also, in order to maintain the α-1,6-fucosyltransferase activity, GMD activity, Fx activity or GFPP activity of the protein to be used in the present invention, it has at least 80% or more, preferably 85% or more, more preferably 90% or more, still more preferably 95% or more, far more preferably 97% or more, and most preferably 99% or more, of homology with the amino acid sequence represented by SEQ ID NO:23, 24, 71, 72 or 73, when calculated using an analyzing soft such as BLAST [*J. Mol. Biol.,* 215, 403 (1990)], FASTA [*Methods in Enzymology,* 183, 63 (1990)] or the like.

Examples of the CHO cell of the present invention include a cell in which the enzyme activity is decreased or deleted.

The cell in which the enzyme activity is decreased or deleted include cells in which the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain is decreased or deleted. As the method for obtaining such cells, any technique can be used, so long as it can reduce or delete the enzyme activity of interest. Examples of the technique for reducing or deleting the enzyme activity include:

(a) a gene disruption technique targeting a gene encoding the enzyme, (b) a technique for introducing a dominant negative mutant of a gene encoding the enzyme, (c) a technique for introducing mutation into the enzyme, (d) a technique for inhibiting transcription and/or translation of a gene encoding the enzyme, (e) a technique for selecting a cell line resistant to a lectin which recognizes a sugar chain in which 1-position of fucose is bound to 6-position of N-acetylglucosamine in the reducing end through α-bond in the complex N-glycoside-linked sugar chain, and the like.

Herein, the lectin-resistant cell line can be obtained by culturing a cell line in a medium comprising a predetermined concentration of lectin and then by selecting a cell line which acquires such a property that its survival rate is increased at least 2 times, preferably 3 times, and more preferably 5 times or more, than the parent cell line with statistical significance. Also, it can also be obtained by culturing a cell line in a medium comprising lectin and then by selecting a cell line which can be cultured at a certain survival rate, e.g., 80% survival rate, at a lectin concentration of at least 2 times, preferably 5 times, more preferably 10 times, and most preferably 20 times or more, than the patent cell line.

As the lectin which recognizes a sugar chain structure in which 1-position of fucose is bound to 6-position of N-acetylglucosamine in the reducing end through α-bond in the N-glycoside-linked sugar chain, any lectin which can recognize the sugar chain structure can be used. Examples include a *Lens culinaris* lectin LCA (lentil agglutinin derived from *Lens culinaris*), a pea lectin PSA (pea lectin derived from *Pisum sativum*), a broad bean lectin VFA (agglutinin derived from *Vicia faba*), an *Aleuria aurantia* lectin AAL (lectin derived from *Aleuria aurantia*) and the like.

The CHO cell of the present invention can produce an antibody composition having higher ADCC activity than that of an antibody composition produced by the parent CHO cell before applying the technique for decreasing or deleting the enzyme activity of interest.

Also, the CHO cell of the present invention can produce an antibody composition having higher ADCC activity than that of an ant%body composition in which, among the total complex N-glycoside-linked sugar chains bound to the Fc region contained in the antibody composition, the ratio of a sugar chain in which fucose is not bound to N-acetylglucosamine in the reducing end in the sugar chain is less than 20%.

An example of the parent cell line to be used in the present invention is a cell in which the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain is not decreased. Specifically, a cell which is not treated to decrease or delete the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain is used.

In the present invention, the ADCC activity is a cytotoxic activity in which an antibody bound to a cell surface antigen on a tumor cell in the living body activate an effector cell through an Fc receptor existing on the antibody Fc region and effector cell surface and thereby obstruct the tumor cell and the like [*Monoclonal Antibodies: Principles and Applications*, Wiley-Liss, Inc., Chapter 2.1 (1955)]. Examples of the effector cell include a killer cell, a natural killer cell, an activated macrophage and the like.

The present invention also relates to a cell in which the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain is decreased by a genetic engineering technique (hereinafter referred to as "the host cell of the present invention"). The host cell of the present invention is useful as a host cell for producing an antibody composition having high ADCC activity.

The host cell of the present invention may be any host, so long as it can express an antibody molecule. Examples include a yeast cell, an animal cell, an insect cell, a plant cell and the like. Examples of the cells include those which will be later in the item 3. Among animal cells, preferred examples include a CHO cell derived from a Chinese hamster ovary tissue, a rat myeloma cell line YB2/3HL.P2.G11.16Ag.20 cell, a mouse myeloma cell line NS0 cell, a mouse myeloma SP2/0-Ag14 cell, a BHK cell derived from a syrian hamster kidney tissue, an antibody producing-hybridoma cell, a human leukemia cell line Namalwa cell, an embryonic stem cell, a fertilized egg cell and the like.

The present invention is described below in detail.

1. Preparation of the Host Cell of the Present Invention

The host cell of the present invention can be prepared by the following techniques.

(1) Gene Disruption Technique Targeting at a gene Encoding an Enzyme

The host cell of the present invention can be prepared using a gene disruption technique by targeting at an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain. Examples of the enzyme relating to the synthesis of an intracellular sugar nucleotide, GDP-fucose include GMD, Fx, GFPP, fucokinase and the like. Examples of the enzyme relating to the modification of a sugar chain wherein 1-position of fucose is bound to 6-position of N-acetylglucosamine in the reducing end through α-bond in the complex N-glycoside-linked sugar chain include α-1,6-fucosyltransferase, α-L-fucosidase and the like.

The gene as used herein includes DNA and RNA.

The gene disruption method may be any method, so long as it can disrupt the gene of the target enzyme is included. Examples include an antisense method, a ribozyme method, a homologous recombination method, an RDO method, an RNAi method, a retrovirus-employed method, a transposon-employed method and the like. The methods are specifically described below.

(a) Preparation of the Host Cell of the Present Invention by the Antisense Method or the Ribozyme Method The host cell of the present invention can be prepared by the ribozyme method described in *Cell Technology*, 12, 239 (1993); *BIO/TECHNOLOGY*, 17, 1097 (1999); *Hum. Mol. Genet.*, 5, 1083 (1995); *Cell Technology*, 13, 255 (1994); *Proc. Natl. Acad. Sci. USA*, 96, 1886 (1999); or the like, e.g., in the following manner by targeting at an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain.

A cDNA or a genome DNA encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain is prepared.

The nucleotide sequence of the prepared cDNA or genome DNA is determined.

Based on the determined DNA sequence, an appropriate length of an antisense gene or ribozyme construct comprising a DNA moiety which encodes the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain a part of its non-translation region or an intron, is designed.

In order to express the antisense gene or ribozyme in a cell, a recombinant vector is prepared by inserting a fragment or total length of the prepared DNA into downstream of the promoter of an appropriate expression vector.

A transformant is obtained by introducing the recombinant vector into a host cell suitable for the expression vector.

The host cell of the present invention can be obtained by selecting a transformant using, as a marker, the activity of the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain. The host cell of the present invention can also be obtained by selecting a transformant as a measure of the sugar chain structure of a glycoprotein on the cell membrane or the sugar chain structure of the produced antibody molecule.

As the host cell used for the production of the host cell of the present invention, any cell such as yeast, animal cell, insect cell or plant cell can be used, so long as it has a gene encoding the target enzyme relating to the synthesis of an intracellular sugar nucleotide, GDP-fucose or the target enzyme relating to the modification of a sugar chain wherein 1-position: of fucose is bound to 6-position of N-acetylglucosamine in the reducing end through α-bond in the complex N-glycoside-linked sugar chain. Examples include host cells which will be described later in the item 3.

As the expression vector, a vector which is autonomously replicable in the host cell or can be integrated into the chromosome and comprises a promoter at such a position that the designed antisense gene or ribozyme can be transferred is used. Examples include expression vectors which will be described later in the item 3.

Regarding the method for introducing a gene into various host cells, the methods for introducing recombinant vectors suitable for various host cells, which will be described later in the item 3, can be used.

The following method can be exemplified as the method for selecting a transformant as a measure of the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain.

Method for Selecting Transformant

Examples of the method for selecting a cell in which the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain is decreased include biochemical methods or genetic engineering techniques described in *New Biochemical Experimentation Series* 3-*Saccharides I, Glycoprotein* (Tokyo Kagaku Dojin), edited by Japanese Biochemical society (1988); *Cell Engineering, Supplement, Experimental Protocol Series, Glycobiology Experimental Protocol, Glycoprotein, Glycolipid and Proteoglycan* (Shujun-sha), edited by Naoyuki Taniguchi, Akemi Suzuki, Kiyoshi Furukawa and Kazuyuki Sugawara (1996);, *Molecular Cloning,* Second Edition; *Current Protocols in Molecular Biology;* and the like. Examples of the biochemical method include a method in which the enzyme activity is evaluated using an enzyme-specific substrate and the like. Examples of the genetic engineering technique include the Northern analysis, RT-PCR and the like which measures the amount of mRNA of a gene encoding the enzyme.

Examples of the method for selecting a transformant using the sugar chain structure of a glycoprotein on the cell membrane as a marker include the methods which will be described later in the item 1(5). Examples of the method for selecting a transformant using the sugar chain structure of a produced antibody molecule as a marker include the methods which will be described later in the items 5 and 6.

As the method for preparing cDNA encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain, the following method is exemplified.

Preparation of DNA

A total RNA or mRNA is prepared from a human or non-human animal tissue or cell.

A cDNA library is prepared from the prepared total RNA or mRNA.

Degenerative primers are produced based on the amino acid sequence of an enzyme relating go the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain, and a gene fragment encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain is obtained by PCR using he prepared cDNA library as the template.

A DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain can be obtained by screening the cDNA library using the obtained gene fragment as a probe.

Regarding the mRNA of a human or non-human tissue or cell, a commercially available product (e.g., manufactured by Clontech) may be used or it may be prepared from a human or non-human animal tissue or cell in the following manner.

Examples of the method for preparing a total RNA from a human or non-human animal tissue or cell include the guanidine thiocyanate-cesium trifluoroacetate method (*Methods in Enzymology,* 154, 3 (1987)), the acidic guanidine thiocyanate phenol chloroform (AGPC) method [*Analytical Biochemistry,* 162, 156 (1987); *Experimental Medicine,* 9, 1937 (1.991)] and the like.

Also, examples of the method for preparing mRNA from a total RNA as poly(A)* RNA include an oligo(dT)-immobilized cellulose column method (*Molecular Cloning,* Second Edition) and the like.

In addition, mRNA can be prepared using a kit such as Fast Track mRNA Isolation Kit (manufactured by Invitrogen), Quick Prep mRNA Purification Kit (manufactured by Pharmacia) or the like.

A cDNA library is prepared from the prepared mRNA of a human or non-human animal tissue or cell. Examples of the method for preparing cDNA libraries include the methods described in *Molecular Cloning,* Second Edition; *Current Protocols in Molecular Biology; A Laboratory Manual,* Second Edition (1989); and the like, or methods using commercially available kits such as SuperScript Plasmid System for cDNA Synthesis and Plasmid Cloning (manufactured by Life Technologies), ZAP-cDNA Synthesis Kit (manufactured by STRATAGENE) and the like.

As the cloning vector for use in the preparation of the cDNA library, any vector such as a phage vector, a plasmid vector or the like can be used, so long as it is autonomously replicable in *Escherichia coli* K12. Examples include ZAP Express [manufactured by STRATAGENE, *Strategies,* 5, 58 (1992)], pBluescript II SK(+) [*Nucleic Acids Research,* 17, 9494 (1989)], Lambda ZAP II (manufactured by STRATAGENE), λgt10 and λgt11 [*DNA Cloning, A Practical Approach,* 1, 49 (1985)], λTriplEx (manufactured by Clontech), λExCell (manufactured by Pharmacia), pcD2 *[Mol. Cell. Biol.,* 3, 280 (1983)], pUC18 (Gene, 33, 103 (1985)] and the like.

Any microorganism can be used as the host microorganism, but *Escherichia coli* is preferably used. Examples include *Escherichia coli* XL1-Blue MRF' [manufactured by STRATAGENE, *Strategies,* 5, 81 (1992)], *Escherichia coli* C600 *[Genetics,* 39 , 440 (1954)], *Escherichia coli* Y1088 *[Science,* 222, 778 (1983)], *Escherichia coli* Y1090 *[Science,* 222, 778 (1983)], *Escherichia coli* NM522 *[J. Mol. Biol.,* 166, 1 (1983)], *Escherichia coli* K802 *[J. Mol. Biol.,* 16, 118 (1966)], *Escherichia coli* JM105 *[Gene,* 38, 275 (1985)] and the like The cDNA library may be used as such in the succeeding analysis, and in order to obtain a full length cDNA as efficient as possible by decreasing the ratio of an infull length cDNA, a cDNA library prepared using the oligo cap method developed by Sugano et al. (*Gene,* 138, 171 (1994); *Gene,* 200 , 149 (1997); *Protein, Nucleic Acid and Protein,* 41, 603 (1996); *Experimental Medicine,* 11, 2491 (1993); *cDNA Cloning* (Yodo-sha) (1996); *Methods for Preparing Gene Libraries* (Yodo-sha) (1994)] may be used in the following analysis.

Degenerative primers specific for the 5'-terminal and 3'-terminal nucleotide sequences of a nucleotide sequence presumed to encode the amino acid sequence are prepared based on the amino acid sequence of the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain, and DNA is amplified by PCR [*PCR Protocols,* Academic Press (1990)] using the prepared cDNA library as the template to obtain a gene fragment encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain.

It can be confirmed that the obtained gene fragment is a DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain, by a method usually used for analyzing a nucleotide, such as the dideoxy method of Sanger et al. [*Proc. Natl. Acad. Sci. USA,* 74, 5463 (1977)], a nucleotide sequence analyzer such as ABIPRISM 377 DNA Sequencer (manufactured by PE Biosystems) or the like.

A DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex M-glycoside-linked sugar chain can be obtained by carrying out colony hybridization or plaque hybridization (*Molecular Cloning,* Second Edition) for the cDNA or cDNA library synthesized from the mRNA contained in the human or non-human animal tissue or cell, using the gene fragment as a DNA probe.

Also, a DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain can also be obtained by carrying out screening by PCR using the cDNA or cDNA library synthesized from the mRNA contained in a human or non-human animal tissue or cell as the template and using the primers used for obtaining the gene fragment encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain.

The nucleotide sequence of the obtained DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain is analyzed from its terminus and determined by a method usually used for analyzing a nucleotide, such as the dideoxy method of Sanger et al. [*Proc. Natl. Acad. Sci. USA,* 74, 5463 (1977)], a nucleotide sequence analyzer such as ABIPRISM 377 DNA Sequencer (manufactured by PE Biosystems) or the like.

A gene encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain can also be determined from genes in data bases by searching nucleotide sequence data bases such as GenBank, EMBL, DDBJ and the like using a homology retrieving program such as BLAST based on the determined cDNA nucleotide sequence.

Examples of the nucleotide sequence of the gene obtained by the method encoding the enzyme relating to the synthesis of an intracellular sugar nucleotide, GDP-fucose include the nucleotide sequence represented by SEQ ID NO:48, 51 or 65. Examples of the nucleotide sequence of the gene encoding the enzyme relating to the modification of a sugar chain wherein 1-position of fucose is bound to 6-position of N-acetylglucosamine in the reducing end through α-bond in the complex N-glycoside-linked sugar chain include the nucleotide sequence represented by SEQ ID NO:1 or 2.

The cDNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain can also be obtained by chemically synthesizing it with a DNA synthesizer such as DNA Synthesizer model 392 manufactured by Perkin Elmer or the like using the phosphoamidite method, based on the determined DNA nucleotide sequence.

As an example of the method for preparing a genome DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain, the method described below is exemplified.

Preparation of Genome DNA

Examples of the method for preparing genome DNA include known methods described in *Molecular Cloning*, Second Edition; *Current Protocols in Molecular Biology;* and the like. In addition, a genome DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain can also be isolated using a kit such as Genome DNA Library Screening System (manufactured by Genome Systems), Universal GenomeWalker™ sits (manufactured by CLONTECH) or the like.

Examples of the nucleotide sequence of the genome DNA obtained by the method encoding the enzyme relating to the synthesis of an intracellular sugar nucleotide, GDP-fucose include the nucleotide sequence represented by SEQ ID NO:67 or 70. Examples of the nucleotide sequence of the genome DNA encoding the enzyme relating to the modification of a sugar chain wherein 1-position of fucose is bound to 6-position of N-acetylglucosamine in the reducing end through α-bond in the complex N-glycoside-linked sugar chain include the nucleotide sequence represented by SEQ ID NO:3.

In addition, the host cell of the present invention can also be obtained without using an expression vector, by directly introducing an antisense oligonucleotide or ribozyme into a host cell, which is designed based on the nucleotide sequence encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain.

The antisense oligonucleotide or ribozyme can be prepared in the usual method or using a DNA synthesizer. Specifically, it can be prepared based on the sequence information of an oligonucleotide having a corresponding sequence of continued 5 to 150 bases, preferably 5 to 60 bases, and more preferably 10 to 40 bases, among nucleotide sequences of a cDNA and a genome DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain, by synthesizing an oligonucleotide which corresponds to a sequence complementary to the oligonucleotide (antisense oligonucleotide) or a ribozyme comprising the oligonucleotide sequence.

Examples of the oligonucleotide include oligo RNA and derivatives of the oligonucleotide (hereinafter referred to as "oligonucleotide derivatives").

Examples of the oligonucleotide derivatives include oligonucleotide derivatives in which a phosphodiester bond in the oligonucleotide is converted into a phosphorothioate bond, an oligonucleotide derivative in which a phosphodiester bond in the oligonucleotide is converted into an N3'-P5' phosphoamidate bond, an oligonucleotide derivative in which ribose and a phosphodiester bond in the oligonucleotide are converted into a peptide-nucleic acid bond, an oligonucleotide derivative in which uracil in the oligonucleotide is substituted with C-5 propynyluracil, an oligonucleotide derivative in which uracil in the oligonucleotide is substituted with C-5 thiazoleuracil, an oligonucleotide derivative in which cytosine in the oligonucleotide is substituted with C-5 propynylcytosine, an oligonucleotide derivative in which cytosine in the oligonucleotide is substituted with phenoxazine-modified cytosine, an oligonucleotide derivative in which ribose in the oligonucleotide is substituted with 2'-O-propylribose and an oligonucleotide derivative in which ribose in the oligonucleotide is substituted with 2'-methoxyethoxyribose [*Cell Technology*, 16, 1463 (1997)].

(b) Preparation of the Host Cell of the Present Invention by Homologous Recombination The host cell of the present invention can be produced by modifying a target gene on chromosome through a homologous recommbiniation technique, using a gene encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain as the target gene.

The target gene on the chromosome can be modified by using a method described in *Manipulating the House Embryo, A Laboratory Manual*, Second Edition, Cold Spring Harbor Laboratory Press (1994) (hereinafter referred to as "*Manipulating the Mouse Embryo, A Laboratory Manual*"); *Gene Targeting, A Practical Approach*, IRL Press at Oxford University Press (1993); *Biomanual Series* 8, *Gene Targeting, Preparation of Mutant Mice using ES Cells,* Yodo-sha (1995) (hereinafter referred to as "*Preparation of Mutant Mice using ES Cells*"); or the like, for example, as follows.

A genome DNA encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain is prepared.

Based on the nucleotide sequence of the genome DNA, a target vector is prepared for homologous recombination of a target gene to be modified (e.g., structural gene of the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain, or a promoter gene).

The host cell of the present invention can be produced by introducing the prepared target vector into a host cell and selecting a cell in which homologous recombination occurred between the target gene and target vector.

As the host cell, any cell such as yeast, animal cell, insect cell or plant cell can be used, so long as it has a gene encoding the enzyme relating to the synthesis of an intracellular sugar nucleotide, GDP-fucose or the enzyme relating to the modification of a sugar chain wherein 1-position of fucose is bound to 6-position of N-acetylglucosamine n the reducing end through α-bond in the complex N-glycoside-linked sugar chain. Examples include the host cells which will be described later in the item 3.

Examples of the method for preparing a genome DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain include the methods described in the preparation of genome DNA in the item 1(1)(a) and the like.

Examples of the nucleotide sequence of genome DNA encoding the enzyme relating to the synthesis of an intracellular sugar nucleotide, GDP-fucose include the nucleotide sequence represented by SEQ ID NO:67 or 70. Examples of the nucleotide sequence of genome DNA encoding the enzyme relating to the modification of a sugar chain wherein 1-position of fucose is bound to 6-position of N-acetylglucosamine in the reducing end through α-bond in the complex N-glycoside-linked sugar chain include the nucleotide sequence represented by SEQ ID NO;3.

The target vector for use in the homologous recombination of the target gene can be prepared in accordance with a method described in *Gene Targeting, A Practical Approach*, IRL Press at Oxford University Press (1993); *Biomanual Series* 8, *Gene Targeting, Preparation of Mutant Mice using ES Cells*, Yodo-sha (1995); or the like. The target vector can be used as either a replacement type or an insertion type.

For introducing the target vector into various host cells, the methods for introducing recombinant vectors suited for various host cells, which will be described later in the item 3, can be used.

Examples of the method for efficiently selecting a homologous recombinant include a method such as the positive selection, promoter selection, negative selection or polyA selection described in *Gene Targeting, A Practical Approach*, IRL Press at Oxford University Press (1993); *Biomanual Series* 8, *Gene Targeting, Preparation of Mutant Mice using ES Cells*, Yodo-sha (1995); or the like. Examples of the method for selecting the homologous recombinant of interest from the selected cell lines include the Southern hybridization method for genome DNA (*Molecular Cloning*, Second Edition), PCR [*PCR Protocols*, Academic Press (1990)], and the like.

(c) Preparation of the Host Cell of the Present Invention by RDO Method

The host cell of the present invention can be prepared by an RDO (RNA-DNA oligonucleotide) method by targeting at a gene encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain, for example, as follows A cDNA or a genome DNA encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain is prepared.

The nucleotide sequence of the prepared cDNA or genome DNA is determined.

Based on the determined DNA sequence, an appropriate length of an RDO construct comprising a DNA moiety which encodes the enzyme relating to the syntheses of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain or a part of its non-translation region or an intron, is designed and synthesized.

The host cell of the present invention can be obtained by introducing the synthesized RDO into a host cell and then selecting a transformant in which a mutation occurred in the target enzyme, namely the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the-complex N-glycoside-linked sugar chain.

As the host cell, any cell such as yeast, animal cell, insect cell or plant cell can be used, so long as it has a gene encoding the target enzyme relating to the synthesis of an intracellular sugar nucleotide, GDP-fucose or of the target enzyme relating to the modification of a sugar chain wherein 1-position of fucose is bound to 6-position of N-acetylglucosamine in the reducing end through α-bond in the complex N-glycoside-linked sugar chain. Examples include the host cells which will be described later in the item 3.

Examples of the method for introducing RDO into various host cells include the methods for introducing recombinant vectors suited for various host cells, which will be described later in the item 3.

Examples of the method for preparing cDNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain include the methods described in the preparation of DNA in the item 1(1)(a) and the like.

Examples of the method for preparing a genome DNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain include the methods in preparation of genome DNA described in the item 1(1)(a) and the like.

The nucleotide sequence of the DNA can be determined by digesting it with appropriate restriction enzymes, cloning the fragments into a plasmid such as pBluescript SK(–) (manufactured by Stratagene) or the like, subjecting the clones to the reaction generally used as a method for analyzing a nucleotide sequence such as the dideoxy method [*Proc. Natl. Acad. Sci. USA*, 74, 5463 (1977)] of Sanger et al. or the like, and then analyzing the clones using an automatic nucleotide sequence analyzer such as A.L.F. DNA Sequencer (manufactured by Pharmacia) or the like.

The RDO can be prepared by a usual method or using a DNA synthesizer.

Examples of the method for selecting a cell in which a mutation occurred, by introducing the ROD into the host cell, in the gene encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain include the methods for directly detecting mutations in chromosomal genes described in *Molecular Cloning, Second Edition, Current Protocols in Molecular Biology* and the like;

the methods described in the item 1(1)(a) for selecting a transformant through the evaluation of the activity of the introduced enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain; the method for selecting a transformant using the sugar structure of a glycoprotein on the cell membrane which will be described later in the item 1(5); and the method for selecting a transformant as a measure of the sugar structure of the produced antibody molecule which will be described later in the item 5 or 6, and the like.

The construct of the ROD can be designed in accordance with the methods described in Science, 273, 1386 (1996); *Nature Medicine*, 4, 285 (1998); *Hepatology*, 25, 1462 (1997); *Gene Therapy*, 5, 1960 (1999); *J. Mol. Med.*, 75, 829 (1997); *Proc. Natl. Acad. Sci. USA*, 96, 8774 (1999); *Proc. Natl. Acad. Sci. USA*, 96, 8768 (1999); *Nuc. Acids. Res.*, 27, 1323 (1999); *Invest. Dematol.*, 111, 1172 (1998); *Nature Biotech.*, 16, 1343 (1998); *Nature Biotech.*, 18, 43 (2000); *Nature Biotech.*, 18, 555 (2000); and the like.

(d) Preparation of the Host Cell of the Present Invention by RNAi Method

The host cell of the present invention can be prepared by the RNAi (RNA interference) method by targeting at a gene of an enzyme relating to the synthesis of an intracellular sugar nucleotide, GDP-fucose or of an enzyme relating to the modification of a sugar chain wherein 1-position of fucose is bound to 6-position of N-acetylglucosamine in the reducing end through α-bond in the complex N-glycoside-linked sugar chain, for example, as follows.

A cDNA encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain is prepared.

The nucleotide sequence of the prepared cDNA is determined.

Based on the determined DNA sequence, an appropriate length of an RNAi gene construct comprising the DNA coding moiety encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain or a part of its non-translation region, is designed.

In order to express the RNAi gene in a cell, a recombinant vector is prepared by inserting a fragment or full length of the prepared DNA into downstream of the promoter of an appropriate expression vector.

A transformant is obtained by introducing the recombinant vector into a host cell suitable for the expression vector.

The host cell of the present invention can be obtained by selecting a transformant as a measure of the activity of the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain, or the sugar chain structure of a glycoprotein on the cell membrane or of the produced antibody molecule.

As the host cell, any cell such as yeast, animal cell, insect cell or plant cell can be used, so long as it has a gene encoding the target enzyme relating to the synthesis of an intracellular sugar nucleotide, GDP-fucose or the target enzyme relating to the modification of a sugar chain wherein 1-position of fucose is bound to 6-position of N-acetylglucosamine in the reducing end through α-bond in the complex N-glycoside-linked sugar chain. Examples include the host cells which will be described later in the item 3.

As the expression vector, a vector which is autonomously replicable in the host cell or can be integrated into the chromosome and comprises a promoter at such a position that the designed RNAi gene can be transferred is used. Examples include the expression vectors which will be described later in the item 3.

As the method for introducing a gene into various host cells, the methods for introducing recombinant vectors suitable for various host cells, which will be described later in the item 3, can be used.

Examples of the method for selecting a transformant as a measure of the activity of the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain include the methods described in the item 1(1)(a).

Examples of the method for selecting a transformant as a measure of the sugar chain structure of a glycoprotein on the cell membrane include the methods which will be described later in the item 1(5). Examples of the method for selecting a transformant as a measure of the sugar chain structure of a produced antibody molecule include the methods which will be described later in the item 5 or 6.

Examples of the method for preparing cDNA encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain include the methods described in preparation of DNA in the item 1(1)(a) and the like.

In addition, the host cell of the present invention can also be obtained without using an expression vector, by directly introducing an RNAi gene designed based on the nucleotide sequence encoding the enzyme relating to the synthesis of an intracellular sugar nucleotide, GDP-fucose or the enzyme relating to the modification of a sugar chain wherein 1-position of fucose is bound to 6-position of N-acetylglucosamine in she reducing end through α-bond in the complex N-glycoside-linked sugar chain.

The RNAi gene can be prepared in the usual method or using a DNA synthesizer.

The RNAi gene construct can be designed in accordance with the methods described in *Nature*, 391, 806 (1998); *Proc. Natl. Acad. Sci. USA*, 95, 15502 (1998); *Nature*, 395, 854

(1998); *Proc. Natl. Acad. Sci. USA,* 96, 5049 (1999); *Cell,* 95, 1017 (1998); *Proc. Natl. Acad. Sci. USA,* 96, 1451 (1999); *Proc. Natl. Acad. Sci. USA,* 95, 13959 (1998); *Nature Cell Biol.,* 2, 70 (2000); and the like.

(e) Preparation of the Host Cell of the Present Invention by a Method Using Transposon The host cell of the present invention can be prepared by inducing mutation using a transposon system described in *Nature Genet.,* 25, 35 (2000) or the like, and then by selecting a mutant as a measure of the activity of the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain, or the sugar chain structure of a glycoprotein of a produced antibody molecule or on the cell membrane.

The transposon system is a system in which a mutation is induced by randomly inserting an exogenous gene into chromosome, wherein an exogenous gene interposed between transposons is generally used as a vector for inducing a mutation, and a transposase expression vector for randomly inserting the gene into chromosome its introduced into the cell at the same time.

Any transposase can se used, so long as it is suitable for the sequence of the transposon to be used.

As the exogenous gene, any gene can be used, so long as it can induce a mutation in the DNA of a host cell.

As the host cell, any cell such as yeast, animal cell, insect cell or plant cell can be used, so long as it has a gene encoding the target enzyme relating to the synthesis of an intracellular sugar nucleotide, GDP-fucose or of the target enzyme relating to the modification of a sugar chain wherein 1-position of fucose is bound to 6-position of N-acetylglucosamine in the reducing end through α-bond in the complex N-glycoside-linked sugar chain. Examples include the host cells which will be described later in the item 3. For introducing the gene into various host cells, the method for introducing recombinant vectors suitable for various host cells, which will be described later in the item 3, can be used.

Examples of the method for selecting a mutant as a measure of the activity of the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain include the methods described in the item 1(1)(a).

Examples of the method for selecting a mutant as a measure of the sugar chain structure of a glycoprotein on the cell membrane include the methods which will be described later in the item 1(5). Examples of the method for selecting a mutant as a measure of the sugar chain structure of a produced antibody molecule include the methods which will be described later in the item 5 or 6.

(2) Method for Introducing a Dominant Negative Mutant of a Gene Encoding an Enzyme The host cell of the present invention can be prepared by targeting a gene encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain, using a technique for introducing a dominant negative mutant of the enzyme. Examples of the enzyme relating to the synthesis of an intracellular sugar nucleotide, GDP-fucose Include GMD, Fx, GFPP, fucokinase and the like. Examples of the enzyme relating to the modification of a sugar chain wherein 1-position of fucose is bound to 6-position of N-acetylglucosamine In the reducing end through α-bond in the complex N-glycoside-linked sugar chain include α-1,6-fucosyltransferase, α-L-fucosidase and the like.

The enzymes catalyze specific reactions having substrate specificity, and dominant negative mutants of the enzymes can be prepared by disrupting the active center of the enzymes which catalyze the catalytic activity having substrate specificity. The method for preparing a dominant negative mutant is specifically described as follows with reference to GMD among the target enzymes.

As a result of the analysis of the three-dimensional structure of *E. coli*-derived GMD, it has been revealed that 4 amino acids (threonine at position 133, glutamic acid at position 135, tyrosine at position 157 and lysine at position 161) have an important function on the enzyme activity (*Structure,* 8, 2, 2000). That is, when mutants were prepared by substituting the 4 amino acids with other different amino acids based on the three-dimensional structure information, the enzyme activity of all of the mutants was significantly decreased. On the other hand, changes in the ability of GMD to bind to GMD coenzyme NADP and its substrate GDP-mannose were hardly observed in the mutants. Accordingly, a dominant negative mutant can be prepared by substituting the 4 amino acids which control the enzyme activity of GMD. For example, in GMD (SEQ ID NO:65) derived from CHO cell, a dominant negative mutant can be prepared by substituting threonine position 155, glutamic acid at position 157, tyrosine at position 179 and lysine at position 183 with other amino acids, by comparing the homology and predicting the three-dimensional structure using the amino acid sequence information based on the results of the *E. coli*-derived GMD. Such a gene into which amino acid substitution is introduced can be prepared by t-he site-directed mutagenesis described in *Molecular Cloning,* Second Edition, *Current Protocols in Molecular Biology* or the like.

The host cell of the present invention can be prepared in accordance with the method described in *Molecular Cloning,* Second Edition, *Current Protocols in Molecular Biology* or the like, using the prepared dominant negative mutant gene of the target enzyme, for example, as follows.

A gene encoding a dominant negative mutant (hereinafter referred to as "dominant negative mutant gene") of the enzyme relating to the syntheses of an intracellular sugar nucleotide, GDP-fucose or the enzyme relating to the modification of a sugar chain wherein 1-position of fucose s bound to 6-position of N-acetylglucosamine in the reducing end through α-bond in the complex N-glycoside-linked sugar chain is prepared.

Based on the prepared full length DNA of dominant negative mutant gene, a DNA fragment of an appropriate length containing a moiety encoding the protein is prepared, if necessary.

A recombinant vector is produced by inserting the DNA fragment or full length DNA into downstream of the promoter of an appropriate expression vector.

A transformant is obtained by introducing the recombinant vector into a host cell suitable for the expression vector.

The host cell of the present invention can be prepared by selecting a transformant as a measure of the activity of the enzyme relating to the synthesis of an intracellular sugar nucleotide, GDP-fucose or the activity of the enzyme relating to the modification of a sugar chain wherein 1-position of fucose is bound to 6-position of N-acetylglucosamine in the reducing end through α-bond in the complex N-glycoside-linked sugar chain, or the sugar chain structure of a glycoprotein of a produced antibody molecule or on the cell membrane.

As the host cell, any cell such as yeast, animal cell, insect cell or plant cell can be used, so long as it has a gene encoding the target enzyme relating to the synthesis of an intracellular sugar nucleotide, GDP-fucose or of the target enzyme relating to the modification of a sugar chain wherein 1-position of fucose is bound to 6-position of N-acetylglucosamine in the reducing end through α-bond in the complex N-glycoside-linked sugar chain. Examples include the host cells which will be described later in the item 3.

As the expression vector, a vector which is autonomously replicable in the host cell or can be integrated into the chromosome and comprises a promoter at a position where transcription of the DNA encoding the dominant negative mutant of interest can be effected is used. Examples include the expression vectors which will be described later in the item 3.

For introducing the gene into various host cells, the method for introducing recombinant vectors suitable for various host cells, which will be described later in the item 3, can be used.

Examples of the method for selecting a transformant as a measure of the activity of the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain include the methods described in the item 1(1)(a).

Examples of the method for selecting a transformant as a measure of the sugar chain structure of a glycoprotein on the cell membrane include the methods which will be described later in the item 1(5). Examples of the method for selecting a transformant as a measure of the sugar chain structure of a produced antibody molecule include the methods which will be described later in the item 5 or 6.

(3) Method for Introducing a Mutation into an Enzyme

The host cell of the present invention can be prepared by introducing a mutation into a gene encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain, and then by selecting a cell line of interest in which the mutation occurred in the enzyme.

Examples of the enzyme relating to the synthesis of an intracellular sugar nucleotide, GDP-fucose include GMD, Fx, GFPP, fucokinase and the like. Examples of the enzyme relating to the modification of a sugar chain wherein 1-position of fucose is bound to 6-position of N-acetylglucosamine in the reducing end through α-bond in the complex N-glycoside-linked sugar chain include α-1,6-fucosyltransferase, α-L-fucosidase and the like.

Examples of the method include 1) a method in which a desired cell line is selected from mutants obtained by a mutation-inducing treatment of a parent cell line with a mutagen or spontaneously generated mutants, as a measure of the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain, 2) a method in which a desired cell line is selected from mutants obtained by a mutation-inducing treatment of a parent cell line with a mutagen or spontaneously generated mutants, as a measure of the sugar chain structure of a produced antibody molecule and 3) a method in which a desired cell line is selected from mutants obtained by a mutation-inducing treatment of a parent cell line with a mutagen or spontaneously generated mutants, as a measure of the sugar chain structure of a glycoprotein on the cell membrane.

As the mutation-inducing treatment, any treatment can be used, so long as it can induce a point mutation or a deletion or frame shift mutation in the DNA of cells of the parent cell line.

Examples include treatment with ethyl nitrosourea, nitrosoguanidine, benzopyrene or an acridine pigment and treatment with radiation. Also, various alkylating agents and carcinogens can be used as mutagens. Examples of the method for allowing a mutagen to act upon cells include the methods described in *Tissue Culture Techniques*, 3rd edition (Asakura Shoten), edited by Japanese Tissue Culture Association (1996), *Nature Genet.*, 24, 314 (2000) and the like.

Examples of the spontaneously generated mutant include mutants which are spontaneously formed by continuing subculture under general cell culture conditions without applying special mutation-inducing treatment.

Examples of the method for measuring the activity of the enzyme relating to the synthesis of an intracellular sugar nucleotide, GDP-fucose or the activity of the enzyme relating to the modification or a sugar chain wherein 1-position of fucose is bound to 6-position of N-acetylglucosamine in the reducing end through α-bond in the complex N-glycoside-linked sugar chain include the methods described in the item 1(1)(a). Examples of the method for discriminating the sugar chain structure of a prepared antibody molecule include the methods which will be described later in the items 5 or 6. Examples of the method for discriminating the sugar chain structure of a glycoprotein on the cell membrane include the methods which will be described later in the item 1(5).

(4) Method for Inhibiting Transcription and/or Translation of a Gene Encoding an Enzyme The host cell of the present invention can be prepared by inhibiting transcription and/or translation of a target gene through a method such as the antisense RNA/DNA technique [*Bioscience and Industry*, 50, 322 (1992); *Chemistry*, 46, 681 (1991); *Biotechnology*, 9, 358 (1992); *Trends in Biotechnology*, 10, 87 (1992); *Trends in Biotechnology*, 10, 152 (1992); *Cell Engineering*, 16, 1463 (1997)], the triple helix technique [*Trends in Biotechnology*, 10, 132 (1992)] or the like, using a gene encoding an enzyme relating to the synthesis of an intracellular sugar nucleotide, GDP-fucose and/or an enzyme relating to the modification of a sugar chain wherein 1-position of fucose is bound to 6-position of N-acetylglucosamine in the reducing end through α-bond in the complex N-glycoside-linked sugar chain, as the target.

Examples of the enzyme relating to the synthesis of an intracellular sugar nucleotide, GDP-fucose include GMD, Fx, GFPP, fucokinase and the like. Examples of the enzyme relating to the modification of a sugar chain wherein 1-position of fucose is bound to 6-position of N-acetylglucosamine in the reducing end through α-bond in the complex N-glycoside-linked sugar chain include α-1,6-fucosyltransferase, α-L-fucosidase and the like.

(5) Method for Selecting a Cell Line Resistant to a Lectin Which Recognizes a Sugar Chain Structure in Which 1-Position of Fucose is Bound to 6-Position of N-Acetylglucosamine in the Reducing End Through α-Bond in the N-Glycoside-Linked Sugar Chain The host cell of the present invention can be prepared by using a method for selecting a cell line resistant to a lectin which recognizes a sugar chain structure in which 1-position of fucose is bound to 6-position of N-acetylglucosamine in the reducing end through α-bond in the N-glycoside-linked sugar chain.

Examples of the method for selecting a cell line resistant to a lectin which recognizes a sugar chain structure in which 1-position of fucose is bound to 6-position of N-acetylglucosamine in the reducing end through α-bond in the N-glycoside-linked sugar chain include the methods using lectin described in *Somatic Cell Mol. Genet.*, 12, 51 (1986) and the like. As the lectin, any lectin can be used, so long as it is a lectin which recognizes a sugar chain structure in which 1-position of fucose is bound to 6-position of N-acetylglucosamine in the reducing end through α-bond in the N-glycoside-linked sugar chain. Examples include a *Lens culinaris* lectin LCA (lentil agglutinin derived from *Lens culinaris*), a pea lectin PSA (pea lectin derived from *Pisum sativum*), a broad bean lectin VFA (agglutinin derived from *Vicia faba*), an *Aleuria aurantia* lectin AAL (lectin derived from *Aleuria aurantia*) and the like.

Specifically, the cell line of the present invention resistant to a lectin which recognizes a sugar chain structure in which 1-posit on of fucose is bound to 6-position of N-acetylglucosamine in the reducing end through α-bond in the N-glycoside-linked sugar chain can be selected by culturing cells for 1 day to 2 weeks, preferably from 1 day to 1 week, using a medium comprising the lectin at a concentration of 1 μg/ml to 1 mg/ml, subculturing surviving cells or picking up a colony and transferring it into a culture vessel, and subsequently continuing the culturing using the lectin-containing medium Examples of the cell line obtained by the method include CHO/CCR4-LCA Nega-13 (FERM BP-7756) obtained in Example 14(2) which will be described later.

2. Preparation of a Transgenic Non-Human Animal or Plant or the Progenies thereof of the Present Invention The transgenic non-human animal or plant or the progenies thereof of the present invention is a transgenic non-human animal or plant or the progenies thereof in which a genome gene is modified in such a manner that the activity of an enzyme relating to the modification of a sugar chain of an antibody molecule can be controlled, and it can be prepared according to the method similar to that in the item 1, using a gene encoding an enzyme relating to the synthesis of an intracellular sugar nucleotide, GDP-fucose or an enzyme relating to the modification of a sugar chain wherein 1-position of fucose is bound to 6-position of N-acetylglucosamine in the reducing end through α-bond in the complex N-glycoside-linked sugar chain, as the target.

In a transgenic non-human animal, the embryonic stem cell of the present invention in which the activity of the enzyme relating to the synthesis of an intracellular sugar nucleotide, GDP-fucose or the activity of the enzyme relating to the modification of a sugar chain wherein 1-position of fucose is bound to 6-position of N-acetylglucosamine in the reducing end through α-bond in the complex N-glycoside-linked sugar chain is controlled can be prepared applying the method similar to that in the item 1 to an embryonic stem cell of the intended non-human animal such as cattle, sheep, goat, pig, horse, mouse, rat, fowl, monkey, rabbit or the like.

Specifically, a mutant clone is prepared in which a gene encoding the enzyme relating to the synthesis of an intracellular sugar nucleotide, GDP-fucose or the enzyme relating to the modification of a sugar chain wherein 1-position of fucose is bound to 6-position of N-acetylglucosamine in the reducing end through α-bond in the complex N-glycoside-linked sugar chain is inactivated or substituted with any sequence, by a known homologous recombination technique [e.g., *Nature*, 326, 6110, 295 (1987); *Cell*, 51, 3, 503 (1987); or the like]. Using the prepared mutant clone, a chimeric individual comprising an embryonic stem cell clone and a normal cell can be prepared by an injection chimera method into blastocyst of fertilized egg of an animal or by an aggregation chimera method. The chimeric individual is crossed with a normal individual, so that a transgenic non-human animal in which the activity of the enzyme relating to the synthesis of an intracellular sugar nucleotide, GDP-fucose or the activity of the enzyme relating to the modification of a sugar chain wherein 1-position of fucose is bound to 6-position of N-acetylglucosamine in the reducing end through α-bond in the complex N-glycoside-linked sugar chain is decreased or deleted in the whole body cells can be obtainer.

Also, a fertilized egg cell of the present invention in which the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain is decreased or deleted can be prepared by applying the method similar to that in the item 1 to fertilized egg of a non-human animal of interest such as cattle, sheep, goat, pig, horse, mouse, rat, fowl, monkey, rabbit or the like.

A transgenic non-human animal in which the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain is decreased can be prepared by transplanting the prepared fertilized egg cell into the oviduct or uterus of a pseudopregnant female using the embryo transplantation method described in *Manipulating Mouse Embryo*, Second Edition or the like, followed by childbirth by the animal.

In a transgenic plant, the callus of the present invention in which the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain is decreased or deleted can be prepared by applying the method similar to that in the item 1 to a callus or cell of the plant of interest.

A transgenic plant in which the activity of an enzyme relating to the synthesis of an intracellular sugar nucleotide, GDP-fucose or the activity of an enzyme relating to the modification of a sugar chain wherein 1-position of fucose is bound to 6-position of N-acetylglucosamine in the reducing end through α-bond in the complex N-glycoside-linked sugar chain is decreased can be prepared by culturing the prepared callus using a medium comprising auxin and cytokinin to redifferentite it in accordance with a known method [*Tissue Culture*, 20 (1994); *Tissue Culture*, 21 (1995); *Trends in Biotechnology*, 15, 45 (1997)].

3. Method for Producing an Antibody Composition

The antibody composition can be obtained by expressing it in a host cell using the methods described in *Molecular Cloning*, Second Edition; *Current Protocols in Molecular Biology; Antibodies, A Laboratory Manual*, Cold Spring Harbor Laboratory, 1988 (hereinafter referred also to as "Antibodies"); *Monoclonal Antibodies: Principles and Practice*, Third Edition, Acad. Press, 1993 (hereinafter referred also to as "*Monoclonal Antibodies*"); and *Antibody Engineering, A Practical Approach*, IRL Press at Oxford University Press (hereinafter referred also to as "*Antibody Engineering*"), for example, as follows.

A full length cDNA encoding an antibody molecule is prepared, and an appropriate length of a DNA fragment comprising a moiety encoding the antibody molecule is prepared.

A recombinant vector is prepared by inserting the DNA fragment or the full length cDNA into downstream of the promoter of an appropriate expression vector.

A transformant which produces the antibody molecule can be obtained by introducing the recombinant vector into a host cell suitable for the expression vector.

As the host cell, any of yeast, animal cell, insect cell, plant cell or the like can be used, so long as it can express the gene of interest.

A cell such as yeast, animal cell, insect cell, plant cell or the like into which an enzyme relating to the modification of an N-glycoside-linked sugar chain which binds to the Fc region of the antibody molecule is introduced by a genetic engineering technique can also be used as the host cell.

As the expression vector, a vector which is autonomously replicable in the host cell or can be integrated into the chromosome and comprises a promoter at such a position that the DNA encoding the antibody molecule of interest can be transferred is used.

The cDNA can be prepared from a human or non-human tissue or cell using, e.g., a probe primer specific for the antibody molecule of interest, in accordance with the methods described in the preparation of DNA in the item 1(1) (a).

When a yeast is used as the host cell, examples of the expression vector include YEP13 (ATCC 37115), YEp24 (ATCC 37051), YCp50 (ATCC 37419) and the like.

Any promoter can be used, so long as it can function in yeast. Examples include a promoter of a gene of the glycolytic pathway such as a hexose kinase gene, etc., PH05 promoter, PGK promoter, GAP promoter, ADH promoter, gal 1 promoter, gal 10 promoter, heat shock protein promoter, MF α1 promoter, CUP 1 promoter and the like.

Examples of the host cell include microorganisms belonging to the genus *Saccharomyces*, the genus *Schizosaccharomyces*, the genus *Kluyveromyces*, the genus *Trichosporon*, the genus *Schwanniomyces* and the like, such as *Saccharomyces cerevisiae*, *Schizosaccharomyces pombe*, *Kluyveromyces lactis*, *Trichosporon pullulans* and *Schwanniomyces alluvius*, etc.

As the method for introducing the recombinant vector, any method can be used, so long as it can introduce DNA into yeast. Examples include electroporation [*Methods in Enzymology*, 194, 182 (1990)], spheroplast method [*Proc. Natl. Acad. Sci. USA*, 84, 1929 (1978)], lithium acetate method [*J. Bacteriol.*, 153, 163 (1983)], a method described in *Proc. Natl. Acad. Sci. USA*, 75, 1929 (1978) and the like.

When an animal cell is used as the host, examples of the expression vector include pcDNAI, pcDM8 (available from Funakoshi), pAGE107 [Japanese Published Examined Patent Application No. 22979/91; *Cytotechnology*, 3, 133 (1990)], pAS3-3 (Japanese Published Examined Patent Application No. 227075/90), pCDM8 [*Nature*, 329, 840 (1987)], pcDNAI/Amp (manufactured by Invitrogen), pREP4, (manufactured by Invitrogen), pAGE103 [*J. Biochemistry*, 101, 1307 (1987)], pAGE210 and the like.

Any promoter can be used, so long as it can function in an animal cell. Examples include a promoter of IE (immediate early) gene of cytomegalovirus (CMV), an early promoter of SV40, a promoter of retrovirus, a promoter of metallothionein, a heat shock promoter, an SRα promoter and the like.

Also, an enhancer of the IE gene of human CMV may be used together with the promoter.

Examples of the host cell include a human cell such as Namalwa cell, a monkey cell such as COS cell, a Chinese humster cell such as CHO cell or HBT5637 (Japanese Published Examined Patent Application No. 299/88), a rat myeloma cell, a mouse myeloma cell, a cell derived from Syrian hamster kidney, an embryonic stem cell, a fertilized egg cell and the like.

As the method for introducing the recombinant vector, any method can be used, so long as at can introduce DNA into an animal cell. Examples include electroporation [*Cytotechnology*, 3, 133 (1990)], the calcium phosphate method (Japanese Published Examined Patent Application No. 227075/90), the lipofection method [*Proc. Natl. Acad. Sci. USA*, 84, 7413 (1987)], the injection method [*Manipulating the Mouse Embryo, A Laboratory Manual*], a method using particle gun (gene gun) (Japanese Patent No. 2606856, Japanese Patent No. 2517813), the DEAE-dextran method [*Biomanual Series 4-Gene Transfer and Expression Analysis* (Yodo-sha), edited by Takashi Yokota and Kenichi Arai (1994)], the virus vector method [*Manipulating Mouse Embryo*, Second Edition] and the like.

When an insect cell is used as the host, the protein can be expressed by the method described in *Current Protocols in Molecular Biology, Baculovirus Expression Vectors, A Laboratory Manual*, W.H. Freeman and Company, New York (1992), *Bio/Technology*, 6, 47 (1988) or the like.

That is, the protein can be expressed by simultaneously introducing a recombinant gene-introducing vector and a baculovirus into an insect cell to obtain a recombinant virus in an insect cell culture supernatant and then infecting the insect cell with the recombinant virus.

Examples of the gene introducing vector used in the method include pVL1392, pVL1393, pBlueBacIII (all manufactured by Invitrogen) and the like.

Examples of the baculovirus include *Autographa californica* nuclear polyhedrosis virus which is infected with an insect of the family Barathra.

Examples of the insect cell include *Spodoptera frugiperda* oocytes Sf9 and Sf21 [*Current Protocols in Molecular Biology, Baculovirus Expression Vectors, A Laboratory Manual*, W.H. Freeman and Company, New York (1992)], a *Trichoplusia ni* oocyte High 5 (manufactured by Invitrogen) and the like.

Examples of the method for the simultaneously introducing the recombinant gene-introducing vector and the baculovirus for preparing the recombinant virus include the calcium phosphate method (Japanese Published Examined Patent Application No. 227075/90), the lipofection method [*Proc. Natl. Acad. Sci. USA*, 84, 7413 (1987)] and the like.

When a plant cell is used as the host, examples of the expression vector include Ti plasmid, tobacco mosaic virus and the like.

As the promoter, any promoter can be used, so long as it can function in a plant cell. Examples include cauliflower mosaic virus (CaMV) 35S promoter, rice actin 1 promoter and the like.

Examples of the host cell include plant cells of tobacco, potato, tomato, carrot, soybean, rape, alfalfa, rice, wheat, barley, etc., and the like.

As the method for introducing the recombinant vector, any method can be used, so long as it can introduce DNA into a plant cell. Examples include a method using *Agrobacterium* (Japanese Published Examined Patent Application No. 140885/84, Japanese Published Examined Patent Application No. 70080/85, WO 94/00977), electroporation (Japanese Published Examined Patent Application. No. 251887/85), a method using a particle gun (gene gun) (Japanese Patent No. 2606856, Japanese Patent No. 2517813) and the like.

As the method for expressing a gene, secretion production, expression of a fusion protein of the Fc region with other protein and the like can be carried out in accordance with the method described in *Molecular Cloning*, Second Edition or the like, in addition to the direct expression.

When a gene is expressed by a bacterium, a yeast, an animal cell, an insect cell or a plant cell into which a gene relating to the synthesis of a sugar chain is introduced, an antibody molecule to which a sugar or a sugar chain is added by the introduced gene can be obtained.

An antibody composition can be obtained by culturing the obtained transformant in a medium to produce and accumulate the antibody molecule in the culture and then recovering it from the resulting culture. The method for culturing the transformant using a medium can be carried out in accordance with a general method which is used for the culturing of host cells.

As the medium for culturing a transformant obtained using a prokaryote such as *Escherichia coil* etc. or a eukaryote such as yeast etc. as the host cell, the medium may be either a natural medium or a synthetic medium, so long as it comprises materials such as a carbon source, a nitrogen source, an inorganic salt and the like which can be assimilated by the organism and culturing of the transformant can be efficiently carried out.

As the carbon source, those which can be assimilated by the organism can be used. Examples include carbohydrates such as glucose, fructose, sucrose, molasses containing them, starch, starch hydrolysate, etc.; organic acids such as acetic acid, propionic acid; etc.; alcohols such as ethanol, propanol, etc.; and the like.

Examples of the nitrogen source include ammonia; ammonium salts of inorganic acid or organic acid such as ammonium chloride, ammonium sulfate, ammonium acetate, ammonium phosphate, etc.; other nitrogen-containing compounds; peptone; meat extract; yeast extract; corn steep liquor; casein hydrolysate; soybean meal; soybean meal hydrolysate; various fermented cells and hydrolysates thereof; and the like.

Examples of the inorganic material include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like The culturing is carried out generally under aerobic conditions such as a shaking culture, submerged-aeration stirring culture or the like. The culturing temperature is preferably 15 to 40° C., and the culturing time is generally 16 hours to 7 days. During the culturing, the pH is maintained at 3.0 to 9.0. The pH is adjusted using an inorganic or organic acid, an alkali solution, urea, calcium carbonate, ammonia or the like.

If necessary, an antibiotic such as ampicillin, tetracycline or the like may be added to the medium during the culturing.

When a microorganism transformed with a recombinant vector obtained using an inducible promoter as the promoter is cultured, an inducer may be added to the medium, if necessary. For example, when a microorganism transformed with a recombinant vector obtained using lac promoter is cultured, isopropyl-β-D-thiogalactopyranoside may be added to the medium, and when a microorganism transformed with a recombinant vector obtained using trp promoter is cultured, indoleacrylic acid may be added to the medium.

When a transformant obtained using an animal cell as the host cell is cultured, examples of the medium include generally used RDMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)] and Whitten's medium [*Developmental Engineering Experimentation Manual-Preparation of Transgenic Mice* (Kodan-sha), edited by M. Katshuki (1987)], the media to which fetal calf serum, etc. is added, and the like.

The culturing is carried out generally at a pH of 6 to 8 and 30 to 40° C. for 1 to 7 days in the presence of 5%. $CO_2$. If necessary, an antibiotic such as kanamycin, penicillin or the like may be added to the medium during the culturing.

Examples of the medium for use in the culturing of a transformant obtained using an insect cell as the host include usually used TNM-FH medium (manufactured by Pharmingen), Sf-900 II SFM medium (manufactured by Life Technologies), ExCell 400 and ExCell 405 (both manufactured by JRH Biosciences), Grace's Insect Medium [*Nature*, 195, 788 (1962)] and the like.

The culturing is carried out generally at a medium pH of 6 to 7 and 25 to 30° C. for 1 to 5 days.

In addition, antibiotics such as gentamicin may be added to the medium during the culturing as occasion demands.

A transformant obtained using a plant cell as the host can be cultured as a cell or by differentiating it into a plant cell or organ. Examples of the medium for culturing the transformant include generally used Murashige and Skoog (MS) medium and White medium, the media to which a plant hormone such as auxin; cytokinin, etc. is added, and the like.

The culturing is carried out generally at a pH of 5 to 9 and 20 to 40° C. for 3 to 60 days.

If necessary, an antibiotic such as kanamycin, hygromycin or the like may be added to the medium during the culturing.

Accordingly, an antibody composition can be produced by culturing a transformant derived from a microorganism, an animal cell or a plant cell, which comprises a recombinant vector into which a DNA encoding an antibody molecule is inserted, in accordance with a general culturing method, to thereby produce and accumulate the antibody composition, and then recovering the antibody composition from the culture.

As the method for expressing the gene, secretion production, expression of a fusion protein and the like can be carried out in accordance with the method described in *Molecular Cloning*, Second Edition, in addition to the direct expression.

Examples of the method for producing an antibody composition include a method of intracellular expression in a host cell, a method of extracellular secretion from a host cell, and a method of production on a host cell membrane outer envelope. The method can be selected by changing the host cell used or the structure of the antibody composition produced.

When the antibody composition of the present invention is produced in a host cell or on a host cell membrane outer envelope, it can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Examined Patent Application No. 336963/93 and Japanese Published Examined Patent Application No. 823021/94 and the like.

That is, an antibody molecule of interest can be positively secreted extracellularly from a host cell by inserting a DNA encoding the antibody molecule and a DNA encoding a signal peptide suitable for the expression of the antibody molecule into an expression vector using a gene recombination technique, introducing the expression vector into the host cell and then expressing the antibody molecule.

Also, its production amount can be increased in accordance with the method described in Japanese Published Examined Patent Application No. 227075/90 using a gene amplification system using a dihydrofolate reductase gene.

In addition, the antibody composition can also be produced using a gene-introduced animal individual (transgenic non-human animal) or a plant individual (transgenic plant) which is constructed by the redifferentiation of an animal or plant cell into which the gene is introduced.

When the transformant is an animal individual or a plant individual, an antibody composition can be produced in accordance with a general method by rearing or cultivating it to thereby produce and accumulate the antibody composition and then recovering the antibody composition from the animal or plant individual.

Examples of the method for producing an antibody composition using an animal individual include a method in which the antibody composition of interest is produced in an animal constructed by introducing a gene in accordance with a known method [*American Journal of Clinical Nutrition*, 52, 627S (1996); *Bio/Technology*, 9, 830 (1991)].

In the case of an animal individual, an antibody composition can be produced by rearing a transgenic non-human animal into which a DNA encoding an antibody molecule is introduced to thereby produce and accumulate the antibody composition in the animal, and then recovering the antibody composition from the animal. Examples of the place of the animal where the composition is produced and accumulated include milk (Japanese Published Examined Patent Application No. 309192/88) and eggs of the animal. As the promoter used in this case, any promoter can be used, so long as it can function in an animal. Preferred examples include mammary gland cell-specific promoters such as α casein promoter, β casein promoter, β lactoglobulin promoter, whey acidic protein promoter and the like.

Example of the method for producing an antibody composition using a plant individual include a method in which an antibody composition is produced by cultivating a transgenic plant into which a DNA encoding an antibody molecule is introduced by a known method [*Tissue Culture*, 20 (1994); *Tissue Culture*, 21 (1995); *Trends in Biotechnology*, 15, 45 (1997)] to produce and accumulate the antibody composition in the plant, and then recovering the antibody composition from the plant.

Regarding purification of an antibody composition produced by a transformant into which a gene encoding an antibody molecule is introduced, for example, when the antibody composition is intracellularly expressed in a dissolved state, the cells after culturing are recovered by centrifugation, suspended in an aqueous buffer and then disrupted using ultrasonic oscillator, French press, Manton Gaulin homogenizer, dynomill or the like to obtain a cell-free extract. A purified product of the antibody composition can be obtained from a supernatant obtained by centrifuging the cell-free extract, by using a general enzyme isolation purification techniques such as solvent extraction; salting out; desalting with ammonium sulfate, etc.; precipitation with an organic solvent; anion exchange chromatography using a resin such as diethylaminoethyl (DEAE)-Sepharose, DIAION HPA-75 (manufactured by Mitsubishi Chemical), etc.; cation exchange chromatography using a resin such as S-Sepharose FF (manufactured by Pharmacia), etc.; hydrophobic chromatography using a resin such as butyl-Sepharose, phenyl-Sepharose, etc.; gel filtration using a molecular sieve; affinity chromatography; chromatofocusing; electrophoresis such as isoelectric focusing, etc.; and the like which may be used alone or in combination.

Also, when the antibody composition is expressed intracellularly by forming an insoluble body, the cells are recovered, disrupted and centrifuged in the same manner, and the insoluble body of the antibody composition is recovered as a precipitation fraction. The recovered insoluble body of the antibody composition is solubilized using a protein denaturing agent. The antibody composition is made into a normal three-dimensional structure by diluting or dialyzing the solubilized solution, and then a purified product of the antibody composition is obtained by the same isolation purification method.

When the antibody composition is secreted extracellularly, the antibody composition or derivatives thereof can be recovered from the culture supernatant. That is, the culture is treated by a technique such as centrifugation or the like to obtain a soluble fraction, and a purified preparation of the antibody composition can be obtained from the soluble fraction by the same isolation purification method.

Examples of the thus obtained antibody composition include an antibody, the fragment of the antibody, a fusion protein comprising the Fc region of the antibody, and the like.

As an example for obtaining the antibody composition, a method for producing a composition of a humanized antibody is described below in detail, but other antibody compositions can also be obtained in a manner similar to the method.

(1) Construction of Vector for Humanized Antibody Expression

A vector for humanized antibody expression is an expression vector for animal cell into which genes encoding the heavy chain (H chain) and light chain (L chain) C regions of a human antibody are inserted, which can be constructed by cloning each of genes encoding the H chain and L chain C regions of a human antibody into an expression vector for animal cell.

The C regions of a human antibody may be the H chain and L chain of any human antibody. Examples include the C region belonging to IgG1 subclass in the H chain of a human antibody (hereinafter referred to as "hCγ1"), the C region belonging to κ class in the L chain of a human antibody (hereinafter referred to as "hCκ"), and the like.

As the genes encoding the H chain and L chain C regions of a human antibody, a chromosomal DNA comprising an exon and an intron can be used or a cDNA can also be used.

As the expression vector for animal cell, any vector can be used, so long as a gene encoding the C region of a human antibody can be inserted thereinto and expressed therein. Examples include pAGE 107 [*Cytotechnology*, 3, 133 (1990)], pAGE 103 [*J. Biochem.*, 101, 1307 (1987)], pHSG274 [*Gene*, 27, 223 (1984)], pKCR [*Proc. Natl. Acad. Sci. USA*, 78, 1527 (1981), pSG1 β d2-4 [*Cytotechnology*, 4, 173 (1990)] and the like. Examples of the promoter and enhancer in the expression vector for animal cell include SV40 early promoter and enhancer [*J. Biochem.*, 101, 1307 (1987)], Moloney mouse leukemia virus LTR promoter [*Biochem. Biophys. Res. Commun.*, 149, 960 (1987)], immunoglobulin H chain promoter [*Cell*, 41, 479 (1985)] and enhancer [*Cell*, 33, 717 (1983)], and the like.

The humanized antibody expression vector may be either of a type in which genes encoding the H chain and L chain of an antibody exist on separate vectors or of a type in which both genes exist on the same vector (tandem type). In respect of easiness of construction of a humanized antibody expression vector, easiness of introduction into animal cells, and balance between the expression amounts of the H and L chains of an antibody in animal cells, a tandem type of the humanized antibody expression vector is more preferred [*J. Immunol. Methods*, 167, 271 (1994)].

The constructed humanized antibody expression vector can be used for expression of a human chimeric antibody and a human CDR-grafted antibody in animal cells.

(2) Preparation of cDNA Encoding V Region of Antibody Derived from Animal Other than Human cDNAs encoding the H chain and L chain V regions of an antibody derived from an animal other than human, such as a mouse antibody, can be obtained in the following manner.

A cDNA is synthesized by extracting mRNA from a hybridoma cell which produces the mouse antibody of interest. The synthesized cDNA is cloned into a vector such as a phage or a plasmid to obtain a cDNA library. Each of a recombinant phage or recombinant plasmid comprising a cDNA encoding the H chain V region and a recombinant phage or recombinant plasmid comprising a cDNA encoding the L chain V region is isolated from the library using a C region part or a V region part of an existing mouse antibody as the probe. Full nucleotide sequences of the H chain and L chain V regions of the mouse antibody of interest on the recombinant phage or recombinant plasmid are determined, and full amino acid sequences of the H chain and L chain V regions are deduced from the nucleotide sequences.

As the animal other than human, any animal such as mouse, rat, hamster, rabbit or the like can be used so long as a hybridoma cell can be produced therefrom.

Examples of the method for preparing total RNA from a hybridoma cell include the guanidine thiocyanate-cesium trifluoroacetate method [*Methods in Enzymology*, 154, 3 (1987)] and the like, and examples of the method for preparing mRNA from total RNA, an oligo (dT)-immobilized cellulose column method (*Molecular Cloning*, Second Edition) and the like. In addition, examples of a kit for preparing mRNA from a hybridoma cell include Fast Track mRNA Isolation Kit (manufactured by Invitrogen), Quick Prep mRNA Purification Kit (manufactured by Pharmacia) and the like.

Examples of the method for synthesizing cDNA and preparing a cDNA library include the usual methods (*Molecular Cloning*, Second Edition, *Current Protocols in Molecular Biology*, Supplement 1-34), methods using a commercially available kit such as SuperScript™, Plasmid System for cDNA Synthesis and Plasmid Cloning (manufactured by GIBCO BRL) or ZAP-cDNA Synthesis Kit (manufactured by Stratagene), and the like.

In preparing the cDNA library, the vector into which a cDNA synthesized using mRNA extracted from a hybridoma cell as the template is inserted may be any vector so long as the cDNA can be, inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning, A Practical Approach*, I, 49 (1985)], Lambda BlueMid (manufactured by Clontech), λExCell, pT7T3. 18U (manufactured by Pharmacia), pcD2 [*Mol. Cell. Biol.*, 3, 280 (1983)], pUC18 [*Gene*, 33, 103 (1985)] and the like.

As *Escherichia coli* into which the cDNA library constructed from a phage or plasmid vector is introduced, any *Escherichia coli* can be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

As the method for selecting a cDNA clone encoding the H chain and L chain V regions of an antibody derived from an animal other than human from the cDNA library, a colony hybridization or a plaque hybridization using an isotope—or fluorescence-labeled probe can be used (*Molecular Cloning*, Second Edition). The cDNA encoding the H chain and L chain V regions can also be prepared by preparing primers and carrying out polymerase chain reaction (hereinafter referred to as "PCR"; *Molecular Cloning*, Second Edition; *Current Protocols in Molecular Biology*, supplement 1-34) using a cDNA synthesized from mRNA or a cDNA library as the template.

The nucleotide sequences of the cDNAs can be determined by digesting the selected cDNAs with appropriate restriction enzymes, cloning she fragments into a plasmid such as pBluescript SK(−) (manufactured by Stratagene) or the like, carrying out the reaction of a generally used nucleotide sequence analyzing method such as the dideoxy method [*Proc. Natl. Acad. Sci. USA*, 74, 5463 (1977)] of Sanger et al. or the like and then analyzing the clones using an automatic nucleotide sequence analyzer such as A.L.F. DNA Sequencer (manufactured by Pharmacia) or the like. Whether or not the obtained cDNAs are encoding the full amino acid sequences of the H chain and L chain V regions of the antibody containing a secretory signal sequence can be confirmed by deducing the full amino acid sequences of the H chain and L chain V regions from the determined nucleotide sequence and comparing them with the full amino acid sequences of the H chain and L chain V regions of known antibodies [*Sequences of Proteins of Immunological Interest*, US Dep. Health and Human Services (1991)].

(3) Analysis of Amino Acid Sequence of V Region of Antibody Derived from Animal Other Than Human Regarding the full amino acid sequences of the H chain and L chain V regions of the antibody containing a secretory signal sequence, the length of the secretory signal sequence and the N-terminal amino acid sequences can be deduced and subgroups to which they belong can also be found, by comparing them with the full amino acid sequences of the H chain and L chain V regions of known antibodies [*Sequences of Proteins of Immunological Interest*, US Dep. Health and Human Services, (1991)]. In addition, the amino acid sequences of the H chain and L chain V regions of each CDR can also be found by comparing them with the amino acid sequences of the H chain and L chain V regions of known antibodies [*Sequences of Proteins of Immunological Interest*, US Dep. Health and Human Services, (1991)].

(4) Construction of Human Chimeric Antibody Expression Vector

A human chimeric antibody expression vector can be constructed by cloning cDNAs encoding the H chain and L chain V regions of an antibody derived from an animal other than human into upstream of genes encoding the H chain and L chain C regions of a human antibody in the vector for humanized antibody expression constructed in the item 3(1). For example, a human chimeric antibody expression vector can be constructed by linking each of cDNAs encoding the H chain and L chain V regions of an antibody derived from an animal other than human to a synthetic DNA comprising nucleotide sequences at the 3'-terminals of the H chain and L chain V regions of an antibody derived from an animal other than human and nucleotide sequences at the 5'-terminals of the H chain and L chain C regions of a human antibody and also having a recognition sequence of an appropriate restriction enzyme at both terminals, and by cloning them into upstream of genes encoding the H chain and L chain C regions of a human antibody contained in the vector for humanized antibody expression constructed described in the item 3(1).

(5) Construction of cDNA Encoding V Region of Human CDR-Grafted Antibody cDNAs encoding the H chain and L chain V regions of a human CDR-grafted antibody can be obtained as follows. First, amino acid sequences of the frameworks (hereinafter referred to as "FR") of the H chain and L chain V regions of a human antibody for grafting CDR of the H chain and L chain V regions of an antibody derived from an animal other than human is selected. As the amino acid sequences of FRs of the H chain and L chain V regions of a human antibody, any amino acid sequences can be used so long as they are derived from a human antibody. Examples include amino acid sequences of FRs of the H chain and L chain V regions of human antibodies registered at databases such as Protein Data Bank, etc., amino acid sequences common in each subgroup of FRs of the H chain and L chain V regions of human antibodies [*Sequences of Proteins of Immunological Interest*, US Dep. Health and Human Services (1991)] and the like. But in order to produce a human CDR-grafted antibody having potent activity, it is preferable to select an amino acid sequence having a homology as high as possible (at least 60% or more) with amino acid sequences of the H chain and L chain V regions of an antibody of interest derived from an animal other than human.

Next, the amino acid sequences of CDRs of the H chain and L chain V regions of the antibody of interest derived from an animal other than human are grafted to the selected amino acid sequences of FRs of the H chain and L chain V regions of a human antibody to design amino acid sequences of the H chain and L chain V regions of the human CDR-grafted antibody. The designed amino acid sequences are converted into DNA sequences by considering the frequency of codon usage found in nucleotide sequences of antibody genes [*Sequences of Proteins of Immunological Interest*, US Dep. Health and Human Services (1991)], and the DNA sequences encoding the amino acid sequences of the H chain and L chain V regions of the human CDR-grafted antibody are designed. Based on the designed DNA sequences, several synthetic DNA fragments having a length of about 100 bases are synthesized, and PCR is carried out using them. In this case, it is preferable in each of the H chain and the L chain that 6 synthetic DNAs are designed in view of the reaction efficiency of PCR and the lengths of DNAs which can be synthesized.

Also, they can be easily cloned into the vector for humanized antibody expression constructed in the item 3(1) by introducing recognition sequences of an appropriate restriction enzyme into the 5'-terminals of the synthetic DNA present on both terminals. After the PCR, the amplified product is cloned into a plasmid such as pBluescript SK(−) (manufactured by Stratagene) or the like and the nucleotide sequences are determined by the method in the item 3(2) to thereby obtain a plasmid having DNA sequences encoding the amino acid sequences of the H chain and L chain V regions of the desired human CDR-grafted antibody.

(6) Construction of Human CDR-Grafted Antibody Expression Vector

A human CDR-grafted antibody expression vector can be constructed by cloning the cDNAs encoding the H chain and L chain V regions of the human CDR-grafted antibody constructed in the item 3(5) into upstream of the gene encoding H chain and L chain C regions of a human antibody in the vector for humanized antibody expression described in the item 3(1). For example, the human CDR-grafted antibody expression vector can be constructed by introducing recognizing sequences of an appropriate restriction enzyme into the 5'-terminals of both terminals of a synthetic DNA fragment, among the synthetic DNA fragments which are used when PCR is carried out in the item 3(5) for constructing the H chain and L chain V regions of the human CDR-grafted antibody, so that they are cloned into upstream of the genes encoding the H chain and L chain C regions of a human antibody in the vector for humanized antibody expression described in the item 3(1) in such a manner that they can be expressed in a suitable form.

(7) Stable Production of Humanized Antibody

A transformant capable of stably producing a human chimeric antibody and a human CDR-grafted antibody (both hereinafter referred to as "humanized antibody") can be obtained by introducing the humanized antibody expression vectors described in the items 3(4) and (6) into an appropriate animal cell.

Examples of the method for introducing a humanized antibody expression vector into an animal cell include electroporation [Japanese Published Examined Patent Application No. 257891/90, *Cytotechnology*, 3, 133. (1990)] and the like.

As the animal cell into which a humanized antibody expression vector is introduced, any cell can be used so long as it is an animal cell which can produce the humanized antibody.

Examples include mouse myeloma cells such as NS0 cell and SP2/0 cell, Chinese hamster ovary cells such as CHO/dhfr⁻ cell and CHO/DG44 cell, rat myeloma such as YB2/0 cell and IR983F cell, BHK cell derived from a syrian hamster kidney, a human myeloma cell such as Namalwa cell, and the like, and a Chinese hamster ovary cell CHO/DG44 cell, a rat myeloma YB2/0 cell and the host cells of the present invention described in the item 5 are preferred.

After introduction of the humanized antibody expression vector, a transformant capable of stably producing the humanized antibody can be selected using a medium for animal cell culture comprising an agent such as G418 sulfate (hereinafter referred to as "G418"; manufactured by SIGMA) and the like in accordance with the method disclosed in Japanese Published Examined Patent Application No. 257891/90. Examples of the medium for animal cell culture include RPMI 1640 medium (manufactured by Nissui Pharmaceutical), GIT medium (manufactured by Nihon Pharmaceutical), EX-CELL 302 medium (manufactured by JRH), IMDM medium (manufactured by GIBCO BRL), Hybridoma-SFM medium (manufactured by GIBCO BRL) media obtained by adding various additives such as fetal bovine serum (hereinafter referred to as "FBS") to these media, and the like. The humanized antibody can be produced and accumulated in the culture supernatant by culturing the obtained transformant in a medium. The expression level and antigen binding activity of the humanized antibody in the culture supernatant can be measured by a method such as enzyme-linked immunosorbent assay [hereinafter referred to as "ELISA"; *Antibodies. A Laboratory Manual*, Cold Spring Harbor Laboratory, Chapter 14 (1998), *Monoclonal Antibodies: Principles and Practice*, Academic Press Limited (1996)] or the like. Also, the expression level of the humanized antibody by the transformant can be increased using a DHFR gene amplification system in accordance with the method disclosed in Japanese Published Examined Patent Application No. 257891/90.

The humanized antibody can be purified from a culture supernatant of the transformant using a protein A column [*Antibodies, A Laboratory Manual*, Cold spring Harbor Laboratory, Chapter 8 (1988), *Monoclonal Antibodies: Principles and Practice*, Academic Press Limited (1996)]. In addition, purification methods generally used for the purification of proteins can also be used. For example, the purification can be carried out through the combination of a gel filtration, an ion exchange chromatography and an ultrafiltration. The molecular weight of the H chain, L chain or antibody molecule as a whole of the purified humanized antibody can be measured, e.g., by polyacrylamide gel electrophoresis [hereinafter referred to as "SDS-PAGE"; *Nature*, 227, 680 (1970)], Western blotting [*Antibodies, A Laboratory Manual*, Cold Spring Harbor Laboratory, Chapter 12, (1988), *Monoclonal Antibodies: Principles and Practice*, Academic Press Limited (1996)] or the like.

Thus, methods for producing an antibody composition using an animal cell as the host have been described, but, as described above, the antibody composition can also be produced by a yeast, an insect cell, a plant cell, an animal individual or a plant individual by the same methods on the animal cell.

When a host cell has the ability to express an antibody molecule innately, the antibody composition of the present invention can be produced by preparing a cell expressing an antibody molecule using the method described in the item 1, culturing the cell and then purifying the antibody composition of interest from the resulting culture.

4. Activity Evaluation of Antibody Composition

As the method for measuring the amount of the purified antibody composition, the activity to bind to an antibody and the effector function of the purified antibody composition, the known method described in *Monoclonal Antibodies, Antibody Engineering* and the like can be used.

As the examples, when the antibody composition is a humanized antibody, the binding activity with an antigen and the binding activity with an antigen-positive cultured cell line can be measured by methods such as ELISA, an immunofluorescent method [*Cancer Immunol. Immunother.*, 36, 373 (1993)] and the like. The cytotoxic activity against an antigen-positive cultured cell line can be evaluated by measuring CDC activity, ADCC activity [*Cancer Immunol. Immunother.*, 36, 373 (1993)] and the like.

Also, safety and therapeutic effect of the antibody composition in human can be evaluated using an appropriate model of animal species relatively close to human, such as *Macaca fascicularis* or the like.

5. Analysis of Sugar Chains Binding to Antibody Molecules Expressed in Various Cells The sugar chain structure binding to an antibody molecule expressed in various cells can be analyzed in accordance with the general analysis of the sugar chain structure of a glycoprotein. For example, the sugar chain which is bound to IgG molecule comprises a neutral sugar such as galactose, mannose, fucose or the like, an amino sugar such as N-acetylglucosamine or the like and an acidic sugar such as sialic acid or the like, and can be analyzed by a method such as a sugar chain structure analysis or the like using sugar composition analysis, two dimensional sugar chain mapping or the like.

(1) Analysis of Neutral Sugar and Amino Sugar Compositions

The sugar chain composition binding to an antibody molecule can be analyzed by carrying out acid hydrolysis of sugar chains with an acid such as trifluoroacetic acid or the like to release a neutral sugar or an amino sugar and measuring the composition ratio.

Example include a method using a sugar composition analyzer (BioLC) manufactured by Dionex. The BioLC is an apparatus which analyzes a sugar composition by HPAEC-PAD (high performance anion-exchange chromatography-pulsed amperometric detection) [*J. Liq. Chromatogr.*, 6, 1577 (1983)].

The composition ratio can also be analyzed by a fluorescence labeling method using 2-aminopyridine. Specifically, the compositional ratio can be calculated in accordance with a known method [*Agric. Biol. Chem.*, 55 (1), 283-284 (1991)], by labeling an acid-hydrolyzed sample with a fluorescence with 2-aminopyridylation and then analyzing the composition by HPLC.

(2) Analysis of Sugar Chain Structure

The sugar chain structure binding to an antibody molecule can be analyzed by the two dimensional sugar chain mapping method [*Anal. Biochem.*, 171, 73 (1988), *Biochemical Experimentation Methods* 23—*Methods for Studying Glycoprotein Sugar Chains* (Japan Scientific Societies Press) edited by Reiko Takahashi (1989)]. The two dimensional sugar chain mapping method is a method for deducing a sugar chain structure by, e.g., plotting the retention time or elution position of a sugar chain by reverse phase chromatography as the X axis and the retention time or elution position of the sugar chain by normal phase chromatography as the Y axis, respectively, and comparing them with such results of known sugar chains.

Specifically, sugar chains are released from an antibody by subjecting the antibody to hydrazinolysis, and the released sugar chain is subjected to fluorescence labeling with 2-aminopyridine (hereinafter referred to as "PA") [*J. Biochem.*, 95, 197 (1984)], and then the sugar chains are separated from an excess PA-treating reagent by gel filtration, and subjected to reverse phase chromatography. Thereafter, each peak of the separated sugar chains are subjected to normal phase chromatography. The sugar chain structure can be deduced by plotting the results on a two dimensional sugar chain map and comparing them with the spots of a sugar chain standard (manufactured by Takara Shuzo) or a literature [*Anal. Biochem.*, 171, 73 (1988)].

The structure deduced by the two dimensional sugar chain mapping method can be confirmed by further carrying out mass spectrometry such as MALDI-TOF-MS of each sugar chain or the like.

6. Immunological Determination Method for Discriminating Sugar Chain Structure of Antibody Molecule An antibody composition comprises an antibody molecule in which sugar chains binding to the Fc region of the antibody are different in structure. The antibody composition in which the ratio of a sugar chain in which fucose is not bound to N-acetylglucosamine in the reducing end in the sugar chain is 20% or more among the total complex N-glycoside-linked sugar chains binding to the Fc region in the antibody composition reducing end has potent ADCC activity. The antibody composition can be identified by using the method for analyzing the sugar chain structure of an antibody molecule described in the item 6. Also, it can also be identified by an Immunological determination method using a lectin.

The sugar chain structure of an antibody molecule can be identified by the Immunological determination method using a lectin in accordance with the known Immunological determination method such as Western staining, IRA (radioimmunoassay), VIA (viroimmunoassay), EIA (enzymoimmunoassay), FIA (fluoroimmunoassay), MIA (metalloimmunoassay) and the like described in *Monoclonal Antibodies: Principles and Applications*, Wiley-Liss, Inc. (1995); Immunoassay, 3rd Ed., Igakushoin (1987); *Enzyme Antibody Method*, Revised Edition, Gakusai Kikaku (1985); and the like.

A lectin which recognizes the sugar chain structure of an antibody molecule comprised in an antibody composition is labeled, and the labeled lectin is allowed to react with an antibody composition which is a sample. Then, the amount of the complex of the labeled lectin with the antibody molecule is measured.

Examples of the lectin used for identifying the sugar chain structure of an antibody molecule include WGA (wheat-germ agglutinin derived from *T. vulgaris*), ConA (cocanavalin A derived from *C. ensiformis*), RIC (a toxin derived from *R. communis*), L-PHA (leucoagglutinin derived from *P. vulgaris*), LCA (lentil agglutinin derived from *L. culinaris*), PSA (pea lectin derived from *P. sativum*), AAL (*Aleuria aurantia* lectin), ACL (*Amaranthus caudatus* lectin), BPL (*Bauhinia purpurea* lectin), DSL (*Datura stramonium* lectin), DBA (*Dolichos biflorus* agglutinin), EBL (elderberry balk lectin), ECL (*Erythrina cristagalli* lectin), EEL (*Euonymus eoropaeus* lectin), GNL (*Galanthus nivalis* lectin), GSL (*Griffonia simplicifolia* lectin), HPA (*Helix pomatia* agglutinin), HHL (*Hippeastrum hybrid* lectin), Jacalin, LTL (*Lotus tetragonolobus* lectin), LEL (*Lycopersicon esculentum* lectin), MAL (*Maackia amurensis* lectin), MPL (*Maclura pominfera* lectin), NPL (*Narcissus pseudonarcissus* lectin), PNA (peanut agglutinin), E-PHA (*Phaseolus vulgaris* erythroagglutinin), PTL (*Psophocarpus tetragonolobus* lectin), RCA (*Ricinus communis* agglutinin), STL (*Solanum tuberosum* lectin), SJA (*Sophora japonica* agglutinin), SBA (soybean agglutirin), UEA (*Ulex europaeus* agglutinin), VVL (*Vicia villosa* lectin) and WFA (*Wisteria floribunda* agglutinin).

It is preferable to use a lectin which specifically recognizes a sugar chain structure wherein fucose binds to the N-acetylglucosamine in the reducing end in the complex N-glycoside-linked sugar chain. Examples include *Lens culinaris* lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*)

7. Application of Antibody Molecule of the Present Invention

The antibody composition of the present invention has potent antibody-dependent cell-mediated cytotoxic activity. An antibody having potent antibody-dependent cell-mediated cytotoxic activity is useful for preventing and treating various diseases including cancers, inflammatory diseases, immune diseases such as autoimmune diseases, allergies and the like, circulatory organ diseases and viral or bacterial infections.

In the case of cancers, namely malignant tumors, cancer cells grow. General anti-tumor agents inhibit the growth of cancer cells. In contrast, an antibody having potent antibody-dependent cell-mediated cytotoxic activity can treat cancers by injuring cancer cells through its cell killing effect, and therefore, it is more effective as a therapeutic agent than the general anti-tumor agents. At present, in the therapeutic agent for cancers, an anti-tumor effect of an antibody medicament alone is insufficient so that combination therapy with chemotherapy has been carried out [*Science*, 280, 1197 (1998)]. If more potent anti-tumor effect is found by the antibody composition of the present invention alone, the dependency on chemotherapy will be decreased and side effects will be reduced.

In immune diseases such as inflammatory diseases, autoimmune diseases, allergies and the like, in vivo reactions of the diseases are induced by the release of a mediator molecule by immunocytes, so that the allergy reaction can be inhibited by eliminating immunocytes using an antibody having potent antibody-dependent cell-mediated cytotoxic activity.

Examples of the circulatory organ diseases include arteriosclerosis and the like. The arteriosclerosis is treated using balloon catheter at present, but circulatory organ diseases can be prevented and treated by inhibiting growth of arterial cells in restricture after treatment using an antibody having potent antibody-dependent cell-mediated cytotoxic activity.

Various diseases including viral and bacterial infections can be prevented and treated by inhibiting proliferation of cells infected with a virus or bacterium using an antibody having potent antibody-dependent cell-mediated cytotoxic activity.

Examples of an antibody which recognizes a tumor-related antigen, an antibody which recognizes an allergy- or inflammation-related antigen, an antibody which recognizes circulatory organ disease-related antigen and an antibody which recognizes a viral or bacterial infection-related antigen are described below.

Examples of the antibody which recognizes a tumor-related antigen include anti-GD2 antibody (Ohta et al., *Anticancer Res.*, 13, 331-336, 1993), anti-GD3 antibody (Ohta et al., *Cancer Immunol. Immunother.*, 36, 260-266, 1993), anti-GM2 antibody (Nakamura et al., *Cancer Res.*, 54, 1511-1516, 1994), anti-HER2 antibody (Carter et al., *Proc. Natl. Acad. Sci. USA*, 89, 4285-4289, 1992), anti-CD52 antibody (Carter et al., *Proc. Natl. Acad. Sci. USA*, 89, 4285-4289, 1992), anti-MAGE antibody (Jungbluth et al., *British J. Cancer*, 83, 493-497, 2000), anti-HM1.24 antibody (Ono et al., *Molecular Immunol.*, 36, 387-395, 1999), anti-parathyroid hormone-related protein (PTHrP) antibody (Ogata et al., *Cancer*, 88, 2909-2911, 2000), anti-basic fibroblast growth factor antibody and anti-FGF8 antibody (Matsuzaki et al., *Proc. Natl. Acad. Sci. USA*, 86, 9911-9915, 1989), anti-basic fibroblast growth factor receptor antibody and anti-FGF8 receptor antibody (Kuo et al., *J. Biol. Chem.*, 265, 16455-16463, 1990), anti-insulin-like growth factor antibody (Yao et al., *J. Neurosci. Res.*, 40, 647-659, 1995), anti-insulin-like growth factor Receptor antibody (Yao et al., *J. Neurosci. Res.*, 40, 647-659, 1995), anti-PMSA antibody (Murphy et al., *J. Urology*, 160, 2396-2401, 1998), anti-vascular endothelial cell growth factor antibody (Presta et al., *Cancer Res.*, 57, 4593-4599, 1997), anti-vascular endothelial cell growth factor receptor antibody (Kanno et al., *Oncogene*, 12, 2138-2146, 2000) and the like.

Examples of the antibody which recognizes an allergy- or inflammation-related antigen include anti-interleukin 6 antibody (Abrams et al., *Immunol. Rev.*, 127, 5-24, 1992), anti-interleukin 6 receptor antibody (Sato et al., *Molecular Immunol.*, 31, 371-381, 1994), anti-interleukin 5 antibody (Abrams et al., *Immunol. Rev.*, 127, 5-24, 1992), anti-interleukin 5 receptor antibody and anti-interleukin 4 antibody (Biord et al., *Cytokine*, 3, 562-567, 1991), anti-tumor necrosis factor antibody (Tempest et al., *Hybridoma*, 13, 183-190, 1994), anti-tumor necrosis factor receptor antibody (Amrani et al., *Molecular Pharmacol.*, 58, 237-245, 2000), anti-CCR4 antibody (Campbell et al., *Nature*, 400, 776-780, 1999), anti-chemokine antibody (Peri et al., *J. Immuno. Meth.*, 174, 249-257, 1994), anti-chemokine receptor antibody (Wu et al., *J. Exp. Med.*, 186, 1373-1381, 1997) and the like. Examples of the antibody which recognizes a circulatory organ disease-related antigen include anti-GpIIb/IIIa antibody (Co et al., *J. Immunol.*, 152, 2968-2976, 1994), anti-platelet-derived growth factor antibody (Ferns et al., *Science*, 253, 1129-1132, 1991), anti-platelet-derived growth factor receptor antibody (Shulman et al., *J. Biol. Chem.*, 277, 17400-17404, 1997) and anti-blood coagulation factor antibody (Peter et al., *Circulation*, 101, 1158-1164, 2000) and the like.

Examples of the antibody which recognizes a viral or bacterial infection-related antigen include anti-gp120 antibody (Tugarinov et al., *Structure*, 8, 385-395, 2000), anti-CD4 antibody (Schulze-Koops et al., *J. Rheumatology*, 25, 2065-2076, 1998), anti-CCR4 antibody and anti-Vero toxin antibody (Karnali et al., *J. Clin. Microbial.*, 37, 396-399, 1999) and the like.

These antibodies can be obtained from public organizations such as ATCC (The American Type Culture Collection), RIKEN Gene Bank at The Institute of Physical and Chemical Research, National Institute of Bioscience and Human Technology, Agency of Industrial Science and Technology (present name, International Patent Organism Depositary, National Institute of Advanced Industrial Science and Technology) and the like, or private reagent sales companies such as Dainippon Pharmaceutical, R & D SYSTEMS, PharMingen, Cosmo Bio, Funakoshi and the like.

The medicament comprising the antibody composition of the present invention can be administered as a therapeutic agent alone, but generally, it is preferable to provide it as a pharmaceutical formulation produced by an appropriate method well known in the technical field of manufacturing pharmacy, by mixing it with at least one pharmaceutically acceptable carrier.

It is desirable to select a route of administration which is most effective in treatment. Examples include oral administration and parenteral administration, such as buccal, tracheal, rectal, subcutaneous, intramuscular, intravenous or the like. In an antibody preparation, intravenous administration is preferable.

The dosage form includes sprays, capsules, tablets, granules, syrups, emulsions, suppositories, injections, ointments, tapes and the like.

Examples of the pharmaceutical preparation suitable for oral administration include emulsions, syrups, capsules, tablets, powders, granules and the like.

Liquid preparations, such as emulsions and syrups, can be produced using, as additives, water; saccharides, such as sucrose, sorbitol, fructose, etc.; glycols, such as polyethylene glycol, propylene glycol, etc.; oils, such as sesame oil, olive oil, soybean oil, etc.; antiseptics, such as p-hydroxybenzoic acid esters, etc.; flavors, such as strawberry flavor, peppermint, etc.; and the like.

Capsules, tablets, powders, granules and the like can be produced using, as additive, fillers, such as lactose, glucose, sucrose, mannitol, etc.; disintegrating agents, such as starch, sodium alginate, etc.; lubricants, such as magnesium stearate, talc, etc.; binders, such as polyvinyl alcohol, hydroxypropylcellulose, gelatin, etc.; surfactants, such as fatty acid ester, etc.; plasticizers, such as glycerine, etc.; and the like.

Examples of the pharmaceutical preparation suitable for parenteral administration include injections, suppositories, sprays and the like.

Injections may be prepared using a carrier, such as a salt solution, a glucose solution, a mixture of both thereof or the like. Also, powdered injections can be prepared by freeze-drying the antibody composition in the usual way and adding sodium chloride thereto.

Suppositories may be prepared using a carrier such as cacao butter, hydrogenated fat, carboxylic acid or the like.

Also, sprays may be prepared using the antibody composition as such or using a carrier which does not stimulate the buccal or airway mucous membrane of the patient and can facilitate absorption of the antibody composition by dispersing it as fine particles.

Examples of the carrier include lactose, glycerol and the like. Depending on the properties of the antibody composition and the carrier, it is possible to produce pharmaceutical preparations such as aerosols, dry powders and the like. In addition, the components exemplified as additives for oral preparations can also be added to the parenteral preparations.

Although the clinical dose or the frequency of administration varies depending on the objective therapeutic effect, administration method, treating period, age, body weight and the like, it is usually 10 µg/kg to 20 mg/kg per day and per adult.

Also, as the method for examining antitumor effect of the antibody composition against various tumor cells, in vitro tests include CDC activity measuring method, ADCC activity measuring method and the like, and in vivo tests include antitumor experiments using a tumor system in an experimental animal such as a mouse, etc. and the like.

CDC activity and ADCC activity measurements and antitumor experiments can be carried out in accordance with the methods described in *Cancer Immunology Immunotherapy*, 36, 373 (1993); *Cancer Research*, 54, 1511 (1994) and the like.

The present invention will be described below in detail based on Examples; however, Examples are only simple illustrations, and the scope of the present invention is not limited thereto.

EXAMPLE 1

Production of Anti-ganglioside GD3 Human Chimeric Antibody

1. Construction of Tandem Expression Vector pChiLHGM4 for Anti-ganglioside GD3 Human Chimeric Antibody A plasmid pChi641LGM40 was constructed by ligating a fragment of about 4.03 kb containing an L chain cDNA, obtained by digesting an L chain expression vector, pChi641LGM4 [*J. Immunol. Methods*, 167, 271 (1994)] for anti-ganglioside GD3 human chimeric antibody (hereinafter referred to as "anti-GD3 chimeric antibody") with restriction enzymes MluI (manufactured by Takara Shuzo) and SalI (manufactured by Takara Shuzo) with a fragment of about 3.40 kb containing a G418-resistant gene and a splicing signal, obtained by digesting an expression vector pAGE 107 [*Cytotechnology*, 3, 133 (1990)] for animal cell with restriction enzymes MluI (manufactured by Takara Shuzo) and SalI (manufactured by Takara Shuzo) using DNA Ligation Kit (manufactured by Takara Shuzo), and then transforming *E. coli* HB101 (*Molecular Cloning*, Second Edition) with the ligated product.

Next, a fragment of about 5.68 kb containing an L chain cDNA, obtained by digesting the constructed plasmid pChi641LGM40 with a restriction enzyme ClaI (manufactured by Takara Shuzo), blunt-terminating it using DNA Blunting Kit (manufactured by Takara Shuzo) and further digesting it with MluI (manufactured by Takara Shuzo), was ligated with a fragment of about 8.40 kb containing an H chain cDNA, obtained by digesting an anti-GD3 chimeric antibody H chain expression vector, pChi641HGM4 [*J. Immunol. Methods* 167, 271 (1994)] with a restriction enzyme XhoI (manufactured by Takara Shuzo), blunt-terminating it using DNA Blunting Kit (manufactured by Takara Shuzo) and further digesting it with MluI (manufactured by Takara Shuzo), using DNA Ligation Kit (manufactured by Takara Shuzo), and then *E. coli* HB101 (*Molecular Cloning, Second Edition*) was transformed with the ligated product to thereby construct a tandem expression vector pChi641LHGM4 for anti-GD3 chimeric antibody.

2. Preparation of Cells Stably Producing Anti-GD3 Chimeric Antibody

Cells capable of stably producing an anti-GD3 chimeric antibody were prepared using the tandem expression vector pChi641LHGM4 for anti-GD3 chimeric antibody constructed in the item 1 of Example 1, as described below.

(1) Preparation of Antibody-producing Cell Using Rat Myeloma YB2/0 Cell

After introducing 5 μg of the anti-GD3 chimeric antibody expression vector pChi641LHGM4 into $4 \times 10^6$ cells of rat myeloma YB2/0 [ATCC CRL-1662, J. V. Kilmarin et al., *J. Cell. Biol.*, 93, 576-582 (1982)] by electroporation [*Cytotechnology*, 3, 133 (1990)], the cells were suspended in 40 ml of RPMI1640-FBS(10) (RPMI1640 medium comprising 10% FBS (manufactured by GIBCO BRL)) and dispensed in 200 μl/well into a 96 well culture plate (manufactured by Sumitomo Bakelite). After culturing them at 37° C. for 24 hours in a 5% $CO_2$ incubator, G418 was added to a concentration of 0.5 mg/ml, followed by culturing for 1 to 2 weeks. The culture supernatant was recovered from wells in which colonies of transformants showing G418 resistance were formed and growth of colonies was observed, and the antigen binding activity of the anti-GD3 chirmeric antibody in the supernatant was measured by the ELISA shown in the item 3 of Example 1.

Regarding the transformants in wells in which production of the anti-GD3 chimeric antibody was observed in culture supernatants, in order to increase the amount of the antibody production using a DHFR gene amplification system, each of them was suspended in the RPMI1640-FBS(10) medium comprising 0.5 mg/ml G418 and 50 nM DHFR inhibitor, methotrexate (hereinafter referred to as "MTX"; manufactured by SIGMA) to give a density of 1 to $2 \times 10^5$ cells/ml, and the suspension was dispensed in 2 ml into wells of a 24 well plate (manufactured by Greiner). Transformants showing 50 nM MTX resistance were induced by culturing at 37° C. for 1 to 2 weeks in a 5% $CO_2$ incubator. The antigen binding activity of the anti-GD3 chimeric antibody in culture supernatants in wells in which growth of transformants was observed was measured by the ELISA shown in the item 3 of Example 1. Regarding the transformants in wells in which production of the anti-GD3 chimeric antibody was observed in culture supernatants, the MTX concentration was increased to 100 nM and then to 200 nM, and transformants capable of growing in the RPMI1640-FBS(10) medium comprising 0.5 mg/ml G418 and 200 nM MTX and of producing the anti-GD3 chimeric antibody in a large amount were finally obtained by the same method as described above. Among the obtained transformants, suitable cell lines were selected and were made into a single cell (cloning) by limiting dilution twice. Also, using the method for determining the transcription product of an α-1,6-fucosyltransferase gene shown in Example 9, a cell line producing a relatively small amount of the transcription product was selected and used as a suitable cell line.

The obtained anti-GD3 chimeric antibody-producing transformed cell clone 7-9-51 has been deposited on Apr. 5, 1999, as FERM BP-6691 in National Institute of Bioscience and Human Technology, Agency of industrial Science and Technology (Higashi 1-1-3, Tsukuba, Ibaraki, Japan) (present name: International Patent organism Depositary, National Institute of Advanced Industrial Science and Technology (AIST Tsukuba Central 6, 1-1, Higashi 1-Chome Tsukuba-shi, Ibaraki-ken, Japan)).

(2) Preparation of Antibody-Producing Cell Using CHO/DG44 Cell

After introducing 4 μg of the anti-GD3 chimeric antibody expression vector, pChi641LHGM4, into $1.6 \times 10^6$ cells of CHO/DG44 [G. Urlaub and L. A. Chasin, *Proc. Natl. Acad. Sci. USA*, 77, 4216-4220 (1980)] by electroporation [*Cytotechnology*, 1, 133 (1990)], the cells were suspended in 10 ml of IMDM-FBS(10) [IMDM medium comprising 10% FBS and 1× concentration of HT supplement (manufactured by GIBCO BRL)] and dispensed in 200 μl/well into a 96 well culture plate (manufactured by Iwaki Glass). After culturing them at 37° C. for 24 hours in a 5% $CO_2$ incubator, G418 was added to give a concentration of 0.5 mg/ml, followed by culturing for 1 to 2 weeks. The culture supernatant was recovered from wells in which colonies of transformants showing G418 resistance were formed and growth of colonies was observed, and the antigen binding activity of the anti-GD3 chimeric antibody in the supernatant was measured by the ELISA shown in the item 3 of Example 1.

Regarding the transformants in wells in which production of the anti-GD3 chimeric antibody was observed in culture supernatants, in order to increase the amount of the antibody production using a DHFR gene amplification system, each of them was suspended in an IMDM-dFBS(10) medium [IMDM medium comprising 10% dialyzed fetal bovine serum (hereinafter referred to as "dFBS"; manufactured by GIBCO BRL)] comprising 0.5 mg/ml G418 and 10 nM MTX to give a density of 1 to $2 \times 10^5$ cells/ml, and the suspension was dispensed in 0.5 ml into wells of a 24 well plate (manufactured by Iwaki Glass). Transformants showing 10 nM MTX resistance were induced by culturing at 37° C. for 1 to 2 weeks in a 5% $CO_2$ incubator. Regarding the transformants in wells in which their growth was observed, the MTX concentration was increased to 100 nM, and transformants capable of growing in the IMDM-dFBS(10) medium comprising 0.5 mg/ml G418 and 100 nM MTX and of producing the anti-GD3 chimeric antibody in a large amount were finally obtained by the same method as described above. Among the obtained transformants, suitable cell lines were selected and were made into a single cell (cloning) by limiting dilution twice. Also, using the method for determining the transcription product of an α-1,6-fucosyltransferase gene shown in Example 9, a cell line producing a relatively small amount of the transcription product was selected and used as a suitable cell line.

(3) Preparation of Antibody-producing Cell Using Mouse Myeloma NS0 Cell

After introducing 5 μg of the anti-GD3 chimeric antibody expression vector pChi641LHGM4 into $4 \times 10^6$ cells of mouse myeloma NS0 by electroporation [*Cytotechnology*, 3, 133 (1990)], the cells were suspended in 40 ml of EX-CELL302-FBS(10) (EX-CELL302 medium comprising 10% FBS and 2 mM L-glutamine [hereinafter referred to as "L-Gln"; manufactured by GIBCO BRL)] and dispensed in 200 μl/well into a 96 well culture plate (manufactured by Sumitomo Bakelite). After culturing them at 37° C. for 24 hours in a 5% $CO_2$ incubator, G418 was added to give a concentration of 0.5 mg/ml, followed by culturing for 1 to 2 weeks. The culture supernatant was recovered from wells in which colonies of transformants showing G418 resistance were formed and growth of colonies was observed, and the antigen binding activity of the anti-GD3 chimeric antibody in the supernatant was measured by the ELISA shown in the item 3 of Example 1.

Regarding the transformants in wells in which production of the anti-GD3 chimeric antibody was observed in culture supernatants, in order to increase the amount of the antibody production using a DHFR gene amplification system, each of them was suspended in an EX-CELL302-dFBS(10) medium (EX-CELL302 medium comprising 10% dFBS and 2 mM L-Gln) comprising 0.5 mg/ml G418 and 50 nM MTX to give a density of 1 to $2\times10^5$ cells/ml, and the suspension was dispensed in 2 ml into wells of a 24 well plate (manufactured by Greiner). Transformants showing 50 nM MTX resistance were induced by culturing at 37° C. for 1 to 2 weeks in a 5% $CO_2$ incubator. The antigen binding activity of the anti-GD3 chimeric antibody in culture supernatants in wells in which growth of transformants was observed was measured by the ELISA shown in the item 3 of Example 1. Regarding the transformants in wells in which production of the anti-GD3 chimeric antibody was observed in culture supernatants, the MTX concentration was increased to 100 nM and then to 200 nM, and transformants capable of growing in the EX-CELL302-dFBS(10) medium comprising 0.5 mg/ml G418 and 200 nM MTX and of producing the anti-GD3 chimeric antibody in a large amount was finally obtained by the same method as described above. Among the obtained transformants, elite cell lines were selected and were made into a single cell (cloning) by limiting dilution twice Also, using the method for determining the transcription product of an α-1,6-fucosyltransferase gene shown in Example 9, a cell line producing a relatively small amount of the transcription product was selected and used as a suitable cell line.

3. Measurement of Binding Activity of Antibody to GD3 (ELISA)

The binding activity of the antibody to GD3 was measured as described below.

In 2 ml of ethanol solution containing 10 μg of dipalmitoylphosphatidylcholine (manufactured by SIGMA) and 5 μg of cholesterol (manufactured by SIGMA), 4 nmol of GD3 was dissolved. Into each well of a 96 well plate for ELISA (manufactured by Greiner), 20 μl of the solution (40 pmol/well in final concentration) was dispensed, followed by air-drying, 1% bovine serum albumin (hereinafter referred to as "BSA"; manufactured by SIGMA)—containing PBS (hereinafter referred to as "1% BSA-PBS") was dispensed in 100 μl/well, and then the reaction was carried out at room temperature for 1 hour for blocking remaining active groups. After discarding 1% BSA-PBS, a culture supernatant of a transformant or a diluted solution of a human chimeric antibody was dispensed in 50 μl/well to carry out the reaction at room temperature for 1 hour. After the reaction, each well was washed with 0.05% Tween 20 (manufactured by Wako Pure Chemical Industries)-containing PBS (hereinafter referred to as "Tween-PBS"), a peroxidase-labeled goat anti-human IgG (H & L) antibody solution (manufactured by American Qualex) diluted 3,000 times with 1% BSA-PBS was dispensed in 50 μl/well as a secondary antibody solution, and then the reaction was carried out at room temperature for 1 hour. After the reaction and subsequent washing with Tween-PBS, ABTS substrate solution [solution prepared by dissolving 0.55 g of 2,2'-azino-bis(3-ethylbenzothiazoline-6-sulfonic acid) ammonium salt in 1 liter of 0.1 M citrate buffer (pH 4.2) and adding 1 μl/ml of hydrogen peroxide to the solution just before use (hereinafter the same solution was used)] was dispensed in 50 μl/well for color development, and then absorbance at 415 nm (hereinafter referred to as "OD415") was measured.

4. Purification of Anti-GD3 Chimeric Antibody (1) Culturing of Antibody-Producing Cell Derived from YB2/0 Cell and Purification of Antibody The anti-GD3 chimeric antibody-producing transformed cell clone obtained in the item 2(1) of Example 1 was suspended in the Hybridoma-SFM medium comprising 0.2% BSA, 200 nM MTX and 100 nM triiodothyronine (hereinafter referred to as "T3"; manufactured by SIGMA) to give a density of $3\times10^5$ cells/ml and cultured using a 2.0.liter capacity spinner bottle (manufactured by Iwaki Glass) under agitating at a rate of 50 rpm. After culturing them at 37° C. for 10 days in a temperature-controlling room, the culture supernatant was recovered. The anti-GD3 chimeric antibody was purified, from the culture supernatant using a Prosep-A (manufactured by Bioprocessing) column in accordance with the manufacture's instructions. The purified anti-GD3 chimeric antibody was named YB2/0-GD3 chimeric antibody.

(2) Culturing of Antibody-Producing Cell Derived from CHO/DG44 Cell and Purification of Antibody The anti-GD3 chimeric antibody-producing transformed cell clone obtained in the item 2(2) of Example 1 was suspended in the EX-CELL302 medium comprising 3 mM L-Gln, 0.5% fatty acid concentrated solution (hereinafter referred to as "CDLC"; manufactured by GIBCO BRL) and 0.3% Pluronic F68 (hereinafter referred to as "PF68"; manufactured by GIBCO BRL) to give a density of $1\times10^6$ cells/ml, and the suspension was dispensed in 50 ml into 175 mm$^2$ flasks (manufactured by Greiner). After culturing them at 37° C. for 4 days in a 5% $CO_2$ incubator, the culture supernatant was recovered. The anti-GD3 chimeric antibody was purified from the culture supernatant using a Prosep-A (manufactured by Bioprocessing) column in accordance with the manufacturer's instructions. The purified anti-GD3 chimeric antibody was named CHO/DG44-GD3 chimeric antibody.

(3) Culturing of Antibody-producing Cell Derived from NS0 Cell and Purification of Antibody The anti-GD3 chimeric antibody-producing transformed cell clone obtained in the item 2(3) of Example 1 was suspended in the EX-CELL302 medium comprising 2 mM L-Gln, 0.5 mg/ml G418, 200 nM MTX and 1% FBS, to give a density of $1\times10^6$ cells/ml, and the suspension was dispensed in 200 ml into 175 mm$^2$ flasks (manufactured by Greiner). After culturing them at 37° C. for 4 days in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions The purified anti-GD3 chimeric antibody was named NS0-GD3 chimeric antibody (302).

Also, the transformed cell clone was suspended in the GIT medium comprising 0.5 mg/ml G418 and 200 nM MTX to give a density of $3\times10^5$ cells/ml, and the suspension was dispensed in 200 ml into 175 mm$^2$ flasks (manufactured by Greiner) After culturing them at 37° C. for 10 days in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named NS0-GD3 chimeric antibody (GIT).

(4) Culturing of Antibody-producing Cell Derived from SP210 Cell and Purification of Antibody The anti-GD3 chimeric antibody-producing transformed cell clone (KM-871 (FERM BP-3512)) described in Japanese Published Unexamined Patent Application No. 304989/93

(EP 533199) was suspended in the GIT medium comprising 0.5 mg/ml G418 and 200 nM MTX to give a density of $3 \times 10^5$ cells/ml, and the suspension was dispensed in 200 ml into 175 mm² flasks (manufactured by Greiner). After culturing them at 37° C. for 8 days in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named SP2/0-GD3 chimeric antibody.

5. Analysis of Purified Anti-GD3 Chimeric Antibody

Figure 1B:
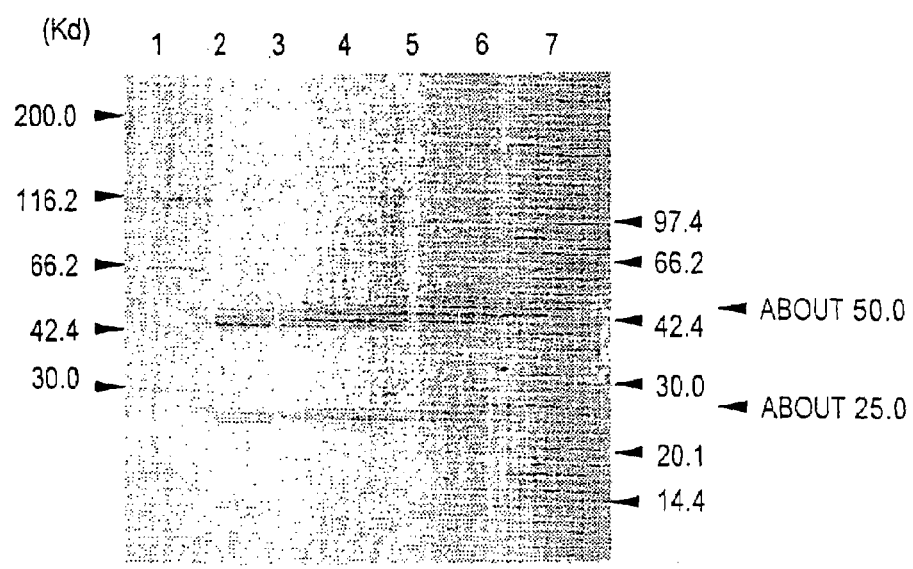

In accordance with a known method [*Nature*, 227, 680 (1970)], 4 μg of each of the five kinds of the anti-GD3 chimeric antibodies produced by and purified from respective animal cells, obtained in the item 4 of Example 1, was subjected to SOS-PAGE to analyze the molecular weight and purification degree. The results are shown in FIG. 1. As shown in FIG. 1, a single band of about 150 kilodaltons (hereinafter referred to as "Kd") in molecular weight was found under non-reducing conditions, and two bands of about 50 Kd and about 25 Kd under reducing conditions, in each of the purified anti-GD3 chimeric antibodies. The molecular weights almost coincided with the molecular weights deduced from the cDNA nucleotide sequences of H chain and L chain of the antibody (H chain: about 49 Kd, L chain: about 23 Kd, whole molecule: about 144 Kd), and also coincided with the reports stating that the IgG antibody has a molecular weight of about 150 Kd under non-reducing conditions and is degraded into H chains having a molecular weight of about 50 Kd and L chains having a molecular weight of about 25 Kd under reducing conditions due to cutting of the disulfide bond (hereinafter referred to as "S—S bond") in the molecule [*Antibodies: A Laboratory Manual*, Cold Spring Harbor Laboratory, Chapter 14 (1998); *Monoclonal Antibodies: Principles and Practice*, Academic Press Limited (1996)], so that it was confirmed that each anti-GD3 chimeric antibody was expressed and purified as an antibody molecule having the true structure.

EXAMPLE 2

Activity Evaluation of Anti-GD3 Chimeric Antibody

1. Binding Activity of Anti-GD3 Chimeric Antibody to GD3 (ELISA)

Figure 2:
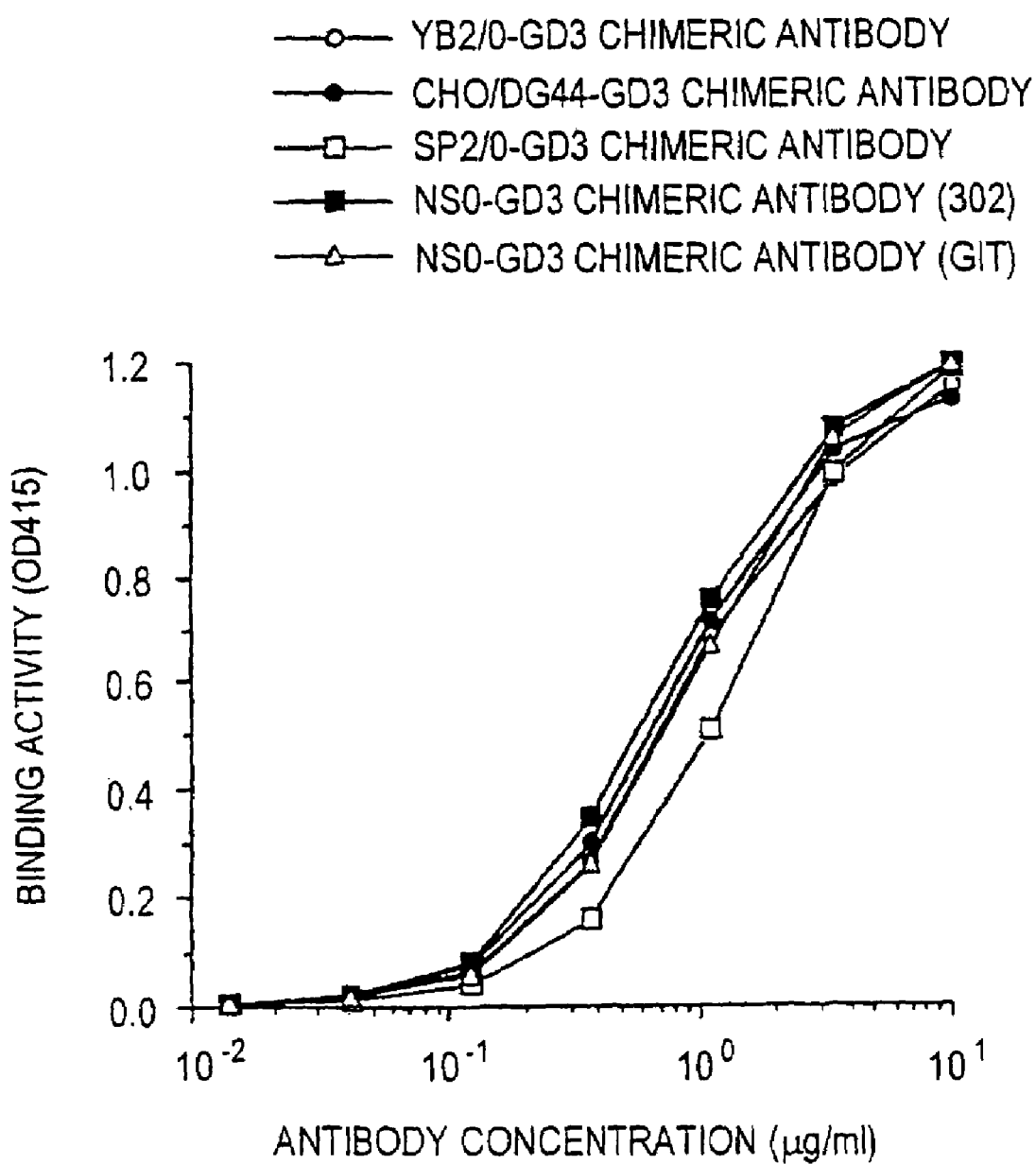
FIG. 2 shows activities of five purified anti-GD3 chimeric antibodies to bind to GD3, measured by changing the antibody concentration. The ordinate and the abscissa show the binding activity with GD3 and the antibody concentration, respectively. "○", "●", "58", "■" and "Δ" show the activities of YB2/0-GD3 chimeric antibody, CHO/DG44-GD3 chimeric antibody, SP2/0-GD3 chimeric antibody, NS0-GD3 chimeric antibody (302) and NS0-GD3 chimeric antibody (GIT), respectively.

The activity of the five kinds of the purified anti-GD3 chimeric antibodies obtained in the item 4 of Example 1 to bind to GD3 (manufactured by Snow Brand Milk Products) was measured by the ELISA shown in the item 3 of Example 1. FIG. 2 shows a result of the examination of the binding activity measured by changing the concentration of the anti-GD3 chimeric antibody to be added. As shown in FIG. 2, the five kinds of the anti-GD3 chimeric antibodies showed almost the same binding activity to GD3. The result shows that antigen binding activities of these antibodies are constant independently of the antibody-producing animal cells and their culturing methods. Also, it was suggested from the comparison of the NS0-GD3 chimeric antibody (302) with the NS0-GD3 chimeric antibody (GIT) that the antigen binding activities are constant independently of the media used in the culturing.

2. In Vitro Cytotoxic Activity (ADCC activity) of Anti-GD3 Chimeric Antibody

In order to evaluate in vitro cytotoxic activity of the five kinds of the purified anti-GD3 chimeric antibodies obtained in the item 4 of Example 1, the ADCC activity was measured in accordance with the following method.

(1) Preparation of Target Cell Solution

A human melanoma cultured cell line G-361 (ATCC CRL 1424) was cultured using the RPMI1640-FBS(10) medium to prepare $1 \times 10^6$ cells, and the cells were radioisotopes labeled by reacting them with 3.7 MBq equivalents of a radioactive substance $Na_2{}^{51}CrO_4$ at 37° C. for 1 hour. After the reaction, the cells were washed three times through their suspension in the RPMI1640-FBS(10) medium and centrifugation, re-suspended in the medium and then incubated at 4° C. for 30 minutes in ice for spontaneous dissolution of the radioactive substance. After centrifugation, the precipitate was adjusted to $2 \times 10^5$ cells/ml by adding 5 ml of the RPMI1640-FBS(10) medium and used as the target cell solution.

(2) Preparation of Effector Cell Solution

From a healthy person, 50 ml of venous blood was collected, and gently mixed with 0.5 ml of heparin sodium (manufactured by Takeda Pharmaceutical). The mixture was cenrtrifuged to isolate a mononuclear cell layer using Lymphoprep (manufactured by Nycomed Pharma AS) in accordance with the manufacture's instructions. After washing with the RPMI1640-FBS(10) medium by centrifugation three times, the resulting precipitate was re-suspended to give a density of $2 \times 10^6$ cells/ml using the medium and used as the effector cell solution.

(3) Measurement of ADCC Activity

Into each well of a 96 well U-shaped bottom plate (manufactured by Falcon), 50 μl of the target cell solution prepared in the above (1) ($1 \times 10^4$ cells/well) was dispensed. Next, 100 μl of the effector cell solution prepared in the above (2) was added thereto ($2 \times 10^5$ cells/well, the ratio of effector cells to target cells becomes 20:1). Subsequently, each of the anti-GD3 chimeric antibodies was added to give a final concentration from 0.0025 to 2.5 μg/ml, followed by reaction at 37° C. for 4 hours. After the reaction, the plate was centrifuged, and the amount of $^{51}Cr$ in the supernatant was measured using a γ-counter. The amount of spontaneously released $^{51}Cr$ was calculated by the same operation using only the medium instead of the effector cell solution and the antibody solution, and measuring the amount of $^{51}Cr$ in the supernatant. The amount of total released $^{51}Cr$ was calculated by the same operation using only the medium instead of the antibody solution and adding 1 N hydrochloric acid instead of the effector cell solution, and measuring the amount of $^{51}Cr$ in the supernatant The ADCC activity was calculated from the following equation (II):

$$ADCC \text{ activity } (\%) = \frac{{}^{51}Cr \text{ in sample supernatant} - \text{spontaneously released } {}^{51}Cr}{\text{total released } {}^{51}Cr - \text{spontaneously released } {}^{51}Cr} \times 100 \qquad (II)$$

Figure 3:
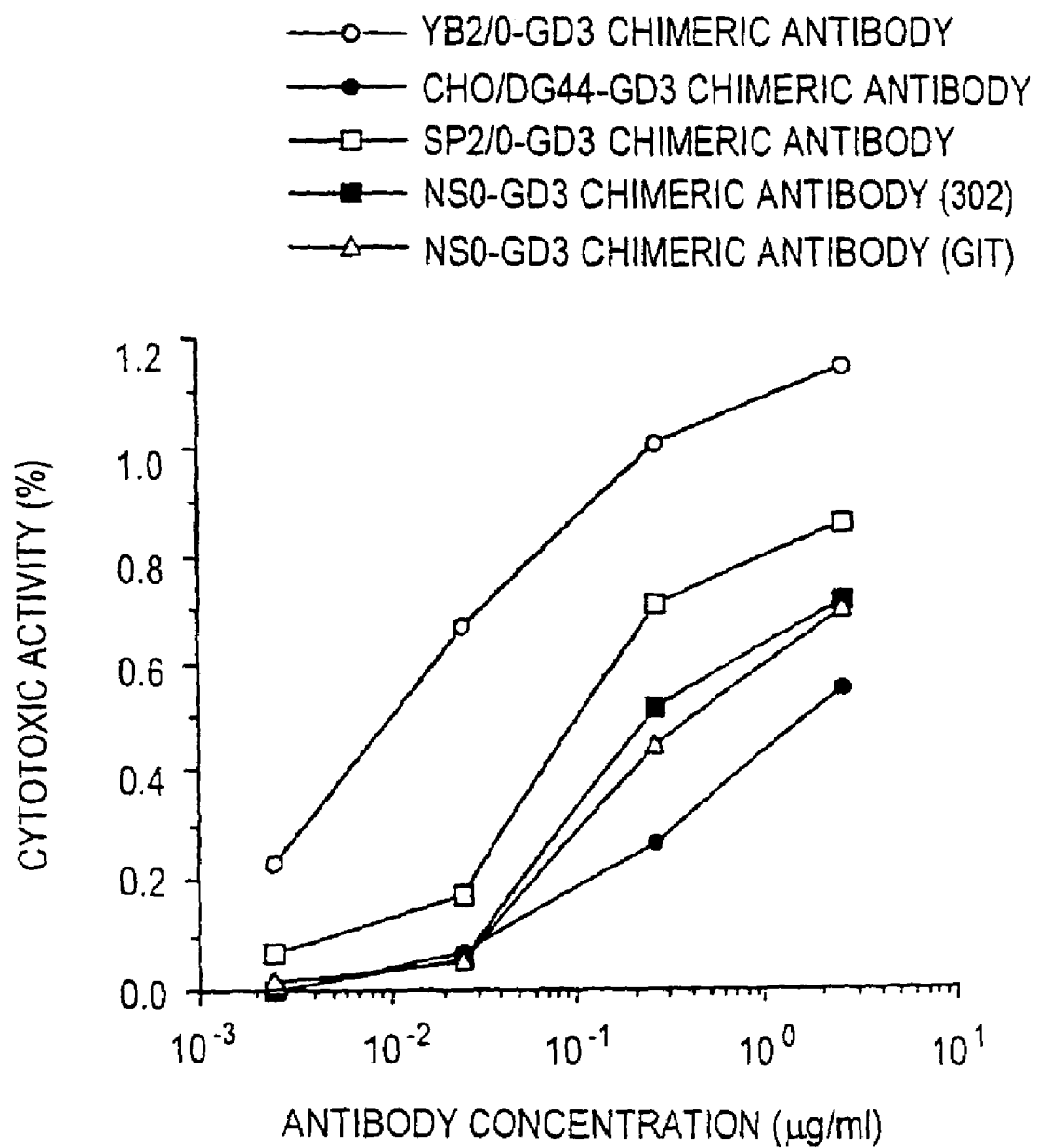
FIG. 3 shows ADCC activities of five purified anti-GD3 chimeric antibodies for a human melanoma cell line G-361. The ordinate and abscissa show the cytotoxic activity and the antibody concentration, respectively. "○", "●", "□", "■" and "Δ" show the activities of YB2/0-GD3 chimeric antibody, CHO/DG44-GD3 chimeric antibody, SP2/0-GD3 chimeric antibody, NS0-GD3 chimeric antibody (302) and NS0-GD3 chimeric antibody (GIT), respectively.

The results are shown in FIG. 3. As shown in FIG. 3, among the five kinds of the anti-GD3 chimeric antibodies, the YB2/0-GD3 chimeric antibody showed the most potent ADCC activity, followed by the SP2/0-GD3 chimeric antibody, NS0-GD3 chimeric antibody and CHO-GD3 chimeric antibody in that order. No difference in the ADCC activity was found between the NS0-GD3 chimeric antibody (302) and NS0-GD3 chimeric antibody (GIT) prepared using different media in the culturing. The above results show that the ADCC activity of antibodies greatly varies depending on the kind of the animal cells to be used in their production. As its mechanism, since their antigen binding activities were identical, it was considered that it is caused by a difference in the structure binding to the antibody Fc region.

EXAMPLE 3

Preparation of Anti-human Interleukin 5 Receptor α Chain Human CDR-Grafted Antibody 1. Preparation of Cell Stably Producing Anti-Human Interleukin 5 Receptor α Chain Human CDR-Grafted Antibody (1) Preparation of Antibody-Producing Cell Using Rat Myeloma YB2/0 Cell Using the anti-human interleukin 5 receptor α chain human CDR-grafted antibody (hereinafter referred to as "anti-hIL-5Rα CDR-grafted antibody") expression vector, pKANTEX1259HV3LV0, described in WO 97/10354, cells capable of stably producing anti-hIL-5Rα CDR-grafted antibody were prepared as described below.

After introducing 5 μg of the anti-hIL-5Rα CDR-grafted antibody expression vector pKANTEX1259HV3LV0 into $4 \times 10^6$ cells of rat myeloma YB2/0 by electroporation [*Cytotechnology*, 3, 133 (1990)], the cells were suspended in 40 ml of RPMI1640-FBS(10) and dispensed in 200 μl/well into a 96 well culture plate (manufactured by Sumitomo Bakelite). After culturing them at 37° C. for 24 hours in a 5% $CO_2$ incubator, G418 was added to give a concentration of 0.5 mg/ml, followed by culturing for 1 to 2 weeks. The culture supernatant was recovered from wells in which colonies of transformants showing G418 resistance were formed and growth of colonies was observed, and the antigen binding activity of the anti-hIL-5Rα CDR-grafted antibody in the supernatant was measured by the ELISA shown in the item 2 of Example 3.

Regarding the transformants in wells in which production of the anti-hIL-5Rα CDR-grafted antibody was observed in culture supernatants, in order to increase amount of the antibody production using a DHFR gene amplification system, each of the them was suspended in the RPMI1640-FBS(10) medium comprising 0.5 mg/ml G418 and 50 nM MTX to give a density of 1 to $2 \times 10^5$ cells/ml, and the suspension was dispensed in 2 ml into wells of a 24 well plate. (manufactured by Greiner). Transformants showing 50 nM MTX resistance were induced by culturing at 37° C. for 1 to 2 weeks in a 5% $CO_2$ incubator. The antigen binding activity of the anti-hIL-5Rα CDR-grafted antibody in culture supernatants in wells in which growth of transformants was observed was measured by the ELISA shown in the item 2 of Example 3. Regarding the transformants in wells in which production of the anti-hIL-5Rα CDR-grafted antibody was observed in culture supernatants, the MTX concentration was increased to 100 nm and then to 200 nM, and transformants capable of growing in the RPMI1640-FBS(10) medium comprising 0.5 mg/ml G418 and 200 nM MTX and of producing the anti-hIL-5Rα CDR-grafted antibody in a large amount were finally obtained in the same manner as described above. Among the obtained transformants, elite cell lines were selected and were made into a single cell (cloning) by limiting dilution twice. Also, using the method for determining the transcription product of an α-1,6-fucosyltransferase gene shown in Example 9, a cell line producing a relatively small amount of the transcription product was selected and used as a suitable cell line. The obtained anti-hIL-5Rα CDR-grafted antibody-producing transformed cell clone No. 3 has been deposited on Apr. 5, 1999, as FERM BP-6690 in National Institute of Bioscience and Human Technology, Agency of Industrial Science and Technology (Higashi 1-1-3, Tsukuba, Ibaraki, Japan) (present name: International Patent Organism Depositary, National Institute of Advanced Industrial Science and Technology (AIST Tsukuba Central 6, 1-1, Higashi 1-Chome. Tsukuba-shi, Ibaraki-ken, Japan)).

(2) Preparation of Antibody-producing Cell Using CHO/dhfr⁻ Cell

After introducing 4 μg of the anti-hIL-5Rα CDR-grafted antibody expression vector pKANTEX1259HV3LV0 described in WO 97/10354 into $1.6 \times 10^6$ cells of CHO/dhfr⁻ by electroporation [*Cytotechnology*, 3, 133 (1990)], the cells were suspended in 10 ml of IMDM-FBS(10) and dispensed in 200 μl/well into a 96 well-culture plate (manufactured by Iwaki Glass). After culturing them at 37° C. for 24 hours in a 5% $CO_2$ incubator, G418 was added to give a concentration of 0.5 mg/ml, followed by culturing for 1 to 2 weeks. The culture supernatant was recovered from respective well in which colonies of transformants showing G418 resistance were formed and growth of colonies was observed, and the antigen binding activity of the anti-hIL-5Rα CDR-grafted antibody in the supernatant was measured by the ELISA shown in the item 2 of Example 3.

Regarding the transformants in wells in which production of the anti-hIL-5Rα CDR-grafted antibody was observed in culture supernatants, in order to increase amount of the antibody production using a DHFR gene amplification system, each of the transformants was suspended in an IMDM-dFBS (10) medium comprising 0.5 mg/ml G418 and 10 nM MTX to give a density of 1 to $2 \times 10^5$ cells/ml, and the suspension was dispensed in 0.5 ml into wells of a 24 well plate (manufactured by Iwaki Glass). Transformants showing 10 nM MTX resistance were induced by culturing at 37° C. for 1 to 2 weeks in a 5% $CO_2$ incubator. Regarding the transformants in wells in which their growth was observed, the MTX concentration was increased to 100 nM and then to 500 nm, and transformants capable of growing in the IMDM-dFBS(10) medium comprising 0.5 mg/ml G418 and 500 nM MTX and of producing the anti-hIL-5Rα CDR-grafted antibody in a large amount were finally obtained in the same manner as described above. Among the obtained transformants, elite cell lines were selected and were made into a single cell (cloning) by limiting dilution twice. Also, using the method for determining the transcription product of an α-1,6-fucosyltransferase gene shown in Example 9, a cell line producing a relatively small amount of the transcription product was selected and used as a suitable cell line.

(3) Production of Antibody-Producing Cell Using Mouse Myeloma NS0 Cell

An anti-hIL-5Rα CDR-grafted antibody expression vector was prepared in accordance with the method of Yarranton et al. [*BIO/TECHNOLOGY*, 10, 169 (1992)] and using the antibody H chain cDNA and L chain cDNA on the anti-hIL-5Rα CDR-grafted antibody expression vector pKANTEX1259HV3LV0 described in WO 97/10354, and NS0 cell was transformed to obtain transformants capable of producing the anti-hIL-5Rα CDR-grafted antibody in a large amount. Among the obtained transformants, elite cell lines were selected and were made into a single cell (cloning) by limiting dilution twice. Also, using the method for determining the transcription production of an α-1,6-fucosyltransferase gene shown in Example 9, a cell line producing a relatively small amount of the transcription product was selected and used as a suitable cell line.

2. Measurement of Binding Activity of Antibody to hIL-5Rα (ELISA)

The binding activity of the antibody to hIL-5Rα was measured as described below.

A solution was prepared by diluting the anti-hIL-5Rα mouse antibody KM1257 described in WO 97/10354 with PBS to give a concentration of 10 μg/ml, and 50 μl of the resulting solution was dispensed into each well of a 96 well plate for ELISA (manufactured by Greiner), followed by reaction at 4° C. for 20 hours. After the reaction, 1% BSA-PBS was dispensed in 100 μl/well, and then the reaction was carried out at room temperature for 1 hour to block remaining active groups. After discarding 1% BSA-PBS, a solution prepared by diluting the soluble hIL-5Rα described in WO 97/10354 with 1% BSA-PBS to give a concentration of 0.5 μg/ml was dispensed in 50 μl/well, followed by reaction at 4° C. for 20 hours. After the reaction, each well was washed with Tween-PBS, culture supernatants of transformants or diluted solutions of a purified human CDR-grafted antibodies were dispensed in 50 μg/well to carry out the reaction at room temperature for 2 hours. After the reaction, each well was washed with Tween-PBS, a peroxidase-labeled goat anti-human IgG (H & L) antibody solution (manufactured by American Qualex) diluted 3,000 times with 1% BSA-PBS was dispensed in 50 μl/well as a secondary antibody solution, followed by reaction at room temperature for 1 hour. After the reaction and subsequent washing with Tween-PBS, the ABTS substrate solution was dispensed in 50 μl/well for color development, and then the absorbance at OD415 was measured.

3. Purification of Anti-hIL-5Rα CDR-grafted Antibody (1) Culturing of Antibody-Producing Cell Derived from YB2/0 Cell and Purification of Antibody The anti-hIL-5Rα CDR-grafted antibody-producing transformed cell clone obtained in the item 1(1) of Example 3 was suspended in the GIT medium comprising 0.5 mg/ml G418 and 200 nM MTX to give a density of $3 \times 10^5$ cells/ml and dispensed in 200 ml into 175 mm² flasks (manufactured by Greiner). After culturing them at 37° C. for 8 days in a 5% $CO_2$ incubator, the culture supernatant was recovered. The anti-hIL-5Rα CDR-grafted antibody was purified from the culture supernatant using ion exchange chromatography and a gel filtration method. The purified anti-hIL-5Rα CDR-grafted antibody was named YB2/0-hIL-5R CDR antibody.

(2) Culturing of Antibody-Producing Cell Derived from CHO/dhfr⁻ Cell and Purification of Antibody The anti-hIL-5Rα CDR-grafted antibody-producing transformed cell clone obtained in the item 1(2) of Example 3 was suspended in the EX-CELL302 medium comprising 3 mM L-Gln, 0.5% CDLC and 0.3% PF68 to give a density of $3 \times 10^5$ cells/ml and cultured using a 4.0 liter capacity spinner bottle (manufactured by Iwaki Glass) under agitating at a rate of 100 rpm. After culturing them at 37° C. for 10 days in a temperature-controlling room, the culture supernatant was recovered. The anti-hIL-5Rα CDR-grafted antibody was purified from the culture supernatant using ion exchange chromatography and a gel filtration method. The purified anti-hIL-5Rα CDR-grafted antibody was named CHO/d-hIL-5R CDR antibody.

(3) Culturing of Antibody-Producing Cell Derived from NS0 Cell and Purification of Antibody The anti-hIL-5Rα CDR-grafted antibody-producing transformed cell clone obtained in the item 1(3) of Example 3 was cultured in accordance with the method of Yarranton et al. [*BIO/TECHNOLOGY*, 10, 169 (1992)] and then a culture supernatant was recovered. The anti-hIL-5Rα CDR-grafted antibody was purified from the culture supernatant using ion exchange chromatography and the gel filtration method. The purified anti-hIL-5Rα CDR-grafted antibody was named NS0-hIL-5R CDR antibody.

4. Analysis of Purified Anti-hIL-5Rα CDR-Grafted Antibodies

Figure 4A:
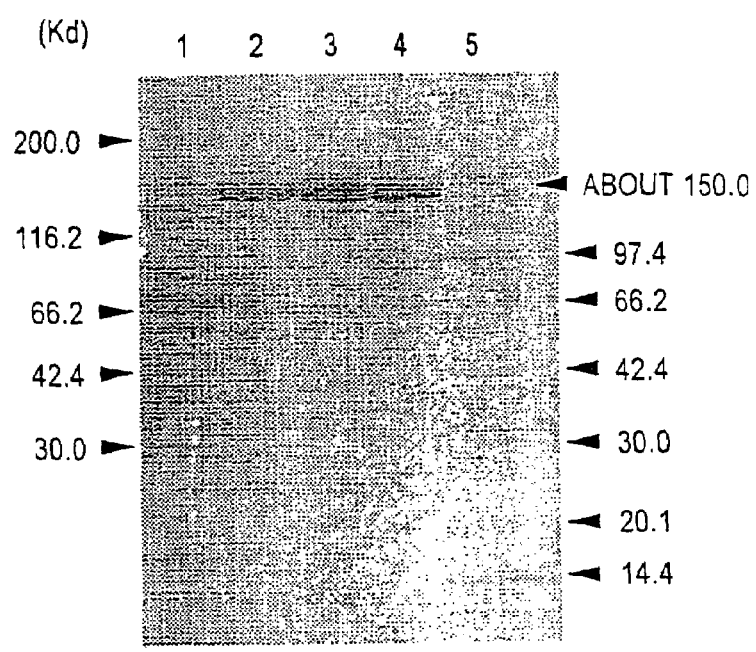
FIG. 4A and FIG. 4B show results of the electrophoresis carried out under non-reducing conditions and those under reducing conditions, respectively. Lanes 1 to 5 show electrophoresis patterns of high molecular weight markers, YB2/0-hIL-5R CDR antibody, CHO/d-hIL-5R CDR antibody, NS0-hIL-5R CDR antibody and low molecular weight markers, respectively.
Figure 4B:
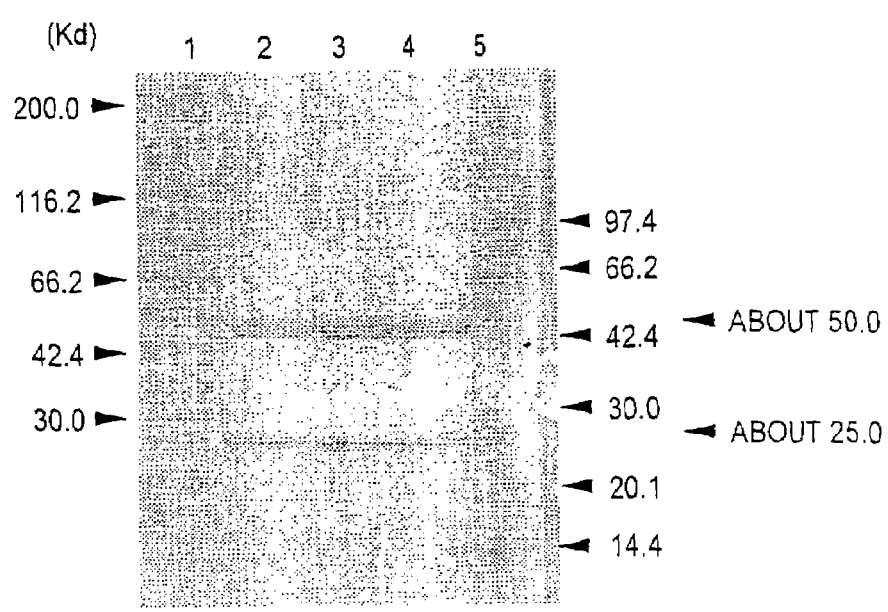

In accordance with a known method [*Nature*, 2, 680 (1970)], 4 μg of each of the three kinds of the anti-hIL-5Rα CDR-grafted antibodies produced by and purified from each animal cells, obtained in the item 3 of Example 3, was subjected to SDS-PAGE to analyze the molecular weight and purification degree. The results are shown in FIG. 4. As shown in FIG. 4, a single band of about 150 Kd in molecular weight was found under non-reducing conditions, and two bands of about 50 Kd and about 25 Kd under reducing conditions, in each of the purified anti-hIL-5Rα CDR-grafted antibodies. The molecular weights almost coincided with the molecular weights deduced from the cDNA nucleotide sequences of H chain and L chain of the antibody (H chain: about 49 Kd, L chain: about 23 Kd, whole molecule: about 144 Kd), and also coincided with the reports stating that the IgG antibody has a molecular weight of about 150 Kd under non-reducing conditions and is degraded into H chains having a molecular weight of about 50 Kd, and L chains having a molecular weight of about 25 Kd under reducing conditions due to cutting of the S—S bond in the molecule [*Antibodies: A Laboratory Manual*, Cold Spring Harbor Laboratory, Chapter 14 (1998); *Monoclonal Antibodies: Principles and Practice*, Academic Press Limited (1996)], so that it was confirmed that each anti-hIL-5Rα CDR-grafted antibody was expressed and purified as an antibody-molecule having the true structure.

EXAMPLE 4

Activity Evaluation of Anti-hIL-5Rα CDR-Grafted Antibody

1. Binding Activity of Anti-hIL-5Rα CDR-Grafted Antibody to hIL-5Rα (ELISA)

The activity of the three kinds of the purified anti-hIL-5Rα CDR-grafted antibodies obtained in the item 3 of Example 3 to bind to hIL-5Rα was measured by the ELISA shown in the item 2 of Example 3. FIG. 5 shows a result of the examination of the binding activity measured by changing concentration of the anti-hIL-5Rα CDR-grafted antibody to be added. As shown in FIG. 5, the three kinds of the anti-hIL-5Rα CDR-grafted antibodies showed almost the same binding activity to hIL-5Rα. The result shows that the antigen binding activities of these antibodies are constant independently of the antibody-producing animal cells and their culturing methods, similar to the result of the item 1 of Example 2.

2. In Vitro Cytotoxic Activity (ADCC Activity) of Anti-hIL-5Rα CDR-Grafted Antibody In order to evaluate in vitro cytotoxic activity of the three kinds of the purified anti-hIL-5Rα CDR-grafted antibodies obtained in the item 3 of Example 3, the ADCC activity was measured in accordance with the following method.

(1) Preparation of Target Cell Solution

A mouse T cell line CTLL-2(h5R) expressing the hIL-5Rα chain and β chain described in WO 97/10354 was cultured using the RPMI1640-FBS(10) medium to give a density of $1 \times 10^6$ cells/0.5 ml, and the cells were radioisotope-labeled by reacting them with 3.7 MBq equivalents of a radioactive substance $Na_2{}^{51}CrO_4$ at 37° C. for 1.5 hours. After the reaction, the cells were washed three times through their suspension in the RPMI1640-FBS(10) medium and centrifugation, resuspended in the medium and then incubated at 4° C. for 30 minutes in ice for spontaneous dissolution of the radioactive substance. After the centrifugation, the precipitate was adjusted to give a density of $2\times10^5$ cells/ml by adding 5 ml of the RPMI1640-FBS(10) medium and used as the target cell solution.

(2) Preparation of Effector Cell Solution

From a healthy person, 50 ml of venous blood was collected and gently mixed with 0.5 ml of heparin sodium (manufactured by Takeda Pharmaceutical). The mixture was centrifuged to separate a mononuclear cell layer using Polymorphprep (manufactured by Nycomed Pharma AS) and in accordance with the manufacture's instructions. After washing with the RPMI1640-FBS(10) medium by centrifugation three times, the resulting cells were resuspended to give a density of $9\times10^4$ cells/ml using the medium and used as the effector cell solution.

(3) Measurement of ADCC Activity

Into each well of a 96 well U-shaped bottom plate (manufactured by Falcon), 50 µl of the target cell solution prepared in the above (1) ($1\times10^4$ cells/well) was dispensed. Next, 100 µl of the effector cell solution prepared in the above (2) was dispensed ($9\times10^5$ cells/well, the ratio of effector cells to target cells becomes 90:1). Subsequently, each of the anti-hIL-5Rα CDR-grafted antibodies was added to give a final concentration of 0.001 to 0.1 µg/ml, followed by reaction at 37° C. for 4 hours. After the reaction, the plate was centrifuged, and the amount of $^{51}Cr$ in the supernatant was measured using a γ-counter. The amount of spontaneously released $^{51}Cr$ was calculated by the same operation using only the medium instead of the effector cell solution and the antibody solution, and measuring the amount of $^{51}Cr$ in the supernatant. The amount of total released $^{51}Cr$ was calculated by the same operation using only the medium instead of the antibody solution and adding 1 N hydrochloric acid instead of the effector cell solution, and measuring the amount of $^{51}Cr$ in the supernatant.

The ADCC activity was calculated from the above equation (II).

Figure 6:
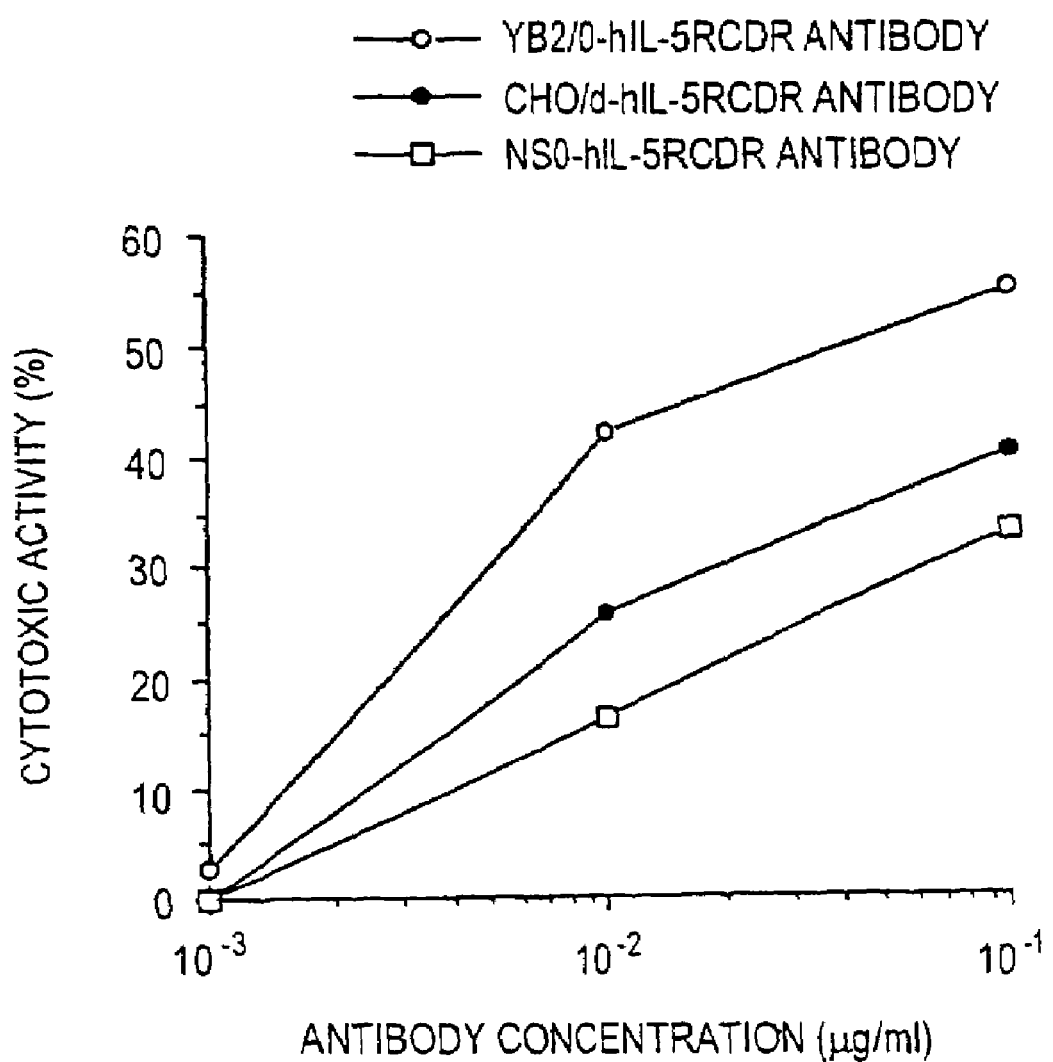
FIG. 6 show ADCC activities of three purified anti-hIL-5Rα CDR-crafted antibodies for an hIL-5R expressing mouse T cell line CTLL-2(h5R). The ordinate and the abscissas show the cytotoxic activity and the antibody concentration, respectively. "○", "●" and "□" show the activities of YB2/0-hIL-5RCDR antibody, CHO/d-hIL-5R CDR antibody and NS0-hIL-5R CDR antibody, respectively.

The results are shown in FIG. 6. As shown in FIG. 6, among the three kinds of the anti-hIL-5Rα CDR-grafted antibodies, the YB2/0-hIL-5R CDR antibody showed the most potent ADCC activity, followed by the CHO/d-hIL-5R CDR antibody and the NS0-hIL-5R CDR antibody in this order. Similar to the result of the item 2 of Example 2, the above results show that the ADCC activity of antibodies greatly varies depending on the animal cells to be used in their production. In addition, since the antibodies produced by the YB2/0 cell showed the most potent ADCC activity in both cases of the two kinds of the humanized antibodies, it was revealed that an antibody having potent ADCC activity can be produced by using the YB2/0 cell.

3. In Vivo Activity Evaluation of Anti-hIL-5Rα CDR-Grafted Antibody

In order to evaluate in vivo activity of the three kinds of the purified anti-hIL-5Rα CDR-grafted antibodies obtained in the item 3 of Example 3, the inhibition activity in an hIL-5-induced eosinophilia increasing model of *Macaca faseicularis* was examined in accordance with the following method.

The hIL-5 (preparation method is described in WO 97/10354) was administered to *Macaca faseicularis* under the dorsal skin at a dose of 1 µg/kg, starting on the first day and once a day for a total of 14 times. Each anti-hIL-5Rα CDR-grafted antibody was intravenously administered at a dose of 0.3 ng/kg one hour before the hIL-5 administration on the day zero. An antibody-non-added group was used as the control.

Figure 7:
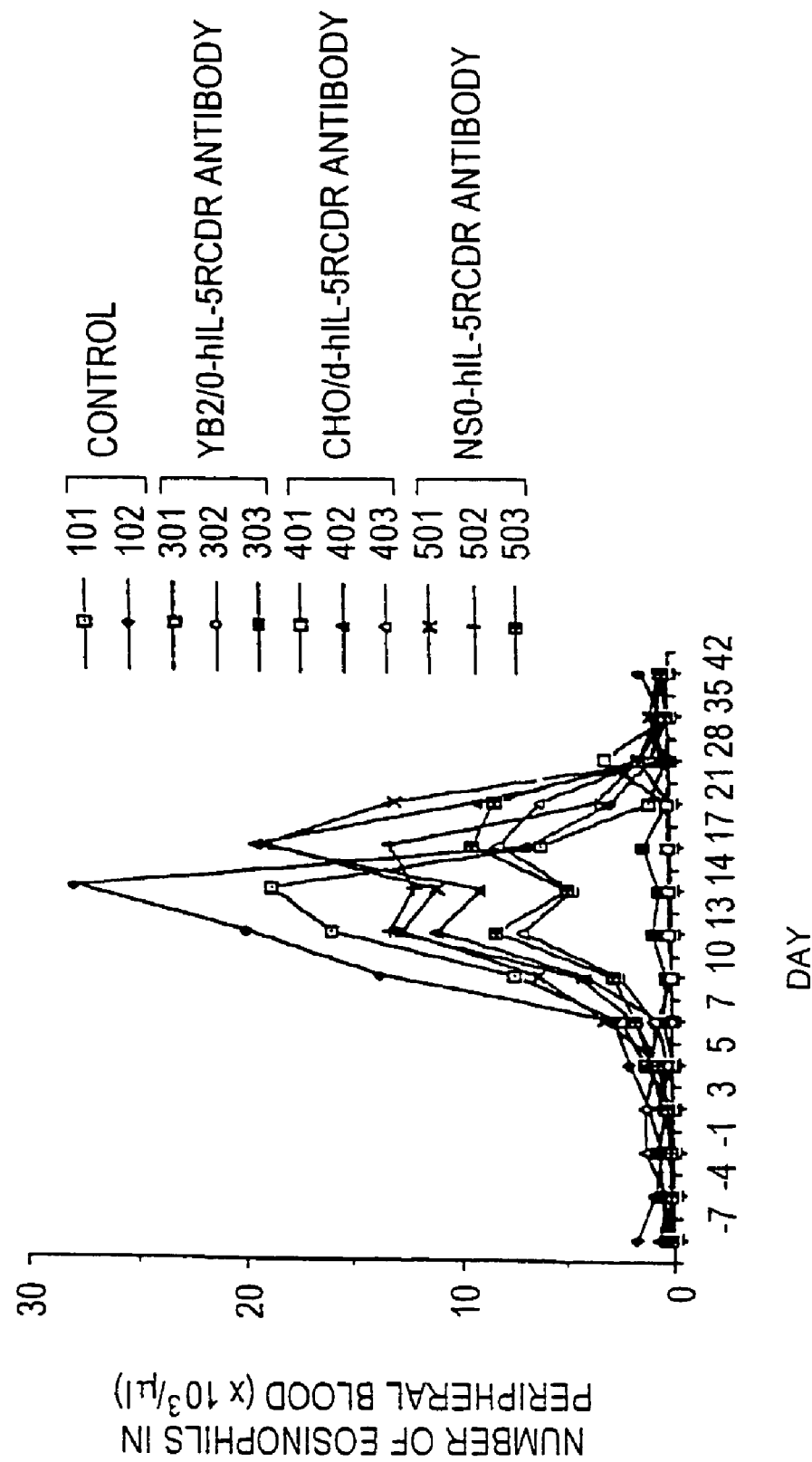
FIG. 7 shows inhibition activities of three purified anti-hIL-5Rα CDR-grafted antibodies in an hIL-5-induced eosinophil increasing model of Macaca faseicularis. The ordinate and the abscissa show the number of eosinophils in peripheral blood and the number of days (the day of the commencement of antibody and hIL-5 administration was defined as 0 day). "101 and 102", "301, 302 and 303", "401, 402 and 403" and "501, 502 and 503" show results in the antibody non-administration group, the YB2/0-hIL-5R CDR antibody administered group, the CHO/d-hIL-5R CDR antibody administered group and the NS0-hIL-5R CDR antibody administered group, respectively.

In the antibody-administered groups, three animals of *Macaca faseicularis* were used in each group (No 301, No. 302, No. 303, No. 401, No. 402, No. 403, No. 501, No. 502 and No. 503), and two animals (No. 101 and No. 102) were used in the antibody-non-added group. Starting 7 days before commencement of the administration and until 42 days after the administration, about 1 ml of blood was periodically collected from a saphena or a femoral vein, and the number of eosinophils in 1 µl of peripheral blood was measured. The results are shown in FIG. 7. As shown in FIG. 7, increase in the blood eosinophil was completely inhibited in the group to which the YB2/0-hIL-5R CDR antibody was administered. On the other hand, complete inhibition activity was found in one animal in the group to which the CH0/d-hIL-5R CDR antibody was administered, but the inhibition activity was not sufficient in two animals. In the group to which NS0-hIL-5R CDR antibody was administered, complete inhibition activity was not found and its effect was not sufficient.

The above results show that the in vivo activity of antibodies greatly varies depending on the animal cells to be used in their production. In addition, since a positive correlation was found between the degree of the in vivo activity of the anti-hIL-SRα CDR-grafted antibody and the degree of its ADCC activity described in the item 2 of Example 4, it was indicated that the degree of ADCC activity is remarkably important for its activity expression.

Based on the above results, it is expected that an antibody having potent ADCC activity is useful also in the clinical field for various diseases in human.

EXAMPLE 5

Analysis of Sugar Chain which Enhances ADCC Activity

1. Preparation of 2-aminopyridine-Labeled Sugar Chain (PA-Treated Sugar Chain)

The humanized antibody of the present invention was aced-hydrolyzed with hydrochloric acid to remove sialic acid. After hydrochloric acid was completely removed, the sugar chain was cleaved from the protein by hydrazinolysis [*Method of Enzymology*, 83, 263 (1982)]. Hydrazine was removed, and N-acetylation was carried out by adding an aqueous ammonium acetate solution and acetic anhydride. After lyophilizing, fluorescence labeling with 2-aminopyridine was carried out [*J. Biochem.*, 95, 197 (1984)]. The fluorescence-labeled sugar chain (PA-treated sugar chain) was separated from impurity using Surperdex Peptide HR 10/30 Column (manufactured by Pharmacia). The sugar chain fraction was dried using a centrifugal concentrator and used as a purified PA-treated sugar chain.

Figure 8A:
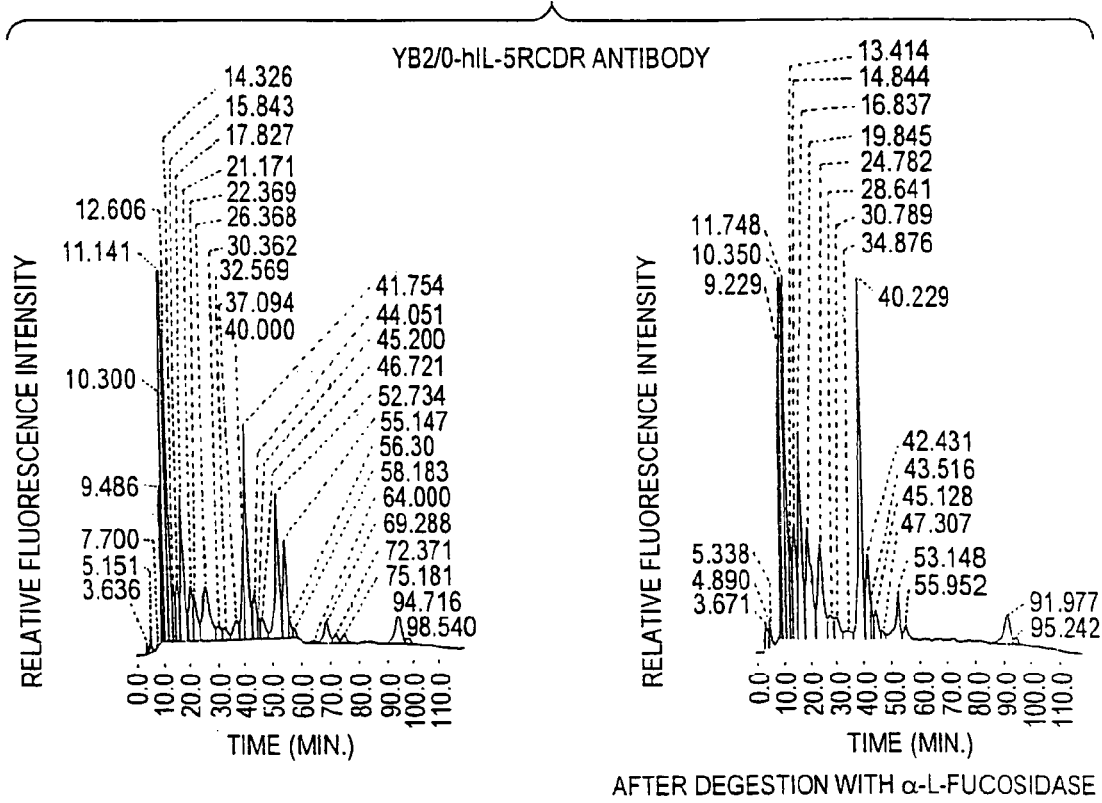
FIG. 8 shows elution patterns of reverse phase HPLC elution of a PA-treated sugar chain (left side), and an elution pattern obtained by treating the PA-treated sugar chain with α-L-fucosidase and then analyzed by reverse phase HPLC (right side), of the purified anti-hIL-5Rα CDR-grafted antibody produced by YB2/0 (FIG. 8A) and the purified anti-hIL-5Rα CDR-grafted antibody produced by NS0 (FIG. 8B). The ordinates and the abscissas show the relative fluorescence intensity and the elution time, respectively.
Figure 8B:
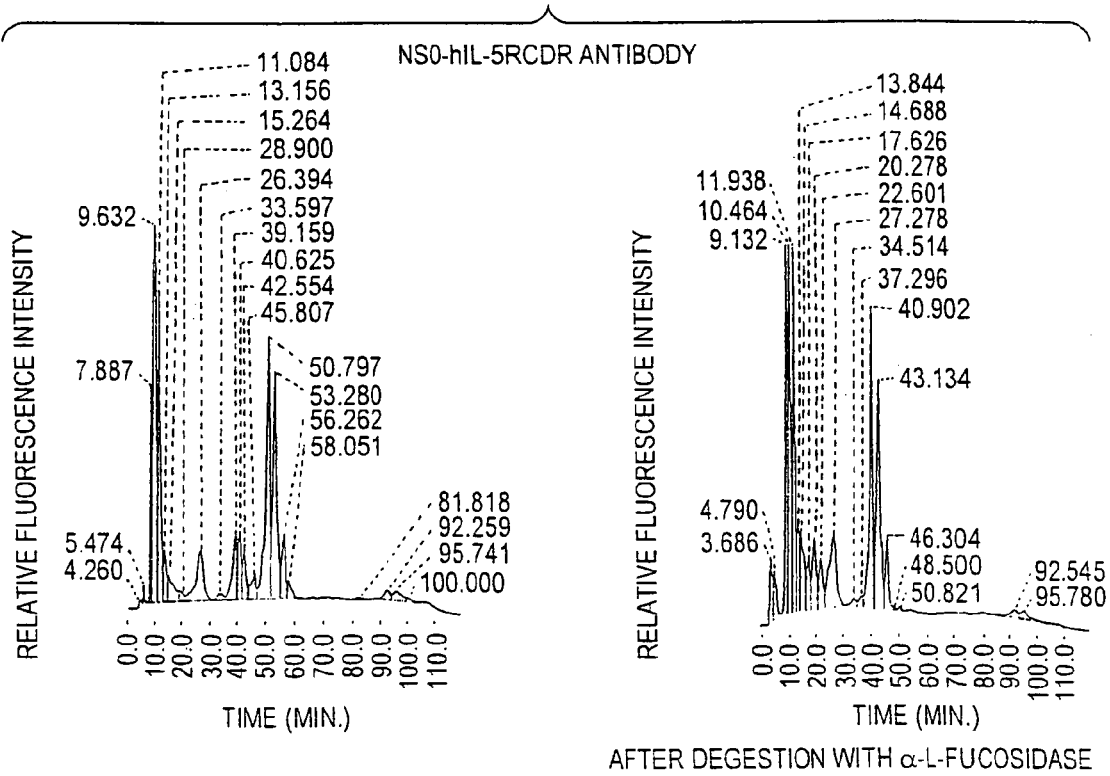

2. Reverse Phase HPLC Analysis of PA-Treated Sugar Chain of Purified Anti-hIL-5Rα CDR-Grafted Antibody According to the method in the item 1 of Example 5, various anti-hIL-5Rα CDR-grafted antibodies produced in Example 3 were subjected to PA-treated sugar chain treatment, and reverse phase HPLC analysis was carried out by CLC-ODS column (manufactured by Shimadzu). An excess amount of α-L-fucosidase (derived from bovine kidney, manufactured by SIGMA) was added to the PA-treated sugar chain for digestion (37° C., 15 hours), and then the products were analyzed by reverse phase HPLC (FIG. 8). It was confirmed that the asparagine-linked sugar chain is eluted for 30 minutes to 80 minute using PA-treated sugar chain standards manufactured by Takara Shuzo. The ratio of sugar chains whose reverse phase HPLC elution positions were shifted (sugar chains eluted for 48 minutes to 78 minutes) by the α-L-fucosidase digestion was calculated. The results are shown in Table 1.

TABLE 1

| Antibody-producing cell | α-1,6-Fucose-linked sugar chain (%) |
|---|---|
| YB2/0 | 47 |
| NS0 | 73 |

About 47% of the anti-hIL-5R CDR-grafted antibody produced by the YB2/0 cell and a-out 73% of the anti-hIL-SR CpR-grafted antibody produced by the NS0 cell were sugar chains in which 1-position of fucose is bound to 6-position of N-acetylglucosamine in the reducing end through α-bond in the N-glycoside-linked sugar chain (hereinafter referred to as "sugar chain having α-1,6-fucose"). Thus, the ratio of sugar chains in which 1-position of fucose is not bound to 6-position of N-acetylglucosamine in the reducing end through α-bond in the N-glycoside-linked sugar chain (hereinafter referred to as "α-1,6-fucose-free sugar chain") is higher in the antibody produced by the YB2/0 cell than in the antibody produced by the NS0 cell.

3. Analysis of Monosaccharide Composition of Purified Anti-hIL-5Rα CDR-Grafted Antibody Sugar chains of anti-hIL-5Rα CDR-grafted antibodies produced by the YB2/0 cell, NS0 cell and CHO/d cell were hydrolyzed into monosaccharides by acid hydrolysis with trifluoroacetic acid, and monosaccharide composition analysis was carried out using BioLC (manufactured by Diorex).

Among N-glycoside-linked sugar chains, there are 3 mannose units in one sugar chain in the complex type N-glycoside-linked sugar chain. A relative ratio of each monosaccharide obtained by calculating the number of mannose as 3 is shown in Table 2.

TABLE 2

| Antibody-producing cell | Fuc | GlcNAc | Gal | Man | ADCC activity (%)* |
|---|---|---|---|---|---|
| YB2/0 | 0.60 | 4.98 | 0.30 | 3.00 | 42.27 |
| NS0 | 1.06 | 3.94 | 0.66 | 3.00 | 16.22 |
| CHO/dhFr⁻ | 0.85 | 3.59 | 0.49 | 3.00 | 25.73 |
| CHO/dhFr⁻ | 0.91 | 3.80 | 0.27 | 3.00 | 25.73 |

*Antibody concentration: 0.01 µg/ml

Since the relative ratios of fucose were in an order of YB2/0<CHO/d<NS0, the sugar chain produced in the antibody produced by YB2/0 cell showed the lowest fucose content as also shown in the present results.

4. Sugar Chain Analysis of Antibody Produced by CHO/dhfr⁻ Cell

Figure 9:
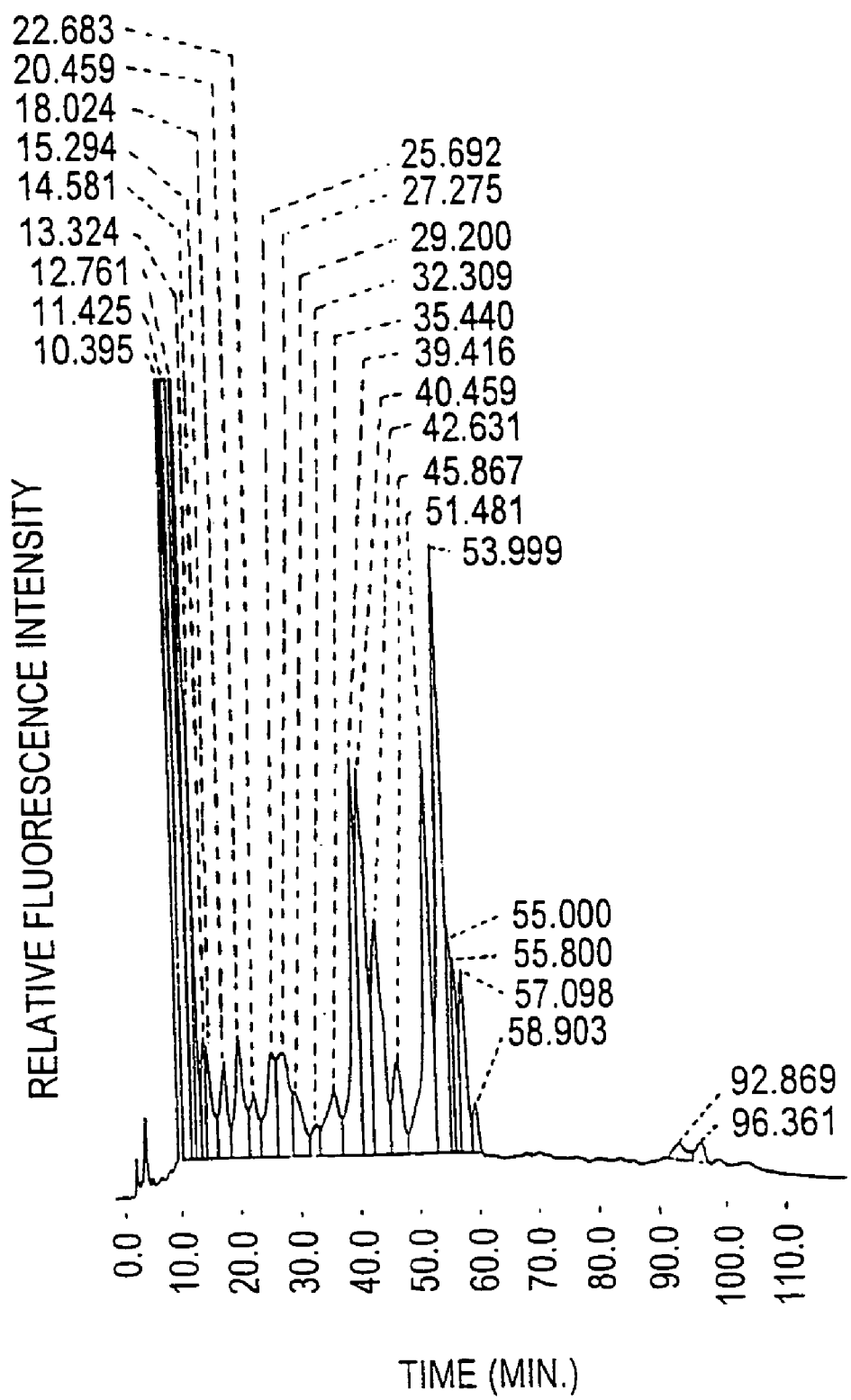
FIG. 9 shows an elution pattern obtained by preparing a PA-treated sugar chain from the purified anti-hIL-5Rα CDR-grafted antibody produced by CHO/d cell and analyzing it by reverse phase HPLC. The ordinate and the abscissa show the relative fluorescence intensity and the elution time, respectively.

PA-treated sugar chains were prepared from purified anti-hIL-5Rα CDR-grafted antibody produced by CHO/dhfr⁻ cell, and reverse phase HPLC analysis was carried out using CLC-ODS column (manufactured by Shimadzu) (FIG. 9). In FIG. 9, an elution time from 35 to 45 minutes corresponded to sugar chains having no fucose and an elution time from 45 to 60 minutes corresponded to sugar chains having fucose. Similar to the case of the antibody produced by mouse myeloma NS0 cell, the anti-hIL-5Rα CDR-grafted antibody produced by CHO/dhfr⁻ cell had less fucose-free sugar chain content than the antibody produced by rat myeloma YB2/0 cell.

EXAMPLE 6

Separation of Potent ADCC Activity Antibody

Figure 10A:
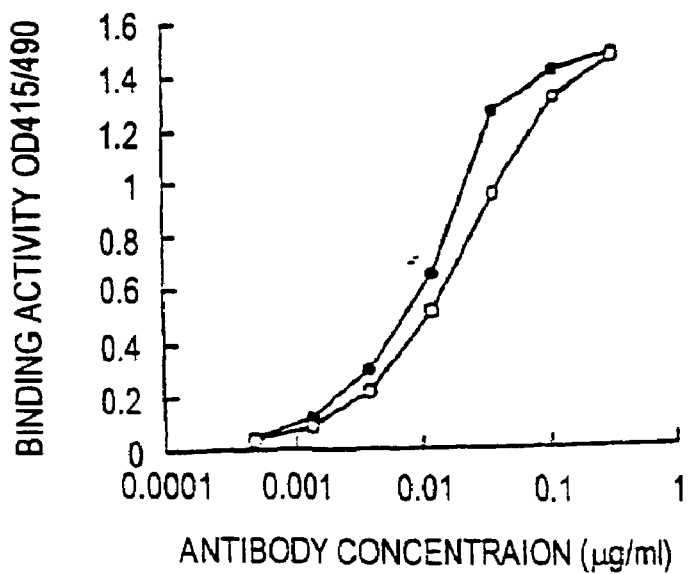
FIG. 10A shows the GD3-binding activities of a non-adsorbed fraction and a part of an adsorbed fraction, measured by changing the antibody concentration. The ordinate and the abscissa show the binding activity with GD3 and the antibody concentration, respectively. "●" and "○" show the non-adsorbed fraction and a part of the adsorbed fraction, respectively.
Figure 10B:
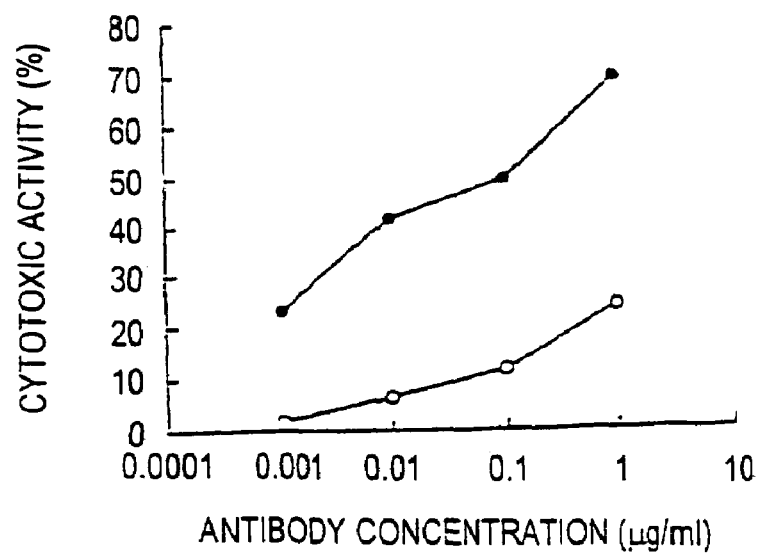
FIG. 10B shows the ADCC activities of the non-adsorbed fraction and a part of the adsorbed fraction for a human melanoma line G-361. The ordinate and the abscissa show the cytotoxic activity and the antibody concentration, respectively. "●" and "○" show the non-adsorbed fraction and a part of the adsorbed fraction, respectively.
Figure 11B:
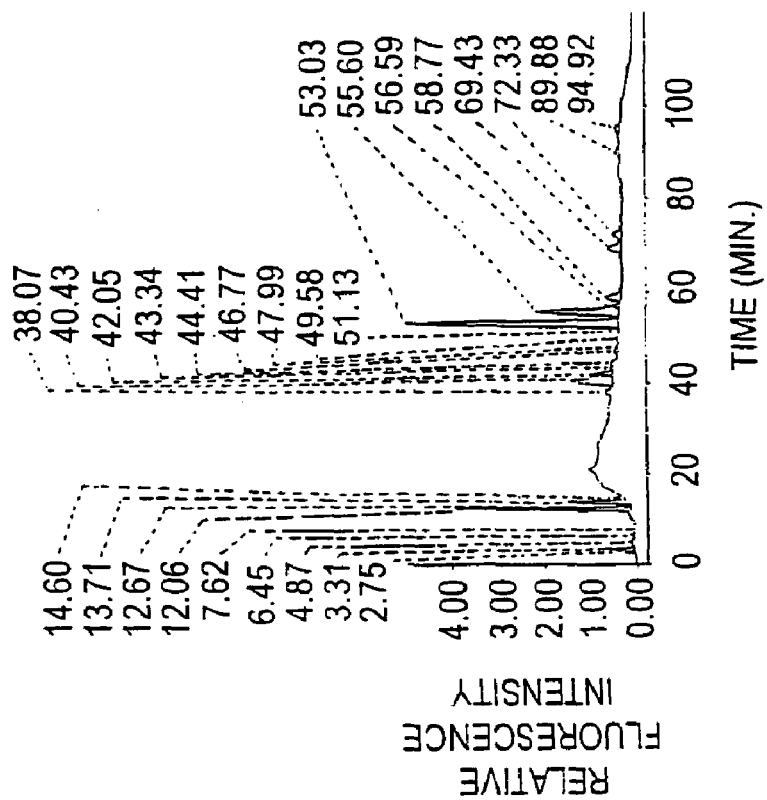
FIG. 11A and FIG. 11B show an elution pattern of the non-adsorbed fraction and an elution pattern of a part of the adsorbed fraction, respectively. The ordinates and the abscissas show the relative fluorescence strength and the elution time, respectively.
Figure 11A:
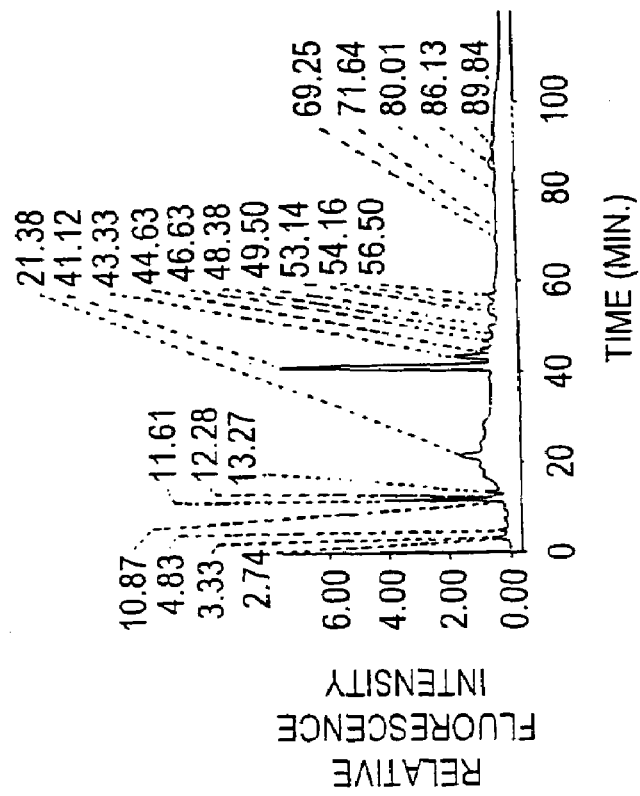
Figure 12A:
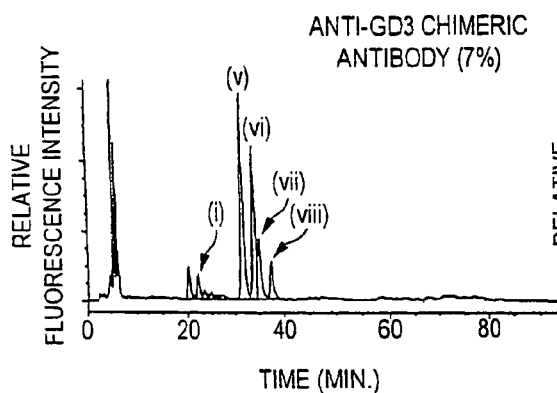
FIG. 12 shows elution patterns of PA-treated sugar chains prepared from 6 anti-GD3 chimeric antibodies (FIG. 12A to FIG. 12F), obtained by analyzing them by reverse phase HPLC. The ordinates and the abscissas show the relative fluorescence intensity and the elution time, respectively.
Figure 12B:
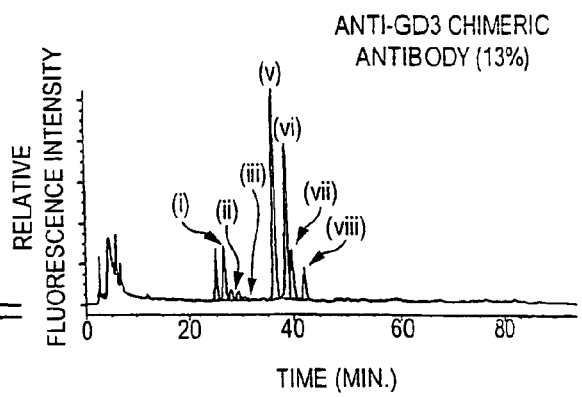
Figure 12C:
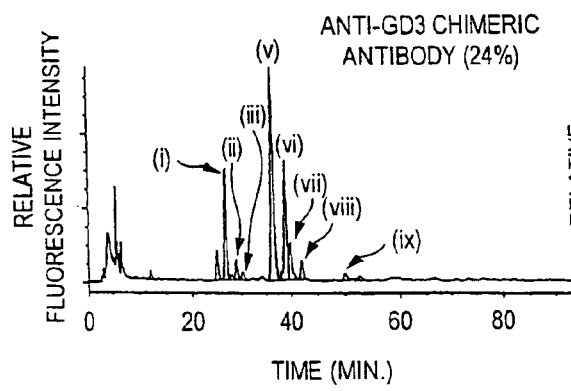
Figure 12D:
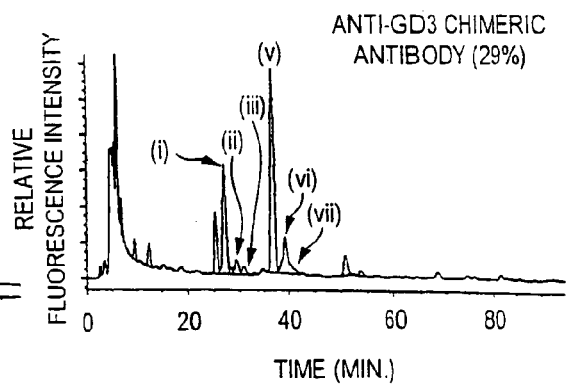
Figure 12E:
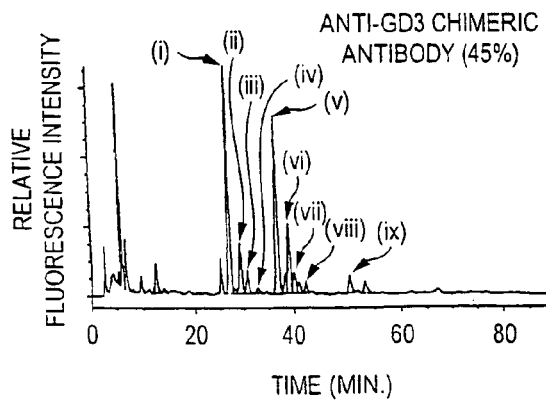
Figure 12F:
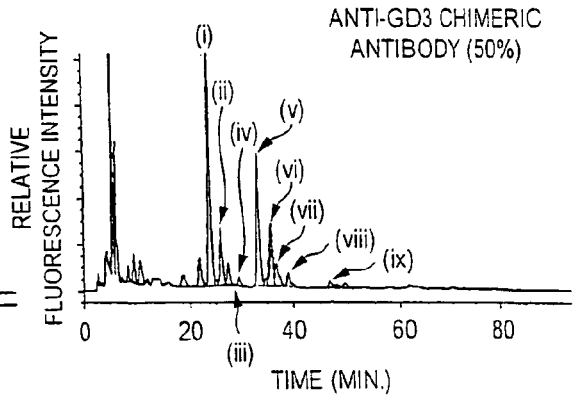

The anti-hIL-SRα CDR-grafted antibody produced by rat myeloma YB2/0 cell was separated using a lectin column which binds to sugar chains having fucose. HPLC was carried out using LC-6A manufactured by Shimadzu at a flow rate of 1 ml/min and at room temperature as the column temperature. After equilibration with 50 mM Tris-sulfate buffer (pH 7.3), the purified anti-hIL-5Rα CDR-grafted antibody was injected and then eluted by a linear density gradient (60 minutes) of 0.2 M α-methylmannoside (manufactured by Nakalai Tesque). The anti-hIL-5Rα CDR-grafted antibody was separated into non-adsorbed fraction and adsorbed fraction. When the non-adsorbed fraction and a part of the adsorbed fraction were sampled and their binding activity to hIL-5Rα was measured, they showed similar binding activity (FIG. 10A). When the ADCC activity was measured, the non-adsorbed fraction showed potent ADCC activity (100 to 1000 folds) than that of the part of adsorbed fraction (FIG. 10B). In addition, PA-treated sugar chains were prepared from the non-adsorbed fraction and a part of the adsorbed fraction, and reverse HPLC analysis was carried out using CLC-ODS column (manufactured by Shimadzu) (FIG. 11). In the non-adsorbed fraction, an antibody binding to fucose-free sugar chains was mainly present, and in the part of adsorbed fraction, an antibody binding to sugar chains having fucose was mainly present.

EXAMPLE 7

Activity Evaluation of Anti-GD3 Chimeric Antibody Having Different Ratio of α-1,6-fucose-Free Sugar Chain 1. Preparation of Anti-GD3 Chimeric Antibodies Having Different Ratio of α-1,6-fucose-Free Sugar Chain In accordance with the method described in the item 2(1) of Example 1, transformed clones derived from YB2/0 cell capable of producing an anti-GD3 chimeric antibody was obtained. Antibodies were prepared from the transformed clones derived from YB2/0 cell and named lot 1, lot 2 and lot 3. Each sugar chain which is bound to the anti-GD3 chimeric antibodies of lot 1, lot 2 and lot 3 was analyzed in accordance with the method of Example 11(6), and it was found that the ratios of α-1,6-fucose-free sugar chains were 50%, 45% and 29%, respectively. Herein, these samples are referred to as anti-GD3 chimeric antibody (50%), anti-GD3 chimeric antibody (45%) and anti-GD3 chimeric antibody (29%).

Also, sugar chains of the anti-GD3 chimeric antibody derived from the CHO/DG44 cell prepared in the item 2(2) of Example 1 were analyzed in accordance with the method of Example 11(6), and it was found that the ratio of α-1,6-fucose-free sugar chains was 7%. Herein, the sample is referred to as anti-GD3 chimeric antibody (7%).

The anti-GD3 chimeric antibody (45%) and anti-GD3 chimeric antibody (7%) were mixed at a ratio of anti-GD3 chimeric antibody (45%) : anti-GD3 chimeric antibody (7%) =5:3 or 1:7. Sugar chains of the samples were analyzed in accordance with the method of Example 10(6), and it was found that samples having the ratio of α-1,6-fucose-free sugar chains of 24% and 13% (calculated, value) were prepared. Herein, they are referred to as anti-GD3 chimeric antibody (24%) and anti-GD3 chimeric antibody (13%).

Results of the sugar chain analysis of each of the samples are shown in FIG. 12. The ratio of α-1,6-fucose-free sugar chains was shown as an average value of the result of two sugar chain analyses.

2. Evaluation of Binding Activity to GD3 (ELISA)

Figure 13:
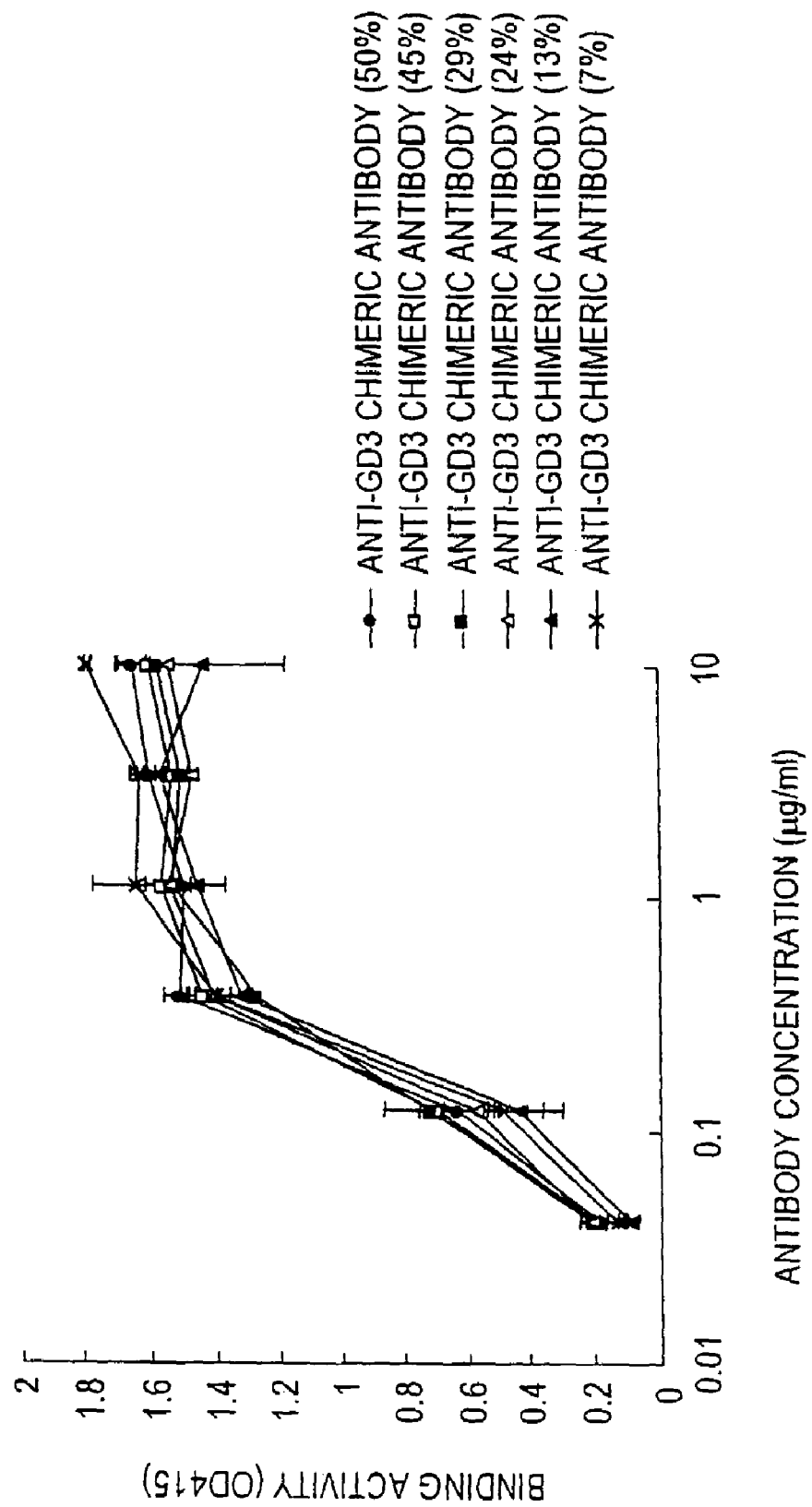
FIG. 13 shows GD3-binding activities of 6 anti-GD3 chimeric antibodies having a different ratio of α-1,6-fucose-free sugar chains measured by changing the antibody concentration. The ordinate and the abscissa show the binding activity with GD3 and the antibody concentration, respectively. "●", "○", "Δ", "▲" and "x" show the activities of anti-GD3 chimeric antibody (50%), anti-GD3 chimeric antibody (45%), anti-GD3 chimeric antibody (29%), anti-GD3 chimeric antibody (24%), anti-GD3 chimeric antibody (13%) and anti-GD3 chimeric antibody (7%), respectively.

The binding activities of the six kinds of the anti-GD3 chimeric antibodies having a different ratio of α-1,6-fucose-free sugar chains prepared in the item 1 of Example 7 against GD3 (manufactured by Snow Brand Milk Products) were measured by the ELISA shown in the item 3 of Example 1. As a result, all of the six kinds of the anti-GD3 chimeric antibodies showed almost the same GD3-binding activity as shown in FIG. 13, and it was found that the ratio of the α-1,6-fucose-free sugar chains does not have influence on the antigen binding activity of the antibody.

3. Evaluation of ADCC Activity on Human Melanoma Cell Line

The ADCC activity of anti-GD3 chimeric antibodies on a human melanoma cell line G-361 (ATCC CRL 1424) was measured as follows.

(1) Preparation of Target Cell Suspension $1 \times 10^6$ cells of a human melanoma cell line G-361 were prepared, a 3.7 MBq equivalent of a radioactive substance $Na_2{}^{51}CrO_4$ was added thereto and the mixture was allowed to react at 37° C. for 1 hour to label the cells with the radioisotope. After the reaction, the cells were washed three times by a procedure of their suspension in a medium and subsequent centrifugation, re-suspended in the medium and then incubated at 4° C. for 30 minutes in ice to effect spontaneous dissociation of the radioactive substance. After centrifugation, the cells were adjusted to $2 \times 10^5$ cells/ml by adding 5 ml of the medium and used as a target cell suspension.

(2) Preparation of Human Effector Cell Suspension

A 50 ml portion of peripheral blood was collected from a healthy person and gently mixed with 0.5 ml of heparin sodium (manufactured by Shimizu Pharmaceutical). Using Lymphoprep (manufactured by AXIS SHIELD), this was centrifuged (800 g, 20 minutes) in accordance with the manufacturers instructions to separate a mononuclear cell layer. The cells were washed by centrifuging (1,200 rpm, 5 minutes) three times using a medium and then re-suspended in the medium to give a density of $2 \times 10^6$ cells/ml and used as a human effector cell suspension.

(3) Measurement of ADCC Activity

The target cell suspension prepared in the (1) was dispensed in 50 μl ($1 \times 10^4$ cells/well) into each well of a 96 well U-bottom plate (manufactured by Falcon). Next, 100 μl of the human effector cell suspension prepared in the (2) was added thereto ($2 \times 10^5$ cells/well, ratio of the human effector cells to the target cells was 20:1). Each of the anti-GD3 chimeric antibodies was added thereto to give a final concentration of 0.0005 to 5 μg/ml, followed by reaction at 37° C. for 4 hours. After the reaction, the plate was centrifuged and the amount of $^{51}Cr$ in the supernatant was measured using a γ-counter. An amount of the spontaneously dissociated $^{51}Cr$ was calculated by carrying out the same procedure using the medium alone instead of the human effector cell suspension and antibody solution, and measuring the amount of $^{51}Cr$ in the supernatant. An amount of the total dissociated $^{51}Cr$ was calculated by carrying out the same procedure using the medium alone instead of the antibody solution and a 1 mol/l hydrochloric acid solution instead of the human effector cell suspension, and measuring the amount of $^{51}Cr$ in the supernatant. The cytotoxic activity (%) was calculated using equation (II).

Figure 14:
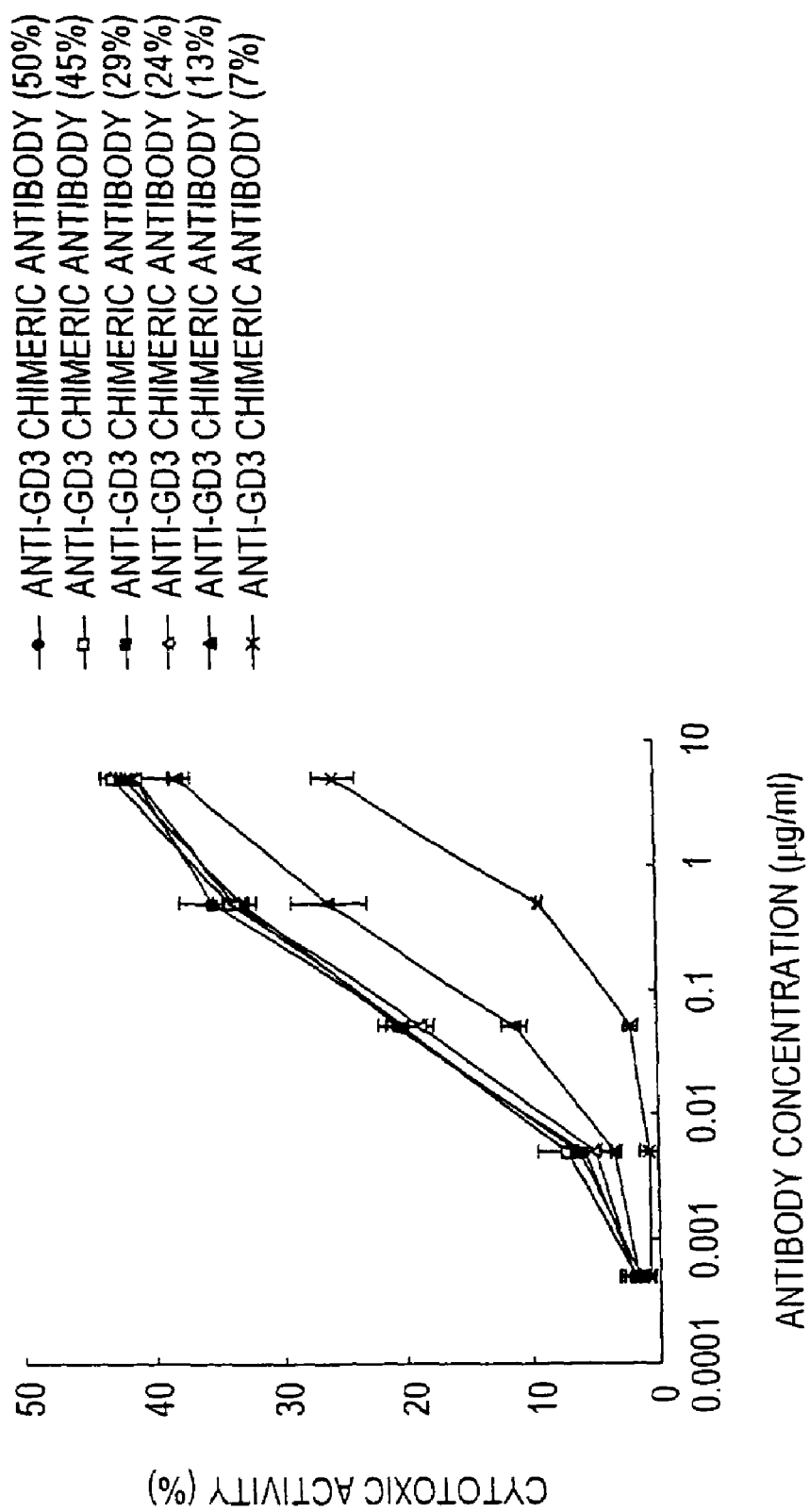
FIG. 14 shows ADCC activities of six kinds of anti-GD3 chimeric antibodies having a different ratio of α-1,6-fucose-free sugar chains against a human melanoma cell line G-361, using an effector cell of the donor A. The ordinate and the abscissa show the cytotoxic activity and the antibody concentration, respectively. "●", "□", "■", "Δ", "." and "x" show the activities of anti-GD3 chimeric antibody (50%), anti-GD3 chimeric antibody (45%), anti-GD3 chimeric antibody (29%), anti-GD3 chimreric antibody (24%), anti-GD3 chimeric antibody (13%) and anti-GD3 chimeric antibody (7%), respectively.
Figure 15:
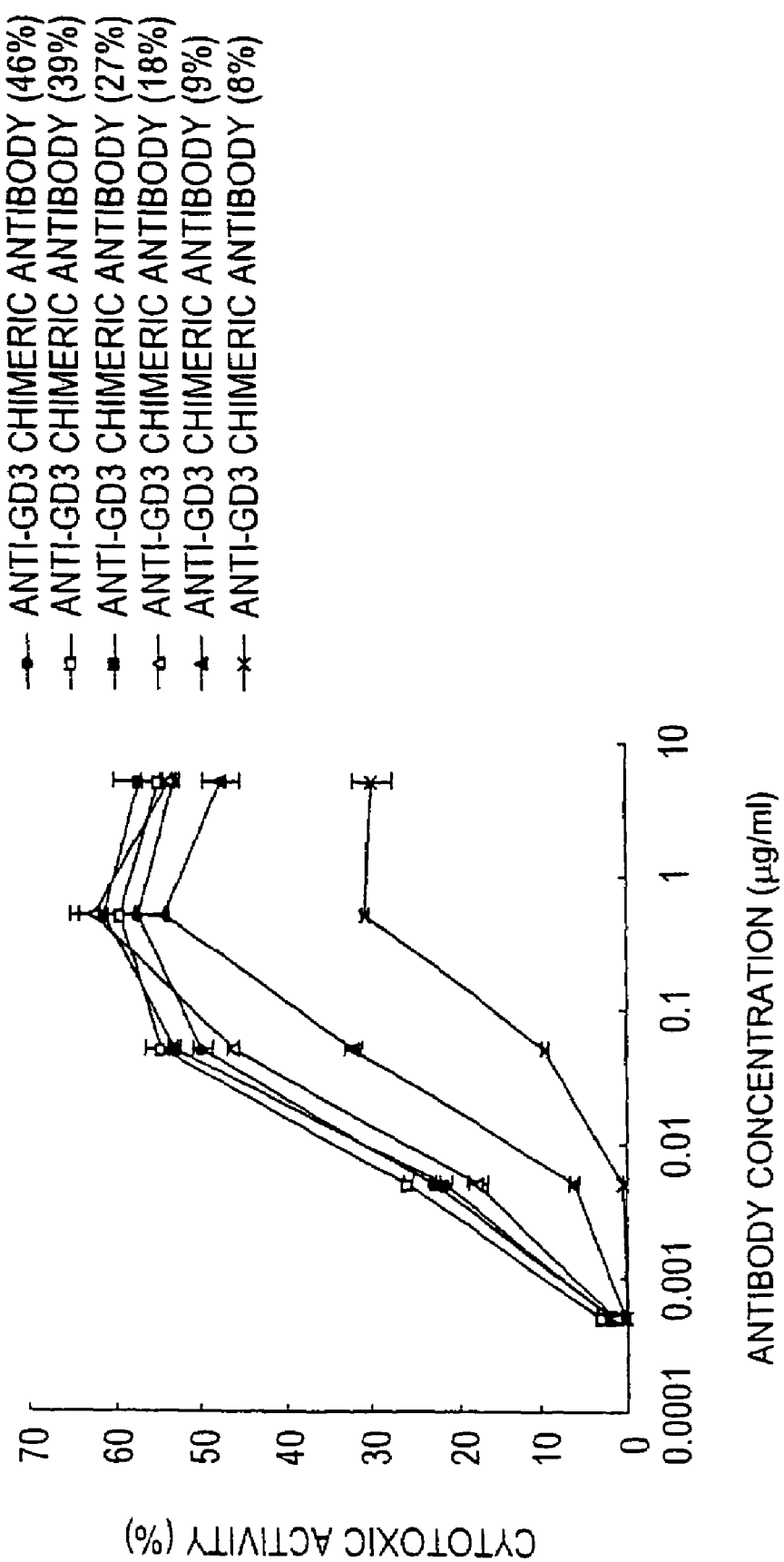
FIG. 15 shows ADCC activities of six kinds of anti-GD3 chimeric antibodies having a different ratio of α-1,6-fucose-free sugar chains against a human melanoma cell line G-361, using an effector cell of the donor B. The ordinate and the abscissa show the cytotoxic activity and the antibody concentration, respectively. "●", "□", "■", "Δ", "." and "x" show the activities: of anti-GD3 chimeric antibody (50%), anti-GD3 chimeric antibody (45%), anti-GD3 chimeric antibody (29%), anti-GD3 chimeric antibody (24%), anti-GD3 chimeric antibody (13%) and anti-GD3 chimeric antibody (7%), respectively.
Figure 16A:
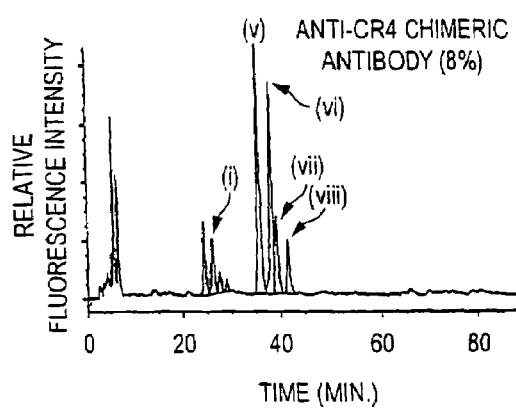
FIG. 16. shows elution patterns of PA-treated sugar chains prepared from six kinds of anti-GD3 chimeric antibodies, obtained by analyzing them by reverse phase HPLC. The ordinates and the abscissas show the relative fluorescence intensity and the elution time, respectively.
Figure 16B:
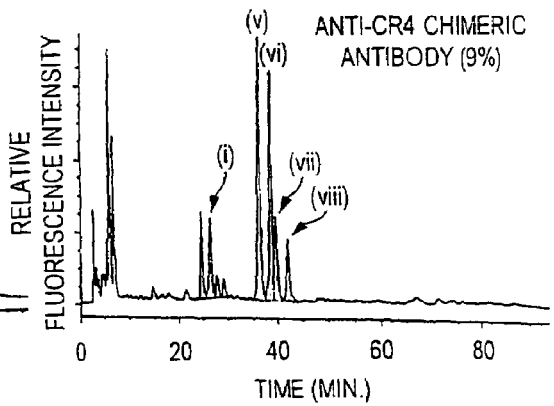
Figure 16C:
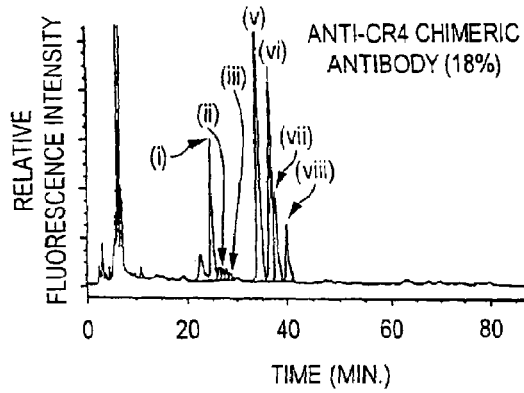
Figure 16D:
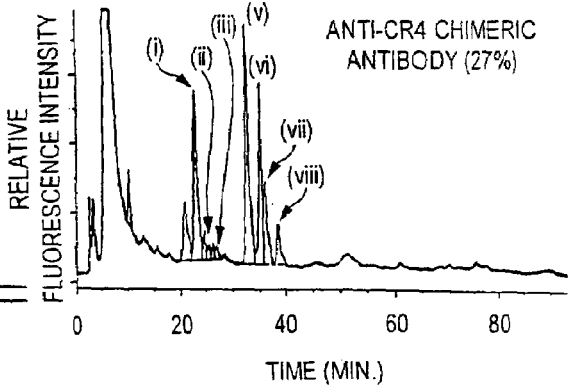
Figure 16E:
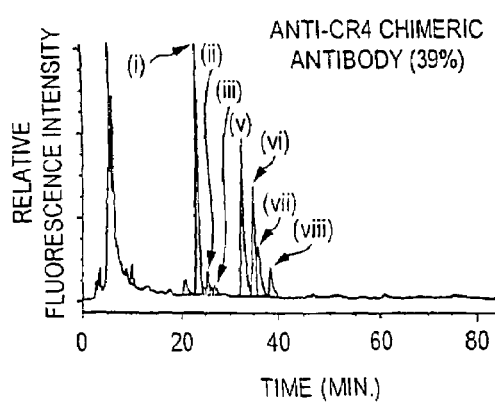
Figure 16F:
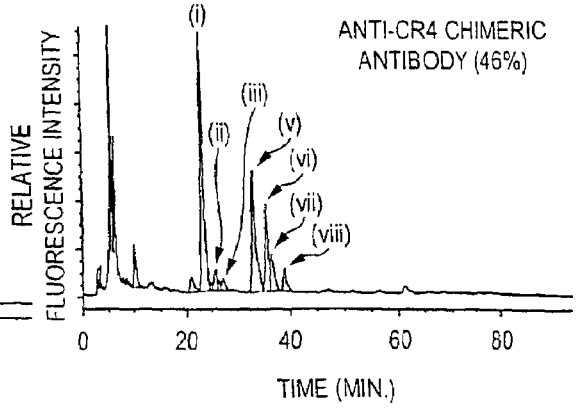

FIGS. 14 and 15 show results of the measurement of ADCC activity of the six kinds of the anti-GD3 chimeric antibodies having a different ratio of α-1,6-fucose-free sugar chains at various concentrations (0.0005 to 5 μg/ml) using effector cells of two healthy donors (A and B), respectively. As shown in FIGS. 14 and 15, ADCC activity of the anti-Gb3 chimeric antibodies showed a tendency to increase in proportion to the ratio of α-1,6-fucose-free sugar chains at each antibody concentration. The ADCC activity decreases when the antibody concentration is low. At an antibody concentration of 0.05 μg/ml, the antibody in which the ratio of α-1,6-fucose-free sugar chains is 24%, 29%, 45% or 50% showed almost the same potent ADCC activity but the ADCC activity was low in the antibody (13%) or (7%) in which the ratio of α-1,6-fucose-free sugar chains is less that 20%. These results were the same when the effector cell donor was changed.

EXAMPLE 8

Activity Evaluation of Anti-CCR4 Chimeric Antibody Having Different Ratio of α-1,6-fucose-Free Sugar Chain 1. Production of Cells Stably Producing Anti-CCR4 Chimeric Antibody Cells which capable of stably producing an anti-CCR4 chimeric antibody were prepared as follows using a tandem type expression vector pKANTSX2160 for an anti-CCR4 chimeric antibody described in WO 01/64754.

(1) Preparation of Antibody-Producing Cell Using Rat Myeloma YB2/0 Cell

After introducing 10 μg of the anti-CCR4 chimeric antibody expression vector pKANTEX2160 into $4 \times 10^6$ cells of rat myeloma YB2/0 cell (ATCC CRL 1662) by electroporation [*Cytotechnology*, 3, 133 (1990)], the cells were suspended in 40 ml of Hybridoma-SFM-FBS(5) [Hybridoma-SFM medium (manufactured by Invitrogen) comprising 5% FBS (manufactured by PAA Laboratories)) and dispensed in 200 μl/well into a 96 well culture plate (manufactured by Sumitomo Bakelite). After culturing them at 37° C. for 24 hours in a 5% $CO_2$ incubator, G418 was added to give a concentration of 1 mg/ml, followed by culturing for 1 to 2 weeks. Culture supernatant was recovered from wells in which growth of transformants showing G418 resistance was observed by the formation of colonies, and antigen binding activity of the anti-CCR4 chimeric antibody in the supernatant was measured by the ELISA described in the item 2 of Example 8.

Regarding the transformants in wells in which production of the anti-CCR4 chimeric antibody was observed in culture supernatants, in order to increase an amount of the antibody production using a DHFR gene amplification system, each of them was suspended in the Hybridoma-SFM-FBS(5) medium comprising 1 mg/ml G418 and 50 nM DHFR inhibitor MTX (manufactured by SIGMA) to give a density of 1 to $2 \times 10^5$ cells/ml, and the suspension was dispensed in 1 ml portions into wells of a 24 well plate (manufactured by Greiner). After culturing them at 37° C. for 1 to 2 weeks in a 5% $CO_2$ incubator, transformants showing 50 nM MTX resistance were induced. Antigen binding activity of the anti-CCR4 chimeric antibody in culture supernatants in wells in which growth of transformants was observed was measured by the ELISA described in the item 2 of Example 8.

Regarding the transformants in wells in which production of the anti-CCR4 chimeric antibody was observed in culture supernatants, the MTX concentration was increased by the same method, and a transformant capable of growing in the Hybridoma-SFM-FBS(5) medium comprising 200 nM MTX and of producing the anti-CCR4 chimeric antibody in a large amount was finally obtained. The obtained transformant was made into a single cell (cloning) by limiting dilution twice, and the obtained cloned cell line was named KM2760 #58-35-16. In this case, using the method for determining the transcription product of an α-1,6-fucosyltransferase gene shown in Example 9, a cell line producing a relatively small amount of the transcription product was selected and used as a suitable cell line.

(2) Preparation of Antibody-Producing Cell Using CHO/DG44 Cell

After introducing 4 4g of the anti-CCR4 chimeric antibody expression vector pKANTEX2160 into 1.6×10⁶ cells of CHO/DG44 cell by electroporation [*Cytotechnology*, 3, 133 (1990)], the cells were suspended in 10. ml of IMDM-dFBS (10)-HT(1) [IMDM medium (manufactured by Invitrogen) comprising 10% dFBS (manufactured by Invitrogen) and 1× concentration of HT supplement (manufactured by Invitrogen)] and dispensed in 100 µl/well into a 96 well culture plate (manufactured by Iwaki Glass). After culturing them at 37° C. for 24 hours in a 5% $CO_2$ incubator, the medium was changed to IMDM-dFBS(10) (IMDM medium comprising 10% of dialyzed FBS), followed by culturing for 1 to 2 weeks. Culture supernatant was recovered from wells in which the growth was observed due to formation of a transformant showing HT-independent growth, and an expression level of the anti-CCR4 chimeric antibody in the supernatant was measured by the ELISA described in the item 2 of Example 8.

Regarding the transformants in wells in which production of the anti-CCR4 chimeric antibody was observed in culture supernatants, in order to increase an amount of the antibody production using a DHFR gene amplification system, each of them was suspended n the IMDM-dFBS(10) medium comprising 50 nM MTX to give a density of 1 to 2×10⁵ cells/ml, and the suspension was dispensed in 0.5 ml into wells of a 24 well plate (manufactured by Iwaki Glass). After culturing them at 37° C. for 1 to 2 weeks in a 5% $CO_2$ incubator, transsformants showing 50 nM MTX resistance were induced. Regarding the transformants in wells in which the growth was observed, the MTX concentration was increased to 200 nM by the same method, and a transformant capable of growing in the IMDM-dFBS(10) medium comprising 200 nM MTX and of producing the anti-CCR4 chimeric antibody in a large amount was finally obtained. The obtained transformant was named 5-03. In this case, using the method for determining the transcription product of an α-1,6-fucosyltransferase gene shown in Example 9, a cell line producing a relatively small amount of the transcription product was selected and used as a suitable cell line.

2. Antibody Binding Activity to CCR4 Partial Peptide (ELISA)

Compound 1 (SEQ ID NO:25) was selected as a human CCR4 extracellular region peptide capable of reacting with the anti-CCR4 chimeric antibody. In order to use it in the activity measurement by ELISA, a conjugate with BSA (bovine serum albumin) (manufactured by Nakalai Tesque) was prepared by the following method and used as the antigen. That is, 100 ml of a DMSO solution comprising 25 mg/ml SMCC [4-(N-maleimidomethyl)-cyclohexane-1-carboxylic acid N-hydroxysuccinimide ester] (manufactured by Sigma) was added dropwise to 900 ml of a 10 mg BSA-containing PBS solution under stirring using a vortex, followed by gently stirring for 30 minutes. A 1 ml portion of the reaction solution was applied to a gel filtration column such as NAP-10 column or the like equilibrated with 25 ml of PBS, and then eluted with 1.5 ml of PBS and the resulting eluate was used as a BSA-SMCC solution (BSA concentration was calculated based on $Al_{280}$ measurement). Next, 250 ml of PBS was added to 0.5 mg of Compound 1 and then completely dissolved by adding 250 ml of DMF, and the BSA-SMCC solution was added thereto under vortex, followed by gently stirring for 3 hours. The reaction solution was dialyzed against PBS at 4° C. overnight, sodium azide was added thereto to give a final concentration of 0.05%, and the mixture was filtered through a 0.22 mm filter to be used as a BSA-compound 1 solution.

The prepared conjugate was dispensed at 0.05 µg/ml and 50 µl/well into a 96 well EIA plate (manufactured by Greiner) and incubated for adhesion at 4° C. overnight. After washing each well with PBS, 1% BSA-PBS was added thereto in 100 µl/well and allowed to react at room temperature to block the remaining active groups. After washing each well with PBS containing 0.05% Tween 20 (hereinafter referred to as "Tween-PBS"), a culture supernatant of a transformant was added at 50 µl/well and allowed to react at room temperature for 1 hour. After the reaction, each well was washed with Tween-PBS, and then a peroxidase-labeled goat anti-human IgG(γ) antibody solution (manufactured by American Qualex) diluted 6000 times with 1% BSA-PBS as the secondary antibody was added at 50 µl/well-and allowed to react at room temperature for 1 hour. After the reaction and subsequent washing with Tween-PBS, the ABTS substrate solution was added at 50 µl/well for color development, and 20 minutes thereafter, the reaction was stopped by adding a 5% SDS solution at 50 µl/well. Thereafter, the absorbance at $OD_{415}$ was measured. The anti-CCR4 chimeric antibody obtained in the item 1 of Example 8 showed the binding activity to CCR4.

3. Purification of Anti-CCR4 Chimeric Antibody (1) Culturing of Antibody-Producing Cell Derived from YB2/0 Cell and Purification of Antibody The anti-CCR4 chimeric antibody-expressing transformant cell clone KM2760 # 58-35-16 obtained in the item 1 (1) of Example 8 was suspended in Hybridoma-SFM. (manufactured by Invitrogen) medium comprising 200 nM MTX and 5% of Daigo's GF21 (manufactured by Wako Pure Chemical Industries) to give a density of 2×10⁵ cells/ml and subjected to fed-batch shaking culturing using a spinner bottle (manufactured by Iwaki Glass) in a constant temperature chamber of 37° C. After culturing them for 8 to 10 days, the anti-CCR4 chimeric antibody was purified from the culture supernatant recovered using Prosep-A (manufactured by Millipore) column and gel filtration. The purified anti-CCR4 chimeric antibody was named KM2760-1.

(2) Culturing of Antibody-Producing Cell Derived from CHO-DG44 Cell and Purification of Antibody The anti-CCR4 chimeric antibody-producing transformant cell line 5-03 obtained in the item 1(2) of Example 8 was cultured at 37° C. in a 5% $CO_2$ incubator using IMDM-dFBS (10) medium in a 182 cm² flask (manufactured by Greiner). When the cell density reached confluent after several days, the culture supernatant was discarded, and the cells were washed with 25 ml of PBS buffer and then mixed with 35 ml of EXCELL 301 medium (manufactured by JRH). After culturing them at 37° C. for 7 days in a 5% $CO_2$ incubator, the culture supernatant was recovered. The anti-CCR4. chimeric ant-body was purified from the culture supernatant using Prosep-A (manufactured by Millipore) column in accordance with the manufacture's instructions. The purified anti-CCR4 chimeric antibody was named KM3060.

When the binding activity to CCR4 of KM2760-1 and KM3060 was measured by ELISA, they showed equivalent binding activity.

4. Analysis of Purified Anti-CCR4 Chimeric Antibodies

Each (4 µg) of the two kinds of the anti-CCR4 chimeric antibodies produced by and purified from in different animal cells, obtained in the item 1 of this Example was subjected to SDS-PAGE in accordance with a known method [*Nature*, 227, 680 (1970)), and the molecular weight and purification degree were analyzed. In each of the purified anti-CCR4 chimeric antibodies, a single band corresponding to the molecular weight of about 150 Kd was found under non-reducing conditions, and two bands of about 50 Kd and about 25 Kd were found under reducing conditions. The molecular weights almost coincided with the molecular weights deduced from the cDNA nucleotide sequences of antibody H chain and L chain (H chain: about 49 Kd, L chain: about 23 Kd, whole molecule: about 144 Kd) and coincided with reports stating that an IgG type antibody, has a molecular weight of about 150 Kd under non-reducing conditions and is degraded into H chain having a molecular weight of about 50 Kd and L chain having a molecular weight of about 25 Kd under reducing conditions caused by cutting an S—S bond in the molecule [*Antibodies: A Laboratory Manual*, Cold Spring Harbor Laboratory, Chapter 14 (1988), *Monoclonal Antibodies: Principles and Practice*, Academic Press Limited (1996)], thus confirming that the anti-CCR4 chimeric antibody was expressed and purified as an antibody molecule having a correct structure.

5. Preparation of Anti-CCR4 Chimeric Antibody Having Different Ratio of α-1,6-Fucose-Free Sugar Chain Sugar chains which are bound to anti-CCR4 chimeric antibody KM2760-1 derived from YB2/0 cell prepared in the item 3(1) of Example 8 and the anti-CCR4 chimeric antibody KM3060 derived from CHO/DG44 cell prepared in the item 3(2) of Example 8 were analyzed in accordance with the method of Example 10(6). The ratio of α-1,6-fucose-free sugar chains was 87% and 8% in KM2760 and KM3060, respectively. Herein, the samples are referred to as anti-CCR4 chimeric antibody (87%) and anti-CCR4 chimeric antibody (8%).

The anti-CCR4 chimeric antibody (87%) and anti-CCR4 chimeric antibody (8%) were mixed at a ratio of anti-CCR4 chimeric antibody (87%) : anti-CCR4 chimeric antibody (8%)=1:39, 16:67, 22:57, 32:47 or 42:37. Sugar chains of these samples were analyzed in accordance with the method of Example 10(6). The ratio of α-1,6-fucose-free sugar chains was 9%, 18%, 27%, 39% and 46%, respectively. Herein, these samples are referred to as anti-CCR4 chimeric antibody (9%), anti-CCR4 chimeric antibody (18%), anti-CCR4 chimeric antibody (27%), anti-CCR4 chimeric antibody (39%) and anti-CCR4 chimeric antibody (46%).

Results of the sugar chain analysis of each of the samples are shown in FIG. 16. The ratio of α-1,6-fucose-free sugar chains was shown as an average value of the result of two sugar chain analyses.

6. Evaluation of Binding Activity to CCR4 Partial Peptide (ELISA)

Binding activity of the six kinds of the different anti-CCR4 chimeric antibodies having a different α-1,6-fucose-free sugar chain prepared in the item 5 of Example 8 to CCR4 partial peptide was measured in accordance with the method described in the item 2 of Example 8.

Figure 17:
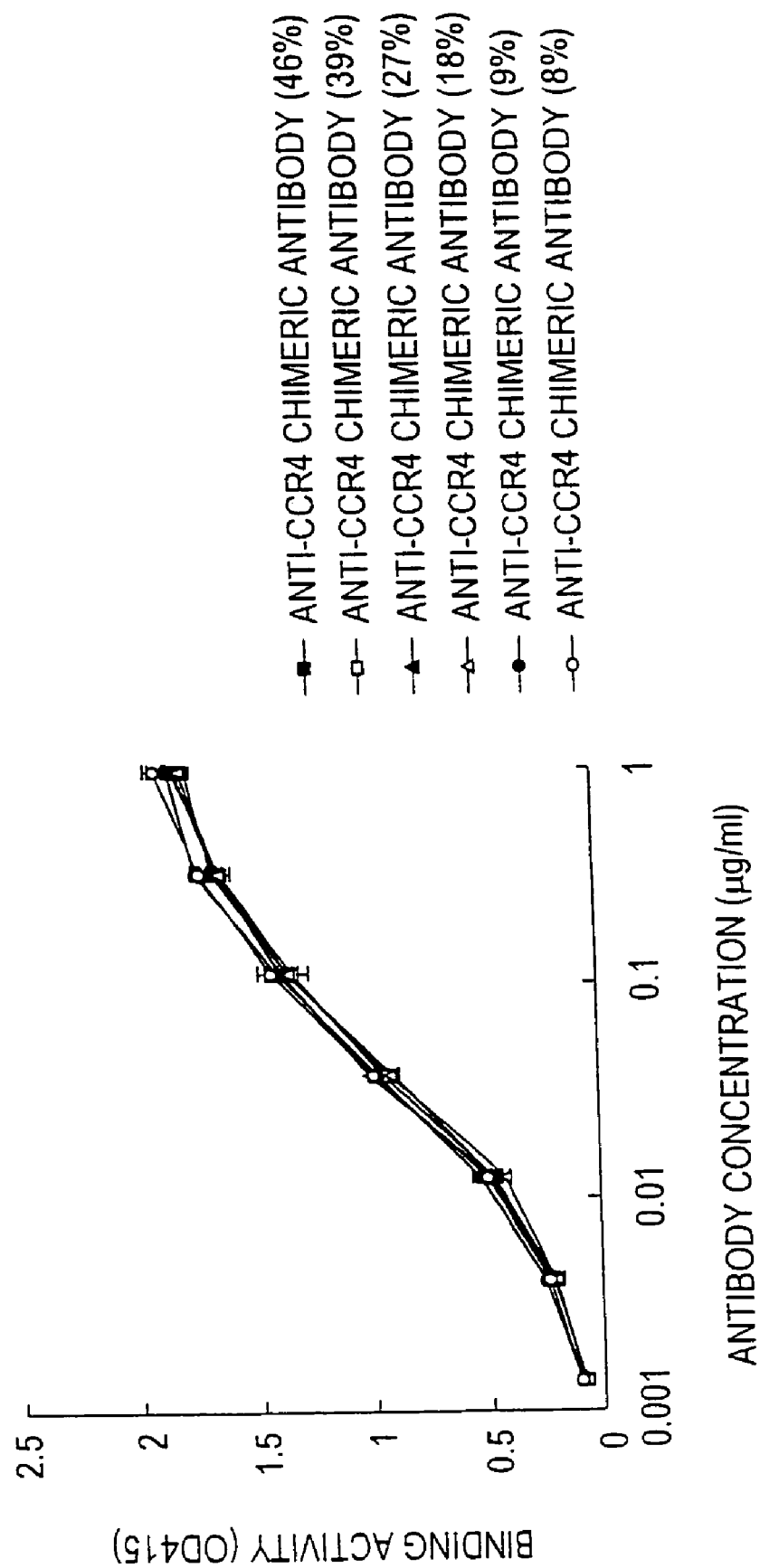
FIG. 17 shows CCR4-binding activities of six kinds of anti-CCR4 chimeric antibodies having a different ratio of α-1,6-fucose-free sugar chains measured by changing the antibody concentration. The ordinate and the abscissa show the binding activity with CCR4 and the antibody concentration, respectively. "■", "□", "▲", "66 ", "●" and "○" show the activities of anti-CCR4 chimeric antibody (46%), anti-CCR4 chimeric antibody (39%), anti-CCR4 chimeric antibody (27%), anti-CCR4 chimeric antibody (18%), anti-CCR4 chimeric antibody (9%) and arti-CCR4 chimeric antibody (8%), respectively.

As a result, as shown in FIG. 17, the six kinds of the anti-CCR4 chimeric antibodies showed almost the same CCR4-binding activity, it was found that the ratio of α-1,6-fucose-free sugar chains does not have influence on the antigen-binding activity of the antibody.

7. Evaluation of ADCC Activity on Human CCR4-High Expressing Cell Line

The ADCC activity of the anti-CCR4 chimeric antibodies against a human CCR4-high expressing cell CCR4/EL-4 cell (WO 01/64754) was measured as follows.

(1) Preparation of Target Cell Suspension

Cells ($1.5 \times 10^6$) of a human CCR4-expressing cell, CCR4/EL-4 cell, described in WO 01/64754 were prepared and a 5.55 MBq equivalent of a radioactive substance $Na_2{}^{51}CrO_4$ was added thereto, followed by reaction at 37° C. for 1.5 hours to thereby label the cells with a radioisotope. After the reaction, the cells were washed three times by suspension in a medium and subsequent centrifugation, resuspended in the medium and then incubated at 4° C. for 30 minutes in ice for spontaneous dissociation of the radioactive substance. After centrifugation, the cells were adjusted to give a density of $2 \times 10^5$ cells/ml by adding 7.5 ml of the medium and used as a target cell suspension.

(2) Preparation of Human Effector Cell Suspension

From a healthy person, 60 ml of peripheral blood was collected, 0.6 ml of heparin sodium (manufactured by Shimizu Pharmaceutical) was added thereto, followed by gently mixing. The mixture was centrifuged (800 g, 20 minutes) to isolate a mononuclear cell layer using Lymphoprep (manufactured by AXIS SHIELD) in accordance with the manufacture's instructions. The cells were washed by centrifuging (1,400 rpm, 5 minutes) three times using a medium and then re-suspended in the medium to give a density of $5 \times 10^6$ cells/ml and used as a human effector cell suspension.

(3) Measurement of ADCC Activity

The target cell suspension prepared in the (1) was dispensed at 50 µl ($1 \times 10^4$ cells/well) into each well of a 96 well U-bottom plate (manufactured by Falcon). Next, 100 µl of the human effector cell suspension prepared in the (2) was added thereto ($5 \times 10^5$ cells/well, ratio of the human effector cells to the target cells was 50:1). Furthermore, each of the anti-CCR4 chimeric antibodies was added thereto to give a final concentration of 0-0001 to 10 µg/ml, followed by reaction at 37° C. for 4 hours. After the reaction, the plate was centrifuged and the amount of $^{51}Cr$ in the supernatant was measured using a γ-counter. An amount of the spontaneously dissociated $^{51}Cr$ was calculated by carrying out the same procedure using the medium alone instead of the human effector cell suspension and antibody solution, and measuring the amount of $^{51}Cr$ in the supernatant. An amount of the total dissociated $^{51}Cr$ was calculated by carrying out the same procedure using a 1 mol/L hydrochloric acid solution instead of the antibody solution and human effector cell suspension, and measuring the amount of $^{51}Cr$ in the supernatant. The ADCC activity (%) was calculated based on equation (II).

Figure 18:
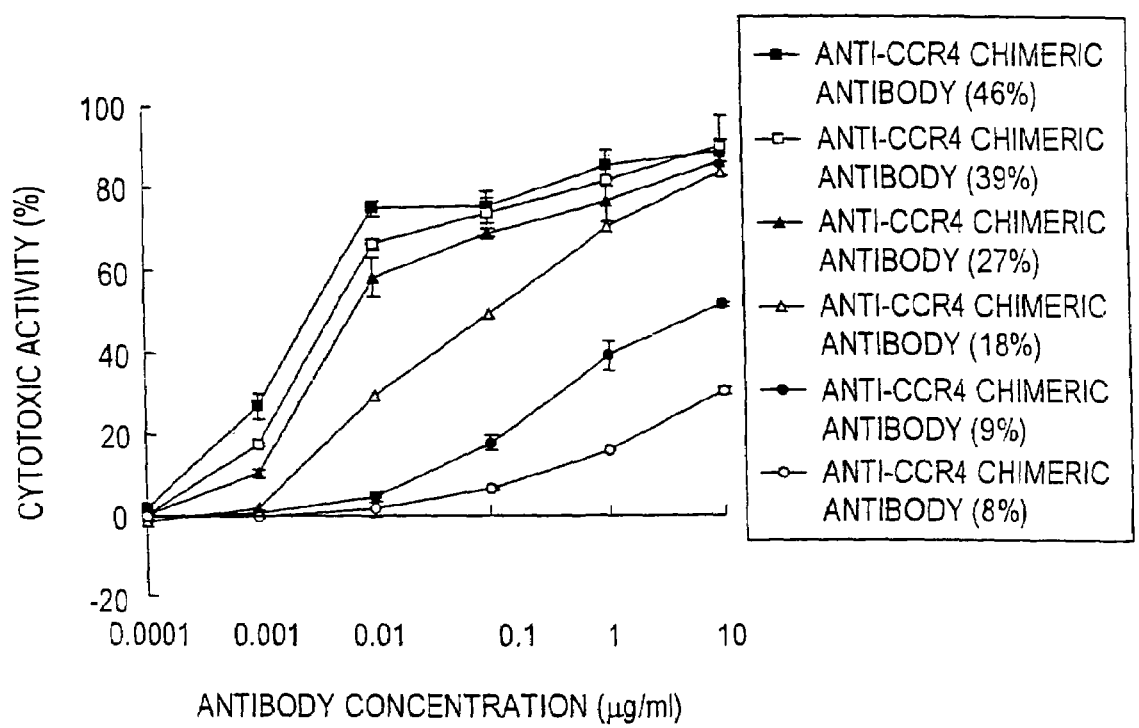
FIG. 18 shows ADCC activities of anti-CCR4 chimeric antibodies having a different ratio of α-1,6-fucose-free sugar chains against CCR4/EL-4 cell, using an effector cell of the donor A. The ordinate and the abscissa show the cytotoxic activity and the antibody concentration, respectively. "■", "□", "▲", "Δ", "●" and "○" show the activities of anti-CCR4 chimeric antibody (46%), anti-CCR4 chimeric antibody (39%), anti-CCR4 chimeric antibody (27%), anti-CCR4 chimeric antibody (18%), anti-CCR4 chimeric antibody (9%) and anti-CCR4 chimeric antibody (8%), respectively. Also.
Figure 19:
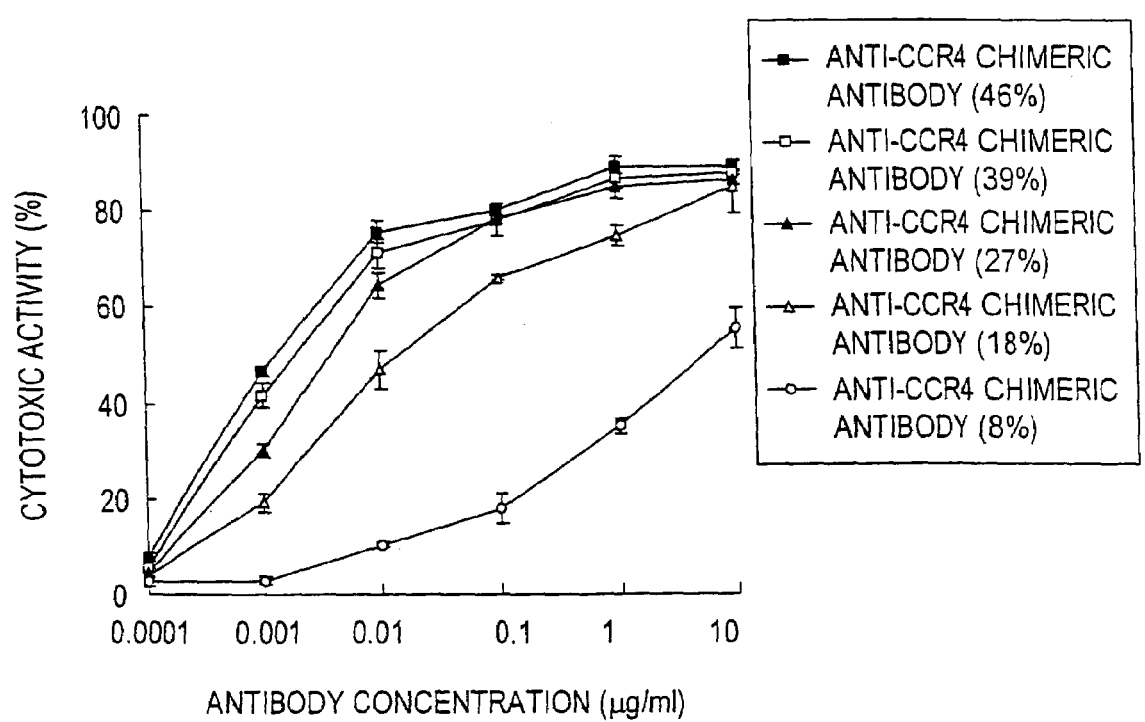
FIG. 19 shows ADCC activities of anti-CCR4 chimeric antibodies having a different ratio of α-1,6-fucose-free sugar chain against CCR4/EL-4 cell, using an effector cell of the donor B. The ordinate and the abscissa show the cytotoxic activity and the antibody concentration, respectively. "■", "□", "▲", "Δ", "●" and "○" show the activities of anti-CCR4 chimeric antibody (46%), anti-CCR4 chimeric antibody (39%), anti-CCR4 chimeric antibody (27%), anti-CCR4 chimeric antibody (18%), anti-CCR4 chimeric antibody (9%) and anti-CCR4 chimeric antibody (8%), respectively.

FIGS. 18 and 19 show results of the measurement of ADCC activity of the anti-CCR4 chimeric antibodies having a different ratio of α-1,6-fucose-free sugar chains at various concentrations (0.001 to 10 µg/ml) using effector cells of two healthy donors (A and B), respectively. As shown in FIGS. 18 and 19, the ADCC activity of the anti-CCR4 chimeric antibodies showed a tendency to increase in proportion to the ratio of α-1,6-fucose-free sugar chains at each antibody concentration. The ADCC activity decreases when the antibody concentration is low. At an antibody concentration of 0.01 µg/ml, the antibody in which the α-1,6-fucose-free sugar chains is 27%, 39% or 46% showed almost the same potent ADCC activity but the ADCC activity was low in the antibody in which the ratio of α-1,6-fucose-free sugar chains is less than 20%. The results were the same as the case when the effector cell donor was changed.

EXAMPLE 9

Determination of Transcription Product of α-1,6-Fucosyltransferase Gene in Host Cell Line (1) Preparation of Single-Stranded cDNA from Various Cell Lines Single-stranded cDNA samples were prepared from dihydrofolate reductase gene (dhfr)-deleted CHO/DG44 cells derived from Chinese hamster ovary and rat myeloma YB2/0 cells by the following procedure.

The CHO/DG44 cells were suspended in IMDM medium (manufactured by Life Technologies) supplemented with 10% fetal bovine serum (manufactured by Life Technologies) and 1× concentration HT supplement (manufactured by Life Technologies), and 15 ml of the suspension was inoculated into T75 flask for adhesion cell culture use (manufactured by Greiner) at a density of $2 \times 10^5$ cells/ml. Also, the YB2/0 cells were suspended in RPMI 1640 medium (manufactured by Life Technologies) supplemented with 10% fetal bovine serum (manufactured by Life Technologies) and 4 mmol/l L-GLN (manufactured by Life Technologies), and 15 ml of the suspension was inoculated into T75 flask for suspension cell culture (manufactured by Greiner) at a density of $2 \times 10^5$ cells/ml. They were cultured at 37° C. in a 5% $CO_2$ incubator, and $1 \times 10^7$ of respective host cells were recovered on the 1st, 2nd, 3rd, 4th and 5th days of the culturing to extract total RNA using RNAeasy (manufactured by QIAGEN) in accordance with the manufacture's instructions.

The total RNA was dissolved in 45 μl of sterile water, 1 μl of RQ1 RNase-Free DNase (manufactured by Promega), 5 μl of the attached 10× DNase buffer and 0.5 μl of RNasin Ribonuclease Inhibitor (manufactured by Promega) were added thereto, followed by reaction at 37° C. for 30 minutes to degrade genome DNA contaminated in the sample. After the reaction, the total RNA was purified again using RNAeasy (manufactured by QIAGEN) and dissolved in 50 μl of sterile water.

In a 20 μl of the reaction mixture using oligo(dT) as a primer, single-stranded cDNA was synthesized from 3 μg of each of the obtained total RNA samples by reverse transcription reaction using SUPERSCRIPT™ Preamplification System for First Strand cDNA Synthesis (manufactured by Life Technologies) and in accordance with the manufacture's instructions. A 1× concentration solution of the reaction solution was used for the cloning of α-1,6-fucosyltransferase (hereinafter referred sometimes to as "FUT8") and β-actin derived from respective host cells, and 50 folds-diluted aqueous solution of the reaction solution for the determination of each gene transcription amount by competitive PCR, and the solutions were stored at −80° C. until use.

(2) Preparation of cDNA Partial Fragments of Chinese Hamster FUT8 and Rat FUT8

Figure 20:
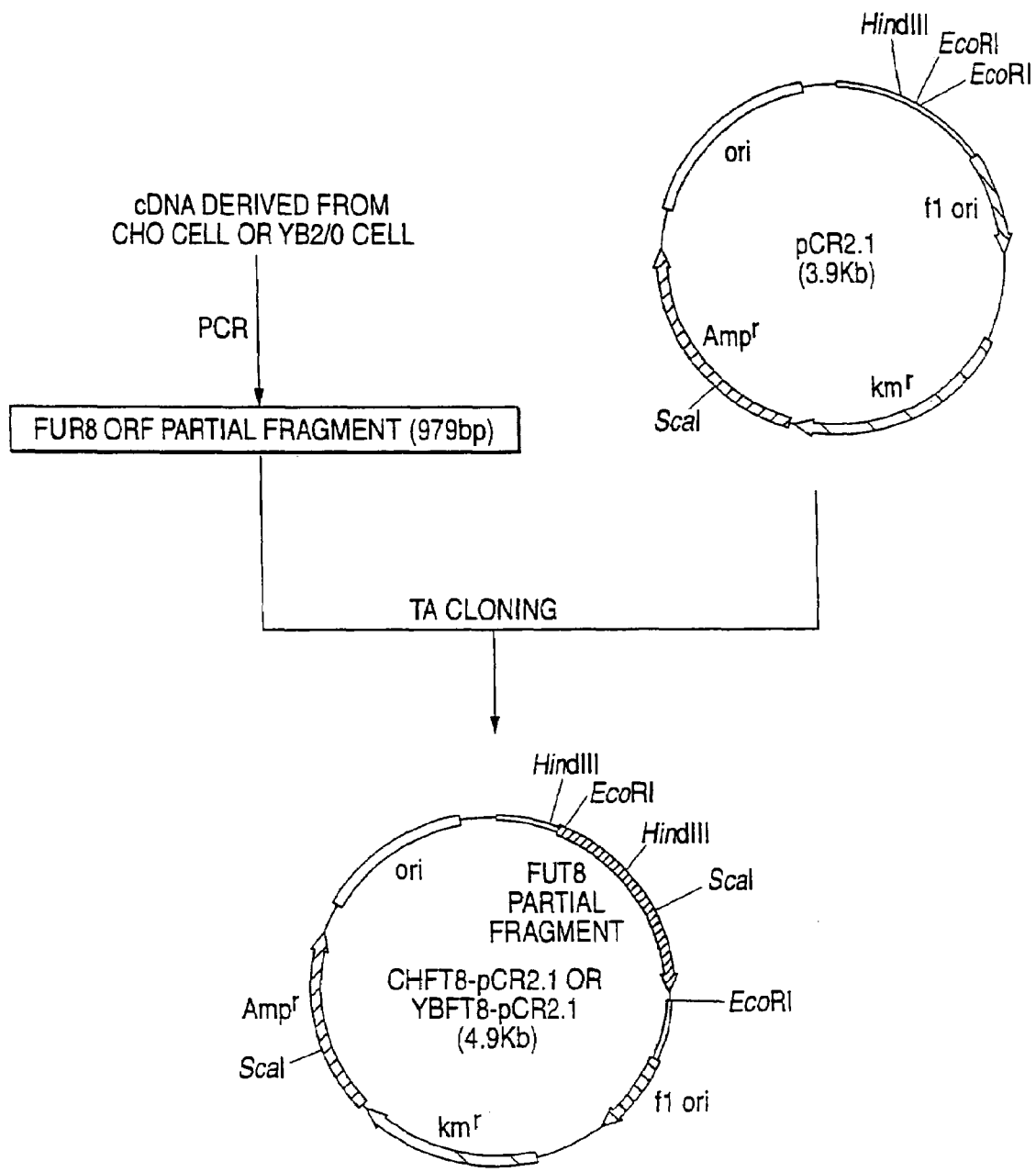
FIG. 20 shows construction of plasmids CHFT8-pCR2.1 and YBFT8-pCR2.1.

Each cDNA partial fragment of Chinese hamster FUT8 and rat FUT8 was prepared by the following procedure (FIG. 20)

First, primers (shown in SEQ ID NOs:4 and 5) specific for nucleotide sequences common to human FUT8 cDNA (*J. Biochem.*, 121, 626 (1997)] and swine FUT8 cDNA [*J. Biol. Chem.*, 211, 27810 (1995)] were designed.

Next, 25 μl of a reaction solution [ExTaq buffer (manufactured by Takara Shuzo), 0.2 mmol/l dNTPs and 0.5 μmol/l gene-specific primers (SEQ ID NOs:4 and 5)] containing 1 μl of each of the cDNA prepared, from CHO cell and cDNA prepared from YB2/0 cell, both obtained in the item (1) 2 days after culturing, and polymerase chain reaction (PCR) was carried out using a DNA polymerase ExTaq (manufactured by Takara Shuzo). The PCR was carried out by heating at 94° C. for 1 minute, subsequent 30 cycles of heating at 94° C. for 30 seconds, 55° C. for 30 seconds and 72° C. for 2 minutes as one cycle, and final heating at 72° C. for 10 minutes.

After the PCR, the reaction solution was subjected to 0.8% agarose gel electrophoresis, and a specific amplified fragment of 979 bp was purified using GENECLEAN Spin Kit (manufactured by BIO 101) and eluted with 10 μl of sterile water (hereinafter, the method was used for the purification of DNA fragments from agarose gel). Into a plasmid pCR2.1, 4 μl of the amplified fragment was employed to insert in accordance with the manufacture's instructions of TOPO TA Cloning Kit (manufactured by Invitrogen), and *E. coli* XL1-Blue was transformed with the reaction solution by the method of Cohen et al. [*Proc. Natl. Acad. Sci. USA*, 69, 2110 (1972)] (hereinafter, the method was used for the transformation of *E. coli*). Plasmid DNA samples were isolated in accordance with a known method [*Nucleic Acids Research*, 7, 1513 (1979)] (hereinafter, the method was used for the isolation of plasmid) from cDNA-inserted 6 clones among the obtained kanamycin-resistant colonies.

The nucleotide sequence of each cDNA inserted into the plasmid was determined using DNA Sequencer 377 (manufactured by Parkin Elmer) and BigDye Terminator Cycle Sequencing FS Ready Reaction kit (manufactured by Parkin Elmer) in accordance with the method of the manufacture's instructions. It was confirmed that all of the inserted cDNAs of which sequences were determined by the method encode the open reading frame (ORF) partial sequences of Chinese hamster FUT8 or rat FUT8 (shown in SEQ ID NOs:6 and 7). Among these, plasmid DNA samples containing absolutely no reading error by the PCR in the sequences were selected. Herein, these plasmids are referred to as CHFUT8-pCR2.1 and YBFUT8-pCR2.1.

(3) Preparation of Chinese Hamster β-Actin and Rat β-Actin cDNA

Figure 21:
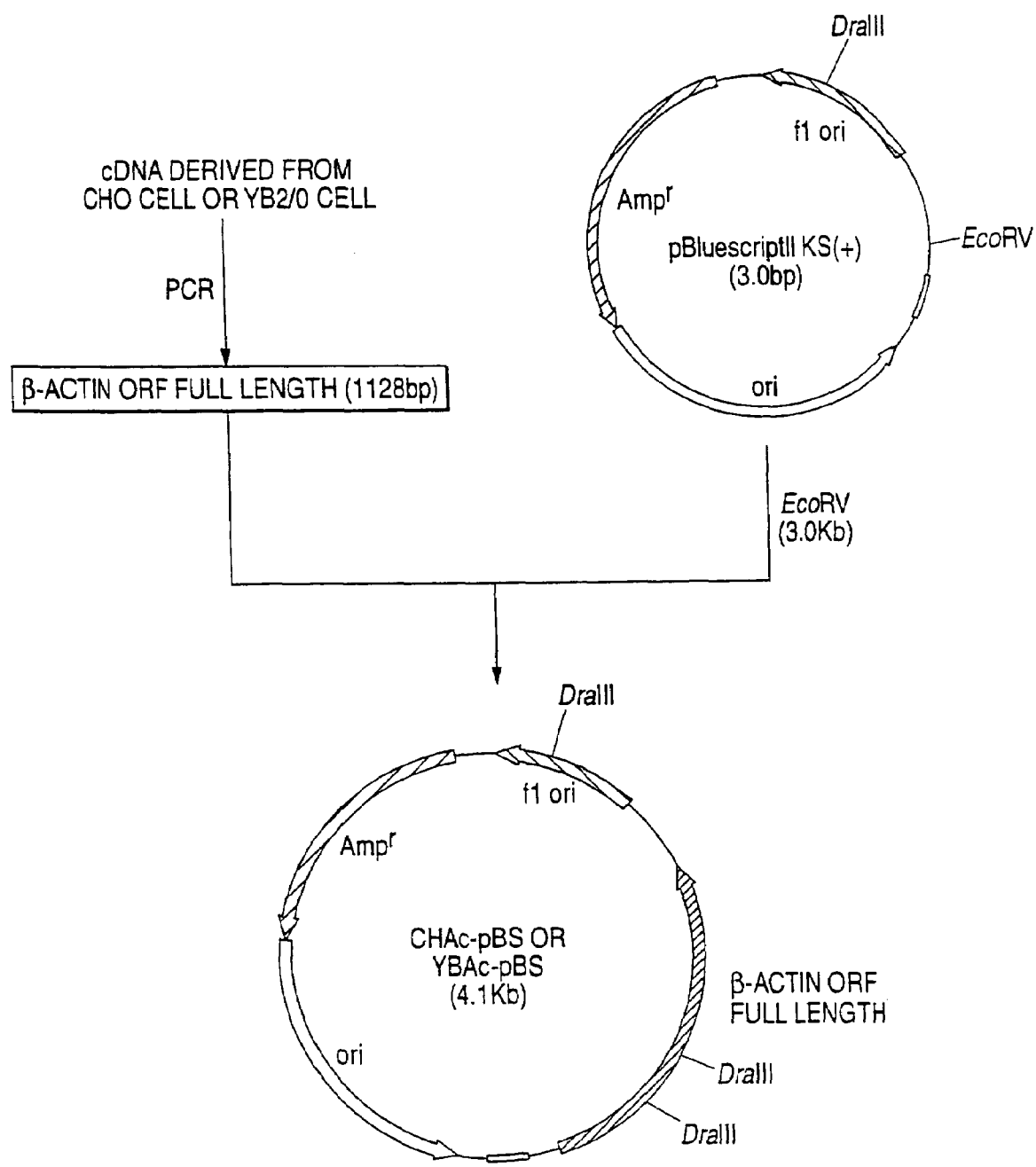
FIG. 21 shows construction of plasmids CHAc-pBS and YBAc-pBS.

Chinese hamster β-actin and rat β-actin cDNA were prepared by the following procedure (FIG. 21).

First, a forward primer specific for a common sequence containing translation Initiation codon (shown in SEQ ID NO:8) and reverse primers specific for respective sequences containing translation termination codon (shown in SEQ ID NOs:9 and 10) were designed from Chinese hamster β-actin genomic sequence (GenBank, U20114) and rat β-actin genomic sequence [*Nucleic Acids Research*, 11, 1759 (1983).

Next, 25 μl of a reaction solution [KOD buffer #1 (manufactured by Toyobo), 0.2 mmol/l dNTPs, 1 mmol/l $MgCl_2$, 0.4 μmol/l gene-specific primers (SEQ ID NOs:8 and 9, or SEQ ID NOs:8 and 10) and 5% DMSO] containing 1 μl of each of the cDNA prepared from CHO cell and cDNA prepared from YB2/0 cell, both obtained in the item (1) 2 days after culturing was prepared, and PCR was carried out using a DNA polymerase KOD (manufactured by Toyobo). The PCR was carried out by heating at 94° C. for 1 minute and subsequent 25 cycles of heating at 98° C. for 15 seconds, 65° C. for 2 seconds and 74° C. for 30 seconds as one cycle.

After the PCR, the reaction solution was subjected to 0.8% agarose gel electrophoresis, and a specific amplified fragment of 1128 bp was purified. The DNA fragment was subjected to DNA 5'-terminal phosphorylation using MEGALABEL (manufactured by Takara Shuzo) in accordance with the manufacture's instructions. The DNA fragment was recovered from the reaction solution using ethanol precipitation method and dissolved in 10 μl of sterile water.

Separately, 3 μg of a plasmid pBluescript II KS(+) (manufactured by Stratagene) was dissolved in 35 μl of NEBuffer 2

(manufactured by New England Biolabs), and 16 units of a restriction enzyme EcoRV (manufactured by Takara Shuzo) were added thereto for digestion reaction at 37° C. for 3 hours. To the reaction solution, 35 µl of 1 mol/l Tris-HCl buffer (pH 8.0) and 3.5 µl of *E. coli* C15-derived alkaline phosphatase (manufactured by Takara Shuzo) were added thereto, followed by reaction at 65° C. for 30 minutes to thereby dephosphorylate the DNA terminus. The reaction solution was extracted with phenol/chloroform, followed by ethanol precipitation, and the recovered DNA fragment was dissolved in 100 µl of sterile water.

Each 4 µl of the amplified fragment prepared from Chinese hamster cDNA or the amplified fragment (1192 bp) prepared from rat cDNA was nixed with 1 µl of the EcoRV-EcoRV fragment (about 3.0 Kb) prepared from plasmid pBluescript II KS(+) and 5 µl of Ligation High (manufactured by Toyobo) for ligation reaction at 16° C. for 30 minutes. Using the reaction solution, *E. coli* XL1-Blue was transformed, and plasmid DNA samples were isolated respectively in accordance with a known method from the obtained ampicillin-resistant clones.

The nucleotide sequence of each cDNA inserted into the plasmid was determined using DNA Sequencer 377 (manufactured by Parkin Elmer) and BigDye Terminator Cycle Sequencing FS Ready Reaction kit (manufactured by Parkin Elmer) in accordance with the method of the manufacture's instructions. It was confirmed that all of the inserted cDNAs of which sequences were determined by the method encode the ORF full sequences of Chinese hamster β-actin or rat β-actin. Among these, plasmid DNA samples containing absolutely no reading error of bases by the PCR in the sequences were selected. Herein, the plasmids are called CHAc-pBS and YBAc-pBS.

(4) Preparation of FUT8 Standard and Internal Control

In order to measure a transcription level of FUT8 gene mRNA in each cell, CHFT8-pCR2.1 or YBF-8-pCR2.1, as plasmids in which cDNA partial fragments prepared in the item (2) from Chinese hamster FUT8 or rat FUT8 were inserted Into pCR2.1, respectively, were digested with a restriction enzyme EcoRI, and the obtained linear DNAs were used as the standards for the preparation of a calibration curve CHFT8d-pCR2.1 and YBFT8d-pCR2.1, which were obtained from the CHFT8-pCR2.1 and YBFT 8-pCR2.1, by deleting 20.3 bp between ScaI and HindIII, an inner nucleotide sequence of Chinese hamster FUT8 and rat FUT8, respectively, were digested with a restriction enzyme EcoRI, and the obtained linear DNAs were used as the internal standards for FUT8 amount determination. Details thereof are described below.

Chinese hamster FUT8 and rat FUT8 standards were prepared as follows. In 40 µl of NEBuffer 2 (manufactured by New England Biolabs), 2 µg of the plasmid CHFT8-pCR2.1 was dissolved, 24 units of a restriction enzyme EcoRI (manufactured by Takara Shuzo) were added thereto, followed by digestion reaction at 37° C. for 3 hours. Separately, 2 µg of the plasmid YBFT8-pCR2.1 was dissolved in 40 µl of NEBuffer 2 (manufactured by New England Biolabs), and 24 units of a restriction enzyme EcoRI (manufactured by Takara Shuzo) were added thereto, followed by digestion reaction at 37° C. for 3 hours. By subjecting a portion of each of the reaction solutions to 0.8% agarose gel electrophoresis, it was confirmed that an EcoRI-EcoRI fragment (about 1 Kb) containing each of cDNA partial fragments of Chinese hamster FUT8 and rat FUT8 was separated from the plasmids CHFT8-pCR2.1 and YBFT8-pCR2.1 by the restriction enzyme digestion reactions. Each of the reaction solutions was diluted with 1 µg/ml of baker's yeast t-RNA (manufactured by SIGMA) to give a concentration of 0.02 fg/µl, 0.2 fg/µl, 1 fg/µl, 2 fg/µl, 10 fg/µl, 20 fg/µl and 100 fg/µl and used as the Chinese hamster FUT8 and rat FUT8 standards.

Internal standards of Chinese hamster FUT8 and rat FUT8 were prepared as follows (FIG. 22). A reaction solution [KOD buffer #1 (manufactured by Toyobo), 0.2 mmol/l dNTPs, 1 mmol/l MgCl$_2$, 0.4 µmol/l gene-specific primers (SEQ ID NOs:11 and 12) and 5% DMSO] containing 5 ng of CHFT8-pCR2.1 or YBFT8-pCR2.1 was prepared, and PCR was carried out using a DNA polymerase KOD (manufactured by Toyobo). The PCR was carried out by heating at 94° C. for 4 minutes and subsequent 25 cycles of heating at 98° C. for 15 seconds, 65° C. for 2 seconds and 74° C. for 30 seconds as one cycle. After the PCR, the reaction solution was subjected to 0.8% agarose gel electrophoresis, and a specific amplified fragment of about 4.7 Kb was purified. The DNA 5'-terminal was phosohorylated using MEGALABEL (manufactured by Takara Shuzo) in accordance with the manufacture's instructions, and then the DNA fragment was recovered from the reaction solution by ethanol precipitation and dissolved in 50 µl of sterile water. The obtained DNA fragment (5 µl, about 4.7 kb) and 5 µl of Ligation High (manufactured by Toyobo) were mixed, followed by self-cyclization reaction at 16° C. for 30 minutes.

Using the reaction solution, *E. coli* DH5α was transformed, and plasmid DNA samples were isolated in accordance with a known method from the obtained ampicillin-resistant clones. The nucleotide sequence of each plasmid DNA was determined using DNA Sequencer 377 (manufactured by Parkin Elmer) and BigDye Terminator Cycle Sequencing FS Ready Reaction kit (manufactured by Parkin Elmer), and it was confirmed that a 203 bp inner nucleotide sequence between ScaI and HindIII of Chinese hamster FUT8 or rat FUT8 was deleted. The obtained plasmids are referred to as CHFT8d-pCR2.1 or YBFT8d-pCR2.1, respectively.

Next, 2 µg of the plasmid CHFT8d-pCR2.1 was dissolved in 40 µl of NEBuffer 2 (manufactured by New England Biolabs), and 24 units of a restriction enzyme EcoRI (manufactured by Takara Shuzo) were added thereto, followed by digestion reaction at 37° C. for 3 hours. Separately, 2 µg of the plasmid YBFT8d-pCR2.1 was dissolved in 40 µl of NEBuffer 2 (manufactured by New England Biolabs), and 24 units of a restriction enzyme EcoRI (manufactured by Takara Shuzo) were added thereto, followed by digestion reaction at 37° C. for 3 hours. A portion of each of the reaction solutions was subjected to 0.8% agarose gel electrophoresis, and it was confirmed that an EcoRI-EcoRI fragment (about 800 bp) containing a fragment from which 203 bp of the inner nucleotide sequences of Chinese hamster FUT8 or rat FUT8 partial fragments was deleted was separated from the plasmids CHFT8d-pCR2.1 or YBFT8d-pCR2.1 by the restriction enzyme digestion reactions. Dilutions of 2 fg/µl were prepared from the reaction solutions using 1 µg/ml baker's yeast t-RNA (manufactured by SIGMA) and used as the Chinese hamster FUT8 or rat FUT8 internal controls.

(5) Preparation of β-Actin Standard and Internal Control

In order to measure the transcription amount of β-actin gene mRNA in various host cells, CHAc-pBS and YBAc-pBS, as plasmids in which the ORF full length of each cDNA of Chinese hamster β-actin and rat β-actin prepared in the item (3) was inserted into pBluescript II KS(+), respectively, were digested with restriction enzymes HindIII and PstI and restriction enzymes HindIII and KpnI, respectively, and the digested linear DNAs were used as the standards for the preparation of a calibration curve-CHAcd-pBS and YBAcd-pBS which were obtained from the CHAc-pBS and YBAc-pBS by deleting 180 bp between DraIII and DraIII of an inner nucleotide sequence of Chinese hamster β-actin and rat β-actin were digested with restriction enzymes HindIII and PstI and restriction enzymes HindIII and KpnI, respectively, and the digested linear DNAs were used as the internal standards for β-actin amount determination. Details thereof are described below.

Chinese hamster β-actin and rat β-actin standards were prepared as follows. In 40 μl of NEBuffer 2 (manufactured by New England Biolabs), 2 μg of the plasmid CHAc-pBS was dissolved, and 25 units of a restriction enzyme HindIII (manufactured by Takara Shuzo) and 20 units of PstI (manufactured by Takara Shuzo) were added thereto, followed by digestion reaction at 37° C. for 3 hours. Separately, 2 μg of the plasmid YBAc-pBS was dissolved in 40 μl of NEBuffer 2 (manufactured by New England Biolabs), and 25 units of a restriction enzyme HindIII (manufactured by Takara Shuzo) and 25 units of KpnI (manufactured by Takara Shuzo) were added thereto, followed by digestion reaction at 37° C. for 3 hours. A portion of each of the reaction solutions was subjected to 0.8% agarose gel electrophoresis, and it was confirmed that a HindIII-PstI fragment and a HindIII-KpnI fragment (about 1.2 Kb) containing the full length ORF of each cDNA of Chinese hamster β-actin and rat β-actin were separated from the plasmids CHAc-pBS and YBAc-pBS by the restriction enzyme digestion reactions. Each of the reaction solutions was diluted with 1 μg/ml baker's yeast t-RNA (manufactured by SIGMA) to give a concentration 2 pg/μl, 1 pg/μl, 200 fg/μl, 100 fg/μl and 20 fg/μl and used as the Chinese hamster β-actin and or β-actin standards.

Figure 23:
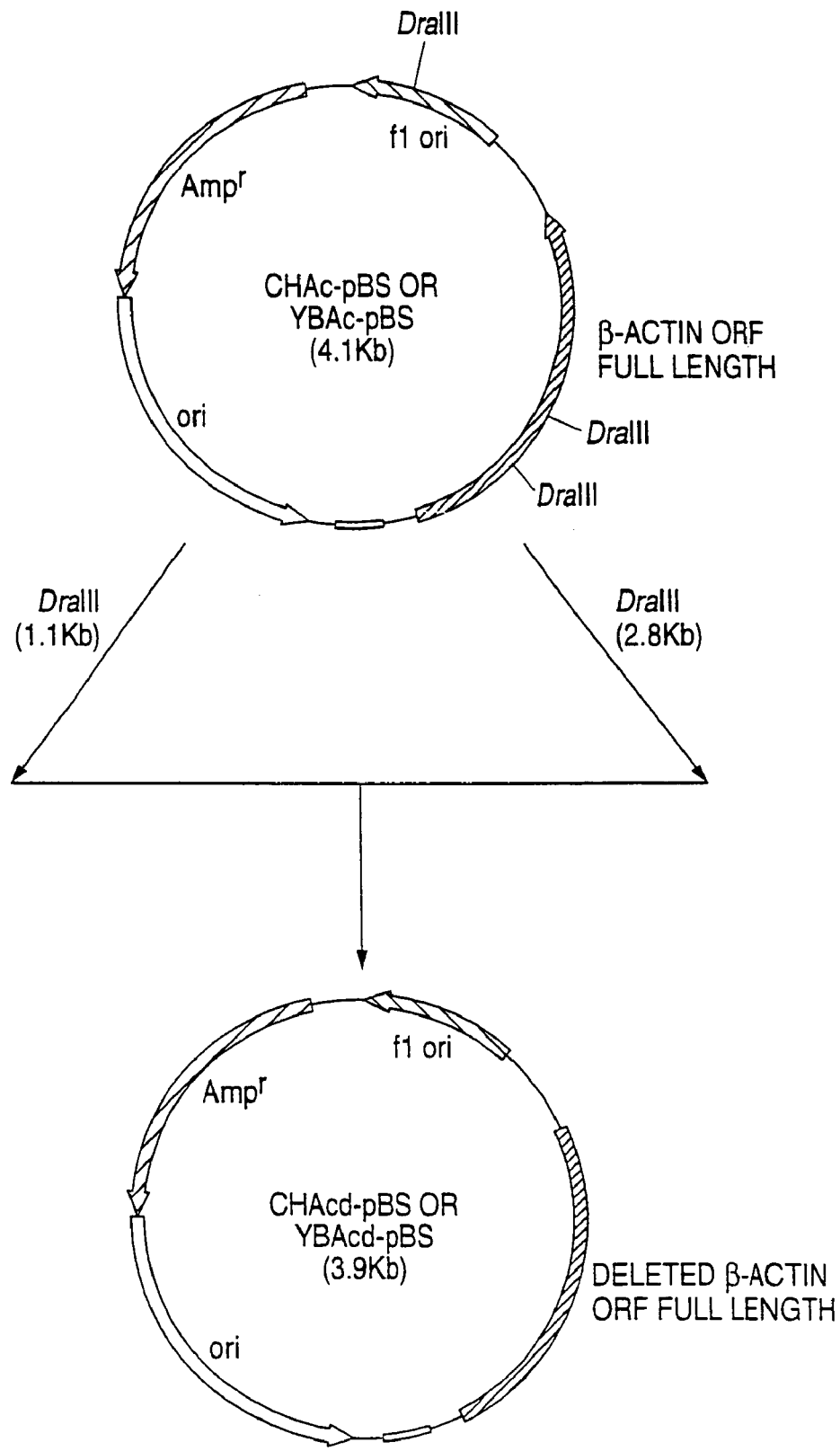
FIG. 23 shows construction of plasmids CHAcd-pBS and YBAcd-pBS.

Chinese hamster β-actin and rat β-actin internal standards were prepared as follows (FIG. 23). In 100 μl of NEBuffer 3 (manufactured by New England Biolabs) containing 100 ng/μl of BSA (manufactured by New England Biolabs), 2 μg of CHAc-pBS was dissolved, and 10 units of a restriction enzyme DraIII (manufactured by New England Biolabs) were added thereto, followed by digestion reaction at 37° C. for 3 hours. DNA fragments were recovered from the reaction solution by ethanol precipitation and the DNA termini were changed to blunt ends using DNA Blunting Kit (manufactured by Takara Shuzo) in accordance with the manufacture's instructions, and then the reaction solution was divided into two equal parts. First, to one part of the reaction solution, 35 μl of 1 mol/l Tris-HCl buffer (pH 8.0) and 3.5 μl of *E. coli* C15-derived alkaline phosphatase (manufactured by Takara Shuzo) were added thereto, followed by reaction at 65° C. for 30 minutes for dephosphorylating the DNA termini. The DNA fragment was recovered by carrying out dephosphorylation treatment, phenol/chloroform extraction treatment and ethanol precipitation treatment and then dissolved in 10 μl of sterile water. The remaining part of the reaction solution was subjected to 0.8% agarose gel electrophoresis to purify a DNA fragment of about 1.1 Kb containing the ORF partial fragment of Chinese hamster β-actin.

The dephosphorylated DraIII-DraIII fragment (4-5 μl), 4.5 μl of the DraIII-DraIII fragment of about 1.1 Kb and 5 μl of Ligation High (manufactured by Toyobo) were mixed, followed by ligation reaction at 16° C. for 30 minutes. Using the reaction solution, *E. coli* DH5α was transformed, and plasmid DNAs were isolated in accordance with a known method from the obtained ampicillin-resistant clones. The nucleotide sequence of each plasmid DNA was determined using DNA Sequencer 377 (manufactured by Parkin Elmer) and BigDye Terminator Cycle Sequencing FS Ready Reaction kit (manufactured by Parkin Elmer), and it was confirmed that a Chinese hamster β-actin DraIII-DraIII 180 bp inserted into the plasmid was deleted. The plasmid is referred to as CHAcd-pBS.

Also, a plasmid in which rat β-actin DraIII-DraIII 180 bp was deleted was prepared via the same steps of CHAcd-pBS. The plasmid is referred to as YBAcd-pBS.

Next, 2 μg of the plasmid CHAcd-pBS was dissolved in 40 μl of NEBuffer 2 (manufactured by New England Biolabs), and 25 units of a restriction enzyme HindIII (manufactured by Takara Shuzo) and 20 units of PstI (manufactured by Takara Shuzo) were added thereto, followed by digestion reaction at 37° C. for 3 hours. Separately, 2 μg of the plasmid YBAcd-pBS was dissolved in 40 μl of NEBuffer 2 (manufactured by New England Biolabs), and 25 units of a restriction enzyme HindIII (manufactured by Takara Shuzo) and 24 units of KpnI (manufactured by Takara Shuzo) were added thereto, followed by digestion reaction at 37° C. for 3 hours. A portion of each of the reaction solutions was subjected to 0.8% agarose gel electrophoress, and it was confirmed that an HindIII-PstI fragment and HindIII-KpnI fragment (about 1.0 Kb) containing a fragment in which 180 bp of the inner nucleotide sequence of the ORF full length of each cDNA of Chinese hamster β-actin and rat β-actin was deleted were separated from the plasmids CHAcd-pBS and YBAcd-pBS by the restriction enzyme digestion reactions. Dilutions of 200 fg/μl were prepared from the reaction solutions using 1 μg/ml baker's yeast t-RNA (manufactured by SIGMA) and used as the Chinese hamster β-actin and rat β-actin internal controls.

(6) Determination of Transcription Amount by Competitive PCR

Competitive PCR was carried out using the FUT8 internal control DNA prepared in the item (4) and the host cell-derived cDNA obtained in the item (1) as the templates, the determined value of the FUT8 transcription product in the host cell line was calculated from the relative value of the amount of the amplified product derived from each template. On the other hand, since it is considered that the β-actin gene is transcribed continuously in each cell and its transcription level is approximately the same between cells, transcription level of the β-actin gene was determined as a measure of the efficiency of synthesis reaction of cDNA in each host cell line. That is, the PCR was carried out using the β-actin internal control DNA prepared in the item (5) and the host cell-derived cDNA obtained in the item (1) as the templates, the determined value of the β-actin transcription product in the host cell line was calculated from the relative value of the amount of the amplified product derived from each template Details thereof are described below.

The FUT8 transcription product was determined by the following procedure. First, a set of sequence-specific primers (shown in SEQ ID NOs:13 and 14) common to the inner sequences of the ORF partial sequences of Chinese hamster FUT8 and rat FUT8 obtained in the item (2) were designed.

Next, PCR was carried out using a DNA polymerase ExTaq (manufactured by Takara Shuzo) in 20 μl in total volume of a reaction solution [ExTaq buffer (manufactured by Takara Shuzo), 0.2 mmol/l dNTPs, 0.5 μmol/l gene-specific primers (SEQ ID NOs:13 and 14) and 5% DMSO] containing 5 μl of 50 folds-diluted cDNA solution prepared from each of respective host cell line in the item (i) and 5 μl (10 fg) of the plasmid for internal control. The PCR was carried out by heating at 94° C. for 3 minutes and subsequent 32 cycles of heating at 94° C. for 1 minute, 60° C. for 1 minute and 72° C. for 1 minute as one cycle.

Also, PCR was carried out in a series of reaction in which 5 μl (0.1 fg, 1 fg, 5 fg, 10 fg, 50 fg, 100 fg, 500 fg or 1 pg) of the FUT8 standard plasmid obtained in the item (4) was added instead of the each host cell line-derived cDNA, and used in the preparation of a calibration curve for the FUT8 transcription level.

The β-actin transcription product was determined by the following procedure. First, two sets of respective gene-specific primers common to the inner sequences of the ORF full lengths of Chinese hamster β-actin and rat β-actin obtained in the item (3) were designed (the former are shown in SEQ ID NOs:15 and 16, and the latter are shown in SEQ ID NOs:17 and 18).

Next, PCR was carried out using a DNA polymerase ExTaq (manufactured by Takara Shtuzo) in 20 μl in total volume of a reaction solution [ExTaq buffer (manufactured by Takara Shuzo), 0.2 mmol/l dNTPs, 0.5 μmol/l gene-specific primers (SEQ ID NOs:15 and 16, or SEQ ID NOs:17 and 18) and 5% DMSO) containing 5 μl of 50 folds-diluted cDNA solution prepared from respective host cell line in the item (1) and 5 μl (1 pg) of the plasmid for internal control. The PCR was carried out by heating at 94° C. for 3 minutes and subsequent 17 cycles of heating at 94° C. for 30 seconds, 65° C. for 1 minute and 72° C. for 2 minutes as one cycle.

Also, PCR was carried out in a series of reaction in which 5 μl (10 pg, 5 pg, 1 pg, 500 fg or 100 fg) of the β-actin standard plasmid obtained in the item (5) was added instead of the each host cell line-derived cDNA, and used in the preparation of a calibration curve for the β-actin transcription level.

TABLE 3

| Target gene | Primer set * | Size (bp) of PCR amplification product | |
|---|---|---|---|
| | | Target | Competitor |
| FUT8 | F: 5'-GTCCATGGTGATCCT GCAGTGTGG-3'<br>R: 5'-CACCAATGATATCTC CAGGTTCC-3' | 638 | 431 |
| β-Actin (Chinese hamster) | F: 5'-GATATCGCTGCGCTC GTTGTCGAC-3'<br>R: 5'-CAGGAAGGAAGGCTG GAAAAGAGC-3' | 789 | 609 |
| β-Actin (Rat) | F: 5'-GATATCGCTGCGCTC GTCGTCGAC-3'<br>R: 5'-CAGGAAGGAAGGCTG GAAGAGAGC-3' | 789 | 609 |

* F: forward primer, R: reverse primer

By carrying out PCR using the primer set described in Table 3, a DNA fragment having a size shown in the target column of Table 3 can be amplified from each gene transcription product and each standard, and a DNA fragment having a size shown in the competitor column of Table 3 can be amplified from each internal control.

A 7 μl portion of each of the solutions after PCR was subjected to 1.75% agarose gel electrophoresis, and then the gel was stained by soaking it for 30 minutes in 1× concentration SYBR Green I Nucleic Acid Gel Stain (manufactured by Molecular Probes). The amount of the amplified DNA fragment was measured by calculating luminescence intensity of each amplified DNA using a fluoro-imager (FluorImacer SI; manufactured by Molecular Dynamics).

The amount of an amplified product formed by PCR using a standard plasmid as the template was measured by the method, and a calibration curve was prepared by plotting the measured values against the amounts of the standard plasmid.

Using the calibration curve, the amount of cDNA of a gene of interest in each cell line was calculated from the amount of the amplified product when each expression cell line-derived cDNA was used as the template, and the amount was defined as the mRNA transcription amount in each cell line.

Figure 24:
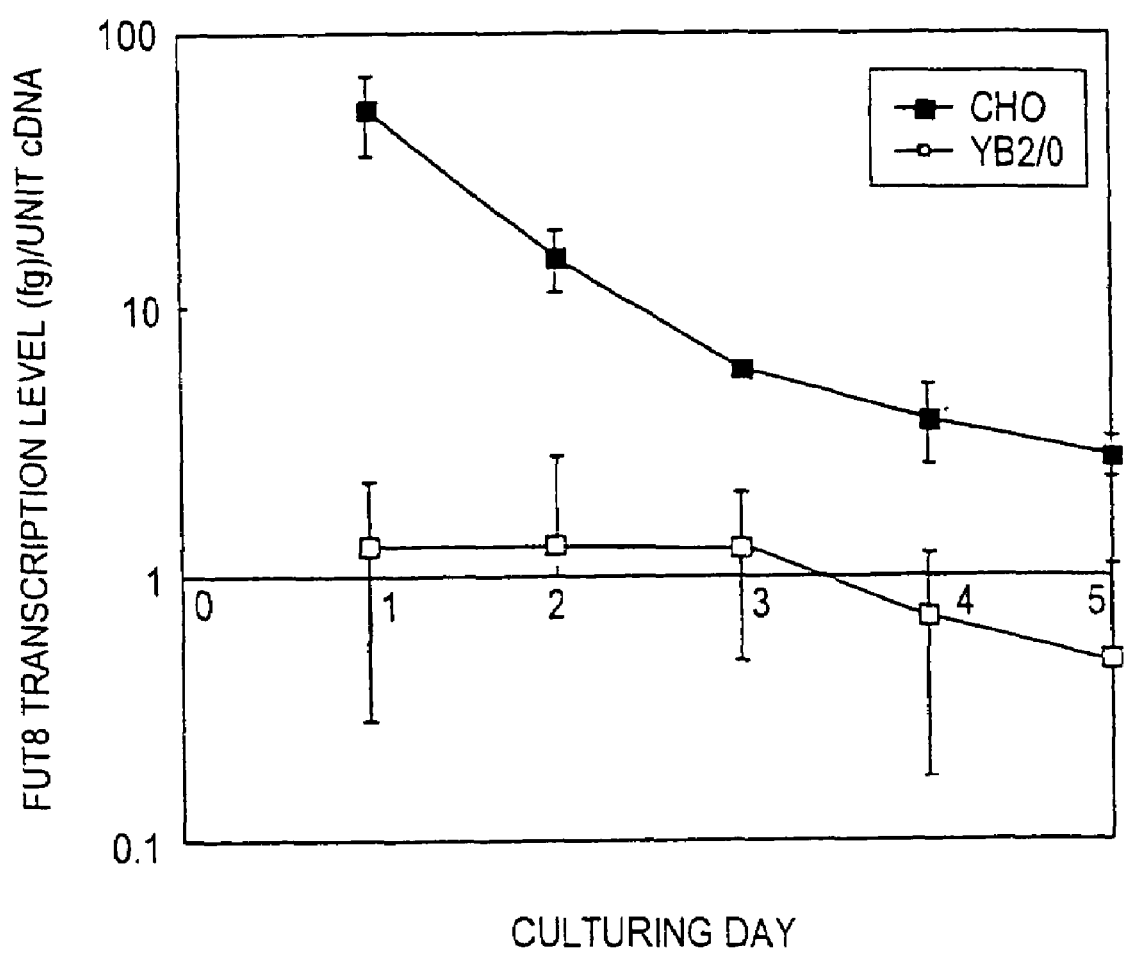
FIG. 24 shows results of determination of an FUT8 transcription product in each host cell line using competitive RT-PCR. Amounts of the FUT8 transcription product in each host cell line when rat FUT8 sequence was used as the standard and internal control are shown. "■" and "□" show results when CHO cell line and YB2/0 cell line, respectively, were used as the host cell.

The amount of the FUT8 transcription product in each host cell line when a rat FUT8 sequence was used in the standard and internal control is shown in FIG. 24. Throughout the culturing period, the CHO cell line showed a transcription amount 10 folds or higher than that of the YB2/0 cell line. The tendency was also found when a Chinese hamster FUT8 sequence was used in the standard and internal control.

Also, the FUT8 transcription amounts are shown in Table 4 as relative values to the amount of the β-actin transcription product. Throughout the culturing period, the FUT8 transcription amount in the YB2/0 cell line was around 0.1% of β-actin while it was 0.5% to 2% in the CHO cell line.

The results shows that the amount of the FUT8 transcription product in YB2/0 cell line was significantly smaller than that in the CHO cell line.

TABLE 4

| Cell line | Culture days | | | | |
|---|---|---|---|---|---|
| | 1st | 2nd | 3rd | 4th | 5th |
| CHO | 1.95 | 0.90 | 0.57 | 0.52 | 0.54 |
| YB2/0 | 0.12 | 0.11 | 0.14 | 0.08 | 0.07 |

EXAMPLE 10

Determination of Transcription Product of A-1,6-Fucosyltransferase (FUT8) Gene in Anti-Ganglioside GD3 Chimeric Antibody-Producing Cell Line (1) Preparation of Single-Stranded cDNA from Various Antibody-Producing Cell Lines Single-stranded cDNA was prepared from anti-ganglioside GD3 chimeric antibody-producing cell lines DCHI01-20 and 61-33 as follows. The DCHI01-20 is a transformant clone derived from the CHO/DG44 cell described in item 2(2) of Example 1. Also, the 61-33 is a clone obtained by carrying out serum-free adaptation of YB2/0-derived transformant cell 7-9-51 (FERM BP-6691, International Patent Organism Depositary, National Institute of Advanced Industrial Science and Technology (AIST Tsukuba Central 6, 1-1, Higashi 1-Chome Tsukuba-shi, Ibaraki-ken 305-8566 Japan)] and then carrying out single cell isolation by two limiting dilution.

Cells of the DCHI01-20 were suspended in EXCELL 302 medium (manufactured by JRH BIOSCIENCES) supplemented with 3 mmol/l L-GLN (manufactured by Life Technologies), 0.3% PLURONIC F-68 (manufactured by Life Technologies), and 0.5% fatty acid concentrate (manufactured by Life Technologies), and 15 ml of the suspension was Inoculated into T75 flask for suspension cell culture use (manufactured by Greiner) at a density of 2×10$^5$ cells/ml. Also, cells of the 61-33 were suspended in Hybridoma-SFM medium (manufactured by Life Technologies) supplemented with 0.2% bovine serum albumin fraction V (manufactured by Life Technologies) (hereinafter referred to as "BSA"), and 15 ml of the suspension was inoculated into T75 flask for suspension cell culture (manufactured by Greiner) at a density of 2×10$^5$ cells/ml. They were cultured at 37° C. in a 5% CO$_2$ incubator, and 1, 2, 3, 4 and 5 days after culturing, 1×10$^7$ of respective host cells were recovered to extract total RNA using RNAeasy (manufactured by QIAGEN) in accordance with the manufacturers instructions.

The total RNA was dissolved in 45 µl of sterile water, and 1 µe of RQ1 RNase-Free DNase (manufactured by Promega), 5 µl of the attached 10× DNase buffer and 0.5 µl of RNasin Ribonuclease Inhibitor (manufactured by Promega) were added thereto, followed by reaction at 37° C. for 30 minutes to degrade genome DNA contaminated in the sample. After the reaction, the total RNA was purified again using RNAeasy (manufactured by QIAGEN) and dissolved in 50 µl of sterile water.

In a 20 µl reaction mixture using oligo(dT) as a primer, single-stranded cDNA was synthesized from 3 µg of each of the obtained total RNA samples by reverse transcription reaction using SUPERSCRIPT™ Preamplification System for First Strand cDNA Synthesis (manufactured by Life Technologies) in accordance with the manufacture's instructions. The reaction solution was diluted 50 folds with water and stored at −80° C. until use.

(2) Determination of Transcription Amounts of Each Gene by Competitive PCR

The transcription amount of each of the genes on the cDNA derived from the antibody-producing cell line obtained in the item (1) was determined by competitive PCR in accordance with Example 9(6).

The FUT8 gene-derived mRNA transcription amount in each of the antibody-producing cell lines was determined by the following procedure.

CHFT8-pCR2.1 and YBFT8-pCR2.1, as plasmids in which cDNA partial fragments prepared in Example 9(2) from Chinese hamster FUT8 and rat FUT8, respectively, were inserted into pCR2.1, were digested with a restriction enzyme EcoRI, and the obtained linear DNAs were used as the standards in the preparation of a calibration curve for determining the FUT8 transcription amount CHFT8d-pCR2.1 and YBFT8d-pCR2.1, which were obtained by deleting 203 bp between ScaI and HindIII of an inner nucleotide sequence of Chinese hamster FUT8 and rat FUT8, respectively, in Example 9(4) were digested with a restriction enzyme EcoRI, and the obtained linear DNAs were used as the internal standards for FUT8 amount determination.

PCR was carried out using a DNA polymerase ExTaq (manufactured by Takara Shuzo) in 20 µl in total volume of a reaction solution [ExTaq buffer (manufactured by Takara Shuzo), 0.2 mmol/l dNTPs, 0.5 mol/l FUT8 gene-specific primers (SEQ ID NOs:13 and 14) and 5% DMSO] containing 5 µl of 50 folds-diluted cDNA solution prepared from each of the antibody-producing cell line in the item (1) and 5 µl (10 fg) of the plasmid for internal control. The PCR was carried out by heating at 94° C. for 3 minutes and subsequent 32 cycles of heating at 94° C. for 1 minute, 60° C. for 1 minute and 72° C. for 1 minute as one cycle.

Also, PCR was carried out in a series of reaction in which 5 µl (0.1 fg, 1 fg, 5 fg, 10 fg, 50 fg, 100 fg, 500 fg or 1 pg) of the FUT8 standard plasmid was added instead of the each antibody-producing cell line-derived cDNA, and used in the preparation of a calibration curve for the FUT8 transcription amount. In this case, 1 µg/ml of a baker's yeast t-RNA (manufactured by SIGMA) was used for the dilution of the standard plasmid.

On the other hand, since it is considered that the β-actin gene is transcribed constantly in each cell and its transcription amount is approximately the same between cells, the transcription amount of the β-actin gene was determined as an index of the efficiency of synthesis reaction of cDNA in each antibody-producing cell line.

CHAc-pBS and YBAc-pBS as plasmids in which the ORF full length of each cDNA of Chinese hamster β-actin and rat β-actin prepared in Example 9(3) were inserted into pBluescript II KS(+), respectively, were digested with restriction enzymes HindIII and KpnI, and the obtained linear DNA samples were used as the standards in the preparation of a calibration curve for determining the β-actin transcription amount.

CHAcd-pBS and YBAcd-pBS which were obtained by deleting 180 bp between DraI and DraI of an inner nucleotide sequence of Chinese hamster β-actin and rat β-actin, respectively in Example 9(5), were digested with restriction enzymes HindIII and KpnI, and the obtained linear DNAs were used as the internal standards for β-actin determination.

PCR was carried out using a DNA polymerase ExTaq (manufactured by Takara Shuzo) in 20 µl in total volume of a reaction solution [ExTaq buffer (manufactured by Takara Shuzo), 0.2 mmol/l dNTPs, 0.5 µmol/l β-actin-specific primers (SEQ ID NOs:17 and 18) and 5% DMSO] containing 5 µl of 50 folds-diluted cDNA solution prepared from each of the antibody-producing cell lines and 5 µl (1 pg) of the plasmid for internal control. The PCR was carried out by heating at 94° C. for 3 minutes and subsequent 17 cycles of heating at 94° C. for 30 seconds, 65° C. for 1 minute and 72° C. for 2 minutes as one cycle. Also, PCR was carried out in a series of reaction in which 10 pg, 5 pg, 1 pg, 500 fg or 100 fg of the β-actin standard plasmid was added instead of the each antibody-producing cell line-derived cDNA, and used in the preparation of a calibration curve for the β-actin transcription amount. In this case, 1 µg/ml of a baker's yeast t-RNA (manufactured by SIGMA) was used for the dilution of standard plasmid.

By PCR using the primer set described in Table 3, a DNA fragment having a size shown in the target column of Table 3 can be amplified from each gene transcription product and each standard, and a DNA fragment having a size shown in the competitor column of Table 3 can be amplified from each internal control.

A 7 µl portion of each of the solutions after PCR was subjected to 1.75% agarose gel electrophoresis, and then the gel was stained by soaking it for 30 minutes in 1× concentration SYBR Green I Nucleic Acid Gel Stain (manufactured by Molecular Probes). The amount of the amplified DNA fragment was measured by calculating luminescence intensity of each amplified DNA using a fluoro-imager (FluorImager SI; manufactured by Molecular Dynamics).

The amount of the amplified product formed by PCR which used a standard plasmid as the template was measured by the method, and a calibration curve was prepared by plotting the measured values against the amounts of the standard plasmid. Using the calibration curve, the amount of cDNA of a gene of interest in each cell line was calculated from the amount of the amplified product when each antibody-producing cell line-derived cDNA was used as the template, and the value was defined as the mRNA transcription amount in each cell line.

The FUT8 transcription amounts are shown in Table 5 as relative values to the amount of the β-actin transcription product. Throughout the culturing period, the FUT8 transcription amount in the YB2/0 cell-derived antibody-producing 61-33 was 0.3% or less of β-actin while it was 0.7% to 1.5% in the CHO cell-derived antibody-producing cell.

The results shows that the amount of the FUT8 transcription product in the YB2/0 cell-derived antibody-producing cell line was significantly less than that in the antibody-producing cell line derived from the CHO cell.

TABLE 5

| Cell line | Culture days | | | | |
|---|---|---|---|---|---|
| | 1st | 2nd | 3rd | 4th | 5th |
| DCHI01-20 | 0.75 | 0.73 | 0.99 | 1.31 | 1.36 |
| 61-33 | 0.16 | 0.19 | 0.24 | 0.30 | <0.10 |

EXAMPLE 11

Preparation of Mouse α-1,6-Fucosyltransferase (FUT8) Gene Over-Expressing Cell Line (1) Construction of Mouse α-1,6-Fucosyltransferase (FUT8) Expression Plasmid Total RNA was extracted from 1×10⁷ cells of a mouse myeloma NS0 cell (RCB0213, Cell Bank at The Institute of Physical and Chemical Research) subcultured using IMDM medium (manufactured by Life Technologies) containing 10% fetal bovine serum (manufactured by Life Technologies), using RNAeasy (manufactured by QIAGEN) in accordance with the manufacture's instructions. The total RNA was dissolved in 45 µl of sterile water, and 1 µl of RQ1 RNase-Free DNase (manufactured by Promega), 5 µl of the attached 10× DNase buffer and 0.5 µl of RNasin Ribonuclease Inhibitor (manufactured by Promega) were added thereto, followed by reaction at 37° C. for 30 minutes to degrade genome DNA contaminated in the sample. After the reaction, the total RNA was purified again using RNAeasy (manufactured by QIAGEEN) and dissolved in 50 µl of sterile water. In a 20 µl reaction mixture using oligo(dT) as a primer, single-stranded cDNA was synthesized from 3 µg of the obtained total RNA by reverse transcription reaction using SUPERSCRIPT™ Preamplification System for First Strand cDNA Synthesis (manufactured by Life Technologies) in accordance with the manufacturers instructions.

Figure 25:
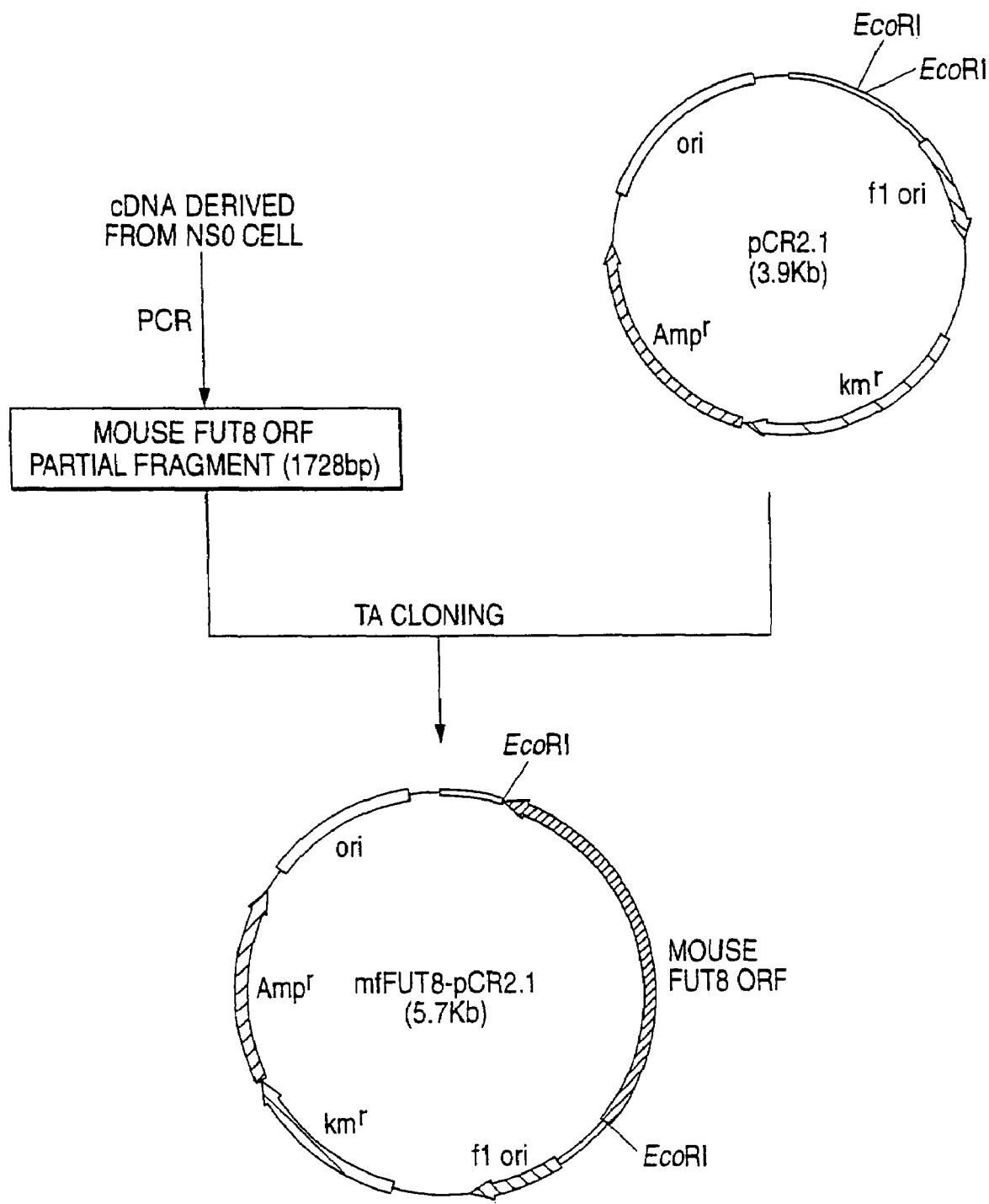
FIG. 25 shows construction of a plasmid mfFUT8-pCR2.1.

Mouse FUT8 cDNA was prepared by the following procedure (FIG. 25).

First, a forward primer specific for a sequence containing a translation initiation codon (shown in SEQ ID NO:19) and a reverse primer specific for a sequence containing translation termination codon (shown in SEQ ID NO:20) were designed from a mouse FUT8 cDNA sequence (GenBank, AB025198).

Next, 25 µl of a reaction solution [ExTaq buffer (manufactured by Takara Shuzo), 0.2 mmol/l dNTPs, 4% DMSO and 0.5 µmol/l specific primers (SEQ ID NO:19 and SEQ ID NO:20)] containing 1 µl of the NS0 cell-derived cDNA was prepared, and PCR was carried out using a DNA polymerase ExTaq (manufactured by Takara Shuzo) The PCR was carried out by heating at 94° C. for 1 minute, subsequent 30 cycles of heating at 94° C. for 30 seconds, 55° C. for 30 seconds and 72° C. for 2 minutes as one cycle, and final heating at 72° C. for 10 minutes.

After the PCR, the reaction solution was subjected to 0.8% agarose gel electrophoresis, and a specific amplified fragment of 1728 bp was purified into a plasmid pCR2.1, 4 µl of the DNA fragment was employed to insert in accordance with the manufacturer's instructions attached to TOPO TA Cloning Kit (manufactured by Invitrogen), and *E. Coli* DH5α was transformed with the reaction solution. Plasmid DNAs were isolated in accordance with a known method from cDNA-inserted 6 clones among the obtained kanamycin-resistant colonies.

The nucleotide sequence of each cDNA inserted into the plasmid was determined using DNA Sequencer 377 (manufactured by Parkin Elmer) and BigDye Terminator Cycle Sequencing FS Ready Reaction kit (manufactured by Parkin Elmer) in accordance with the-method of the manufacture's instructions. It was confirmed that all of the inserted cDNAs of which sequences were determined encode the ORF full sequence of mouse FUT8. Among these, a plasmid DNA containing absolutely no reading error of bases by the PCR in the sequences were selected (its DNA sequence and amino acid sequence are shown in SEQ ID NOs:2 and 24, respectively). Also, inconsistency of 3 bases due to amino acid substitution was found in the sequence when compared with the mouse FUT8 sequence registered on GenBank. Herein, the plasmid is referred to mfFUT8-pCR21.

Figure 26:
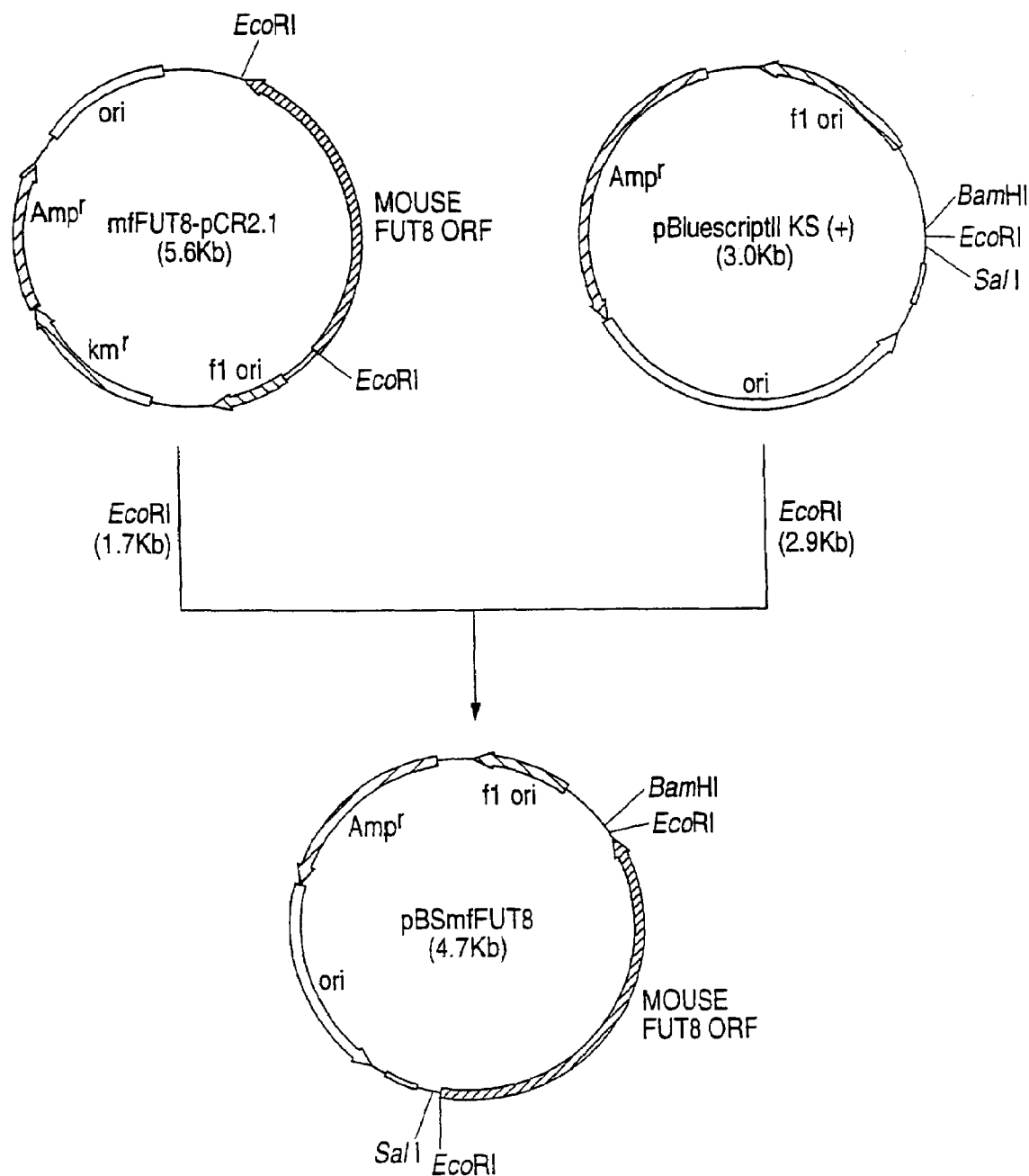
FIG. 26 shows construction of a plasmid pBSmfFUT8.

Next, a plasmid pBSmfFUT8 containing the ORF full sequence of mouse FUT8 was constructed as follows (FIG. 26). First, 1 µg of a plasmid pBluescript II KS(+) (manufactured by Stratagene) was dissolved in 35 µl of NEBuffer 2 (manufactured by New England Biolabs), and 20 units of a restriction enzyme EcoRI (manufactured by Takara Shuzo) were added thereto, followed by digestion reaction at 37° C. for 2 hours. To the reaction solution, 35 µl of 1 mol/l Tris-HCl buffer (pH 8.0) and 3.5 µl of *E. coli* C15-derived alkaline phosphatase (manufactured by Takara Shuzo) were added, followed by reaction at 65° C. for 30 minutes for dephosphorylate the DNA termini. The reaction solution was extracted with phenol/chloroform, followed by ethanol precipitated, and the recovered DNA fragment was dissolved in 10 µl of sterile water.

Separately, 1 µg of the plasmid mfFUT8-pCR2.1 was dissolved in 35 µl of NEBuffer 2 (manufactured by New England Biolabs), and 20 units of a restriction enzyme EcoRI (manufactured by Takara Shuzo) were added thereto, followed by digestion reaction at 37° C. for 2 hours. The reaction solution was subjected to 0.8% agarose gel electrophoresis to purify a DNA fragment of about 1.7 Kb containing the ORF full sequence of mouse FUT8 cDNA.

The obtained plasmid pBluescript II KS(+)-derived EcoRI-EcoRI fragment (1 µl, 2.9 Kb), 4 µl of the EcoRI-EcoRI fragment (17 Kb) prepared from the plasmid mfFUT8-pCR2.1. and 5 µl of Ligation High (manufactured by Toyobo) were mixed, followed by ligation reaction at 16° C. for 30 minutes. Using the reaction solution, *E. coli* DH5α was transformed, and, plasmid DNAs were isolated in accordance with a known method from the obtained ampicillin-resistant clones Herein, the plasmid is referred to pBSmfFUT8.

Figure 27:
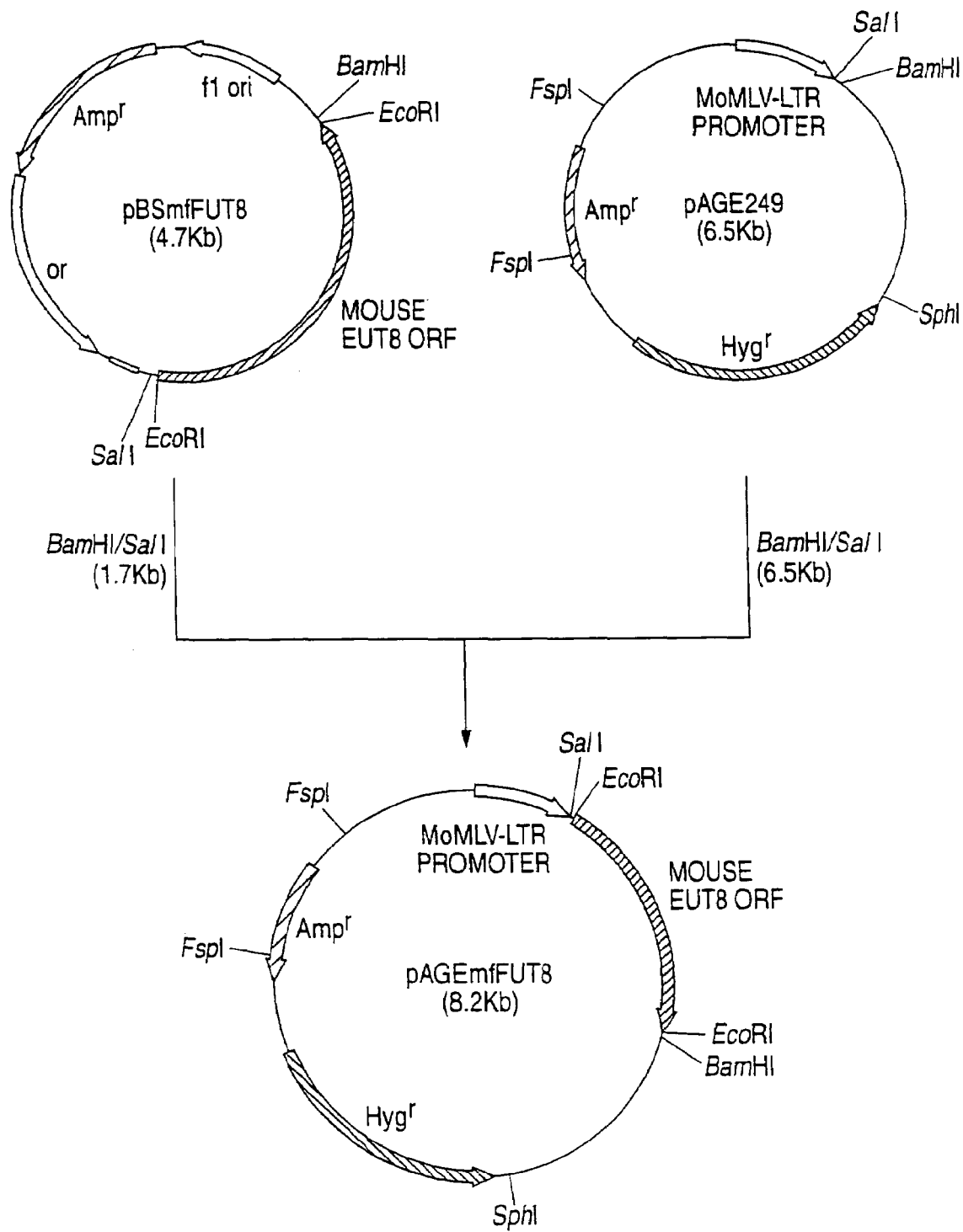
FIG. 27 shows construction of a plasmid pAGEmfFUT8.

Using the pBSmfFUT8 and pAGE249, a mouse FUT8 expression vector pAGEmfFUT8 was constructed by the following procedure (FIG. 27). The pAGE249 is a derivative of pAGE248 [*J. Biol. Chem.*, 269, 14730 (1994)], as a vector in which an SphI-SphI fragment (2.7 Kb) containing a dihydrofolate reductase gene (dhfr) expression unit was removed from the pAGE248.

In 50 µl of Universal Buffer H (manufactured by Takara Shuzo), 1 µg of-the pAGE249 was dissolved, and 20 units of a restriction enzyme SalI (manufactured by New England Biolabs) were added thereto, followed by digestion reaction at 37° C. for 2 hours. A DNA fragment was recovered from the reaction solution by ethanol precipitation and dissolved in 35 µl of NEBuffer 2 (manufactured by New England Biolabs), and 20 units of a restriction enzyme BamHI (manufactured by New England Biolabs) were added thereto, followed by digestion reaction at 37° C. for 2 hours. After the digestion reaction, to the reaction solution, 35 µl of 1 mol/l Tris-HCl buffer (pH 8.0) and 3.5 µl of *E. coli* C15-derived alkaline phosphatase (manufactured by Takara Shuzo) were added thereto, followed by reaction at 65° C. for 30 minutes to dephosphorylate the DNA termini. The reaction solution was extracted with phenol/chloroform extraction, followed by ethanol precipitation, and the recovered DNA fragment was dissolved in 10 µl of sterile water.

Separately, 1 µg of pBSmfFUT8 was dissolved in 50 µl of Universal Buffer H (manufactured by Takara Shuzo), and 20 units of a restriction enzyme SalI (manufactured by New England Biolabs) were added thereto, followed by digestion reaction at 37° C. for 2 hours. A DNA fragment was recovered from the reaction solution by ethanol precipitation and dissolved in 35 µl of NEBuffer 2 (manufactured by New England Biolabs), and 20 units of a restriction enzyme BamHI (manufactured by New England Biolabs) were added thereto, followed by digestion reaction at 37° C. for 2 hours. After the digestion reaction, the solution was subjected to 0-8% agarose gel electrophoresis to purify a DNA fragment of about 1.7 Kb containing the ORF full sequence of mouse FUT8 cDNA.

The obtained plasmid pAGE249-derived BamHI-SalI fragment (1 µl, 6.5 Kb), 4 µl of the BamHI-SalI fragment (1.7 Kb) prepared from the plasmid pBSmfFUT8 and 5 µl of Ligation. High (manufactured by Toyobo) were mixed, followed by ligation reaction at 16° C. for 30 minutes. Using the reaction solution, $E.\ coli$ DH5α was transformed, and a plasmid DNA was isolated in accordance with a known method from the obtained ampicillin-resistant clones. Herein, the plasmid is referred to pAGEmfFUT8.

(2) Preparation of Mouse α-1,6-Fucosyltransferase (FUT8) Gene Over-Expressing Cell Line A stable FUT8 gene-expressing cell line was obtained by introducing the mouse FUT8 expression vector pAGEmfFUT8 constructed in the item (1) into 61-33. The 61-33 is a clone obtained by carrying out serum-free adaptation of a transformant cell 7-9-51 (FERM BP-6691, International Patent Organism Depositary, National Institute of Advanced Industrial Science and Technology) derived from a YB2/0 cell highly producing an anti-ganglioside GD3 chimeric antibody, and then carrying out single cell isolation by two limiting dilution.

The plasmid pAGEmfFUT8 was transferred into 61-33 by the following procedure in accordance with the electroporation [$Cytotechnology$, 3, 133 (1990)] First, 30 µg of the plasmid pAGEmfFUT8 was dissolved in 600 µl of NEBuffer 4 (manufactured by New England Biolabs), and 100 units of a restriction enzyme FspI (manufactured by New England Biolabs) were added thereto, followed by digestion reaction at 37° C. for 2 hours to obtain a linear fragment. The reaction solution was subjected to ethanol precipitation, and the recovered linear plasmid was made into a 1 µg/µl aqueous solution. Next, the 61-33 was suspended in a K-PBS buffer (137 mol/l KCl, 2.7 mol/l NaCl, 8.1 mol/l $Na_2HPO_4$, 1.5 mol/l $KH_2PO_4$, 4.0 mol/l $MgCl_2$) to give a density of $2\times10^7$ cells/ml, and 200 µl of the cell suspension ($4\times10^6$ cells) was mixed with 10 µl (10 Fg) of the linear plasmid. The cell-DNA mixture was transferred into Gene Pulser Cuvette (inter-electrode distance, 2 mm) (manufactured by BIO-RAD) and then electroporation was carried out using a cell fusion apparatus Gene Pulser (manufactured by BIO-RAD) at 0.2 KV pulse voltage and 250 µF electric capacity. The cell suspension was mixed with 10 ml of Hybridoma-SFM medium (manufactured by Life Technologies) supplemented with 5% fetal bovine dialyzed serum (manufactured by Life Technologies) and 0.2% BSA (manufactured by Life Technologies) and dispensed in 100 µl portions into a 96 well plate for suspension cell use (manufactured by Greiner). After culturing them at 37° C. for 24 hours in 5% $CO_2$, 50 µl of the culture supernatant was removed, and Hybridoma-SFM medium (manufactured by Life Technologies) supplemented with 0.5 mg/ml Hygromycin B (manufactured by Wako Pure Chemical Industries), 5% fetal bovine dialyzed serum (manufactured by Life Technologies) and 0.2% BSA (manufactured by Life Technologies) was dispensed at 100 µl. They were cultured for 3 weeks while repeating the medium exchange step at intervals of 3 to 4 days, and 14 cell lines showing hygromycin resistance were obtained.

On the other hand, a negative control cell line was prepared by introducing the plasmid pAGE249 as a parent vector of the pAGEmfFUT8 into the 61-33. According to the above procedure, 10 µg of the plasmid pAGE249 converted into linear form with a restriction enzyme FspI was introduced into $4\times10^6$ cells of the 61-33 using the electroporation. The cells were mixed with 15 ml of Hybridoma-SFM medium (manufactured by Life Technologies) supplemented with 5% fetal bovine dialyzed serum (manufactured by Life Technologies) and 0.2% BSA (manufactured by Life Technologies), transferred into a T75 flask for suspension cell (manufactured by Greiner) and then cultured at 37° C. for 24 hours in 5% $CO_2$. After culturing them, a half of the culture supernatant (7.5 ml) was removed by centrifugation at 600 rpm for 4 minutes, and the cells were suspended in 7.5 ml of Hybridoma-SFM medium (manufactured by Life Technologies) supplemented with 0.5 mg/ml Hygromycin B (manufactured by Wako Pure Chemical Industries), 5% fetal bovine dialyzed serum (manufactured by Life Technologies) and 0.2% BSA (manufactured by Life Technologies) and transferred into the T75 flask for suspension cell (manufactured by Greiner). They were cultured for 3 weeks while repeat:no the medium exchange at intervals of 3 to 4 days, a hygromycin-resistant cell line was obtained.

(3) Analysis of Expression Level of α-1,6-Fucosyltransferase (FUT8) Gene in Cell Lines Over-Expressing the Gene Using 6 cell lines optionally selected from the 14 mouse FUT8-over expressing cell lines prepared from 61-33 in the item (2) and the negative control cell line, the FUT8 expression levels were compared using competitive RT-PCR.

Each of these over-expression cell lines was suspended in Hybridoma-SFM medium (manufactured by Life Technologies) supplemented with 0.5 mg/ml Hygromycin B (manufactured by Wako Pure Chemical Industries), 5% fetal bovine dialyzed serum (manufactured by Life Technologies) and 0.2% BSA (manufactured by Life Technologies) to give a density of $3\times10^5$ cells/ml and then transferred into a T75 flask for suspension cell culture use (manufactured by Greiner). After culturing them at 37° C. for 24 hours in 5% $CO_2$, $1\times10^7$ of intact cells were recovered to extract total RNA using RNAeasy (manufactured by QIAGEN) in accordance with the manufacture's instructions. The total RNA was dissolved in 45 µl of sterile water, and 0-5 U/µl of RQ1 RNase-Free DNase (manufactured by Promega), 5 µl of the attached 10× DNase buffer and 0.5 µl of RNasin Ribonuclease Inhibitor (manufactured by Promega) were added thereto, followed by reaction at 37° C. for 30 minutes to degrade genome DNA contaminated in the sample. After the reaction, the total RNA was purified again using RNAeasy (manufactured by QIAGEN) and dissolved in 50 µl of sterile water.

In a 20 µl reaction mixture using oligo(dT) as a primer, single-stranded cDNA was synthesized from 2.5 µg of the obtained total RNA by reverse transcription reaction using SUPERSCRIPT™ Preamplification System for First Strand cDNA Synthesis (manufactured by Life Technologies) in accordance with the manufacturers instructions. The reaction solution was diluted 50 folds with water and the transcription amount of each gene was determined by the competitive PCR in accordance with Example 9(6).

The FUT8 gene-derived mRNA transcription amount in each expression cell line was determined by the following procedure.

YBFT8-pCR2.1, as a plasmid in which a cDNA partial fragment prepared in Example 9(2) from rat FUT8 was inserted into pCR2.1, was digested with a restriction enzyme EcoRI, and the obtained linear DNA was used as the standard in the preparation of a calibration curve for determining the FUT8 transcription amount.

Among the YBFT8-pCR2.1 prepared in Example 9(4), YBFT8d-pCR2.1 obtained by deleting 203 bp between ScaI and HindIII of an inner nucleotide sequence of rat FUT8 was digested with a restriction enzyme EcoRI, and the obtained linear DNA was used as the internal control for FUT8 determination.

PCR was carried out using a DNA polymerase ExTaq (manufactured by Takara Shuzo) in 20 μl in total volume of a reaction solution [ExTaq buffer (manufactured by Takara Shuzo), 0.2 mmol/l dNTPs, 0.5 μmol/l FUT8 gene-specific primers (SEQ ID NOs.13 and 14) and 5% DMSO) containing 5 μl of 50 folds-diluted cDNA solution prepared from respective expression cell line in the above and 5 μl (10 fg) of the plasmid for internal control. The PCR was carried out by heating at 94° C. for 3 minutes and subsequent 32 cycles of heating at 94° C. for 1 minute, 60° C. for 1 minute and 72° C. for 1 minute as one cycle.

Also, PCR was carried out in a series of reaction in which 5 μl (0.1 fg, 1 fg, 5 fg, 10 fg, 50 fg, 100 fg, 500 fg or 1 pg) of the FUT8 standard plasmid was added instead of the each expression cell line-derived cDNA, and used in the preparation of a calibration curve for the FUT8 transcription amount. In this case, 1 μg/ml baker's yeast t-RNA (manufactured by SIGMA) was used for the dilution of standard plasmid.

On the other hand, since it is considered that the β-actin gene is transcribed constantly in each cell and its transcription level is approximately the same between cells, the transcription amount of the β-actin gene was determined as an index of the efficiency of synthesis reaction of cDNA in each expression cell line.

YBAc-pBS, as a plasmid in which the ORF full sequence of cDNA of rat β-actin was inserted into pBluescript II KS(+) prepared in Example 9(3), was digested with restriction enzymes HindIII and KpnI, and the obtained linear DNA was used as the standard in the preparation of a calibration curve for determining the β-actin gene transcription amount.

YBAcd-pBS obtained from the YBAc-pBS by deleting 180 bp between DraI and DraI of an inner nucleotide sequence of rat β-actin was digested with restriction enzymes HindIII and KpnI, and the obtained linear DNA was used as the internal standards for β-actin amount determination.

PCR was carried out using a DNA polymerase ExTaq (manufactured by Takara Shuzo) in 20 μl in total volume of a reaction solution [ExTaq buffer (manufactured by Takara Shuzo), 0.2 mmol/l dNTPs, 0.5 μmol/l β-actin-specific primers (SEQ ID NOs:17 and 18) and 5% DMSO] containing 5 μl of 50 folds-diluted cDNA solution prepared from each of the expression cell lines and 5 μl (1 pg) of the plasmid for internal control. The PCR was carried out by heating at 94° C. for 3 minutes and subsequent 17 cycles of heating at 94° C. for 30 seconds, 65° C. for 1 minute and 72° C. for 2 minutes as one cycle.

Also, PCR was carried out in a series of reaction in which 10 pg, 5 pg, 1 pg, 500 fg or 100 fg of the β-actin standard plasmid was added instead of the each expression cell line-derived cDNA, and used in the preparation of a calibration curve for the β-actin, transcription amount. In this case, 1 μg/ml baker's yeast t-RNA (manufactured by SIGMA) was used for diluting the standard plasmid.

By carrying out PCR using the primer set described in Table 3, a DNA fragment having a size shown in the target column of Table 3 can be amplified from each gene transcription product and each standard, and a DNA fragment having a size shown in the competitor column of Table 3 can be amplified from each internal control.

Each (7 μl) of the solutions after PCR was subjected to a 1.75% agarose gel electrophoresis, and then the gel was stained by soaking it for 30 minutes in 1× concentration SYBR Green I Nucleic Acid Gel Stain (manufactured by Molecular Probes). By calculating luminescence intensity of each amplified DNA fragment using a fluoro-imager (FluorImager SI; manufactured by Molecular Dynamics), the amount of the amplified DNA fragment was measured.

The amount of an amplified product formed by PCR using the standard plasmid as the template was measured by the method, and a calibration curve was prepared by plotting the measured values against the amounts of the standard plasmid. Using the calibration curve, the amount of cDNA of a gene of interest in each cell line was calculated from the amount of an amplified product when each expression cell line-derived cDNA was used as the template, and the amount was defined as the mRNA transcription amount in each cell line.

Figure 28:
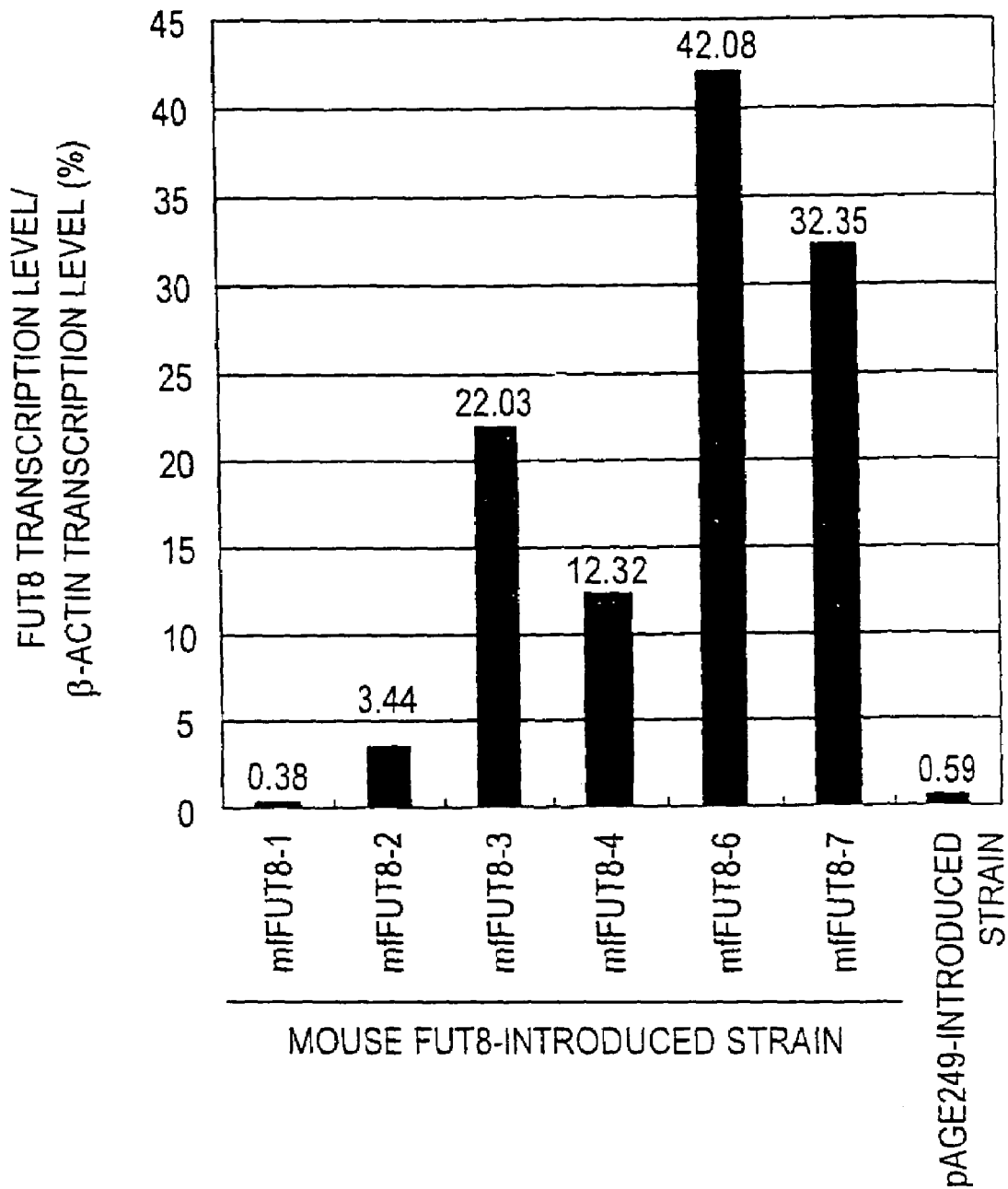
FIG. 28 shows results of analysis of expression levels of FUT8 gene by a cell line excessively expressing the gene using a competitive RT-PCR. The ordinate shows relative values of amounts of FUT8 transcription to amounts of β-actin transcription.

FIG. 28 shows the FUT8 transcription amounts as relative values to the amount of β-actin transcription product. Three cell lines mfFUT8-1, mfFUT8-2 and mfFUT8-4 and the pAGE249-introduced cell line were cell lines having a relatively small FUT8 transcription amount, which was equivalent to 0.3 to 10% of a β-actin transcription amount. On the other hand, other three cell lines mfFUT8-3, mfFUT8-6 and mfFUT8-7 were cell lines having a relatively large FUT8 transcription amount, which was equivalent to 20 to 40% of a β-actin transcription amount.

(4) Purification of Anti-Body Produced by α-1,6-Fucosyltransferase (FUT8) Gene Over-Expressing Cell Line Each of the six FUT8 gene over-expressing cell lines and one negative control cell line obtained in the item (2) was suspended in Hybridoma-SFM medium (manufactured by Life Technologies) supplemented with 200 nmol/l MTX, 0.5 mg/ml Hygromycin B (manufactured by Wako Pure Chemical Industries) and 0.2% BSA (manufactured by Life Technologies) to give a density of $2 \times 10^5$ cells/ml, and then 100 ml in total of the suspension was inoculated into three T225 flasks for suspension cell culture use (manufactured by IWAKI). After culturing them at 37° C. for 7 to 9 days in a 5% $CO_2$ incubator, the number of intact cells was counted to confirm that their viability was almost the same (each 30% or less), and then each cell suspension was recovered. Each of the cell suspensions was centrifuged at 3,000 rpm at 4° C. for 10 minutes, and the recovered supernatant was centrifuged at 10,000 rpm at 4° C. for 1 hour and then filtered using PES Filter Unit (manufactured by NALGENE) having a pore diameter of 0.22 μm with 150 ml capacity.

Prosep-A HighCapacity (manufactured by bioPROCESSING) was packed in a 0.8 cm diameter column to a thickness of 2 cm and washed with 10 ml of 0.1 mol/l citrate buffer (pH 3.0) and 10 ml of 1 mol/l glycine/NaOH-0.15 mol/l NaCl buffer (pH 8.6) in that order to effect equilibration the carrier. Next, 100 ml of each of the culture supernatant was passed through the column and washed with 50 ml of 1 mol/l glycine/NaOH-0.15 mol/l NaCl buffer (pH 8.6). After washing them, the antibody absorbed to Prosep-A was eluted using 2.5 ml of a 0.1 mol/l citrate buffer (pH 3.0), the eluate was fractionated at 500 μl and each fraction was neutralized by mixing with 100 μl of 2 mol/l Tris-HCl (pH 8.5). Two fractions containing the antibody at a high concentration (1.2 ml in total) were selected by the BCA method [*Anal. Biochem.*, 150, 76 (1985)], combined and then dialyzed against 10 mol/l citrate buffer (pH 6.0) at 4° C. for a whole day and night. After the dialysis, the antibody solution was recovered and subjected to sterile filtration using a 0.22 μm pore size Millex GV (manufactured by MILLIPORE).

(5) In vitro Cytotoxic Activity (ADCC Activity) of Antibody Produced by Mouse α-1,6-Fucosyltransferase (FUT8) Gene Over-Expressing Cell Line In order to evaluate in vitro cytotoxic activity of the anti-GD3 antibodies purified in the item (4), ADCC activity was measured using a GD3-positive cell, human melanoma cultured cell line G-361 (RCB0991, Cell Bank at The Institute of Physical and Chemical Research).

The G-361 cells subcultured in RPMI1640 medium (manufactured by Life Technologies) containing 10% fetal bovine serum (manufactured by Life Technologies) (hereinafter referred to as "RPMI1640-FBS(10)") were suspended in 500 μl of RPMI1640-FBS(10) at a density of $1\times10^6$ cells, and 3.7 MBq of $Na_2^{51}CrO$ was added thereto, followed by culturing at 37° C. for 30 minutes for labeling the cells with a radioisotope. After centrifugation at 1,200 rpm for 5 minutes, the supernatant was discarded and the target cells were suspended in 5 ml of RPMI1640-FBS(10). The washing step was repeated three times and then the cell suspension was incubated for 30 minutes on ice for spontaneous dissociation of the radioactive substance. The washing step was again repeated twice and then the cells were suspended in 5 ml of RPMI1640-FBS(10) to thereby prepare $2\times10^5$ cells/ml of a target cell suspension.

On the other hand, 30 ml of peripheral blood was collected from a healthy person and gently mixed with 0.5 ml of heparin sodium (manufactured by Shinizu Pharmaceutical) and then mixed with 30 ml of physiological saline (manufactured by otsuka Pharmaceutical). After the mixing, 10 ml of the mixture was gently overlaid on 4 ml of Lymphoprep (manufactured by NYCOMED PHARMA AS) and centrifuged at room temperature at 2,000 rpm for 30 minutes. The separated mononuclear cell fractions were collected from the centrifugation tubes, combined and then suspended in 30 ml of RPMI1640-FBS(10). After centrifugation at room temperature at 1,200 rpm for 5 minutes, the supernatant was discarded and the cells were suspended in 20 ml of RPMI1640-FBS (10). The washing step was repeated twice and then $2\times10^6$ cells/ml of an effector cell suspension was prepared using RPMI1640-FBS(10).

The target cell suspension was dispensed at 50 μl ($1\times10^4$ cells/well) into each well of a 96 well U-bottom plate (manufactured by Falcon). Subsequently, the effector cell suspension was dispensed at 100 μl ($2\times10^5$ cells/well) into each well to thereby adjust the ratio of the effector cells to the target cells to 20:1. Next, using a 10 M citrate buffer (pH 6.0), a series of dilution solution of 0.01 μg/ml, 0.1 μg/ml, 1 μg/ml and 10 μg/ml of each anti-GD3 antibody obtained in the item (4) was prepared, and the diluted solutions were dispensed at 50 μl into the wells to give final concentrations of 0.0025 μg/ml, 0.025 μg/ml, 0.25 μg/ml and 2.5 μg/ml, respectively. After carrying out the reaction at 37° C. for 4 hours an 5% $CO_2$, the plate was centrifuged at 1,200 rpm for 5 minutes. Into a 12 mm diameter RIA tube (manufactured by IWAKI), 50 μl of the supernatant in each well was transferred and, and the amount of the dissociated $^{51}Cr$ was measured using MINAX-γ auto-gamma counter 5550 (manufactured by PACKARD).

Also, the amount of the spontaneously dissociated $^{51}Cr$ was calculated by carrying out the same reaction in a reaction mixture in which 150 μl of RPMI1640-FBS(10) was added instead of the effector cell suspension and antibody solution. The amount of the total dissociated $^{51}Cr$ was calculated by carrying out the same reaction in a reaction mixture in which 100 μl of 1 N hydrochloric acid and 50 μl of RPMI1640-FBS (10) were added instead of the effector cell suspension and antibody solution. Using these values, the ADCC activity was calculated based on the formula (II) described in the item 2(3) of Example 2.

Figure 29:
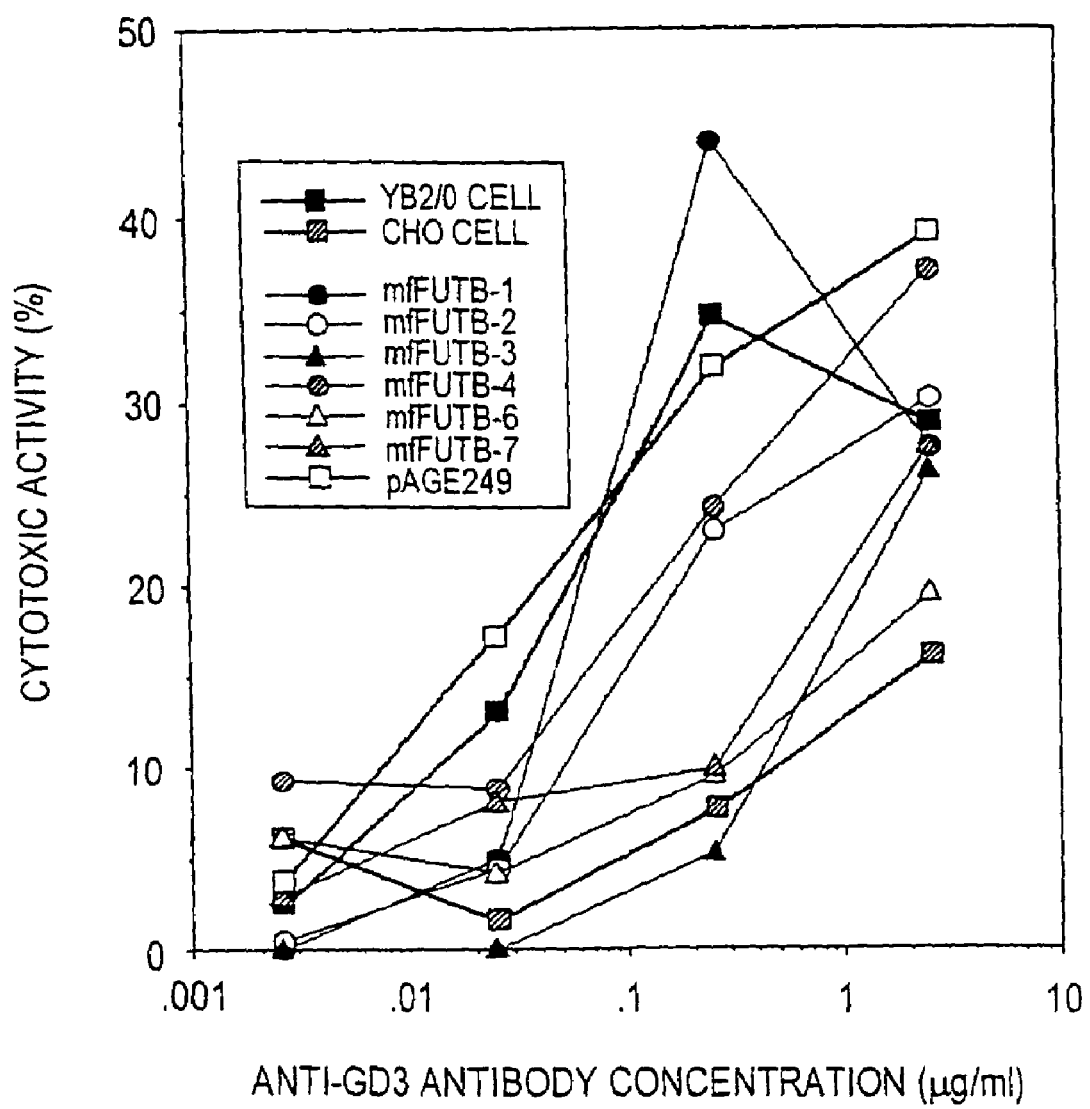
FIG. 29 shows ADCC activities of an anti-GD3 chimeric antibody purified from a cell line excessively expressing FUT8 gene against a human melanoma cell line G-361. The ordinate and the abscissa show the cytotoxic activity and the antibody concentration, respectively.

FIG. 29 shows ADCC activity of each of the anti-GD3 antibodies for G-361 cell. Three cell lines mfFUT8-1, mfFUT8-2 and mfFUT8-4 having a low FUT8 expression level as shown in FIG. 28 showed potent ADCC activity equivalent to that of the negative control pAGE249-introduced cell line. On the other hand, other three cell lines mfFUT8-3, mfFUT8-6 and mfFUT8-7 having a high FUT8 expression level as shown in FIG. 28 showed low ADCC activity equivalent to that of the anti-GD3 antibody produced from CHO cell. Based on these results, it was shown that the ADCC activity of produced antibodies can be controlled by regulating the expression level of FUT8 in host cells.

(6) Sugar Chain Analysis of Antibody Produced by Mouse α-1,6-Fucosyltransferase (FUT8) Gene Over-Expressing Cell Line Sugar chains of the anti-GD3 antibodies purified in the item (4) were analyzed. The sugar chains binding to the antibodies produced by mfFUT8-6 and pAGE249-introduced cell lines were cleaved from proteins by subjecting the antibodies to hydrazinolysis [*Method of Enzymology*, 83, 263 (1982)]. After removing hydrazine by evaporation under a reduced pressure, N-acetylation was carried out by adding an aqueous ammonium acetate solution and acetic anhydride. After freeze-drying, fluorescence labeling by 2-aminopyridine [*J. Biochem.*, 95, 197 (1984)] was carrying out. A fluorescence-labeled sugar chain group (PA-treated sugar chain group) was separated from excess reagents using Superdex Peptide HR 10/30 column (manufactured by Pharmacia). The sugar chain fractions were dried using a centrifugation concentrator and used as a purified PA-treated sugar chain group. Next, the purified PA-treated sugar chain group was subjected to reverse phase HPLC analysis using a CLC-ODS column (manufactured by Shimadzu) (FIG. 30). When calculated from the peak area, the content of α-1,6-fucose-free sugar chains in mfFUT8-6 was 10%, and the content of α-1,6-fucose-bound sugar chains was 90%. The content of α-1,6-fucose-free sugar chains in pAGE249 was 20%, and the content of α-1,6-fucose-bound sugar chains was 80%. Based on these results, it was found that the content of α-1,6-fucose-bound sugar chains of a produced antibody is increased by over-expressing the FUT8 gene.

Figures 30A, 30B:
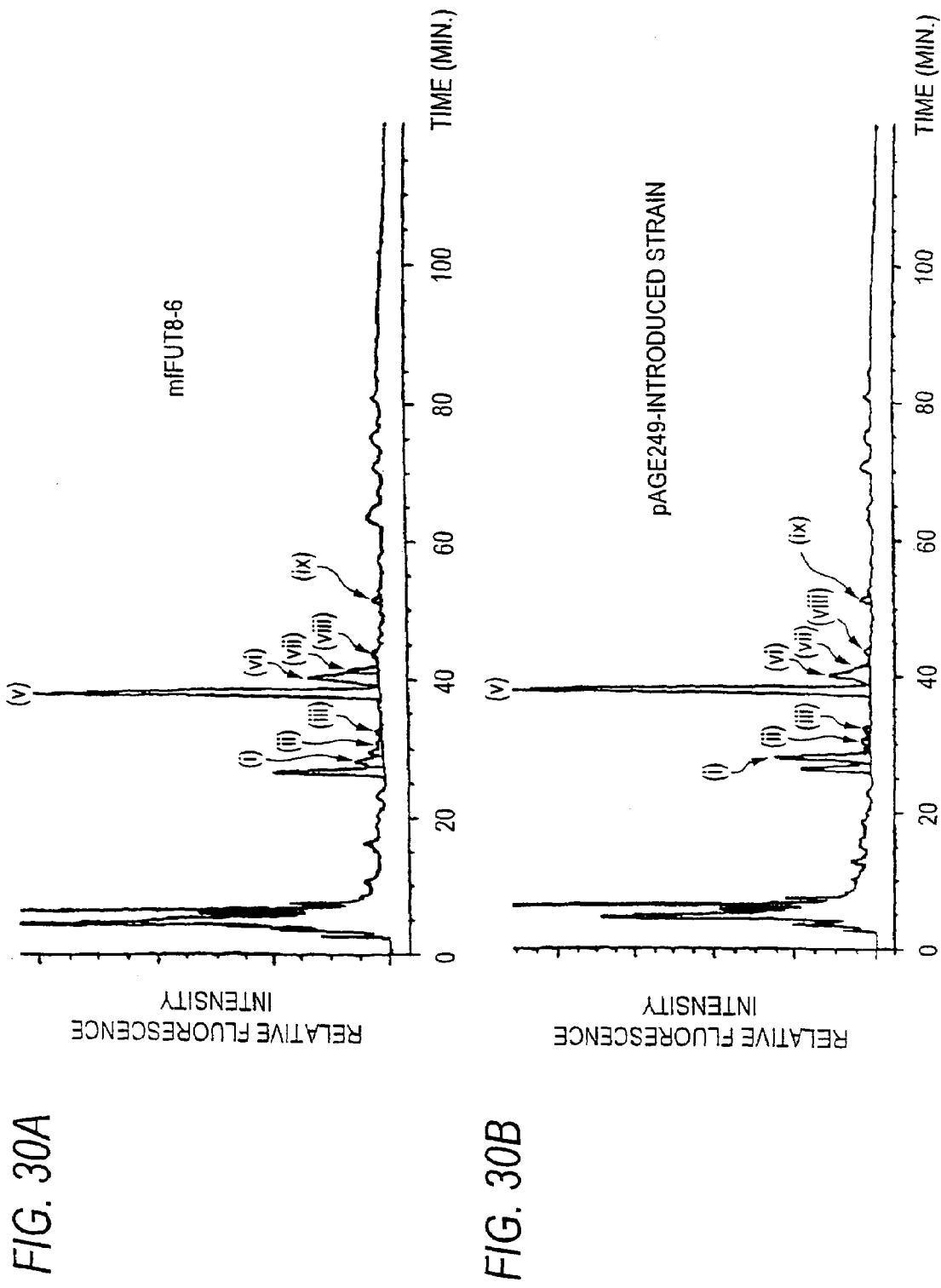
FIG. 30A and FIG. 30B show elution patterns of PA-treated sugar chains prepared from an antibody produced by mfFUT8-6-introduced cell line and PA-treated sugar chains prepared from an antibody produced by pAGE249-introduced cell line, respectively. The ordinate and the abscissa show the relative fluorescence intensity and the elution time, respectively.

FIG. 30 shows elution patterns obtained by carrying out reverse phase HPLC analysis of each of PA-treated sugar chains prepared from antibodies produced by mfFUT8-6 and pAGE249-introduced cell lines. FIGS. 30A and 30B show elution patterns of mfFUT8-6 and pAGE249, respectively. The relative fluorescence intensity and the elution time are plotted as the ordinate and the abscissa, respectively. Using a sodium phosphate buffer (pH 3.8) as buffer A and a sodium phosphate buffer (pH 3.8)+0.5% 1-butanol as buffer B, the analysis was carried out by the following gradient.

| | Time (minute) | | | | |
|---|---|---|---|---|---|
| | 0 | 80 | 90 | 90.1 | 120 |
| Buffer B (%) | 0 | 60 | 60 | 0 | 0 |

Figure 31:
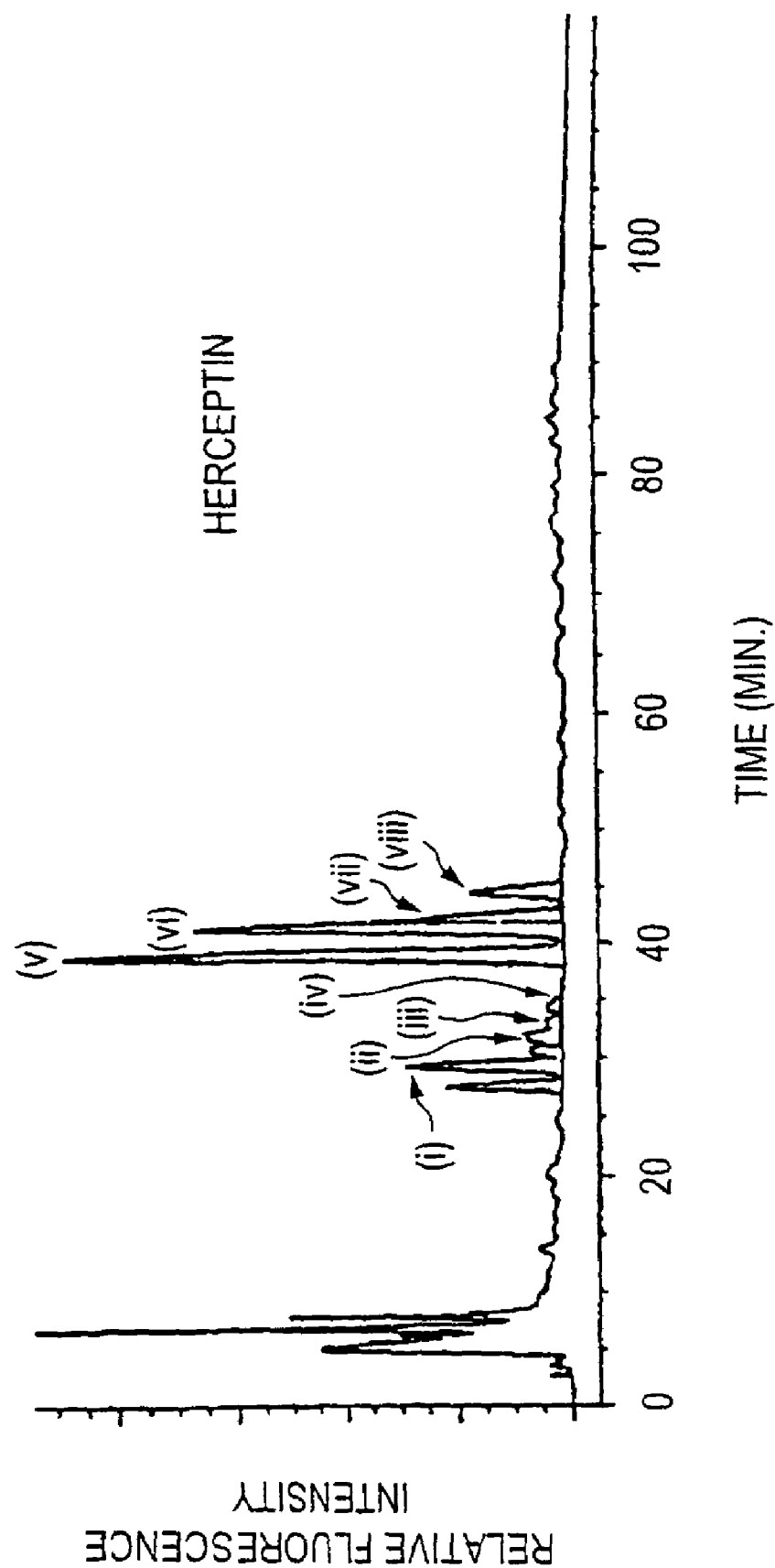
FIG. 31 shows an elution pattern of PA-treated sugar chains prepared from Herceptin, obtained by analyzing them by reverse phase HPLC. The ordinate and the abscissa show the relative fluorescence intensity and the elution time, respectively.

Peaks (i) to (ix) shown in FIG. 30 and FIG. 31 show the following structures.

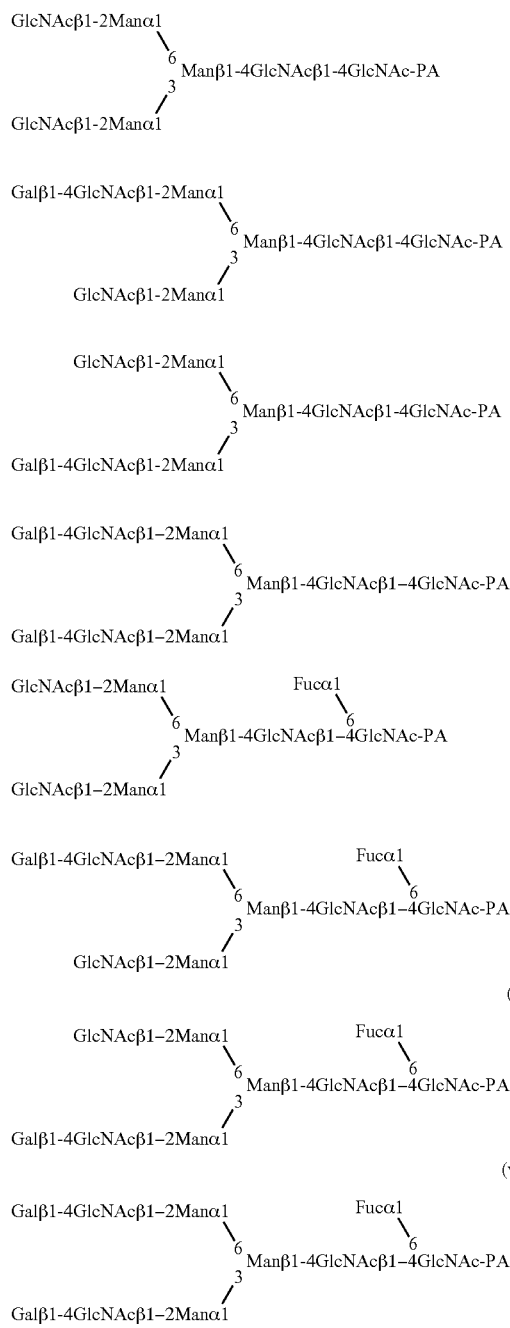

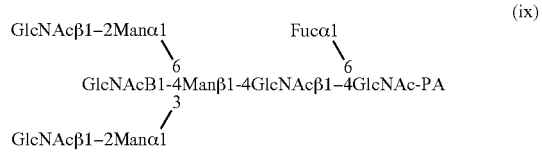

GlcNAc, Gal, Man, Fuc and PA indicate N-acetylglucosamine, galactose, mannose, fucose and a pyridylamino group, respectively. In FIGS. 30 and 31, the ratio of the α-1,6-fucose-free sugar chain group was calculated from the area occupied by the peaks (i) to (iv) among (i) to (ix), and the ratio of the α-1,6-fucose-bound sugar chain group from the area occupied by the peaks (v) to (ix) among (i) to (ix).

EXAMPLE 12

Figure 32:
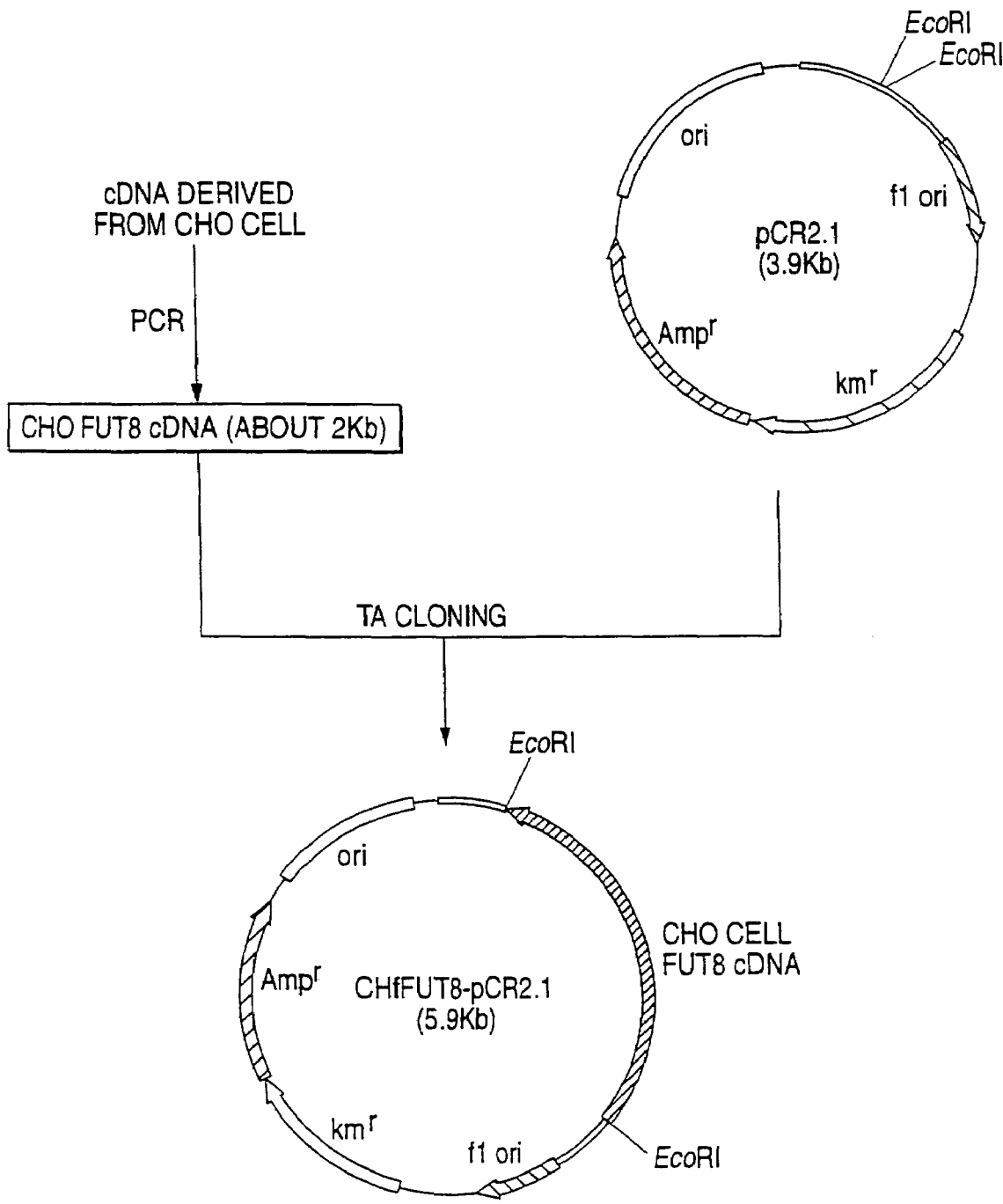
FIG. 32 shows construction of a plasmid CHfFUT8-pCR2.1.

Preparation of CHO Cell α-1,6-fucosyltransferase (FUT8) Gene (1) Preparation of CHO Cell α-1,6-fucosyltransferase (FUT8) cDNA Sequence From a single-stranded cDNA prepared from CHO/DG44 cells on the 2nd day of culturing in Example 9(1), Chinese hamster FUT8 cDNA was obtained by the following procedure (FIG. 32).

First, a forward primer specific for a 5α-terminal non-translation region (shown in SEQ ID NO:21) and a reverse primer specific for a 3α-terminal non-translation region (shown in SEQ ID NO:22) were designed from a mouse FUT8 cDNA sequence (GenBank, AB025198).

Next, 25 μl of a reaction solution [ExTaq buffer (manufactured by Takara Shuzo), 0.2 mmol/l dNTPs, 4% DMSO and 0.5 μmol/l specific primers (SEQ ID NOs:21 and 22)] containing 1 μl of the CHO/DG44 cell-derived cDNA was prepared and PCR was carried out using a DNA polymerase ExTaq (manufactured by Takara Shuzo). The PCR was carried out by heating at 94° C. for 1 minute, subsequent 30 cycles of heating at 94° C. for 30 seconds, 55° C. for 30 seconds and 72° C. for 2 minutes as one cycle, and final heating at 72° C. for 10 minutes.

After the PCR, the reaction solution was subjected to 0.8% agarose gel electrophoresis, and a specific amplified fragment of about 2 Kb was purified. Into a plasmid pCR2.1, 4 μl of the DNA fragment was employed to insert in accordance with the instructions attached to TOPO TA Cloning Kit (manufactured by Invitrogen), and E. coli DH5α was transformed with the reaction solution. Plasmid DNAs were isolated in accordance with a known method from cDNA-inserted 8 clones among the obtained kanamycin-resistant colonies.

The nucleotide sequence of each cDNA inserted into the plasmid was determined using DNA Sequencer 377 (manufactured by Parkin Elmer) and BigDye Terminator Cycle Sequencing FS Ready Reaction Kit (manufactured by Parkin Elmer) in accordance with the method of the manufacture's instructions. It was confirmed by the method that all of the inserted cDNAs encode a sequence containing the full ORF of CHO cell FUT8. Among these, a plasmid DNA containing absolutely no reading error of bases by the PCR in the sequences was selected. Herein, the plasmid is referred to as CHfFUT8-pCR2.1. The determined nucleotide sequence and the amino acid sequence of the cDNA of CHO FUT8 are shown in SEQ ID NOs:1 and 23, respectively.

(2) Preparation of CHO Cell α-1,6-fucosyltransferase (FUT8) Genomic Sequence

Using the ORF full length cDNA fragment of CHO cell FUT8 obtained in the item (1) as a probe, a CHO cell FUT8 genomic clone was obtained in accordance with a known genome screening method described, e.g., in *Molecular Cloning*, Second Edition, *Current Protocols in Molecular Biology, A Laboratory Manual*, Second Edition (1989). Next, after digesting the obtained genomic clone using various restriction enzymes, the Southern hybridization was carried out using an AfaI-Sau3AI fragment (about 280 bp) containing initiation codon of the CHO cell FUT8 cDNA as a probe, and then a XbaI-XbaI fragment (about 2.5 Kb) and a SacI-SacI fragment (about 6.5 Kb) were selected from restriction enzyme fragments showing positive reaction, inserted into pBluescript II KS(+) (manufactured by Stratagene), respectively.

The nucleotide sequence of each of the obtained genomic fragments was determined using DNA Sequencer 377 (manufactured by Parkin Elmer) and BigDye Terminator Cycle Sequencing FS Ready Reaction Kit (manufactured by Parkin Elmer) in accordance with the method of the manufacture's instructions. Thereby, it was confirmed that the XbaI-XbaI fragment encodes a sequence of an upstream intron of about 2.5 Kb containing exon 2 of the CHO cell FUT8, and the SacI-SacI fragment encodes a sequence of a downstream intron of about 6.5 Kb containing exon 2 of the CHO cell FUT8. Herein, the plasmid containing XbaI-XbaI fragment is referred to as pFUT8fgE2-2, and the plasmid containing SacI-SacI fragment is referred to as pFUT8fgE2-4. The determined nucleotide sequence (about 9.0 Kb) of the genome region containing exon 2 of the CHO cell FUT8 is shown in SEQ ID NO:3.

EXAMPLE 13

Preparation of CHO Cell in which α-1,6-fucose Transferase Gene is Disrupted and Production of Antibody Using the Cell A CHO cell from which the genome region comprising the CHO cell α-1,6-fucosyltransferase (FUT8) gene exon 2 was deleted was prepared and the ADCC activity of an antibody produced by the cell was evaluated.

Figure 33:
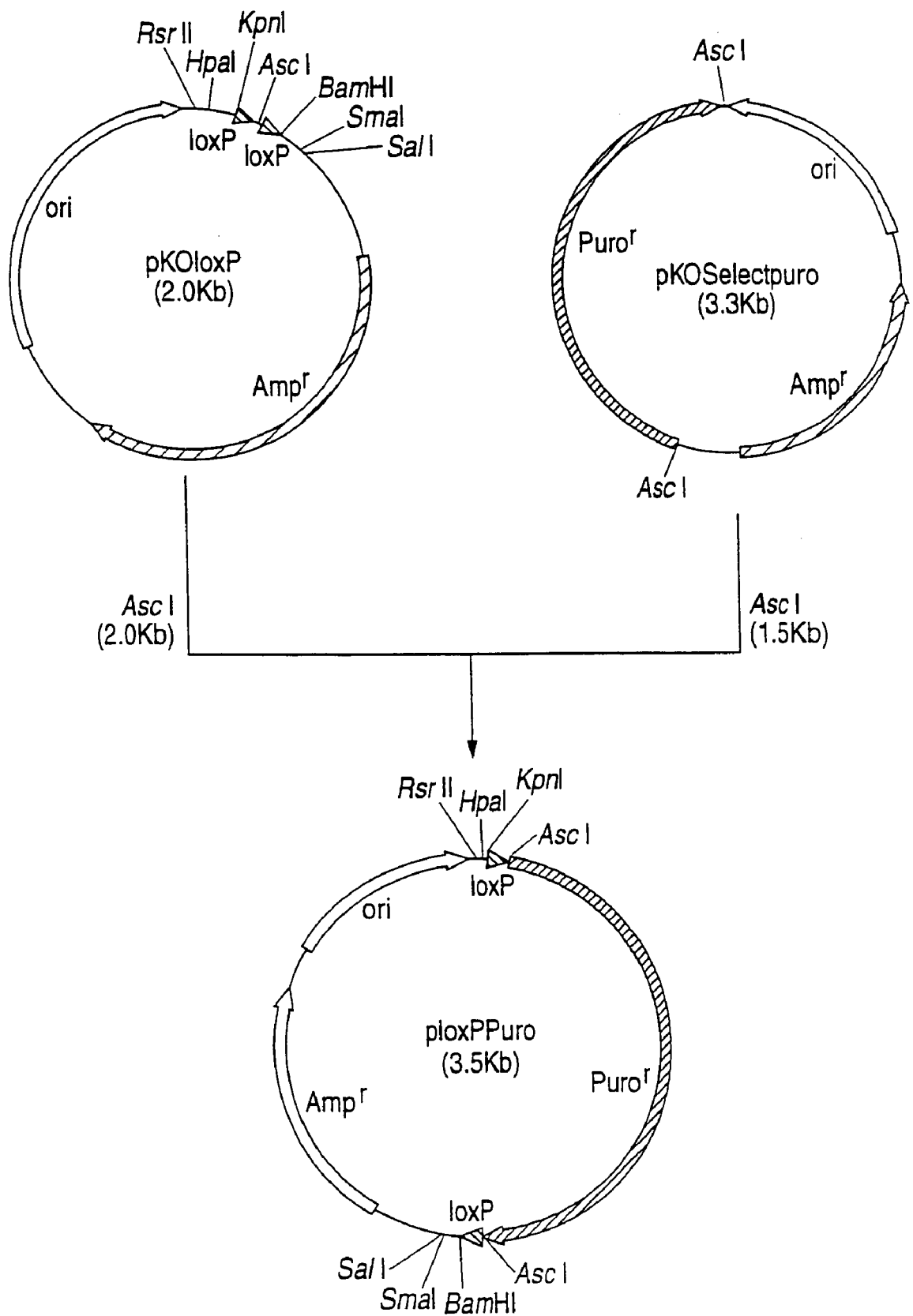
FIG. 33 shows construction of a plasmid ploxPPuro.

1. Construction of Chinese Hamster α-1,6-fucosyltransferase (FUT8) Gene Exon 2 Targeting Vector Plasmid pKOFUT8Puro (1) Construction of Plasmid ploxPPuro A plasmid ploxPPuro was constructed by the following procedure (FIG. 33).

In 35 μl of NEBuffer 4 (manufactured by New England Biolabs), 1.0 μg of a plasmid pKOSelectPuro (manufactured by Lexicon) was dissolved, and 20 units of a restriction enzyme AscI (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 1.5 Kb containing a puromycin resistance gene expression unit.

On the other hand, 1.0 μg of a plasmid ploxP described in Japanese Published Examined Patent Application No. 314512/99 was dissolved in 35 μl of NEBuffer 4 (manufactured by New England Biolabs), and 20 units of a restriction enzyme AscI (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 2.0 Kb.

The obtained AscI-AscI fragment (4.5 μl, about 1.5 Kb) derived from the plasmid pKOSelectPuro, 0.5 μl of the AscI-AscI fragment (about 2.0 Kb) derived from the plasmid ploxP and 5.0 μl of Ligation High (manufactured by Toyobo) were mixed, followed by ligation reaction at 16° C. for 30 minutes. *E. coli* DH5α was transformed using the reaction solution, and a plasmid DNA was isolated in accordance with a known method from the obtained ampicillin-resistant clones. Herein, the plasmid is referred to as ploxPPuro.

(2) Construction of Plasmid pXOFUT8gE2-1

Figure 34:
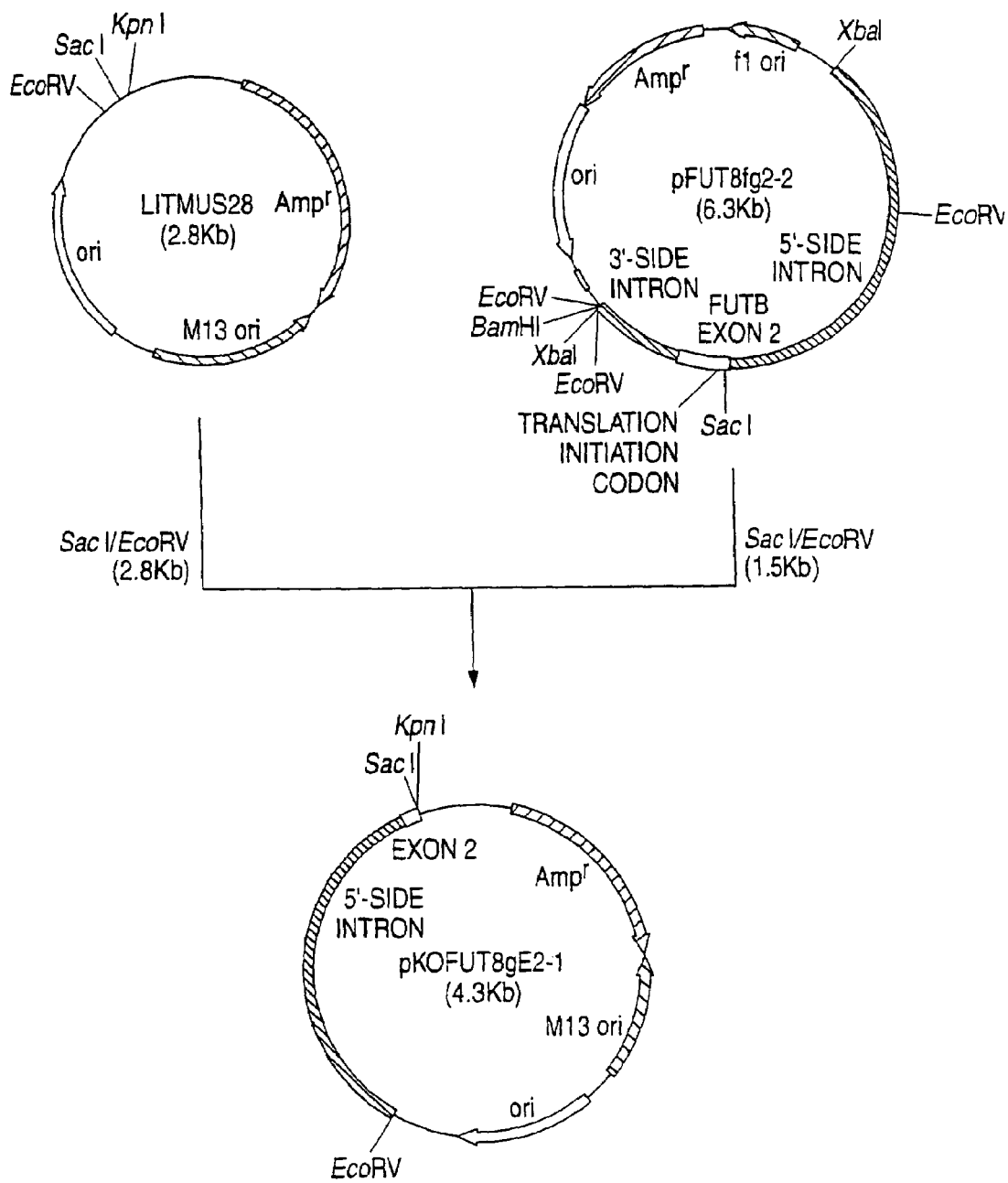
FIG. 34 shows construction of a plasmid pKOFUT8gE2-1.

A plasmid pKOFUT8gE2-1 was constructed by the following procedure (FIG. 34), using the plasmid pFUT8fgE2-2 obtained in Example 12(2) having a genome region comprising exon 2 of Chinese hamster FUT8.

In 35 μl of NEBuffer 1 (manufactured by New England Biolabs) containing 100 μg/ml of BSA (manufactured by New England Biolabs), 2.0 μg of the plasmid pFUT8fgE2-2 was dissolved, and 20 units of a restriction enzyme SacI (manufactured by New England Biolabs) were added thereto, followed by digestion reaction at 37° C. for 2 hours. A DNA fragment was recovered from the reaction solution by ethanol precipitation and dissolved in 35 μl of NEBuffer 2 (manufactured by New England Biolabs) containing 100 μg/ml of BSA (manufactured by New England Biolabs), and 20 units of a restriction enzyme EcoRV (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 1.5 Kb.

Separately, 1 0 μg of a plasmid LITMUS28 (manufactured by New England Biolabs) was dissolved in 35 μl of NEBuffer 1 (manufactured by New England Biolabs) containing 100 μg/ml of BSA (manufactured by New England Biolabs), and 20 units of a restriction enzyme SacI (manufactured by New England Biolabs) were added thereto, followed by digestion reaction at 37° C. for 2 hours. A DNA fragment was recovered from the reaction solution by ethanol precipitation and dissolved in 35 μl of NEBuffer 2 (manufactured by New England Biolabs) containing 100 μg/ml of BSA (manufactured by New England Biolabs), and 20 units of a restriction enzyme EcoRV (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 2.8 Kb.

The obtained EcoRV-SacI fragment (4.5 μl, about 1.5 Kb) derived from the plasmid pFUT8fgE2-2, 0.5 μl of the EcoRV-SacI fragment (about 2.8 Kb) derived from the plasmid LITMUS28 and 5.0 μl of Ligation High (manufactured by Toyobo) were mixed, followed by ligation reaction at 16° C. for 30 minutes. *E. coli* DH5α was transformed using the reaction solution, and a plasmid DNA was isolated in accordance with a known method from the obtained ampicillin-resistant clones. Herein, the plasmid is referred to as pKOFUT8gE2-1.

(3) Construction of Plasmid pKOFUT8gE2-2

Figure 35:
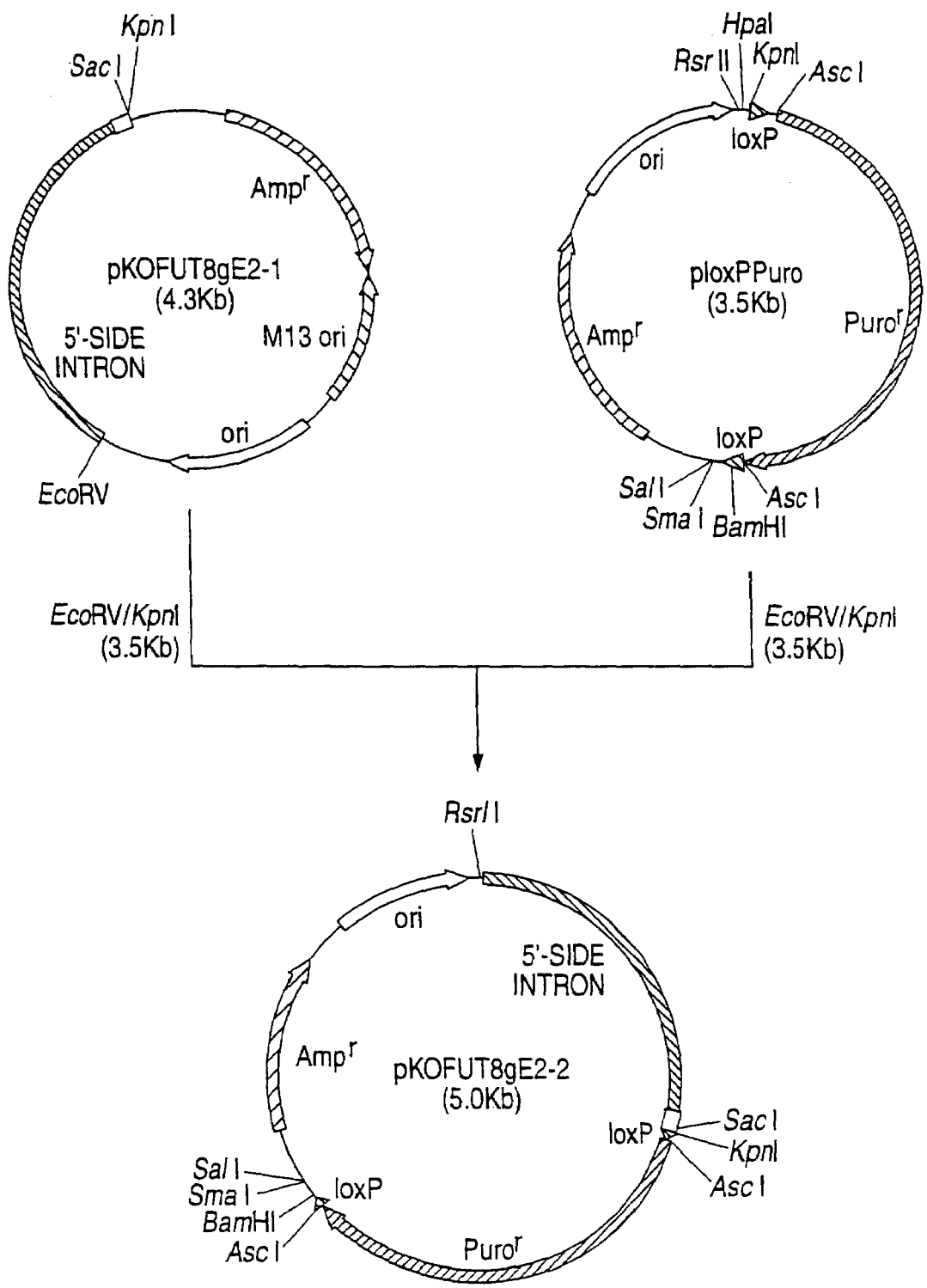
FIG. 35 shows construction of a plasmid pKOFUT8GEE2-2.

A plasmid pKOFUT8gE2-2 was constructed by the following procedure (FIG. 35), using the plasmid pKOFUT8gE2-1 obtained in the item (2).

In 30 μl of NEBuffer 2 (manufactured by New England Biolabs) containing 100 μg/ml of BSA (manufactured by New England Biolabs), 2.0 μg of the plasmid pKOFUT8gE2-1 was dissolved, and 20 units of a restriction enzyme EcoRV (manufactured by New England Biolabs) were added thereto, followed by digestion reaction at 37° C. for 2 hours. A DNA fragment was recovered from the reaction solution by ethanol precipitation and dissolved in 30 μl of NEBuffer 1 (manufactured by New England Biolabs) containing 100 μg/ml of BSA (manufactured by New England Biolabs), and 20 units of a restriction enzyme KpnI (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 1.5 Kb.

Separately, 1.0 μg of the plasmid ploxPPuro was dissolved in 30 μl of NEBuffer 4 (manufactured by New England Biolabs), and 20 units of a restriction enzyme HpaI (manufactured by New England Biolabs) were added thereto, followed by digestion reaction at 37° C. for 2 hours. A DNA fragment was recovered from the reaction solution by ethanol precipitation and dissolved in 30 μl of NEBuffer 1 (manufactured by New England Biolabs) containing 100 μg/ml of BSA (manufactured by New England Biolabs), and 20 units of a restriction enzyme KpnI (manufactured by New England Biolabs) were added thereto, followed by digestion reaction at 37° C. for 2 hours. After the digestion reaction, the solution was subjected to 0 8% (w/v) agarose gel electrophoresis to purify a DNA fragment of about 3.5 Kb.

A 4.0 μl portion of the obtained EcoRV-KpnI fragment (about 1.5 Kb) derived from the plasmid pKOFUTgE2-1, 1.0 μl of the HpaI-KpnI fragment (about 3.5 Kb) derived from the plasmid ploxPPuro and 5.0 μl of Ligation High (manufactured by Toyobo) were mixed and allowed to undergo the ligation reaction at 16° C. for 30 minutes. E. coli DH5α was transformed using the reaction solution, and a plasmid DNA was isolated in accordance with a known method from the obtained ampicillin-resistant clones. Herein, the plasmid is referred to pKOFUT8gE2-2.

(4) Construction of Plasmid pscFUT8gE2-3

Figure 36:
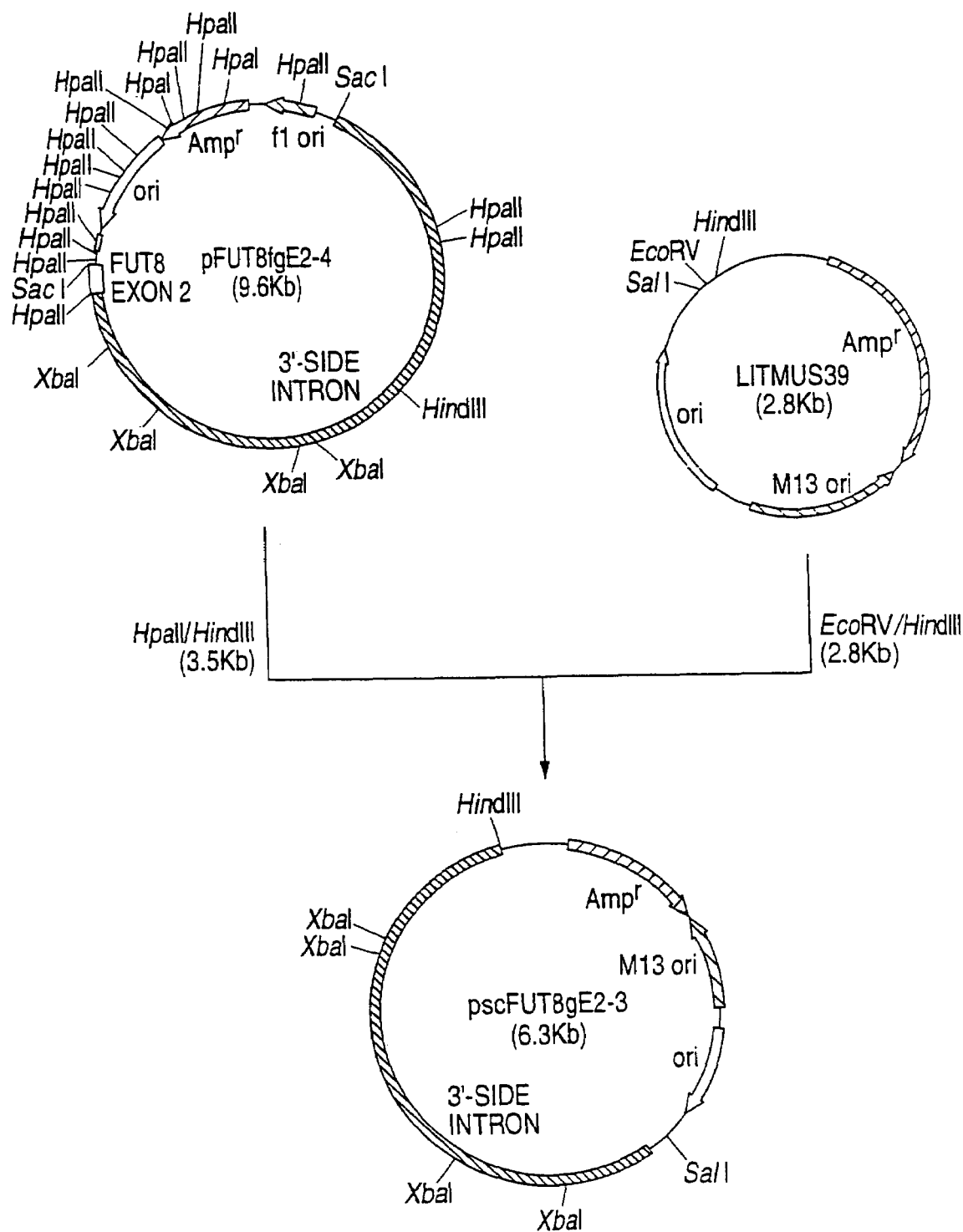
FIG. 36 shows construction of a plasmid pscFUT8GEE2-3.

A plasmid pscFUT8gE2-3 was constructed by the following procedure (FIG. 36), using the plasmid pFUT8fgE2-4 obtained in Example 12(2) having a genome region comprising exon 2 of Chinese hamster FUT8.

In 35 μl of NEBuffer 1 (manufactured by New England Biolabs), 2.0 μg of the plasmid pFUT8fgE2-4 was dissolved, and 20 units of a restriction enzyme HpaII (manufactured by New England Biolabs) were added thereto, followed by digestion reaction at 37° C. for 2 hours. A DNA fragment was recovered from the reaction solution by ethanol precipitation, and then the DNA termini were changed to blunt ends using Blunting High (manufactured by Toyobo) in accordance with the manufacture's instructions. The DNA fragment was recovered by carrying out phenol/chloroform extraction and ethanol precipitation and dissolved in 35 μl of NEBuffer 2 (manufactured by New England Biolabs), and 20 units of a restriction enzyme HindIII (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 3.5 Kb.

On the other hand, 1.0 μg of a plasmid LITMUS39 (manufactured by New England Biolabs) was dissolved in 35 μl of NEBuffer 2 (manufactured by New England Biolabs), and the solution was mixed with 20 units of a restriction enzyme EcoRV (manufactured by New England Biolabs) and 20 units of a restriction enzyme HindIII (manufactured by New England Biolabs) and subjected to the digestion reaction at 37° C. for 2 hours. After the digestion reaction, the solution was subjected to 0.8% (w/v) agarose gel electrophoresis to purify a DNA fragment of about 2.8 Kb.

The obtained HpaII-HindIII fragment (4.0 μl, about 3.5 Kb) derived from the plasmid pFUT8fgE2-4, 1.0 μl of the EcoRV-HindIII fragment (about 2.8 Kb) derived from the plasmid LITMUS39 and 5.0 μl of Ligation High (manufactured by Toyobo) were mixed, followed by ligation reaction at 16° C. for 30 minutes. E. coli DH5α was transformed using the reaction solution, and a plasmid DNA was isolated in accordance with a known method from the obtained ampicillin-resistant clones. Herein, the plasmid is referred to pscFUT8gE2-3.

(5) Construction of Plasmid pKOFUT8gE2-3

Figure 37:
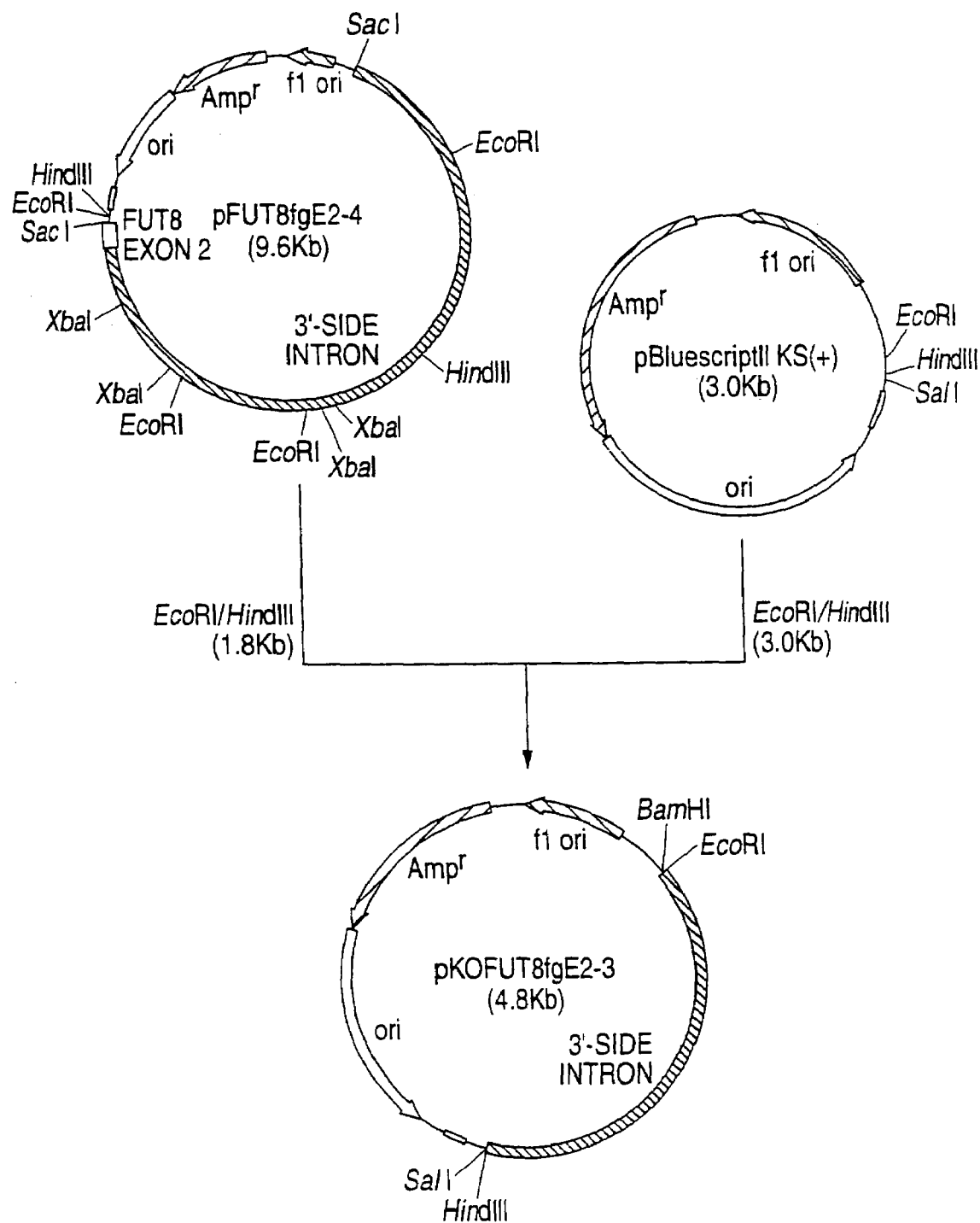
FIG. 37 shows construction of a plasmid pKOFUT8GEE2-3.

A plasmid pKOFUT8gE2-3 was constructed by the following procedure (FIG. 37), using the plasmid pFUT8fgE2-4 obtained in Example 12(2) having a genome region comprising exon 2 of Chinese hamster FUT8.

In 35 μl of NEBuffer for EcoRI (manufactured by New England Biolabs), 2.0 μg of the plasmid pFUT8fgE2-4 was dissolved, and 20 units of a restriction enzyme EcoRI (manufactured by New England Biolabs) and 20 units of a restriction enzyme HindIII (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 1.8 Kb.

Separately, 1.0 μg of a plasmid pBluescript II KS(+) (manufactured by Stratagene) was dissolved in 35 μl of NEBuffer for EcoRI (manufactured by New England Biolabs), and 20 units of a restriction enzyme EcoRI (manufactured by New England Biolabs) and 20 units of a restriction enzyme HindIII (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 3.0 Kb.

The obtained HindIII-EcoRI fragment (44.0 μl, about 1.8 Kb) derived from the plasmid pFUT8fgE2-4, 1.0 μl of the HindIII-EcoRI fragment (about 3.0 Kb) derived from the plasmid pBluescript II KS(+) and 5.0 μl of Ligation High (manufactured by Toyobo) were mixed, followed by ligation reaction at 16° C. for 30 minutes. E. coli DH5α was transformed using the reaction solution, and a plasmid DNA was isolated in accordance with a known method from the obtained ampicillin-resistant clones. Herein, the plasmid is referred to pKOFUT8gE2-3.

(6) Construction of Plasmid pKOFUT8gE2-4

Figure 38:
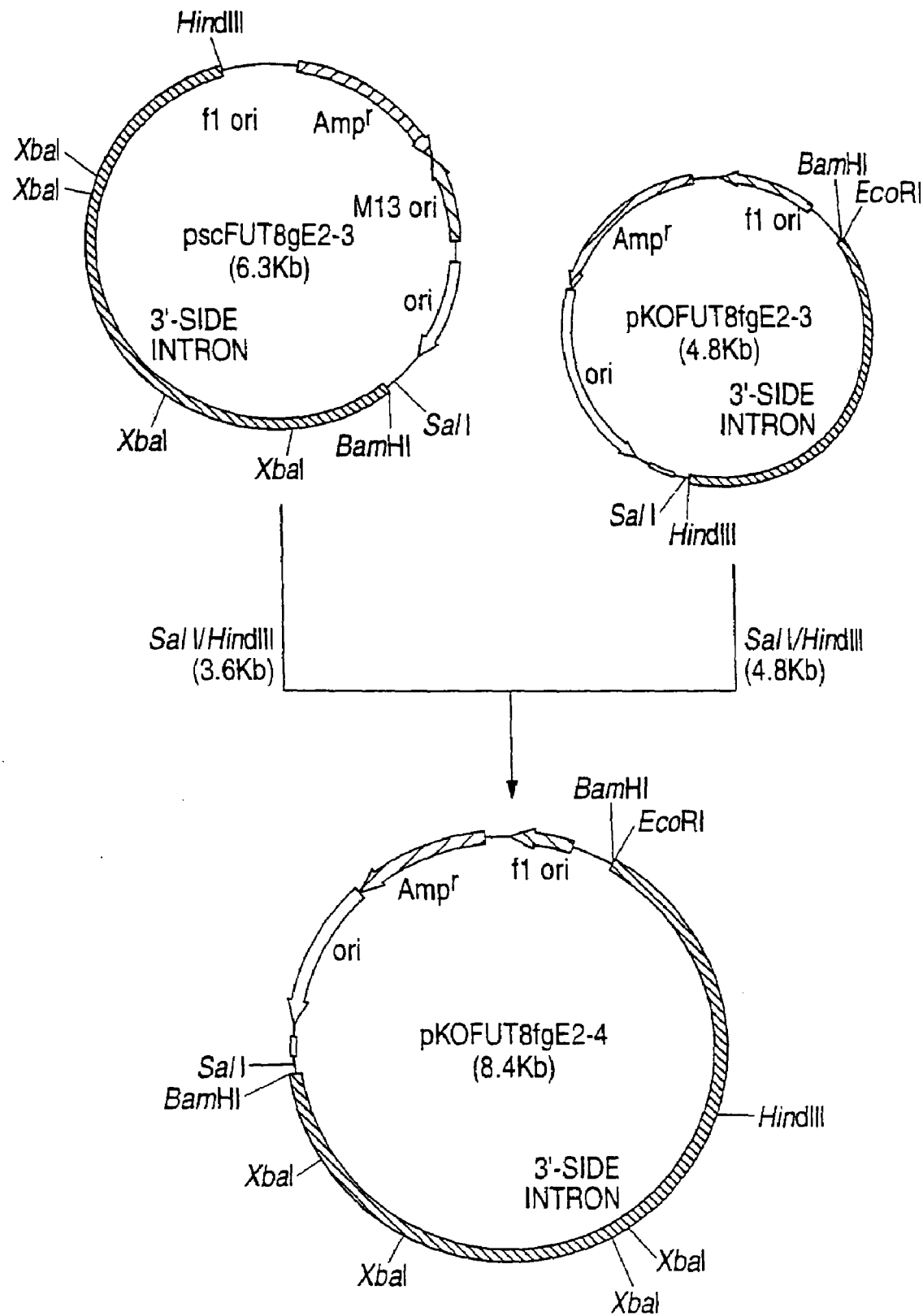
FIG. 38 shows construction of a plasmid pKOFUT8GEE2-4.

A plasmid pKOFUT8gE2-4 was constructed by the following procedure (FIG. 38), using the plasmids pscFUT8fgE2-3 and pKOFUT8gE2-3 obtained in the items (4) and (5).

In 35 μl of NEBuffer for SalI (manufactured by New England Biolabs) containing 100 μg/ml of BSA (manufactured by New England Biolabs), 1.0 μg of the plasmid pscFUT8gE2-3 was dissolved, and 20 units of a restriction enzyme SalI (manufactured by New England Biolabs) were added thereto, followed by digestion reaction at 37° C. for 2 hours. A DNA fragment was recovered from the reaction solution by ethanol precipitation and dissolved in 30 μl of NEBuffer 2 (manufactured by New England Biolabs) containing 100 μg/ml of BSA (manufactured by New England Biolabs), and 20 units of a restriction enzyme HindIII (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 3.6 Kb.

Separately, 1.0 μg of the plasmid pKOFUT8gE2-3 was dissolved in 35 μl of NEBuffer for SalI (manufactured by New England Biolabs), and 20 units of a restriction enzyme SalI (manufactured by New England Biolabs) were added thereto, followed by digestion reaction at 37° C. for 2 hours. A DNA fragment was recovered from the reaction solution by ethanol precipitation and dissolved in 35 µl of NEBuffer 2 (manufactured by New England Biolabs), and 20 units of a restriction enzyme HindIII (manufactured by New England Biolabs) were added thereto, followed by digestion reaction at 37° C. for 2 hours. After the digestion reaction, 35 µl of 1 mol/l Tris-HCl buffer (pH 8.0) and 3.5 µl of *E. coli* C15-derived alkaline phosphatase (manufactured by Takara Shuzo) were added thereto, followed by reaction at 65° C. for 30 minutes to dephosphorylate the DNA termini. After the dephosphorylation treatment, a DNA fragment was recovered by carrying out phenol/chloroform extraction and ethanol precipitation and dissolved in 10 µl of sterile water.

The obtained SalI-HindIII fragment (4.0 µl, about 3.1 Kb) derived from the plasmid pscFUT8gE2-3, 1.0 µl of the SalI-HindIII fragment (about 4.8 Kb) derived from the plasmid pKOFUT8gE2-3 and 5.0 µl of Ligation High (manufactured by Toyobo) were mixed, followed by ligation reaction at 16° C. for 30 minutes *E. coli* DH5α was transformed using the reaction solution, and a plasmid DNA was isolated in accordance with a known method from the obtained ampicillin-resistant clones. Herein, the plasmid is referred to pKOFUT8gE2-4.

(7) Construction of Plasmid pKOFUT8gE2-5

Figure 39:
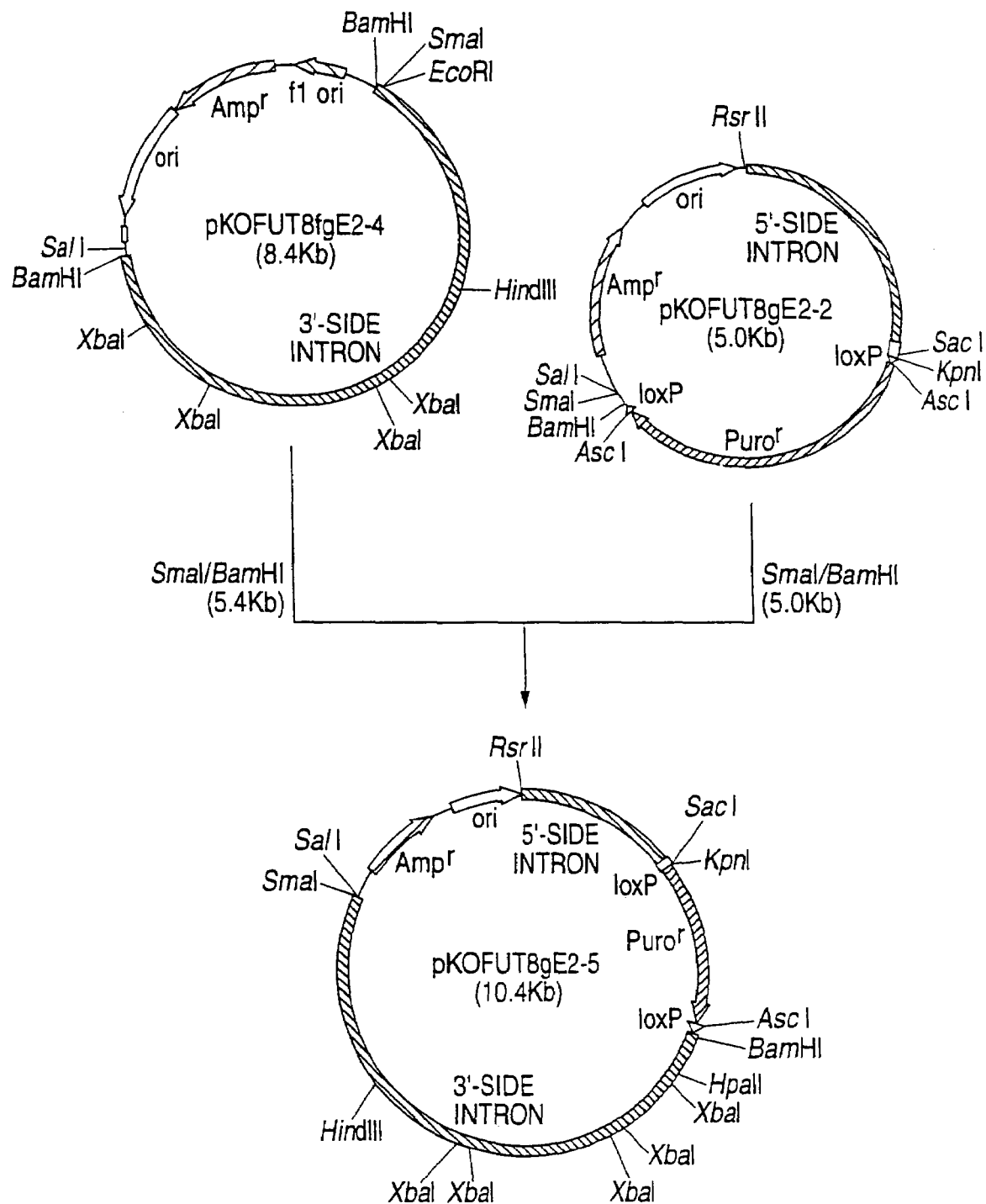
FIG. 39 shows construction of a plasmid pKOFUT8GEE2-5.

A plasmid pKOFUT8gE2-5 was constructed by the following procedure (FIG. 39), using the plasmids pKOFUT8gE2-2 and pKOFUT8gE2-4 obtained in the items (3) and (6).

In 30 µl of NEBuffer 4 (manufactured by New England Biolabs), 1.0 µg of the plasmid pKOFUT8gE2-2 was dissolved, and 20 units of a restriction enzyme SmaI (manufactured by New England Biolabs) were added thereto, followed by digestion reaction at 25° C. for 2 hours. A DNA fragment was recovered from the reaction solution by ethanol precipitation and dissolved in 30 µl of NEBuffer 2 (manufactured by New England Biolabs), and 20 units of a restriction enzyme BamHI (manufactured by New England Biolabs) were added thereto, followed by digestion reaction at 37° C. for 2 hours. After the digestion reaction, 30 µl of 1 mol/l Tris-HCl buffer (pH 8.0) and 3.0 µl of *E. coli* C15-derived alkaline phosphatase (manufactured by Takara Shuzo) were added thereto, followed by reaction at 65° C. for 1 hour to dephosphorylate the DNA termini. After the dephosphorylation treatment, the DNA fragment was recovered by carrying out phenol/chloroform extraction and ethanol precipitation and dissolved in 10 µl of sterile water.

Separately, 1.0 µg of the plasmid pKOFUT8gE2-4 was dissolved in 30 µl of NEBuffer 4 (manufactured by New England Biolabs), and 20 units of a restriction enzyme SmaI (manufactured by New England Biolabs) were added thereto, followed by digestion reaction at 25° C. for 2 hours. A DNA fragment was recovered from the reaction solution by ethanol precipitation and dissolved in 30 µl of NEBuffer 2 (manufactured by New England Biolabs), and 20 units of a restriction enzyme BamHI (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 5.2 Kb.

The obtained SmaI-BamHI fragment (0.5 µl, about 5.0 Kb) derived from the plasmid pKOFUT8gE2-2, 4.5 µl of the SmaI-BamHI fragment (about 5.4 Kb) derived from the plasmid pKOFUT8gE2-4 and 5.0 µl of Ligation High (manufactured by Toyobo) were mixed, followed by ligation reaction at 16° C. for 15 hours. *E. coli* DH5α was transformed using the reaction solution, and a plasmid DNA was isolated in accordance with a known method from the obtained ampicillin-resistant clones. Herein, the plasmid is referred to pKOFUT8gE2-5.

(8) Construction of Plasmid pKOFUT8Puro

Figure 40:
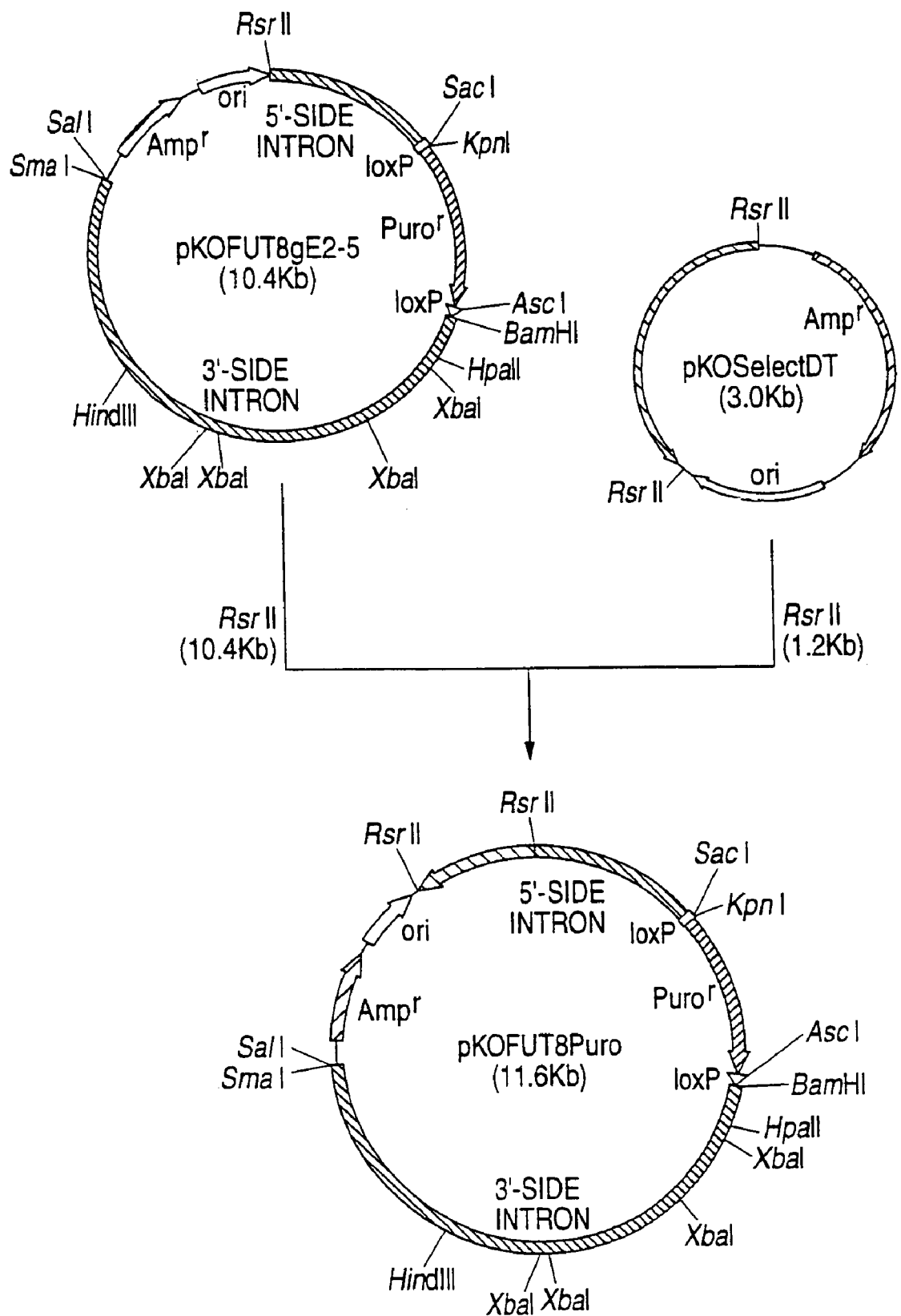
FIG. 40 shows construction of a plasmid pKOFUT8Puro.

A plasmid pKOFUT8Puro was constructed by the following procedure (FIG. 40), using the plasmid pKOFUT8gE2-5 obtained in the item (7).

In 50 µl of NEBuffer 4 (manufactured by New England Biolabs), 1.0 µg of a plasmid pKOSelectDT (manufactured by Lexicon) was dissolved, and 16 units of a restriction enzyme RsrII (manufactured by New England Biolabs) were added thereto, followed by digestion reaction at 37° C. for 2 hours. After the digestion reaction, the solution was subjected to 0.8% (w/v) agarose gel electrophoresis to purify a DNA fragment of about 1.2 Kb comprising a diphtheria toxin expression unit.

Separately, 1.0 µg of the plasmid pKOFUT8gE2-5 was dissolved in 50 µl of NEBuffer 4 (manufactured by New England Biolabs), and 16 units of a restriction enzyme RsrII (manufactured by New England Biolabs) were added thereto, followed by digestion reaction at 37° C. for 2 hours. After the digestion reaction, 30 µl of 1 mol/l Tris-HCl buffer (pH 8.0) and 3.0 µl of *E. col. C15-derived* alkaline phosphatase (manufactured by Takara Shuzo) were added thereto, followed by reaction at 65° C. for 1 hour to dephosphorylate the DNA termini. After the dephosphorylation treatment, the DNA fragment was recovered by carrying out phenol/chloroform extraction and ethanol precipitation and dissolved in 10 µl of sterile water.

The obtained RsrII-RsrII fragment (1.0 µl, about 1.2 Kb) derived from the plasmid pKOSelectDT, 1.0 µl of the RsrII-RsrII fragment (about 10.4 Kb) derived from the plasmid pKOFUT8gE2-5, 3.0 µl of sterile water and 5.0 µl of Ligation High (manufactured by Toyobo) were mixed, followed by ligation reaction at 16° C. for 30 minutes. *E. coli* DH5α was transformed using the reaction solution, and a plasmid DNA was isolated in accordance with a known method from the obtained ampicillin-resistant clones. Herein, the plasmid is referred to pKOFUT8Puro.

2. Preparation of CHO Cell in which One Copy of the Genome Region Containing α-1,6-fucosyltransferase (FUT8) Gene Exon 2 was Disrupted (1) introduction of Targeting Vector A Chinese hamster FUT8 genome region targeting vector pKOFUT8Puro constructed in the item 1 of this Example was introduced into the strain 5-03 prepared in the item 1(2) of Example 8.

A gene of the plasmid pKOFUT8Puro was introduced into the strain 5-03 as described below in accordance with the electroporation method [*Cytotechnology, a*, 133 (1990)). First, 150 µg of the plasmid pKOFUT8Puro was dissolved in 1.8 ml of NEBuffer for SalI (manufactured by New England Biolabs), and 600 units of a restriction enzyme SalI (manufactured by New England Biolabs) were added thereto, followed by digestion reaction at 37° C. for 5 hours to obtain a linear fragment. The reaction solution was extracted with phenol/chloroform extraction, followed by ethanol precipitation, and the recovered linear plasmid was made into a 1 µg/µl aqueous solution. Separately, the strain 5-03 was suspended in a K-PBS buffer (137 mmol/l KCl, 2.7 mmol/l NaCl, 8.1 mmol/l $Na_2HPO_4$, 1.5 mmol/l $KH_2PO_4$, 4.0 mmol/l $MgCl_2$) to give a density of $8\times10^7$ cells/ml. After mixing 200 µl of the cell suspension ($1.6\times10^4$ cells) with 4 µl (4 µg) of the linear plasmid, an entire volume of the cell-DNA mixture was transferred into Gene Pulser Cuvette (inter-electrode distance, 2 mm) (manufactured by BIO-RAD) and then the electroporation was carried out using a cell fusion apparatus Gene Pulser (manufactured by BIO-RAD) at 350 V pulse voltage and 250 µF electric capacity. After carrying out the electroporation using 30 cuvettes in the same manner, the cell suspension was suspended in IMDM medium (manufactured by Life Technologies) supplemented with 10% fetal bovine serum (manufactured by Life Technologies) and 1× concentration HT supplement (manufactured by Life Technologies) and inoculated into 30 adhesion cell culture dishes of 10 cm in diameter (manufactured by Falcon). After culturing them at 37° C. for 24 hours in 5% $CO_2$, the culture supernatant was removed, and IMDM medium (manufactured by Life Technologies) supplemented with 15 µg/ml puromycin (manufactured by SIGMA) and 10% fetal bovine dialyzed serum (manufactured by Life Technologies) was dispensed in 10 ml portions. After culturing them for 10 days while repeating the medium exchange at intervals of 3 to 4 days, puromycin-resistant cell lines were obtained.

(2) Preparation of Targeting Vector-Introduced Cell Lines

Arbitrary 900 colonies were obtained as follows from the puromycin-resistant cell lines obtained in the item (1).

First, culture supernatant was removed from the 10 cm dish in which colony of puromycin-resistant cell lines were formed and 7 ml of a phosphate buffer was added to the dish which was subsequently set under a stereoscopic microscope. Next, each colony was scratched and sucked up using Pipetteman (manufactured by GILSON) and transferred into a 96 well round-bottom plate (manufactured by Falcon). After a trypsin-treatment, each clone was inoculated into a 96 well flat-bottom plate for adhesion cell culture use (manufactured by Iwaki Glass) and cultured for 1 week using IMDM medium (manufactured by Life Technologies) supplemented with 15 µg/ml puromycin (manufactured by SIGMA) and 10% fetal bovine dialyzed serum (manufactured by Life Technologies).

After culturing them, each clone in the plate was subjected to trypsin treatment and then mixed with two volumes of a freeze drying medium (20% DMSO, 40% fetal bovine serum, 40% IMDM). A half of the mixture was inoculated into a 96 well flat-bottom plate for adhesion cell culture (manufactured by Iwaki Glass) as a replica plate, while the remaining half of the mixture was subjected to cryopreservation as master plates. The replica plate was cultured for 1 week using IMDM medium (manufactured by Life Technologies) supplemented with 15 µg/ml of puromycin (manufactured by SIGMA) and 10% fetal bovine dialyzed serum (manufactured by Life Technologies).

(3) Diagnosis of Homologous Recombination by Genomic PCR

Diagnosis of homologous recombination in the 900 clones obtained in the item (2) was carried out by genomic PCR.

First, genome DNA of each clone was prepared from the replica plate prepared in the item (2) in accordance with a known method [*Analytical Biochemistry*, 21, 331 (1992)] and dissolved overnight in 30 µl of a TE-RNase buffer (pH 8.0) (10 mmol/l Tris-HCl, 1 mmol/l EDTA, 200 µg/ml RNase A). Also, a primer (shown in SEQ ID NO:26) which binds to a sequence outside the targeting vector homologous region among the FUT8 genome region obtained in Example 12 and a primer (shown in SEQ ID NO:27) which binds to the loxP sequence in the vector were designed.

Using a DNA polymerase ExTaq (manufactured by Takara Shuzo), 25 µl of a reaction solution (ExTaq buffer (manufactured by Takara Shuzo), 0.2 mmol/l dNTPs and 0.5 µmol/l gene-specific primers (SEQ ID NO;26 and SEQ ID NO:27)] containing 10 µl of each the above-prepared genome DNA solution were prepared, and polymerase chain reaction (PCR) was carried out. The PCR was carried out by heating at 94° C. for 3 minutes and subsequent 38 cycles of heating using the reaction at 94° C. for 1 minute, 60° C. for 1 minute and 72° C. for 2 minutes as one cycle.

After the PCR, the reaction solution was subjected to 0.8% (W/v) agarose gel electrophoresis, and a specifically amplifying fragment of about 1.7 Kb containing a border region between the CHO cell genome region and the targeting vector homologous region was identified as a positive clone One positive clone was found by the method.

(4) Diagnosis of Homologous Recombination by Genome Southern Blotting

Diagnosis of homologous recombination in the 1 clone, whose-positive signal was confirmed in the item (3), was carried out by genome Southern blotting.

Among the master plates cryo-preserved in the item (2), a 96 well plate containing the positive clone found in the item (3) was selected and incubated at 37° C. for 10 minutes in 5% $CO_2$. After the incubation, cells were collected from a well corresponding to the positive clone and inoculated into a 24 well flat bottom plate for adhesion cell (manufactured by Greiner). After culturing them for 1 week using IMDM medium (manufactured by Life Technologies) supplemented with 15 µg/ml of puromycin (manufactured by SIGMA) and 10% fetal bovine dialyzed serum (manufactured by Life Technologies), the cells were inoculated into a 6 well flat bottom plate for adhesion cell (manufactured by Greiner). Genome DNA was prepared from the clone in the plate in accordance with a known method [*Nucleic Acids Research*, 1, 2303 (1976)] and dissolved overnight in 150 µl of a TE-RNase buffer (pH 8.0) (10 mmol/l Tris-HCl, 1 mmol/l EDTA, 200 µg/ml RNase A).

In 120 µl of NEBuffer 3 (manufactured by New England Biolabs), 12 µg of the obtained genome DNA was dissolved, and 25 unites of a restriction enzyme PstI (manufactured by New England Biolabs) were added thereto, followed, by digestion reaction at 37° C. overnight. A DNA fragment was recovered from the reaction solution by ethanol precipitation, dissolved in 20 µl of TE buffer (pH 8.0) (10 mmol/l Tris-HCl, 1 mmol/l EDTA) and then subjected to 0.8% (w/v) agarose gel electrophoresis. After the electrophoresis, the genome DNA was transferred onto a nylon membrane in accordance with a known method [*Proc. Natl. Acad. Sci. USA*, 76, 3683 (1979)]. After completion of the transfer, the nylon membrane was heated at 80° C. for 2 hours.

Separately, a probe used in the Southern blotting was prepared as follows. First, primers (SEQ ID NOs.28 and 29) which bind to a sequence outside the targeting vector homologous region with the FUT8 genome region obtained in Example 12 were designed. Next, using a DNA polymerase ExTaq (manufactured by Takara Shuzo), 20 µl of a reaction solution [ExTaq buffer (manufactured by Takara Shuzo), 0.2 mmol/l dNTPs and 0.5 mol/l gene-specific primers (SEQ ID NOs:28 and 29)] containing 4.0 ng of the plasmid pFUT8fgE2-2 obtained in Example 12(2) was prepared, and polymerase chain reaction (PCR) was carried out. The PCR was carried out by heating at 94° C. for 1 minute and subsequent 25 cycles of heating at 94° C. for 30 seconds, 55° C. for 30 seconds and 74° C. for 1 minute as one cycle. After the PCR, the reaction solution was subjected to 1.75% (w/v) agarose gel electrophoresis to purify a probe DNA fragment of about 230 bp. The obtained probe DNA solution (5 µl) was labeled with a radioisotope using 1.75 MBq of [α-$^{32}$P]dCTP and Megaprime DNA Labeling System, dCTP (manufactured by Amersham Pharmacia Biotech).

The hybridization was carried out as follows. First, the nylon membrane was sealed in a roller bottle, and pre-hybridization was carried out at 65° C. for 3 hours by adding 15 ml of a hybridization solution [5×SSPE, 50× Denhaldt's solution, 0.5% (w/v) SDS, 100 µg/ml salmon sperm DNA). Next, the $^{32}$P-labeled probe DNA was heat-denatured and put into the bottle. Then, the nylon membrane was heated at 65° C. overnight.

After the hybridization, the nylon membrane was soaked in 50 ml of 2×SSC-0.1% (w/v) SDS and heated at 65° C. for 15 minutes. After repeating the washing step twice, the membrane was soaked in 50 ml of 0.2×SSC-0.1% (w/v) SDS and heated at 65° C. for 15 minutes. After the washing, the nylon membrane was exposed to an X-ray film at −80° C. for two nights for development.

By the restriction enzyme PstI treatment, a DNA fragment of about 4.4 Kb is formed from a wild type FUT8 allele. On the other hand, a DNA fragment of about 6.0 Kb is formed from an allele in which homologous recombination with a targeting vector was generated.

By the method, such specific fragments of about 4.4 Kb and about 6.0 Kb were found from the positive clone genome DNA in the item (3). Since the quantitative ratio of both fragments was 1:1, it was confirmed that the clone is a clone in which 1 copy of the FUT8 allele was disrupted. Hereinafter, the clone is referred to as the strain 1st.ΔFUT8 2-46.

3. Deletion of Drug Resistance Gene from CHO cell in Which 1 Copy of the α-1,6-fucosyltransferase (FUT8) Gene was Disrupted (1) Introduction of Cre Recombinase Expression Vector A Cre recombinase expression vector pBS185 (manufactured by Life Technologies) was introduced into the strain 1st.ΔFUT8 2-46 prepared in the item 2 of this Example.

A gene of the plasmid pBS185 was introduced into the strain 1st.ΔFUT8 2-46 as follows in accordance with the electroporation method [*Cytotechnology*, 3, 133 (1990)]. First, the strain 1st.ΔFUT8 2-46 was suspended in a K-PBS buffer (137 mmol/l KCl, 2.7 mmol/l NaCl, 8.1 mmol/l Na$_2$HPO$_4$, 1.5 mmol/l KH$_2$PO$_4$, 4.0 mmol/l MgCl$_2$) to give a density of 8×10$^7$ cells/ml. After mixing 200 µl of the cell suspension (1.6×10$^6$ cells) with 4 µg of the plasmid pBS185, an entire volume of the cell-DNA mixture was transferred into Gene Pulser Cuvette (inter-electrode distance, 2 mm) (manufactured by BIO-RAD) and then the gene transfer was carried out using a cell fusion apparatus Gene Pulser (manufactured by BIO-RAD) at 350 V pulse voltage and 250 µF electric capacity. After the gene transfer, the cell suspension was suspended in 10 ml of IMDM medium (manufactured by Life Technologies) supplemented with 10% fetal bovine serum (manufactured by Life Technologies) and 1× concentration HT supplement (manufactured by Life Technologies) and further diluted 20,000 folds using the same medium. The cells were inoculated into 7 adhesion cell culture dishes of 10 cm in diameter (manufactured by Falcon) and then cultured at 37° C. for 24 hours in 5% CO$_2$. After culturing them, the culture supernatant was removed and IMDM medium (manufactured by Life Technologies) supplemented with 10% fetal bovine dialyzed serum (manufactured by Life Technologies) was dispensed at 10 ml. Culturing was carried out for 10 days while repeating the medium exchange at intervals of 3 to 4 days.

(2) Preparation of Cre Recombinase Expression Vector-Introduced Cell Lines

Arbitrary 400 colonies were obtained as follows from the cell line obtained in the item (1).

First, culture supernatant was removed from the 10 cm dish and 7 ml of a phosphate buffer was added to the dish which was subsequently set under a stereoscopic microscope. Next, each colony was scratched and sucked up using Pipetteman (manufactured by GILSON) and transferred into a 96 well round-bottom plate (manufactured by Falcon). After a trypsin-treatment, each clone was inoculated into a 96 well flat-bottom plate for adhesion cell culture (manufactured by Iwaki Glass) and cultured for 1 week using IMDM medium (manufactured by Life Technologies) supplemented with 10% fetal bovine dialyzed serum (manufactured by Life Technologies).

After the culturing, each clone in the plate was subjected to trypsin treatment and then mixed with two volumes of a freeze drying medium (20% DMSO, 40% fetal bovine serum, 40% IMDM). A half of the mixture was inoculated into a 96 well flat-bottom plate for adhesion cell culture use (manufactured by Iwaki Glass) to prepare a replica plate, while the remaining half was subjected to cryopreservation as a master plate.

Next, the replica plate was cultured for 6 days using IMDM medium (manufactured by Life Technologies) supplemented with 15 µg/ml of puromycin (manufactured by SIGMA) and 10% fetal bovine dialyzed serum (manufactured by Life Technologies). A positive clone from which the puromycin resistance gene interposed between loxP sequences was eliminated by the expression of Cre recombinase dies out in the presence of puromycin. By the selection method, 91 positive clones were found.

(3) Diagnoses of Drug Resistance Gene Elimination by Genome Southern Blotting

Diagnosis of drug resistance gene elimination by the genome Southern blotting was carried out on optional 6 clones among the positive clones found in the item (2).

Among the master plates cryo-preserved in the item (2), 96 well plates containing the 6 positive clones were selected and incubated at 37° C. for 10 minutes in 5% CO$_2$. After the incubation, cells were collected from a well corresponding to each positive clone and inoculated into a 24 well flat bottom plate for adhesion cell use (manufactured by Greiner). After culturing them for 1 week using IMDM medium (manufactured by Life Technologies) supplemented with 10% fetal bovine dialyzed serum (manufactured by Life Technologies), the cells were inoculated into a 6 well flat bottom plate for adhesion cell use (manufactured by Greiner). Genome DNAs were prepared from each clone in the plate in accordance with a known method [*Nucleic Acids Research*, 3, 2303 (1976)] and dissolved overnight in 150 µl of a TE-RNase buffer (pH 8.0) (10 mmol/l Tris-HCl, 1 mmol/l EDTA, 200 µg/ml RNase A).

In 120 µl of NEBuffer for BamHI (manufactured by New England Biolabs), 12 µg of the obtained genome DNA was dissolved, and 20 unites of a restriction enzyme BamHI (manufactured by New England Biolabs) were mixed, followed by digestion reaction at 37° C. overnight. A DNA fragment was recovered from the reaction solution by ethanol precipitation, dissolved in 20 µl of TE buffer (pH 8.0) (10 mmol/l Tris-HCl, 1 mmol/l EDTA) and then subjected to 0.4% (w/v) agarose gel electrophoresis. After the electrophoresis, the genome DNA was transferred onto a nylon membrane in accordance with a known method [*Proc. Natl.*

Acad. Sci USA, 7, 3683 (1979)]. After completion of the transfer, the nylon membrane was heated at 80° C. for 2 hours.

On the other hand, a probe used in the Southern blotting was prepared as follows. First, primers (SEQ ID NOs:30 and 31) which bind to a sequence outside the targeting vector homologous region among the FUT8 genome region obtained in Example 12 were designed. Next, polymerase chain reaction (PCR) was carried out using a DNA polymerase ExTaq (manufactured by Takara Shuzo), by preparing 20 µl of a reaction solution [ExTaq buffer (manufactured by Takara Shuzo), 0.2 mmol/l dNTPs and 0.5 µmol/l gene-specific primers (SEQ ID NOs:30 and 31)] containing 4.0 ng of the plasmid pFUT8fgE2-2 obtained in Example 12(2). The PCR was carried out by heating at 94° C. for 1 minute and subsequent 25 cycles of heating at 94° C. for 30 seconds, 55° C. for 30 seconds and 74° C. for 1 minute as one cycle. After the PCR, the reaction solution was subjected to 1.75% (w/v) agarose gel electrophoresis to purify a probe DNA fragment of about 230 bp. A 5 µl portion of the obtained probe DNA solution was radioisotope-labeled using 1.75 MBq of [α-$^{12}$P] dCTP and Megaprime DNA Labeling System, dCTP (manufactured by Amersham Pharmacia Biotech).

The hybridization was carried out as follows. First, the nylon membrane was sealed in a roller bottle, and pre-hybridization was carried out at 65° C. for 3 hours by adding 15 ml of a hybridization solution (5×SSPE, 50× Denhaldt's solution, 0.5% (w/v) SDS, 100 µg/ml salmon sperm DNA). Next, the $^{32}$P-labeled probe DNA was heat-denatured and put into the bottle and the nylon membrane was heated overnight at 65° C.

After the hybridization, the nylon membrane was soaked in 50 ml of 2×SSC-0.1% (w/v) SDS and heated at 65° C. for 15 minutes. After repeating the washing step twice, the membrane was soaked in 50 ml of 0.2×SSC-0.1% (w/v) SDS and heated at 65° C. for 15 minutes. After washing the nylon membrane, it was exposed to an X-ray film two nights at −80° C. for development.

By the restriction enzyme BamHI treatment, a DNA fragment of about 19.0 Kb was formed from a wild type FUT8 allele. Also, a DNA fragment of about 12.5 Kb was formed from an allele in which homologous recombination with a targeting vector was generated. In addition, when the puromycin resistance gene (about 1.5 Kb) was deleted from the allele in which homologous recombination was generated, a DNA fragment of about 11.0 Kb was formed by the same treatment.

Figure 41:
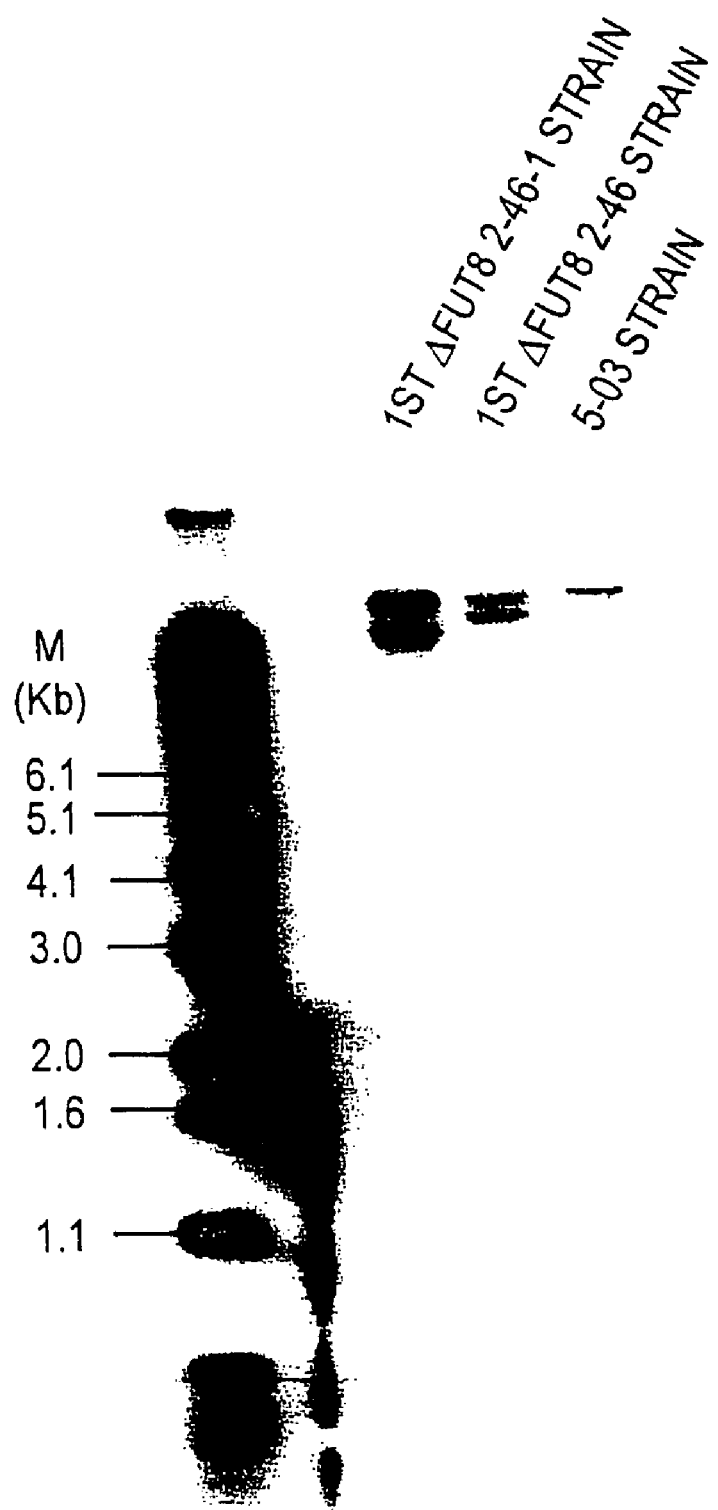
FIG. 41 shows results of genome Southern analyses of 1st.ΔFUT8 2-46-1 and 1st.ΔFUT8 2-46 as α-1,6-fucosyltransferase gene-disrupted CHO cell lines.

By the method, such specific fragments of about 19.0 Kb and about 11.0 Kb were found from the genome DNA of 5 clones among the 6 clones. Since the quantitative ratio of both fragments was 1:1, it was shown that the puromycin resistance gene was deleted from the cell lines in which 1 copy of the FUT8 genome region was disrupted. Hereinafter, one of the clone is called 1st.ΔFUT8 2-46-1. Also, results of the genome Southern blotting of the strain 1st.ΔFUT8 2-46-1, 1st.ΔFUT8 2-46 and 5-03 are shown in FIG. 41. Also, the strain 1st.ΔFUT8 2-46-1, as a name of 2-46-1, has been deposited on Sep. 26, 2001, as FERM BP-7755 in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan)).

4 Purification of Antibody Produced by α-1,6-fucosyltransferase (FUT8) Gene-Disrupted Cell Line 1st.ΔFUT8 2-46-1 obtained in the item 3 of this Example by disrupting one copy of the FUT8 allele was suspended in IMDM medium (manufactured by Life Technologies) supplemented with 15 µg/ml of puromycin (manufactured by SIGMA) and 10% fetal bovine dialyzed serum (manufactured by Life Technologies) to give a density of 3×10$^5$ cells/ml, and then 60 ml in total of the suspension was inoculated into two T182 flasks for adhesion cell culture use (manufactured by Greiner). After culturing them for 3 days, the supernatant was discarded and changed to a total of 60 ml of EXCELL301 medium (manufactured by JRH Biosciences).

After culturing them at 37° C. for 7 days in a 5% CO$_2$ incubator, the number of intact cells was counted to confirm that their viability was almost the same (each 30% or less), and then each cell suspension was recovered. The cell suspension was centrifuged at 3,000 rpm at 4° C. for 10 minutes, and the recovered supernatant was centrifuged at 10,000 rpm at 4° C. for 1 hour and then filtered using 150 ml capacity PES Filter Unit (manufactured by NALGENE) having a pore diameter of 0.22 µm.

Prosep-A HighCapacity (manufactured by bioPROCESSING) was packed in a 0.8 cm diameter column to a thickness of 2 cm and washed with 10 ml of 0.1 mol/l citrate buffer (pH 3.0) and 10 ml of 1 mol/l glycine/NaOH-0.15 mol/l NaCl buffer (pH 8.6) in this order to effect equilibrate the carrier. Next, 100 ml of each of the culture supernatant was passed through the column and washed with 50 ml of 1 mol/l glycine/NaOH-0.15 mol/l NaCl buffer (pH 8.6). After washing it, the antibody absorbed to Prosep-A was eluted using 2.5 ml of 0.1 mol/l citrate buffer (pH 3.0), the eluate was fractionated in 500 µl portions and each fraction was neutralized by mixing with 100 µl of 2 mol/l Tris-HCl (pH 8.5). Two fractions containing the antibody at a high concentration (1.2 ml in total) were selected by the BCA method [*Anal. Biochem.*, 150, 76 (1985)], combined and then dialyzed against 10 mol/l citrate-0.15 mol/l NaCl buffer (pH 6.0) at 4° C. for a whole day and night. After the dialysis, the antibody solution was recovered and subjected to sterile filtration using a 0.22 µm pore size Millex GV (manufactured by MILLIPORE).

5. In Vitro Cytotoxic Activity (ADCC Activity) of Antibody Produced by α-1,6-fucosyltransferase (FUT8) Gene-Disrupted Cell Line In order to evaluate in vitro cytotoxic activity of the anti-CCR4 antibody purified in the item 4 of this Example, ADCC activity was measured using the CCR4-positive cell line CCR4/EL-4 described in Example 8.

The CCR4/EL-4 cells subcultured in RPMI1640 medium (manufactured by Life Technologies) containing 10% fetal bovine serum (manufactured by Life Technologies) (hereinafter referred to as "RPMI1640-FBS(10)") were suspended in 500 µl of RPMI1640-FBS(10) at a density of 1×10$^4$ cells, and 3.7 MBq of Na$_2$$^{51}$CrO$_4$ was added thereto, followed by culturing at 37° C. for 90 minutes to label the cells with a radioisotope. After centrifugation at 1,200 rpm for 5 minutes, the supernatant was discarded and the target cells were suspended in 5 ml of RPMI1640-FBS(10). The washing step was repeated three times and then the cell suspension was incubated for 30 minutes on ice for spontaneous dissociation of the radioactive substance. The washing step was again repeated twice and then the cells were suspended in 5 ml of RPMI1640-FBS(10) to thereby prepare 2.0×10$^5$ cells/ml of a target cell suspension.

Separately, 30 ml of venous blood was collected from a healthy person, gently mixed with 0.5 ml of heparin sodium (manufactured by Shimizu Pharmaceutical) and then mixed with 30 ml of physiological saline (manufactured by Otsuka Pharmaceutical). After mixing them, 10 ml of the mixture was gently overlaid on 4 ml of Lymphoprep (manufactured by NYCOMED PHARMA AS) and centrifuged at room temperature at 2,000 rpm for 30 minutes. The separated mononuclear cell fractions were collected from the centrifugation tubes, combined and then suspended in 30 ml of RPMI1640-FBS(10). After centrifugation at room temperature at 1,200 rpm for 15 minutes, the supernatant was discarded and the cells were suspended in 20 ml of RPMI1640-FBS(10). The washing step was repeated twice and then $2.5 \times 10^6$ cells/ml of an effector cell suspension was prepared using RPMI1640-FBS(10).

The target cell suspension was dispensed at 50 μl ($1 \times 10^4$ cells/well) into each well of a 96 well U-bottom plate (manufactured by Falcon). Subsequently, the effector cell suspension was dispensed at 100 μl ($2.5 \times 10^5$ cells/well) into each well to thereby adjust the ratio of the effector cells to the target cells to 25:1. Next, using RPMI1640-FBS(10), a series of dilution solution of 0.01 μg/ml, 0.1 μg/ml, 1 μg/ml and 10 μg/ml was prepared from each of the anti-CCR4 antibodies obtained in the item 5 of Example 13, and the diluted solutions were dispensed in 50 μl portions into the wells to give final concentrations of 0.0025 μg/ml, 0.025 μg/ml, 0.25 μg/ml and 2.5 μg/ml, respectively. After the reaction at 37° C. for 4 hours in 5% $CO_2$, the plate was centrifuged at 1,200 rpm for 5 minutes. Into a 12 mm diameter RIA tube (manufactured by IWAKI), 75 μl of the supernatant in each well was batched off and the amount of the dissociated $^{51}Cr$ was measured using MINAX-γ auto-gamma counter 5550 (manufactured by PACKARD).

Also, the amount of the spontaneously dissociated $^{51}Cr$ was calculated by carrying out the same reaction in a reaction mixture in which 150 μl of RPMI1640-FBS(10) was added instead of the effector cell suspension and antibody solution. The amount of the total dissociated $^{51}Cr$ was calculated by carrying out the same reaction in a reaction mixture in which 100 μl of 1 N hydrochloric acid and 50 μl of RPMI1640-FBS (10) were added instead of the effector cell suspension and antibody solution. Using these values, the ADCC activity was calculated based on equation (II).

Figure 42:
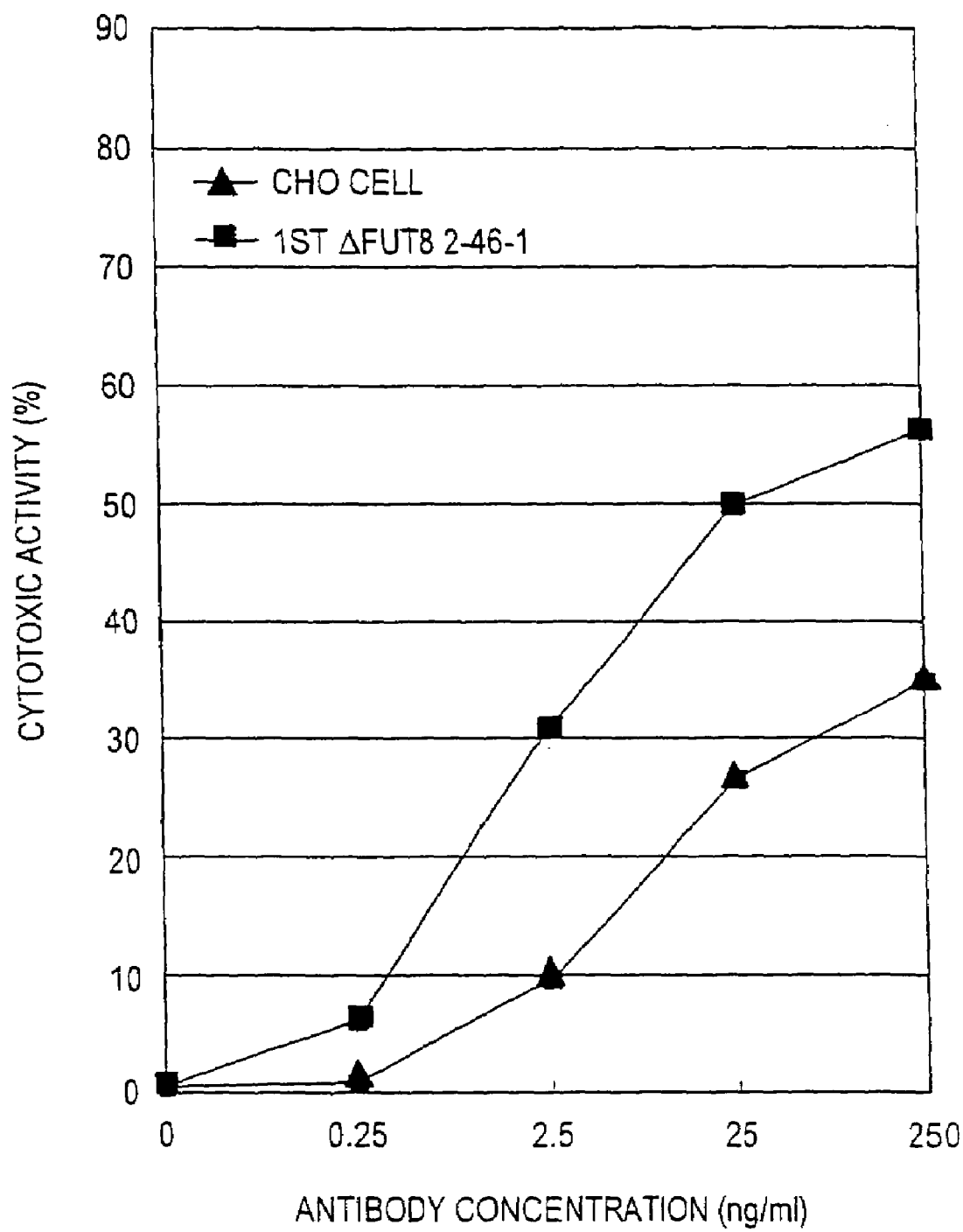
FIG. 42 shows ADCC activities of an anti-CCR4 chimeric antibody purified from an FUT8 allele gene-disrupted cell line. The ordinate and the abscissa show the cytotoxic activity and the antibody concentration. "▲" and "■" show the activities of a purified antibody derived from an anti-CCR4 chimeric antibody-producing CHO cell 5-03 and a purified antibody derived from 1st.ΔFUT8 2-46-1, respectively.

FIG. 42 shows ADCC activity of each of the anti-CCR4 antibodies. The antibody obtained from the strain 1st.ΔFUT8 2-46-1 in which 1 copy of the FUT8 allele was disrupted showed a significantly more potent ADCC activity than the antibody produced by the strain 5-03 which is the CHO cell line before gene disruption. Also, changes in the antigen binding activity of these antibodies were not observed. Based on the results, it was confirmed that the ADCC activity of produced antibodies can be improved by disrupting the FUT8 allele in host cells.

EXAMPLE 14

Preparation of Lectin-Resistant CHO/DG44 Cell and Production of Antibody Using the Cell:

(1) Preparation of Lectin-Resistant CHO/DG44

CHO/DG44 cells were grown until they reached a stage of just before confluent, by culturing in a 75 cm² flask for adhesion culture (manufactured by Greiner) using IMDM-FBS (10) medium [IMDM medium comprising 10% of fetal bovine serum (FBS) and 1× concentration of HT supplement (manufactured by GIBCO BRL)]. After washing the cells with 5 ml of Dulbecco PBS (manufactured by Invitrogen), 1.5 ml of 0.05% trypsin (manufactured by Invitrogen) diluted with Dulbecco PBS was added thereto and incubated at 37° C. for 5 minutes for peel the cells from the flask bottom. The peeled cells were recovered by a centrifugation operation generally used in cell culture and suspended in IMDM-FBS (10) medium to give a density of $1 \times 10^5$ cells/ml, and then 0.1 μg/ml of an alkylating agent N-methyl-N'-nitro-N-nitrosoguanidine (hereinafter referred to as "MNNG", manufactured by Sigma) was added or not added thereto. After incubating them at 37° C. for 3 days in a $CO_2$ incubator (manufactured by TABAI), the culture supernatant was discarded, and the cells were again washed, peeled and recovered by the same operations, suspended in IMDM-FBS(10) medium and then inoculated into an adhesion culture 96 well plate (manufactured by IWAKI Glass) to give a density of 1,000 cells/well. To each well, as the final concentration in medium, 1 mg/ml *Lens culinaris* agglutinin (hereinafter referred to as "LCA", manufactured by Vector), 1 mg/ml *Aleuria aurantia* agglutinin (*Aleuria aurantia* lectin; hereinafter referred to as "AAL", manufactured by Vector) or 1 mg/ml kidney bean agglutinin (*Phaseolus vulgaris* leucoagglutinin; hereinafter referred to as "L-PHA", manufactured by Vector) was added. After culturing them at 37° C. for 2 weeks in a $CO_2$ incubator, the appeared colonies were obtained as lectin-resistant CHO/DG44. Regarding the obtained lectin-resistant CHO/DG44, an LCA-resistant cell line was named CHO-LCA, an AAL-resistant cell line was named CHO-AAL and an L-PHA-resistant cell line was named CHO—PHA. When the resistance of these cell lines to various kinds of lectin was examined, it was found that the CHO-LCA was also resistant to AAL and the CHO-AAL was also resistant LCA In addition, the CHO-LCA and CHO-AAL also showed a resistance to a lectin which recognizes a sugar chain structure identical to the sugar chain structure recognized by LCA and AAL, namely a lectin which recognizes a sugar chain structure in which 1-position of fucose is bound to 6-position of N-acetylglucosamine residue in the reducing end through α-bond in the N-glycoside-linked sugar chain. Specifically, it was found that the CHO-LCA and CHO-AAL can show resistance and survive even in a medium supplemented with 1 mg/ml at a final concentration of a pea agglutinin (*Pisum sativum* agglutinin; hereinafter referred to as "PSA", manufactured by Vector). In addition, even when the alkylating agent MNNG was not added, it was able to obtain lectin-resistant cell lines by increasing the number of cells to be treated. Hereinafter, these cell lines were used in analyses.

(2) Preparation of Anti-CCR4 Human Chimeric Antibody-Producing Cell

An anti-CCR4 human chimeric antibody expression plasmid pKANTEX2160 was introduced into the three lectin-resistant cell lines obtained in the (1) by the method described in Example 8, and gene amplification by a drug MTX was carried out to prepare an anti-CCR4 human chimeric antibody-producing cell line. By measuring an amount of antibody expression by the ELISA described in Example 8-2, antibody-expressing transformants were obtained from each of the CHO-LCA, CHO-AAL and CHO—PHA. Regarding each of the obtained transformants, a transformant derived from CHO-LCA was named CHO/CCR4-LCA, a transformant derived from CHO-AAL was named CHO/CCR4-AAL and a transformant derived from CHO—PHA was named CHO/CCR4-PHA. Also, the CHO/CCR4-LCA, as a name of Nega-13, has been deposited on Sep. 26, 2001, as FERSS BP-7756 in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan)).

(3) Production of Potent ADCC Activity Antibody by Lectin-Resistant CHO Cell

Figure 43:
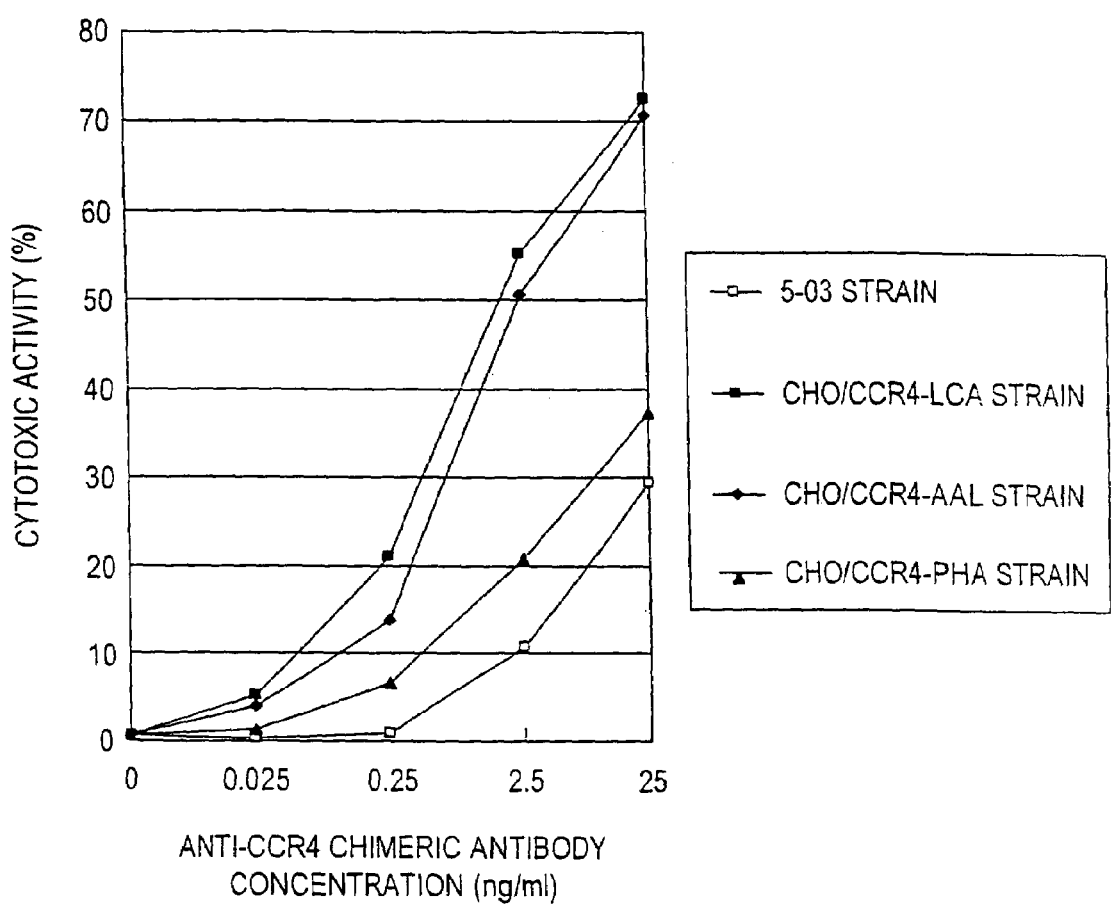
FIG. 43 shows ADCC activities of anti-CCR4 human chimeric antibodies produced by lectin-resistant cell lines. The ordinate and the abscissa show the cytotoxic activity and the antibody concentration. "□", "■", "♦" and "▲" show the activities of antibodies produced by the strain 5-03, CHO/CCR4-LCA, CHO/CCR4-AAL and CHO/CCR4-PHA, respectively.

Using the three transformants obtained in the (2), purified antibodies were obtained by the method described in Example 8-3. The antigen binding activity of each of the purified anti-CCR4 human chimeric antibodies was evaluated using the ELISA described in Example 8-2. The antibodies produced by all transformants showed an antigen binding activity similar to that of the antibody produced by a recombinant cell line (strain 5-03) prepared in Example 8 using general CHO/DG44 cell as the host. Using these purified antibodies, ADCC activity of each of the purified anti-CCR4 human chimeric antibodies was evaluated in accordance with the method described in Example 8-7. The results are shown in FIG. 43. In comparison with the antibody produced by the strain 5-03, about 100 folds-increased ADCC activity was observed in the antibodies produced by the CHO/CCR4-LCA and CHO/CCR4-AAL. On the other hand, no significant increase in the ADCC activity was observed in the antibody produced by the CHO/CCR4-PHA. Also, when ADCC activities of the antibodies produced by the CHO/CCR4-LCA and YB2/0 were compared in accordance with the method described in Example 8-7, it was found that the antibody produced by the CHO/CCR4-LCA shows more potent ADCC activity than the antibody produced by the strain 5-03, similar to the case of the antibody KM2760-1 produced by the YB2/0 cell line prepared in Example 8-1 (FIG. 44).

(4) Sugar Chain Analysis of Antibodies Produced by Lectin-Resistant CHO Cell

Sugar chains of the anti-CCR4 human chimeric antibodies purified in the (3) were analyzed. The solution of each of the purified, antibodies was exchanged to 10 mM $kH_2PO_4$ using Ultra Free 0.5-10K (manufactured by Millipore). The exchange was carried out in such a manner that the exchanging ratio became 80 folds or more. The concentration of the antibodies after the solution exchange was measured using UV-1600 (manufactured by Shimadzu). The molar absorption coefficient was calculated from the amino acid sequence of each antibody based on the following equation (III) [*Advances in Protein Chemistry*, 12, 303 (1962)], and the concentration was determined by defining the absorbance at 280 nm as 1.38 mg/ml.

$$E_{1\ mol/l} = A \times n1 + B \times n2 + C \times n3 \quad (III)$$

$$E_{1\ mol/ml} = E_{1\ mol/l}/MW$$

$E_{1\ mol/l}$: absorption coefficient at 280 nm ($mg^{-1}$ ml $cm^{-1}$)

$E_{1\ mol/ml}$: molar absorption coefficient at 280 nm ($M^{-1}$ $cm^{-1}$)

A: molar absorption coefficient of tryptophan at 280 nm=5550 ($M^{-1}$ $cm^{-1}$)

B: molar absorption coefficient of tyrosine at 280 nm=1340 ($M^{-1}$ $cm^{-1}$)

C: molar absorption coefficient of cystine at 280 nm=200 ($M^{-1}$ $cm^{-1}$)

n1: the number of tryptophan per 1 antibody molecule n2: the number of tyrosine per 1 antibody molecule n3: the number of cystine per 1 antibody molecule MW: molecular weight of antibody (g/mol)

Into Hydraclub S-204 test tube, 100 μg of each antibody was put and dried using a centrifugal evaporator. The dried sample in the test tube was subjected to hydrazinolysis using Hydraclub manufactured by Hohnen. The sample was allowed to react with hydrazine at 110° C. for 1 hour using a hydrazinolysis reagent manufactured by Hohnen hydrazinolysis [*Method of Enzymology*, 83, 263 (1982)]. After the reaction, hydrazine was evaporated under a reduced pressure, and the reaction tube was returned to room temperature by allowing it to stand for 30 minutes. Next, 250 μl of an acetylation reagent manufactured by Hohnen and 25 μl of acetic anhydride were added thereto, followed by thoroughly stirred for reaction at room temperature for 30 minutes. Then, 250 μl of the acetylation reagent and 25 μl of acetic anhydride were further added thereto, followed by thoroughly stirring for reaction at room temperature for 1 hour. The sample was frozen at −80° C. in a freezer and freeze-dried for about 17 hours. Sugar chains were recovered from the freeze-dried sample using Cellulose Cartridge Glycan Preparation Kit manufactured by Takara Syuzo Co., Ltd. The sample sugar chain solution was dried using a centrifugal evaporator and then subjected to fluorescence labeling with 2-aminopyridine [*J. Biochem.*, 9, 197 (1984)]. The 2-aminopyridine solution was prepared by adding 760 μl of HCl per 1 g of 2-aminopyridine (1×PA solution) and diluting the solution 10 folds with reverse osmosis purified water (10-folds diluted PA solution). The sodium cyanoborohydride solution was prepared by adding 20 μl of 1×PA solution and 430 μl of reverse osmosis purified water per 10 mg of sodium cyanoborohydride. To the sample, 67 μl of a 10 folds-diluted PA solution was added, followed by reaction at 100° C. for 15 minutes and spontaneously cooled, and 2 μl of sodium cyanoborohydride was further added thereto, followed by reaction at 90° C. for 12 hours for fluorescence labeling of the sample sugar chains. The fluorescence-labeled sugar chain group (PA-treated sugar chain group) was separated from excess reagent using Superdex Peptide HR 10/30 column (manufactured by Pharmacia). This step was carried out using 10 mM ammonium bicarbonate as the eluent at a flow rate of 0.5 ml/min and at a column temperature of room temperature, and using a fluorescence detector of 320 nm excitation wavelength and 400 nm fluorescence wavelength. The eluate was recovered 20 to 30 minutes after addition of the sample and dried using a centrifugal evaporator to be used as purified PA-treated sugar chains. Next, reverse phase HPLC analysis of the purified PA-treated sugar chains was carried out using CLC-ODS column (manufactured by Shimadzu, φ6.0 nm×159 nm). The step was carried out at a column temperature of 55° C. and at a flow rate of 1 ml/min and using a fluorescence detector of 320 nm excitation wavelength and 400 nm fluorescence wavelength. The column was equilibrated with a 10 mM sodium phosphate buffer (pH 3.8) and elution was carried out for 80 minutes by a 0.5% 1-butanol linear density gradient. Each of the PA-treated sugar chain was identified by post source decay analysis of each peak of the separated PA-treated sugar chains using matrix-assisted laser ionization time of flight mass spectrometry (MALDI-TOF-MS analysis), comparison of elution positions with standards of PA-treated sugar chain manufactured by Takara Syuzo, and reverse phase HPLC analysis after digestion of each PA-treated sugar chain using various enzymes (FIG. 45). Each of the sugar chain content was calculated from each of the peak area of PA-treated sugar chain by reverse HPLC analysis A PA-treated sugar chain whose reducing end is not N-acetylglucosamine was excluded from the peak area calculation, because it is an impurity or a by-product during preparation of PA-treated sugar chain.

The analysis was carried out in the same-manner as in Example 11(6) using a sodium phosphate buffer (pH 3.8) as buffer A and a sodium phosphate buffer (pH 3.8)+0.5% 1-butanol as buffer B.

In FIG. 45, the ratio of the α-1,6-fucose-free sugar chain group was calculated from the area occupied by the peaks (i) to (iv) among (i) to (viii), and the ratio of the α-1,6-fucose-bound sugar chain group from the area occupied by the peaks (v) to (viii) among (i) to (viii).

Results of the sugar chain structure analysis of the purified anti-CCR4 human chimeric antibodies produced by lectin-resistant cell lines are shown in Table 6. The result shows the analysis of sugar chains of the anti-CCR4 human chimeric antibody produced by lectin-resistant cell lines. The ratio of α-1,6-fucose-free sugar chains (%) calculated from peak areas by analyzing by the method described in Example d(4) is shown in the table.

TABLE 6

| Antibody producing cells | α-1,6-Fucose-free complex double-chain sugar chain (%) |
|---|---|
| Strain 5-03 | 9 |
| Strain CHO/CCR4-LCA | 48 |
| Strain CHO/CCR4-AAL | 27 |
| Strain CHO/CCR4-PHA | 8 |

In comparison with the antibody produced by the strain 5-03, the ratio of the α-1,6-fucose-free sugar chains was increased from 9% to 48% in the antibody produced by the CHO/CCR4-LCA when calculated from the analyzed peak area The ratio of α-1,6-fucose-free sugar chains was increased from 9% to 21% in the antibody produced by the CHO/CCR4-AAL. On the other hand, changes in the sugar chain pattern and ratio of the α-1,6-fucose-free sugar chains were hardly found in the PHA-resistant cell line when compared with the strain 5-03.

EXAMPLE 15

Analysis of Lectin-Resistant CHO Cell Line

1. Analysis of Expression Level of GMD Enzyme in an Anti-CCR4 human Chimeric Antibody-Producing Cell Line CHO/CCR4-LCA The expression level of each of the genes of GMD (GDP-mannose 4,6-dehydratase), GFPP (GDP-keto-6-deoxymannose 3,5-epimerase, 4-reductase) and FX (GDP-beta-L-fucose pyrophosphorylase) known as fucose biosynthesis enzymes and FUT8 (α-1,6-fucosyltransferase) as a fucose transferase, in the anti-CCR4 human chimeric antibody-producing cell line CHO/CCR4-LCA obtained in Example 14, was analyzed using RT-PCR method.

(1) Preparation of RNA from Various Cell Lines

Each of the CHO/DG44 cell, the anti-CCR4 human chimeric antibody-producing cell line 5-03 obtained in Example 8-1(2) and the anti-CCR4 human chimeric antibody-producing cell line CHO/CCR4-LCA obtained in Example 14(2) was subcultured at 37° C. in a 5% CO$_2$ incubator and then cultured for 4 days After culturing them, total RNA was prepared from 1×10$^7$ cells of each cell line using RNeasy Protect Mini Kit (manufactured by QIAGEN) in accordance with the manufacture's instructions. Subsequently, single-stranded cDNA was synthesized from 5 μg of each RNA in a 20 μl of a reaction solution using SUPER SCRIPT First-Strand Synthesis System for RT-PCR (manufactured by GIBCO BRL) in accordance with the manufacture's instructions.

(2) Analysis of Expression Level of GMD Gene Using RT-PCR

In order to amplify GMD cDNA by PCR, a 24 mer synthetic DNA primer having the nucleotide sequence shown by SEQ ID NO:32 and a 26 mer synthetic DNA primer having the nucleotide sequence shown by SEQ ID NO:33 were prepared based on the CHO cell-derived GMD cDNA sequence shown in Example 17-1.

Next, 20 μl of a reaction solution [1×Ex Taq buffer (manufactured by Takara Shuzo), 0.2 mM dNTPS, 0.5 unit of Ex Taq polymerase (manufactured by Takara Shuzo) and 0.5 μM of the synthetic DNA primers of SEQ ID NOs:32 and 33) containing 0.5 μl of the single-stranded cDNA prepared from each cell line in the item (1) as the template was prepared, and PCR was carried out using DNA Thermal Cycler 480 (manufactured by Perkin Elmer) by heating at 94° C. for 5 minutes and subsequent 30 cycles of heating of 94° C. for 1 minute and 68° C. for 2 minutes as one cycle. After subjecting 10 μl of the PCR reaction solution to agarose electrophoresis, DNA fragments were stained using Cyber Green (manufactured by BMA) and then the amount of the DNA fragment of about 350 bp was measured using Fluor Imager SI (manufactured by Molecular Dynamics).

(3) Analysis of Expression Level of GFPP Gene Using RT-PCR

In order to amplify GFPP cDNA by PCR, a 27 mer synthetic DNA primer having the nucleotide sequence shown by SEQ ID NO:34 and a 23 mer synthetic DNA primer having the nucleotide sequence shown by SEQ ID NO:35 were prepared based on the CHO cell-derived GFPP cDNA sequence obtained in Example 16-2.

Next, 20 μl of a reaction solution [1× Ex Taq buffer (manufactured by Takara Shuzo), 0.2 mm dNTPs, 0.5 unit of Ex Taq polymerase (manufactured by Takara Shuzo) and 0.5 μM of the synthetic DNA primers of SEQ ID NOs:34 and 35] containing 0.5 μl of the single-stranded cDNA prepared from each cell line in the item (1) as the template was prepared, and PCR was carried out using DNA Thermal Cycler 480 (manufactured by Perkin Elmer) by heating at 94° C. for 5 minutes and subsequent 24 cycles of heating at 94° C. for 1 minute and 68° C. for 2 minutes as one cycle. After subjecting 10 μl of the PCR reaction solution to agarose electrophoresis, DNA fragments were stained using Cyber Green (manufactured by BMA) and then the amount of the DNA fragment of about 600 bp was measured using Fluor Imager SI (manufactured by Molecular Dynamics).

(4) Analysis of Expression Level of FX Gene Using RT-PCR

In order to amplify FX cDNA by PCR, a 28 mer synthetic DNA primer having the nucleotide sequence shown by SEQ ID NO:36 and a 28 mer synthetic DNA primer having the nucleotide sequence shown by SEQ ID NO:37 were prepared based on the CHO cell-derived FX cDNA sequence shown in Example 16-1.

Next, 20 μl of a reaction solution [1× Ex Taq buffer (manufactured by Takara Shuzo), 0.2 mM dNTPs, 0.5 unit of Ex Taq polymerase (manufactured by Takara Shuzo) and 0.5 μM of the synthetic DNA primers of SEQ ID NO:36 and SEQ ID NO:37] containing 0.5 μl of the single-stranded cDNA prepared from each cell line in the item (1) as the template was prepared, and PCR was carried out using DNA Thermal Cycler 480 (manufactured by Perkin Elmer) by heating at 94° C. for 5 minutes and subsequent 22 cycles of heating at 94° C. for 1 minute and 68° C. for 2 minutes as one cycle. After subjecting 10 μl of the PCR reaction-solution to agarose electrophoresis, DNA fragments were stained using Cyber Green (manufactured by BMA) and then the amount of the DNA fragment of about 300 bp was measured using Fluor Imager SI (manufactured by Molecular Dynamics).

(5) Analysis of Expression Level of FUT8 Gene Using RT-PCR

In order to amplify FUT8 cDNA by PCR, 20 μl of a reaction solution [1× Ex Taq buffer (manufactured by Takara Shuzo), 0.2 mM dNTPs, 0.5 unit of Ex Taq polymerase (manufactured by Takara Shuzo) and 0.5 μM of the synthetic DNA primers of SEQ ID NOs:13 and 14] containing 0.5 μl of the single-stranded cDNA prepared from each cell line in the item (1) as the template was prepared, and PCR was carried out using DNA Thermal Cycler 480 (manufactured by Perkin Elmer) by heating at 94° C. for 5 minutes and subsequent 20 cycles of heating at 94° C. for 1 minute and 68° C. for 2 minutes as one cycle. After subjecting 10 μl of the PCR reaction solution to agarose electrophoresis, DNA fragments were stained using Cyber Green (manufactured by BMA) and then amount of the DNA fragment of about 600 bp was measured using Fluor Imager SI (manufactured by Molecular Dynamics).

(6) Analysis of Expression Level of β-actin Gene Using RT-PCR

In order to amplify β-actin cDNA by PCR, 20 μl of a reaction solution [1× Ex Taq buffer (manufactured by Takara Shuzo), 0.2 mM dNTPs, 0.5 unit of Ex Taq polymerase (manufactured by Takara Shuzo) and 0.5 μM of the synthetic DNA primers of SEQ ID NOs;15 and 16] containing 0.5 μl of the single-stranded cDNA prepared from each cell line in the item (1) as the template was prepared, and the reaction was carried out using DNA Thermal Cycler 480 (manufactured by Perkin Elmer) by heating at 94° C. for 5 minutes and subsequent 14 cycles of heating at 94° C. for 1 minute and 68° C. for 2 minutes as one cycle. After subjecting 10 μl of the PCR reaction solution to agarose electrophoresis, DNA fragments were stained using Cyber Green (manufactured by BMA) and then the amount of the DNA fragment of about 800 bp was measured using Fluor Imager SI (manufactured by Molecular Dynamics).

(7) Expression Levels of GMD, GFPP, FX and FUT8 Genes in Each Cell Line

The amount of the PCR-amplified fragment of each gene in the strain 5-03 and the CHO/CCR4-LCA was calculated by dividing values of the amounts of PCR-amplified fragments derived from GMD, GFPP, FX and FUT cDNA in each cell line measured in the items (2) to (6) by the value of the amount of PCR-amplified fragment derived from β-actin cDNA in each cell line, and defining the amount of the PCR-amplified fragments in CHO/DG44 cell as 1. The results are shown in Table 7.

TABLE 7

|  | GMD | GEPP | FX | FUT8 |
|---|---|---|---|---|
| Strain CHO/DG44 | 1 | 1 | 1 | 1 |
| Strain 5-03 | 1.107 | 0.793 | 1.093 | 0.901 |
| Strain 5-03-derived LCA-resistant cell CHO/CCR4-LCA | 0.160 | 0.886 | 0.920 | 0.875 |

As shown in Table 7, the expression level of GMD gene in the CHO/CCR4-LCA was decreased to about 1/10 in comparison with other cell lines. In this case, the test was independently carried out twice, and the average value was used.

Figure 46:
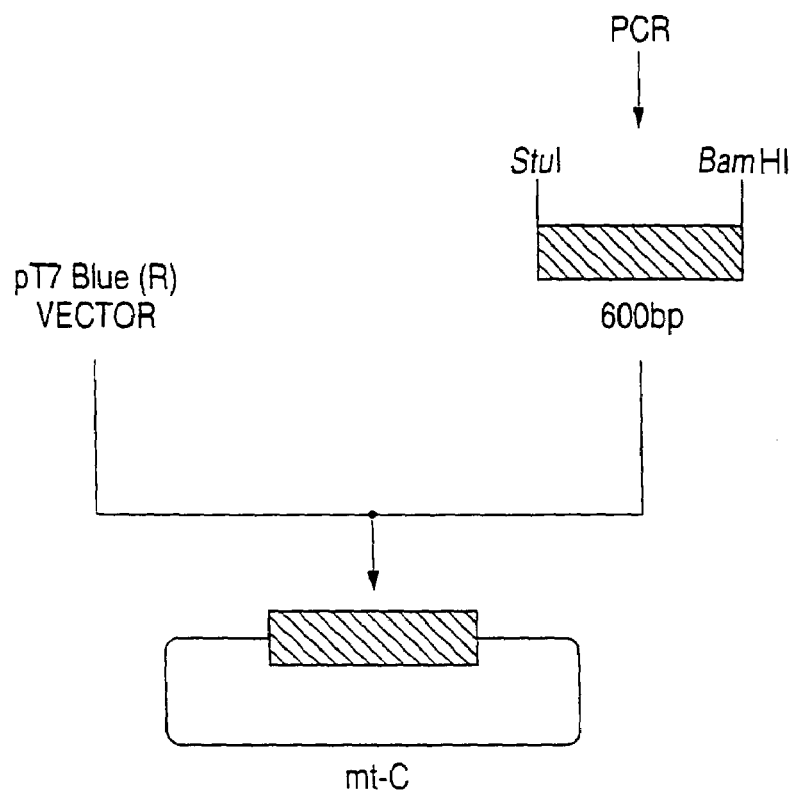
FIG. 46 shows the 1st step of construction of an expression vector of CHO cell-derived GMD (6 steps in total).

2. Analysis Using Anti-CCR4 Human Chimeric Antibody-Producing CHO/CCR4-LCA in Which GMD Gene was Forced to Express (1) Construction of CHO Cell-Derived GMD Gene Expression Vector pAGE249GMD Based on the CHO cell-derived GMD cDNA sequence obtained in Example 17-1, a 28 mer primer having the nucleotide sequence shown by SEQ ID NO:38 and a 29 mer primer having the nucleotide sequence shown by SEQ ID NO:39 were prepared. Next, 20 μl of a reaction solution [1× Ex Taq buffer (manufactured by Takara Shuzo), 0.2 mM dNTPs, 0.5 unit of Ex Taq polymerase (manufactured by Takara Shuzo) and 0.5 μM of the synthetic DNA primers of SEQ ID NOs:38 and 39] containing 0.5 μl of the CHO cell-derived GMD single-stranded cDNA prepared in the item 1(1) of this Example as the template was prepared, and PCR was carried out using DNA Thermal Cycler 480 (manufactured by Perkin Elmer) by heating at 94° C. for 5 minutes and subsequently 8 cycles of heating at 94° C. for 1 minute, 58° C. for 1 minute and 72° C. for 1 minute as one cycle, and then 22 cycles of heating at 94° C. for 1 minute and 68° C. as one cycle. After completion of the reaction, the PCR reaction solution was fractionated by agarose electrophoresis, and then a DNA fragment of about 600 bp was recovered using Gene Clean II Kit (manufactured by BIO 101) in accordance with the manufacture's instructions. The recovered DNA fragment was connected to pT7Blue(R) vector (manufactured by Novagen) using DNA Ligation Kit (manufactured by Takara Shuzo), and E. coli DH5α (manufactured by Toyobo) was transformed using the obtained recombinant plasmid DNA to obtain a plasmid mt-C (cf. FIG. 46).

Figure 47:
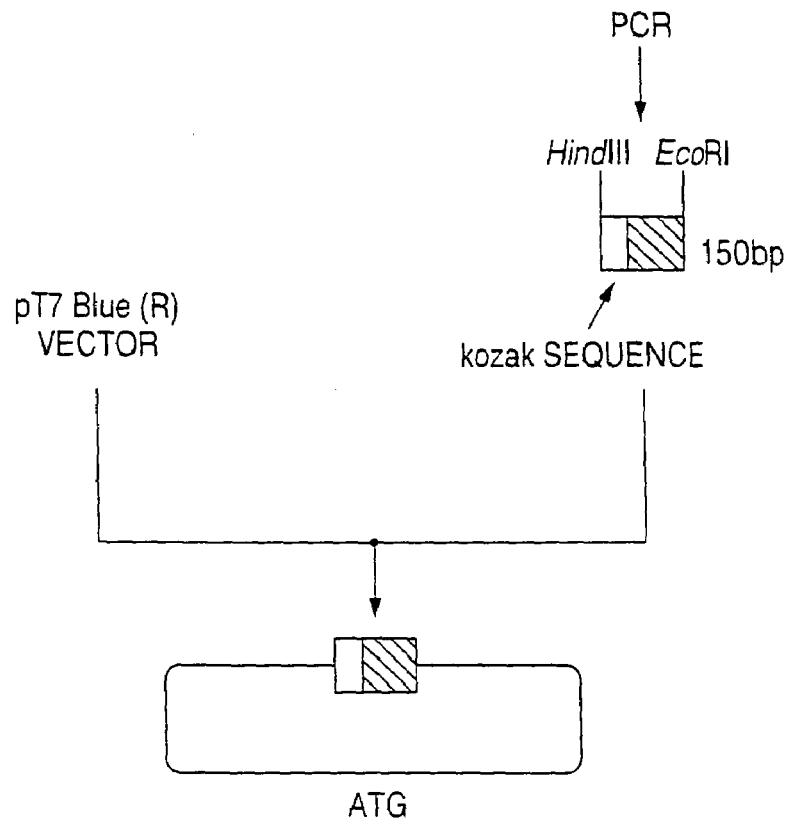
FIG. 47 shows the 2nd step of construction of the expression vector of CHO cell-derived GMD (6 steps in total).

Next, based on the CHO cell-derived GMD cDNA sequence obtained in Example 17-1, a 45 mer primer having the nucleotide sequence shown by SEQ ID NO:40 and a 31 mer primer having the nucleotide sequence shown by SEQ ID NO:41 were prepared. Next, 20 μl of a reaction solution (1× Ex Taq buffer (manufactured by Takara Shuzo), 0.2 mM dNTPs, 0.5 unit of Ex Taq polymerase (manufactured by Takara Shuzo) and 0.5 μm of the synthetic DNA primers of SEQ ID NOs:40 and 41] containing 0.5 μl of the CHO cell-derived GMD single-stranded cDNA prepared in the item 1(1) of this Example as the template was prepared, and PCR was carried out using DNA Thermal Cycler 480 (manufactured by Perkin Elmer) by heating at 94° C. for 5 minutes and subsequently 8 cycles of heating at 94° C. for 1 minute, 57° C. for 1 minute and 72° C. for 1 minute as one cycle, and then 22 cycles of heating at 94° C. for 1 minute and 68° C. for 2 minutes as one cycle. After completion of the reaction, the PCR reaction solution was fractionated by agarose electrophoresis, and then a DNA fragment of about 150 bp was recovered using Gene Clean II Kit (manufactured by BIO 101) in accordance with the manufacture's instructions. The recovered DNA fragment was connected to pT7Blue(R) vector (manufactured by Novagen) using DNA Ligation Kit (manufactured by Takara Shuzo), and E. coli DH5α (manufactured by Toyobo) was transformed using the obtained recombinant plasmid DNA to obtain a plasmid ATG (cf. FIG. 47).

Figure 48:
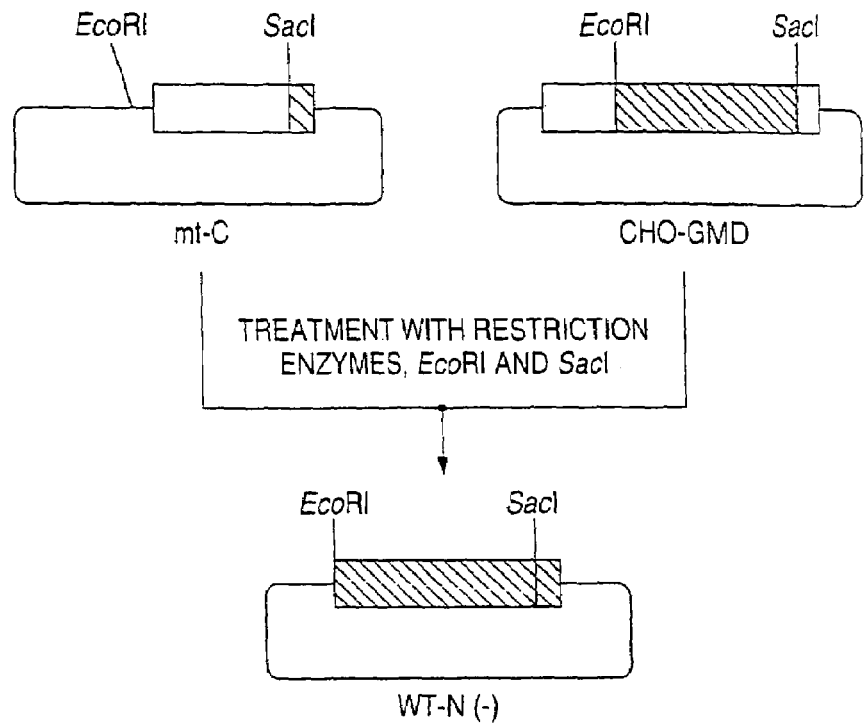
FIG. 48 shows the 3rd step of construction of the expression vector of CHO cell-derived GMD (6 steps in total).

Next, 3 μg of the plasmid CHO-GMD prepared in Example 17-1 was allowed to react with a restriction enzyme SacI (manufactured by Takara Shuzo) at 37° C. for 16 hours, a DNA was recovered by carrying out phenol/chloroform extraction and ethanol precipitation and allowed to react with a restriction enzyme EcoRI (manufactured by Takara Shuzo) at 37° C. for 16 hours, a digest DNA was fractionated by agarose electrophoresis and then a DNA fragment of about 900 bp was recovered using Gene Clean II Kit (manufactured by BIO 101) in accordance with the manufacture's instructions The plasmid mt-C (1.4 μg) was allowed to react with a restriction enzyme SacI (manufactured by Takara Shuzo) at 37° C. for 16 hours, DNA was recovered by carrying out phenol/chloroform extraction and ethanol precipitation and allowed to react with a restriction enzyme EcoRI (manufactured by Takara Shuzo) at 37° C. for 16 hours, the digest was fractionated by agarose electrophoresis and then a DNA fragment of about 3.1 kbp was recovered using Gene Clean II Kit (manufactured by BIO 101) in accordance with the manufacture's instructions The recovered DNA fragments were ligated using DNA Ligation Kit (manufactured by Takara Shuzo), and *E. coli* DH5α was transformed using the obtained recombinant plasmid DNA to obtain a plasmid WT-N(−) (cf. FIG. 48).

Figure 49:
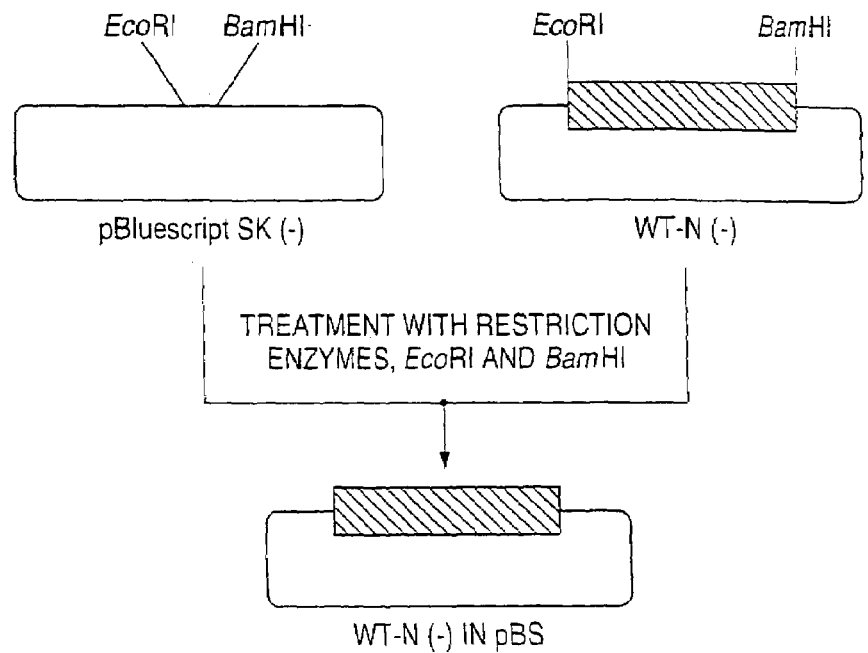
FIG. 49 shows the 4th step of construction of the expression vector of CHO cell-derived GMD (6 steps in total).

Next, 2 µg of the plasmid WT-N(−) was allowed to react with a restriction enzyme BamHI (manufactured by Takara Shuzo) at 37° for 16 hours, DNA was recovered by carrying out phenol/chloroform extraction and ethanol precipitation and allowed to react with a restriction enzyme EcoRI (manufactured by Takara Shuzo) at 37° C. for 16 hours, the digest was fractionated by agarose electrophoresis and then a DNA fragment of about 1 kbp was recovered using Gene Clean II Kit (manufactured by BIO 101) in accordance with the manufacture's instructions. The plasmid pBluescript SK(−) (3 µg; manufactured by Stratagene) was allowed to react with a restriction enzyme BamHI (manufactured by Takara Shuzo) at 37° C. for 16 hours, DNA was recovered by carrying out phenol/chloroform extraction and ethanol precipitation and allowed to react with a restriction enzyme EcoRI (manufactured by Takara Shuzo) at 37° C. for 16 hours, the digest was fractionated by agarose electrophoresis and then a DNA fragment of about 3 kbp was recovered using Gene Clean II Kit (manufactured by BIO 101) in accordance with the manufacture's instructions. The recovered respective DNA fragments were ligated using DNA Ligation Kit (manufactured by Takara Shuzo), and *E. coli* DH5α was transformed using the obtained recombinant plasmid DNA to obtain a plasmid WT-N(−) in pBS (cf. FIG. 49).

Figure 50:
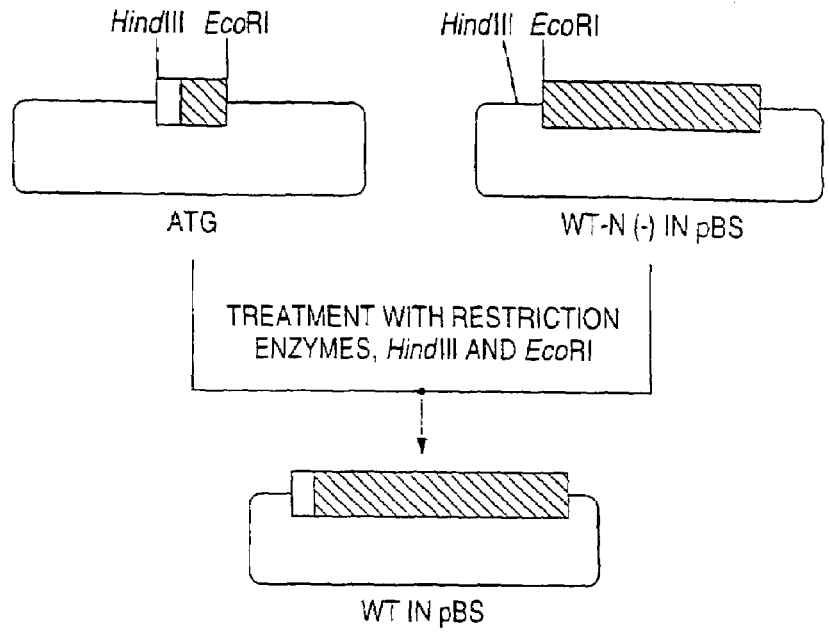
FIG. 50 shows the 5th step of construction of the expression vector of CHO cell-derived GMD (6 steps in total).

Next, 2 µg of the plasmid WT-N(−) in pBS was allowed to react with a restriction enzyme HindIII (manufactured by Takara Shuzo) at 37° C. for 16 hours, DNA was recovered by carrying out phenol/chloroform extraction and ethanol precipitation and allowed to react with a restriction enzyme EcoRI (manufactured by Takara Shuzo) at 37° C. for 16 hours, the digest was fractionated by agarose electrophoresis and then a DNA fragment of about 4 kbp was recovered using Gene Clean II Kit (manufactured by BIO 101) in accordance with the manufacture's instructions. A 2 µg portion of the plasmid ATG was allowed to react with a restriction enzyme HindIII (manufactured by Takara Shuzo) at 37° C. for 16 hours, DNA was recovered by carrying out phenol/chloroform extraction and ethanol precipitation and allowed to react with a restriction enzyme EcoRI (manufactured by Takara Shuzo) at 37° C. for 16 hours, the digest was fractionated by agarose electrophoresis and then a DNA fragment of about 150 bp was recovered using Gene Clean II Kit (manufactured by BIO 101) in accordance with the manufacture's instructions. The recovered respective DNA fragments were ligated using DNA Ligation Kit (manufactured by Takara Shuzo), and *E. coli* DH5α was transformed using the obtained recombinant plasmid DNA to obtain a plasmid WT in pBS (cf. FIG. 50).

Figure 51:
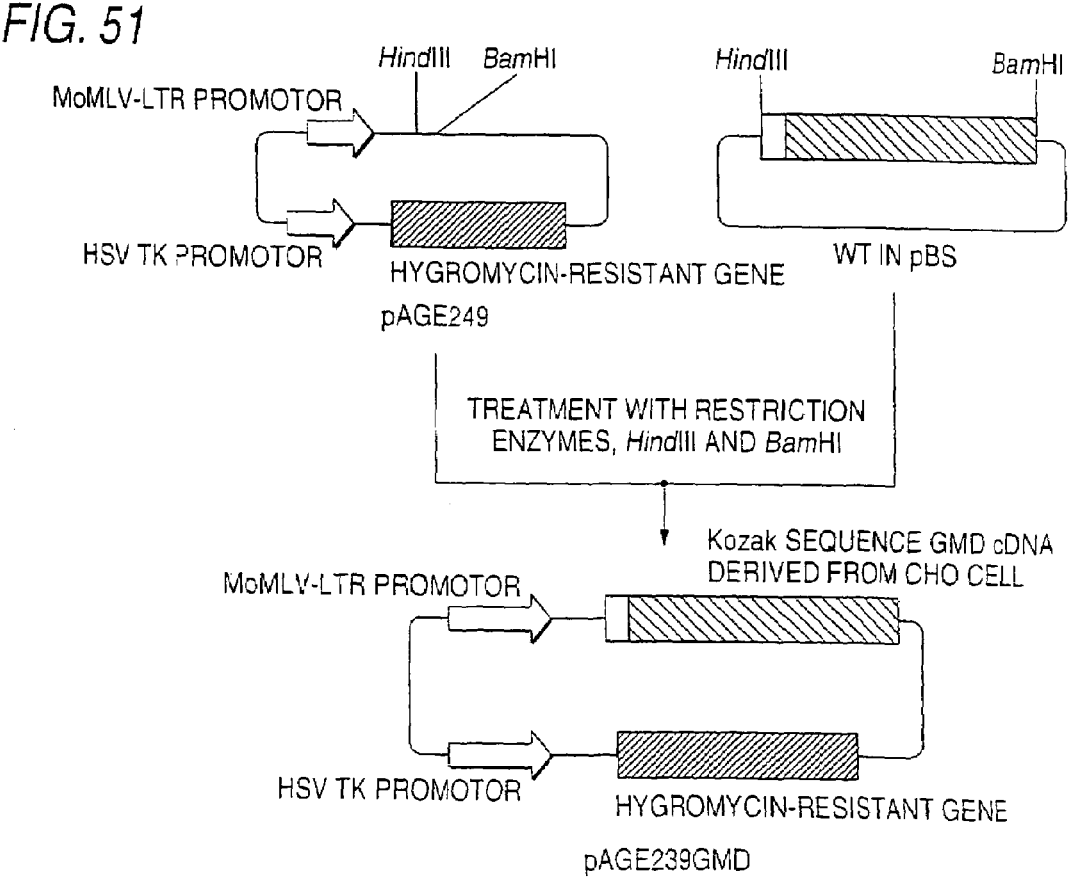
FIG. 51 shows the 6th step of construction of the expression vector of CHO cell-derived GMD (6 steps in total).

Next, 2 µg of the plasmid pAGE249 was allowed to react with restriction enzymes HindIII and BamHI (both manufactured by Takara Shuzo) at 37° C. for 16 hours, the digest was fractionated by agarose electrophoresis and then a DNA fragment of about 6.5 kbp was recovered using Gene Clean II Kit (manufactured by BIO 101) in accordance with the manufacture's instructions. The plasmid WT (2 µg) in pBS was allowed to react with restriction enzymes HindIII and BamHI (both manufactured by Takara Shuzo) at 37° C. for 16 hours, the digest was fractionated by agarose electrophoresis and then a DNA fragment of about 1.2 kbp was recovered using Gene Clean II Kit (manufactured by BIO 101) in accordance with the manufacture's instructions. The recovered respective DNA fragments were ligated using DNA Ligation Kit (manufactured by Takara Shuzo), and *E. coli* DH5α was transformed using the obtained recombinant plasmid DNA to obtain a plasmid pAGE249GMD (cf. FIG. 51).

(2) Stable Expression of GMD Gene in CHO/CCR4-LCA

The CHO cell-derived GMD gene expression vector PAGE249GMD (5 µg) made into linear form by digesting it with a restriction enzyme FspI (manufactured by NEW ENGLAND BIOLABS), which was introduced into $1.6 \times 10^6$ cells of CHO/CCR4-LCA by electroporation [*Cytotechnology*, 3, 133 (1990)]. Then, the cells were suspended in 30 ml of IMDM-dFBS(10) medium [IMDM medium (manufactured by GIBCO BRL) supplemented with 10% of dFBS] containing 200 nM MTX (manufactured by SIGMA), and cultured using a 182 cm² flask (manufactured by Greiner) at 37° C. for 24 hours in a 5% $CO_2$ incubator. After culturing them, the medium was changed to IMDM-dFBS(10) medium containing 0.5 mg/ml hygromycin and 200 nM MTX (manufactured by SIGMA), followed by culturing for 19 days to obtain colonies of hygromycin-resistant transformants.

In the same manner, the pAGE249 vector was introduced into the CHO/CCR4-LCA by the same method to obtain colonies of hygromycin-resistant transformants.

(3) Culturing of GMD Gene-Expressed CHO/CCR4-LCA and Purification of Antibody

Using IMDM-dFBS(10) medium comprising 200 nM MTX (manufactured by SIGMA) and 0.5 mg/ml hygromycin, the GMD-expressing transformant cells obtained in the item (2) were cultured using a 182 cm² flask (manufactured by Greiner) at 37° C. in a 5% $CO_2$ incubator. Several days thereafter, when the cell density reached confluent, the culture supernatant was discarded and the cells were washed with 25 ml of PBS buffer (manufactured by GIBCO BRL) and mixed with 35 ml of EXCELL301 medium (manufactured by JRH). After culturing them at 37° C. in a 5% $CO_2$ incubator for 7 days, the culture supernatant was recovered. An anti-CCR4 chimeric antibody was purified from the culture supernatant using Prosep-A (manufactured by Millipore) in accordance with the manufacture s instructions.

In the same manner, the pAGE249 vector-introduced transformant cells were cultured by the same method and then anti-CCR4 chimeric antibody was recovered and purified from the culture supernatant.

(4) Measurement of Lectin Resistance in Transformed Cells

The GMD-expressing transformant cells obtained in the item (2) were suspended in IMDM-dFBS(10) medium comprising 200 nM MTX (manufactured by SIGMA) and 0.5 mg/ml hygromycin to give a density of $6 \times 10^4$ cells/ml, and the suspension was dispensed in 50 µl/well portions into a 96 well culture plate (manufactured by Iwaki Glass). Next, a medium prepared by suspending at concentrations of 0 mg/ml, 0.4 mg/ml, 1.6 mg/ml or 4 mg/ml LCA (*Lens culinaris* agglutinin: manufactured by Vector Laboratories) in IMDM-dFBS(10) medium containing 200 nM MTX (manufactured by SIGMA) and 0.5 mg/ml hygromycin was added to the plate at 50 µl/well, followed by culturing at 37° C. for 96 hours in a 5% $CO_2$ incubator. After culturing them, WST-I (manufactured by Boehringer) was added at 10 µl/well and incubated at 37° C. for 30 minutes in a 5% $CO_2$ incubator to effect color development, and then the absorbance at 450 nm and 595 nm (hereinafter referred to as "OD450" and "OD595", respectively) was measured using Microplate Reader (manufactured by BIO-RAD). In the same manner, the pAGE249 vector-introduced transformant cells were measured by the same method. The test was carried out twice independently.

Figure 52:
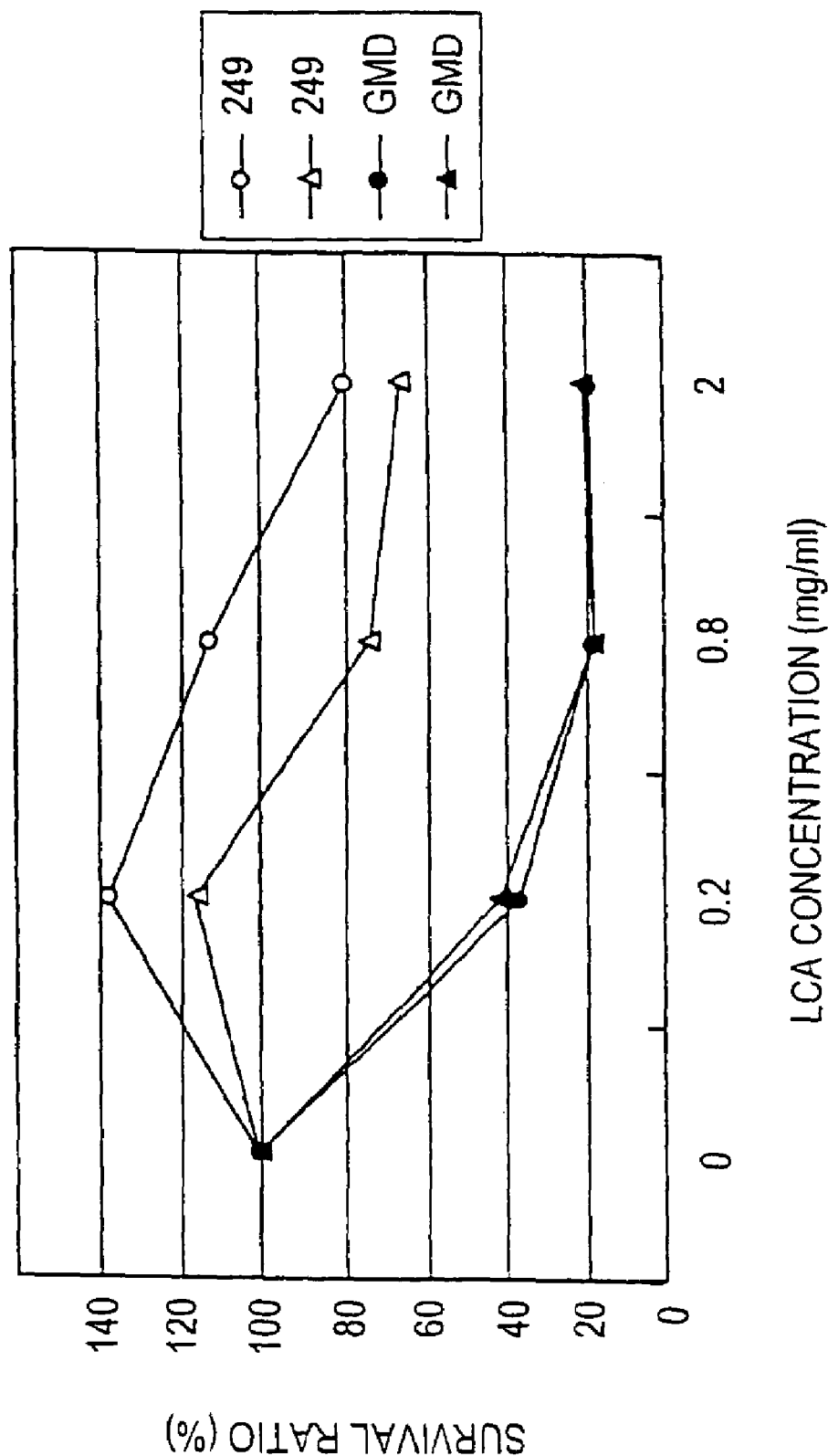
FIG. 52 shows resistance of GMD-expressed CHO/CCR4-LCA for LCA lectin. The measurement was carried out twice by defining the survival rate of a group of cells cultured without adding LCA lectin as 100%. In the drawing, "2491" shows the survival rate of the CHO/CCR4-LCA introduced with an expression vector pAGE249 for LCA lectin. GMD shows resistance of the CHO/CCR4-LCA introduced with a GMD expression vector pAGE249GMD for LCA lectin.

FIG. 52 shows the number of survived cells in each well by percentage when a value calculated by subtracting OD595 from OD450 measured in the above is used as the survived number of each cell group and the number of survived cells in each of the LCA-free wells is defined as 100%. As shown in FIG. 52, decrease in the LCA-resistance was observed in the GMD-expressed CHO/CCR4-LCA, and the survival ratio was about 40% in the presence of 0.2 mg/ml LCA and the survival ratio was about 20% in the presence of 0.8 mg/ml LCA. On the other hand, in the pAGE249 vector-introduced CHO/CCR4-LCA, the survival ratio was 100% in the presence of 0.2 mg/ml LCA and the survival ratio was about 80% even in the presence of 0.8 mg/ml LCA. Based on these results, it was suggested that expression level of GMD gene in the CHO/CCR4-LCA was decreased and, as a result, the resistance against LCA was obtained.

(5) In Vitro Cytotoxic Activity (ADCC Activity) of Anti-CCR4 Chimeric Antibody Obtained from GMD-Expressed CHO/CCR4-LCA In order to evaluate in vitro cytotoxic activity of the purified anti-CCR4 chimeric antibody obtained in the item (3), the ADCC activity was measured in accordance with the following methods.

i) Preparation of Target Cell Suspension

A 3.7 MBq equivalent of a radioactive substance $Na_2^{51}CrO_4$ was added to $1\times10^6$ cells of the CCR4-EL4 (cf. Example 8-7) cultured using a medium prepared by adding 500 µg/ml G418 sulfate (manufactured by Nakalai Tesque) to the RPMI1640-FBS(10) medium, followed by reaction at 37° C. for 90 minutes to thereby label the cells with a radioisotope. After the reaction, the cells were washed three times by suspension in the RPMI1640-FBS(10) medium and subsequent centrifugation, re-suspended in the medium and then incubated at 4° C. for 30 minutes in ice for spontaneous dissociation of the radioactive substance. After centrifugation, the cells were adjusted to $2.5\times10^5$ cells-/ml by adding 5 ml of the RPMI1640-FBS(10) medium and used as a target cell suspension.

ii) Preparation of Effector Cell Suspension

From a healthy person, 50 ml of venous blood was collected and gently mixed with 0.5 ml of heparin sodium (manufactured by Takeda Pharmaceutical). Using Lymphoprep (manufactured by Nycomed Pharma AS), the mixture was centrifuged in accordance with the manufacture's instructions to separate a mononuclear cell layer. The cells were washed three times by centrifuging using the RPMI1640-FBS(10) medium and then resuspended in the medium to give a density of $2\times10^6$ cells/ml and used as a effector cell suspension.

iii) Measurement of ADCC Activity

The target cell suspension prepared in the 1) was dispensed at 50 µl ($1\times10^4$ cells/well) into each well of a 96 well U-bottom plate (manufactured by Falcon). Next, 100 µl of the effector cell suspension prepared in the 2) was added thereto ($2\times10^5$ cells/well, ratio of the effector cells to the target cells was 25:1). Each of various anti-CCR4 chimeric antibodies (the anti-CCR4 chimeric antibody purified in the item (3), and KM2760-1 and KM3060) was further added thereto to give a final concentration of 0.0025 to 2.5 µg/ml, followed by reaction at 37° C. for 4 hours. After the reaction, the plate was centrifuged and the amount of $^{51}Cr$ in the supernatant was measured using a γ-counter. The amount of: the spontaneously dissociated $^{51}Cr$ was calculated by carrying out the same procedure using the medium alone instead of the effector cell suspension and antibody solution, and measuring the amount of $^{51}Cr$ in the supernatant. The amount of the total dissociated $^{51}Cr$ was calculated by carrying out the same procedure using the medium alone instead of the antibody solution and adding 1 N hydrochloric acid instead of the effector cell suspension and measuring the amount of $^{51}Cr$ in the supernatant. The ADCC activity was calculated based on the formula (II).

Figure 53:
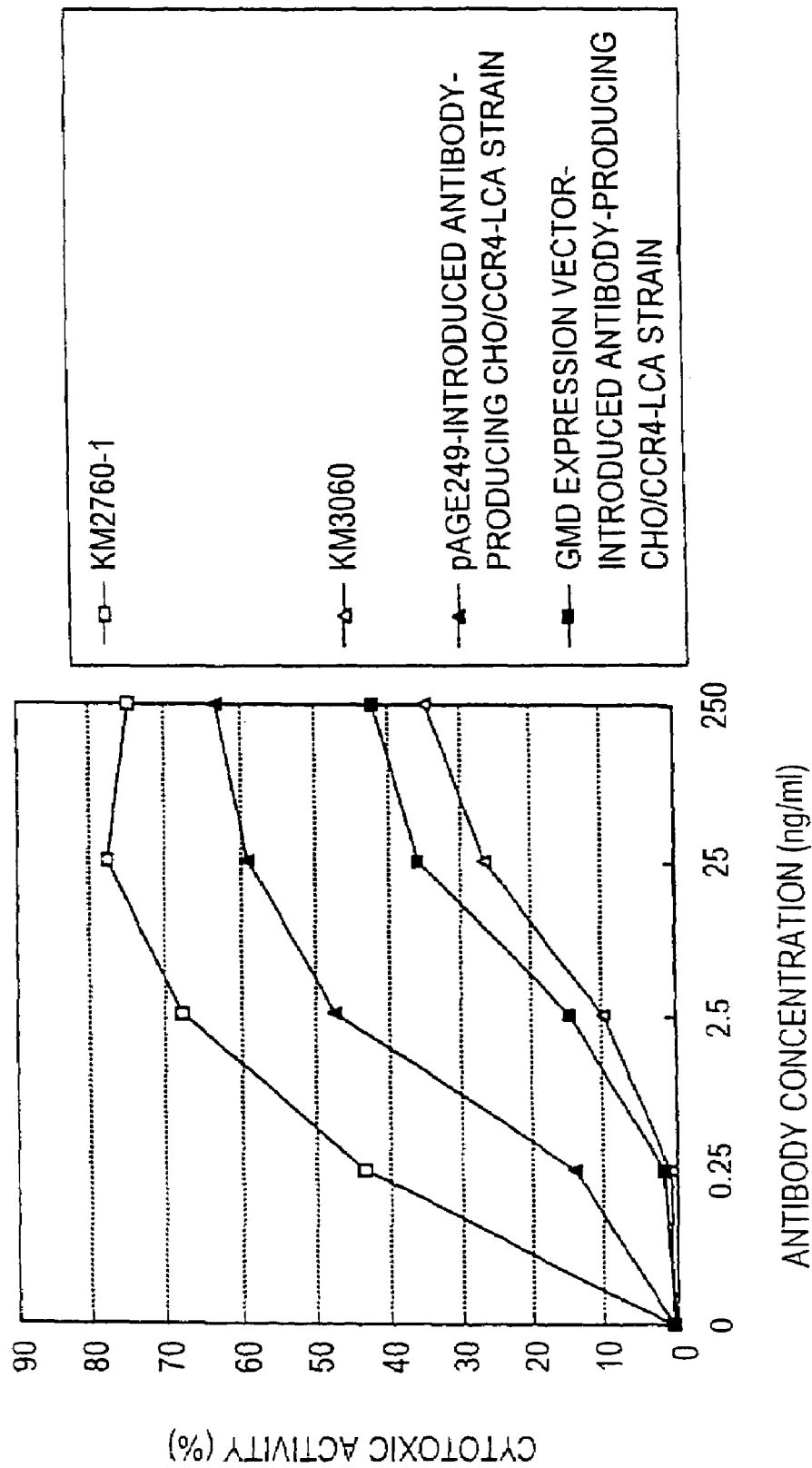
FIG. 53 shows ADCC activities of an anti-CCR4 chimeric antibody produced by cells of GMD-expressed CHO/CCR4-LCA cell lines. The ordinate and the abscissa show the cytotoxic activity and the antibody concentration, respectively.
Figure 55:
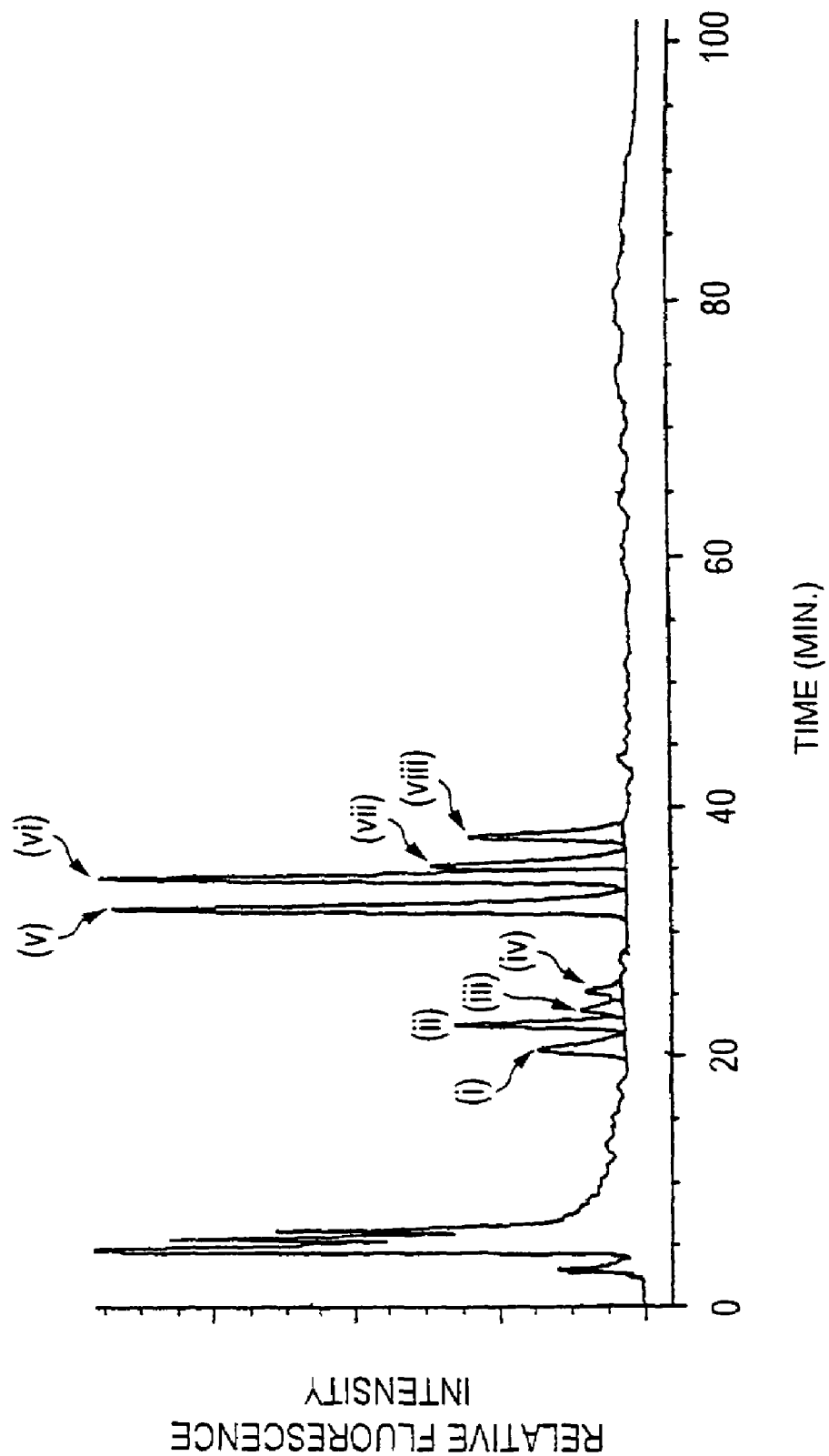
FIG. 55 shows an elution pattern of PA-treated sugar chains prepared from an anti-CCR4 human chimeric antibody purified from GMD gene-expressed CHO/CCR4-LCA, obtained by analyzing them by reverse phase HPLC. The ordinate and the abscissa show the relative fluorescence intensity and the elution time, respectively.

Results of the measurement of ADCC activity are shown in FIG. 53. As shown in FIG. 53, ADCC activity of the purified anti-CCR4 chimeric antibody obtained from the GMD-expressed CHO/CCR4-LCA was decreased to a similar degree to that of the KM3060 obtained in Example 8. On the other hand, ADCC activity of the purified anti-CCR4 chimeric antibody obtained from the pAGE249 vector-introduced CHO/CCR4-LCA showed a similar degree of ADCC activity to that of the purified anti-CCR4 chimeric antibody obtained from the CHO/CCR4-LCA. Based on the results, it was suggested that expression level of GMD gene in the CHO/CCR4-LCA is decreased and, as a result, an antibody having potent ADCC activity can be produced (6) Sugar Chain Analysis of Anti-CCR4 Chimeric Antibody Derived from GMD-Expressed CHO/CCR4-LCA Sugar chains binding to the purified anti-CCR4 chimeric antibody obtained in the item (3) were analyzed in accordance with the method shown in Example 14(4), with the analyzed results shown in FIG. 55. In comparison with the purified anti-CCR4 chimeric antibody prepared from CHO/CCR4-LCA in Example 14, the ratio of sugar chain having no α-1,6-fucose in the purified anti-CCR4 chimeric antibody derived from GMD-expressed CHO/CCR4-LCA was decreased to 9% when calculated from the peak area. Thus, it was shown that the ratio of sugar chain having no α-1,6-fucose in the antibody produced by the cell is decreased to similar level of the antibody produced by the strain 5-03, by expressing GMD gene in the CHO/CCR4-LCA

EXAMPLE 16

Preparation of Various Genes Encoding Enzymes Relating to the Sugar Chain Synthesis in CHO Cell 1. Determination of CHO Cell-Derived FX cDNA Sequence (1) Extraction of Total RNA from CHO/DG44 Cell CHO/DG44 cells were suspended in IMDM medium containing 10% fetal bovine serum (manufactured by Life Technologies) and 1× concentration HT supplement (manufactured by Life Technologies), and 15 ml of the suspension was inoculated into a T75 flask for adhesion cell culture use (manufactured by Greiner) to give a density of $2\times10^5$ cells/ml. On the second day after culturing them at 37° C. in a 5% $CO_2$ incubator, $1\times10^7$ of the cells were recovered and total RNA was extracted therefrom using RNAeasy (manufactured by QIAGEN) in accordance with the manufacture's instructions.

(2) Preparation of Total Single-Stranded cDNA from CHO/DG44 Cell

The total RNA prepared in the (1) was dissolved in 45 µl of sterile water, and 1 µl of RQ1 RNase-Free DNase (manufactured by Promega), 5 µl of the attached 10× DNase buffer and 0.5 µl of RNasin Ribonuclease Inhibitor (manufactured by Promega) were added thereto, followed by reaction at 37° C. for 30 minutes to degrade genome DNA contaminated in the sample. After the reaction, the total RNA was purified again using RNAeasy (manufactured by QIAGEN) and dissolved in 50 µl of sterile water.

In a 20 µl of reaction mixture using oligo(dT) as a primer, single-stranded cDNA was synthesized from 3 µg of the obtained total RNA samples by carrying out reverse transcription reaction using SUPERSCRIPT™ Preamplification System for First Strand cDNA Synthesis (manufactured by Life Technologies) in accordance with the manufacture's instructions. A 50 folds-diluted aqueous solution of the reaction solution was used in the cloning of GFPP and FX. This was stored at −80° C. until use.

(3) Preparation of cDNA Partial Fragment of Chinese Hamster-Derived FX

FX cDNA partial fragment derived from Chinese hamster was prepared by the following procedure.

First, primers (shown in SEQ ID NOs:42 and 43) specific for common nucleotide sequences registered at a public data base, namely a human FX cDNA (Genebank Accession No. U58766) and a mouse cDNA (Genebank Accession No. M30127), were designed.

Next, 25 µl of a reaction solution [ExTaq buffer (manufactured by Takara Shuzo), 0.2 mmol/l dNTPs and 0.5 µmol/l gene-specific primers (SEQ ID NOs:42 and 43)] containing 1 µl of the CHO/DG44-derived single-stranded cDNA prepared in the item (2) was prepared, and polymerase chain reaction (PCR) was carried out using a DNA polymerase ExTaq (manufactured by Takara Shuzo). The PCR was carried out by heating at 94° C. for 5 minutes, subsequent 30 cycles of heating at 94° C. for 1 minute, 58° C. for 2 minutes and 72° C. for 3 minutes as one cycle, and final heating at 72° C. for 10 minutes.

After the PCR, the reaction solution was subjected to 2% agarose gel electrophoresis, and a specific amplified fragment of 301 bp was purified using QuiaexII Gel Extraction Kit (manufactured by Quiagen) and eluted with 20 µl of sterile water (hereinafter, the method was used for the purification of DNA fragments from agarose gel). Into a plasmid pCR2.1, 4 µl of the amplified fragment was employed to insert in accordance with the instructions attached to TOPO TA Cloning Kit (manufactured by Invitrogen), and *E. coli* DH5α was transformed with the reaction solution by the method of Cohen et al. [*Proc. Natl. Acad. Sci USA,* 69, 2110 (1972)] (hereinafter, the method was used for the transformation of *E. coli*). Plasmid DNA was isolated in accordance with a known method [*Nucleic Acids Research,* 1, 1513 (1979)] (hereinafter, the method was used for the isolation of plasmid) from the obtained several kanamycin-resistant colonies to obtain 2 clones into which FX cDNA partial fragments were respectively inserted. They are referred to as pCRFX clone 8 and pCRFX clone 12.

The nucleotide sequence of the cDNA inserted into each of the FX clone 8 and FX clone 12 was determined using DNA Sequencer 377 (manufactured by Parkin Elmer) and BigDye Terminator Cycle Sequencing FS Ready Reaction kit (manufactured by Parkin Elmer) in accordance with the method of the manufacture's instructions. It was confirmed that each of the inserted cDNA whose sequence was determined encodes open reading frame (ORF) partial sequence of the Chinese hamster EX.

(4) Synthesis of Single-Stranded cDNA for RACE

Single-stranded cDNA samples for 5' and 3' RACE were prepared from the CHO/DG44 total RNA extracted in the item (1) using SMART™ RACE cDNA Amplification Kit (manufactured by CLONTECH) in accordance with the manufacture's instructions In the case, PowerScript™ Reverse Transcriptase (manufactured by CLONTECH) was used as the reverse transcriptase. Each single-stranded cDNA after the preparation was diluted 10 folds with the Tricin-EDTA buffer attached to the kit and used as the template of PCR.

(5) Determination of Chinese Hamster-Derived FX Full Length cDNA by RACE Method

Based on the FX partial sequence derived from Chinese hamster determined in the item (3), primers FXGSP1-1 (SEQ ID NO:44) and FXGSP1-2 (SEQ ID NO:45) for the Chinese hamster FX-specific 5' RACE and primers FXGSP2-1 (SEQ ID NO:46) and FXGSP2-2 (SEQ ID NO:47) for the Chinese hamster FX-specific 3' RACE were designed.

Next, polymerase chain reaction (PCR) was carried out using Advantage 2 PCR Kit (manufactured by CLONTECH), by preparing 50 µl of a reaction solution [Advantage2 PCR buffer (manufactured by CLONTECH), 0.2 mM dNTPs, 0.2 µmol/l Chinese hamster FX-specific primers for RACE and 1× concentration of common primers (manufactured by CLONTECH)] containing 1 µl of the CHO/DG44-derived single-stranded cDNA for. RACE prepared in the item (4).

The PCR was carried out by repeating 20 cycles of heating at 94° C. for 5 seconds, 68° C. for 10 seconds and 72° C. for 2 minutes as one cycle.

After completion of the reaction, 1 µl of the reaction solution was diluted 50-folds with the Tricin-EDTA buffer, and 1 µl of the diluted solution was used as a template. The reaction solution was again prepared and the PCR was carried out under the same conditions. The templates, the combination of primers used in the first and second PCRs and the length of amplified DNA fragments by the PCRs are shown in Table 8.

TABLE 8

Combination of primers used in Chinese hamster FX cDNA RACE PCR and the size of PCR products

| | FX-specific primers | Common primers | PCR-amplified product size |
|---|---|---|---|
| 5' RACE | | | |
| First | FXGSP1-1 | UPM (Universal primer mix) | |
| Second | FXGSP1-2 | NUP (Nested Universal primer) | 300 bp |
| 3' RACE | | | |
| First | FXGSP2-1 | UPM (Universal primer mix) | |
| Second | FXGSP2-2 | NUP (Nested Universal primer) | 1,100 bp |

After the PCR, the reaction solution was subjected to 1% agarose gel electrophoresis, and the specific amplified fragment of interest was purified using QiaexII QuiaexII Gel Extraction Kit (manufactured by Qiagen) and eluted with 20 µl of sterile water. Into a plasmid pCR2.1, 4 µl of the amplified fragment was inserted, and *E. coli* DH5α was transformed using the reaction solution in accordance with the instructions attached to TOPO TA Cloning Kit (manufactured by Invitrogen).

Plasmid DNAs were isolated from the appeared several kanamycin-resistant colonies to obtain 5 cDNA clones containing Chinese hamster FX 5' region. They are referred to as FX5' clone 25, FX5' clone 26, FX5' clone 27, FX5' clone 28, FX5' clone 31 and FX5, clone 32.

In the same manner, 5 cDNA clones containing Chinese hamster FX 3' region were obtained. These FX3' clones are referred to as FX3' clone 1, FX3' clone 3, FX3' clone 6, FX3' clone 8 and FX3' clone 9.

The nucleotide sequence of the cDNA moiety of each of the clones obtained by the 5' and 3' RACE was determined using DNA Sequencer 377 (manufactured by Parkin Elmer) in accordance with the method described in the manufacture's instructions. By comparing the cDNA nucleotide sequences determined by the method, reading errors of nucleotide bases due to PCR were excluded and the full length nucleotide sequence of Chinese hamster FX cDNA was determined. The determined sequence is shown in SEQ ID NO 48.

2. Determination of CHO Cell-Derived GFPP cDNA Sequence (1) Preparation of GFPP cDNA Partial Fragment Derived from Chinese Hamster GFPP cDNA partial fragment derived from Chinese hamster was prepared by the following procedure.

First, nucleotide sequences of a human GFPP cDNA (Genebank Accession No. number AF017445), mouse EST sequences having high homology with the sequence (Genebank Accession NOs. AI467195, AA422658, BE304325 and AI466474) and rat EST sequences (Genebank Accession Nos. BF546372, AI058400 and AW144783), registered at public data bases, were compared, and primers GFPP FW9 and GFPP RV9 (SEQ ID NOs:49 and 50) specific for rat GFPP were designed on a highly preserved region among these three species.

Next, polymerase chain reaction (PCR) was carried out using a DNA polymerase ExTaq (manufactured by Takara Shuzo), by preparing 25 µl of a reaction solution (ExTaq buffer (manufactured by Takara Shuzo), 0.2 mM dNTPs and 0.5 µmol/l GFPP-specific primers GFPP FW9 and GFPP RV9 (SEQ ID NOs:49 and 50)] containing 1 µl of the CHO/DG44-derived single-stranded cDNA prepared in the item 1(2) The PCR was carried out by heating at 94° C. for 5 minutes, subsequent 30 cycles of heating at 94° C. for 1 minute, 58° C. for 2 minutes and 72° C. for 3 minutes as one cycle, and final heating at 72° C. for 10 minutes.

After the PCR, the reaction solution was subjected to 2% agarose gel electrophoresis, and a specific amplified fragment of 1.4 Kbp was purified using QuiaexII Gel Extraction Kit (manufactured by Quiagen) and eluted with 20 µl of sterile water. Into a plasmid pCR2-1, 4 µl of the amplified fragment was employed to insert in accordance with the instructions attached to TOPO TA Cloning Kit (manufactured by Invitrogen), and E. coli DH5α was transformed using the reaction solution.

Plasmid DNAs were isolated from the appeared several kanamycin-resistant colonies to obtain 3 clones into which GFPP cDNA partial fragments were respectively integrated. They are referred to as GFPP clone 8, GFPP clone 11 and GFPP clone 12.

The nucleotide sequence of the cDNA inserted into each of the GFPP clone 8, GFPP clone 11 and GFPP clone 12 was determined using DNA Sequencer 377 (manufactured by Parkin Elmer) and BigDye Terminator Cycle Sequencing FS Ready Reaction kit (manufactured by Parkin Elmer) in accordance with the method described in the manufacture's instructions. It was confirmed that the inserted cDNA whose sequence was determined encodes open reading frame (ORF) partial sequence of the Chinese hamster GFPP.

(2) Determination of Chinese Hamster GFPP Full Length cDNA by RACE Method

Based on the Chinese hamster FX partial sequence determined in the item 2(1), primers GFPP GSP1-1 (SEQ ID NO:52) and GFPP GSP1-2 (SEQ ID NO:53) for the Chinese hamster FX-specific 5' RACE and primers GFPP GSP2-1 (SEQ ID NO:54) and GFPP GSP2-2 (SEQ ID NO:55) for the Chinese hamster GFPP-specific 3' RACE were designed.

Next, polymerase chain reaction (PCR) was carried out using Advantage2 PCR Kit (manufactured by CLONTECH), by preparing 50 µl of a reaction solution [Advantage2 PCR buffer (manufactured by CLONTECH), 0.2 mM dNTPs, 0.2 µmol/l Chinese hamster GFPP-specific primers for RACE and 1× concentration of common primers (manufactured by CLONTECH)] containing 1 µl of the CHO/DG44-derived single-stranded cDNA for RACE prepared in the item (4).

The PCR was carried out by repeating 20 cycles of heating at 94° C. for 5 seconds, 68° C. for 10 seconds and 72° C. for 2 minutes as one cycle.

After completion of the reaction, 1 µl of the reaction solution was diluted 50-folds with the Tricin-EDTA buffer, and 1 µl of the diluted solution was used as a template. The reaction solution was again prepared and the PCR was carried out under the same conditions. The templates, the combination of primers used in the first and second PCRs and the size of amplified DNA fragments by the PCRs are shown in Table 9.

TABLE 9

Combination of primers used in Chinese hamster GFPP cDNA RACE PCR and the size of PCR products

|  | GFPP-specific primers | Common primers | PCR-amplified product size |
|---|---|---|---|
| 5' RACE |  |  |  |
| First | GFPPGSP1-1 | UPM (Universal primer mix) |  |
| Second | GFPPGSP1-2 | NUP (Nested Universal primer) | 1,100 bp |
| 3' RACE |  |  |  |
| First | GFPPGSP2-1 | UPM (Universal primer mix) |  |
| Second | GFPPGSP2-2 | NUP (Nested Universal primer) | 1,400 bp |

After the PCR, the reaction solution was subjected to 1% agarose gel electrophoresis, and the specific amplified fragment of interest was purified using QiaexII Gel Extraction Kit (manufactured by Qiagen) and eluted with 20 µl of sterile water. Into a plasmid pCR2.1, 4 µl of the amplified fragment was employed to insert and E. coli DH5α was transformed with the reaction solution in accordance with the instructions attached to TOPO TA Cloning Kit (manufactured by Invitrogen).

Plasmid DNAs were isolated from the obtained several kanamycin-resistant colonies to obtain 4 cDNA clones containing Chinese hamster GFPP 5' region. They are referred to as GFPP5' clone 1, GFPP5' clone 2, GFPP5' clone 3 and GFPP5' clone 4.

In the same manner, 5 cDNA clones containing Chinese hamster GFPP 3' region were obtained. They are referred to as GFPP3' clone 10, GFPP3' clone 16 and GFPP3' clone 20.

The nucleotide sequence of the cDNA of each of the clones obtained by the 5' and 3' RACE was determined using DNA Sequencer 377, (manufactured by Parkin Elmer) in accordance with the method described in the manufacture's instructions. By comparing the cDNA nucleotide sequences after the nucleotide sequence determination, reading errors of bases due to PCR were excluded and the full length nucleotide sequence of Chinese hamster GFPP cDNA was determined. The determined sequence is shown in SEQ ID NO:51.

EXAMPLE 17

Preparation of CHO Cell-Derived GMD Gene

1. Determination of CHO Cell-Derived GMD cDNA Sequence (1) Preparation of CHO Cell-Derived GMD Gene cDNA (Preparation of Partial cDNA Excluding 51- and 30-Terminal Sequences)

Rodents-derived GMD cDNA was searched in a public data base (BLAST) using a human-derived GMD cDNA sequence (GenBank Accession No. AF042377) registered at GenBank as a query, and three kinds of mouse EST sequences were obtained (GenBank Accession Nos. BE986856, BF158988 and BE284785). By ligating these EST sequences, a deduced mouse GMD cDNA sequence was determined.

On the base of the mouse-derived GMD cDNA sequence, a 28 mer primer having the sequence represented by SEQ ID NO:56, a 27 mer primer having the sequence represented by SEQ ID NO:57, a 25 mer primer having the sequence represented by SEQ ID NO: 58, a 24 mer primer having the sequence represented by SEQ ID NO:59 and a 25 mer primer having the sequence represented by SEQ ID NO:60 were generated.

Next, in order to amplify the CHO cell-derived GMD cDNA, PCR was carried out by the following method. A 20 µl portion of a reaction solution [1× Ex Taq buffer (manufactured by Takara Shuzo), 0.2 mM dNTPs, 0.5 unit of Ex Taq polymerase (manufactured by Takara Shuzo) and 0.5 µM of two synthetic DNA primers] containing 0.5 µl of the CHO cell-derived single-stranded cDNA prepared in Example 15-1 (1) as the template was prepared. In this case, combinations of SEQ ID NO:56 with SEQ ID NO.57, SEQ ID NO:58 with SEQ ID NO:57, SEQ ID NO:56 with SEQ ID NO:59 and SEQ ID NO:56 with SEQ ID NO:60 were used as the synthetic DNA primers. The reaction was carried out using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle.

The PCR reaction solution was fractionated by agarose electrophoresis: to find that a DNA fragment of about 1.2 kbp was amplified in the PCR product when synthetic DNA primers of SEQ ID NOs:56 and 57 were used, a fragment of about 1.1 kbp was amplified in the PCR product when synthetic DNA primers of SEQ ID NOs.57 and 59 were used, a fragment of about 350 bp was amplified in the PCR product when synthetic DNA primers of SEQ ID NOs:56 and 59 were used and a fragment of about 1 kbp was amplified in the PCR product when synthetic DNA primers of SEQ ID NOs:56 and 60 were used. The DNA fragments were recovered using Gene Clean II Kit (manufactured by BIO 101) in accordance with the manufacture's instructions. The recovered DNA fragments were ligated to a pT7Blue(R) vector (manufactured by Novagen) using DNA Ligation Kit (manufactured by Takara Shuzo), and *E. coli* DH (manufactured by Toyobo) was transformed using the obtained recombinant plasmid DNA samples to thereby obtain plasmids 22-8 (having a DNA fragment of about 1.2 kbp amplified from synthetic DNA primers of SEQ ID NO:56 and SEQ ID NO:57), 23-3 (having a DNA fragment of about 1.1 kbp amplified from synthetic DNA primers of SEQ ID NO:58 and SEQ ID NO:57), 31-5 (a DNA fragment of about 350 bp amplified from synthetic DNA primers of SEQ ID NO;56 and SEQ ID NO:59) and 34-2 (having a DNA fragment of about 1 kbp amplified from synthetic DNA primers of SEQ ID NO:56 and SEQ ID NO:60). The CHO cell-derived GMD cDNA sequence contained in these plasmids was determined in the usual way using a DNA sequencer ABI PRISM 377 (manufactured by Parkin Elmer) (since a sequence of 28 bases in downstream of the initiation codon nethionine in the 5'-terminal side and a sequence of 27 bases in upstream of the termination codon in the 3'-terminal side are originated from synthetic oligo DNA sequences, they are mouse GMD cDNA sequences).

Figure 54:
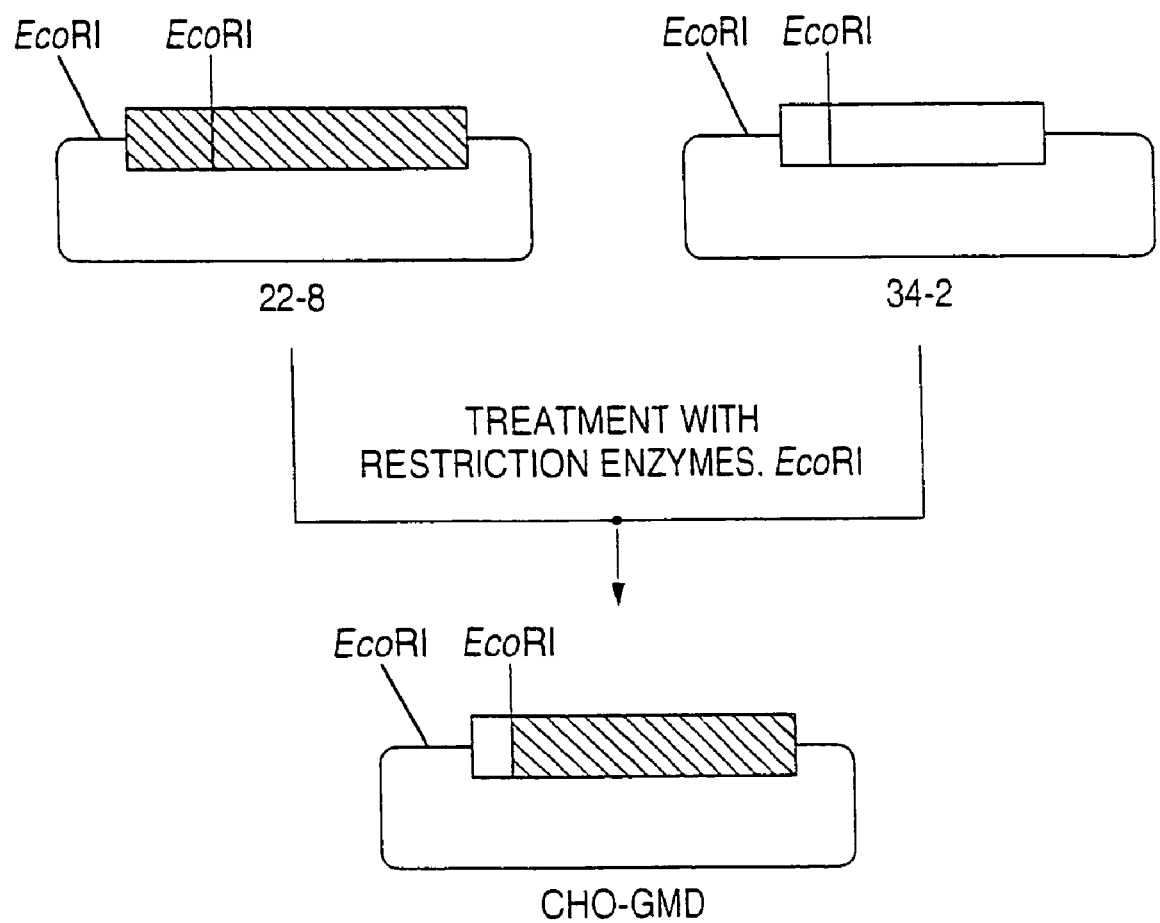
FIG. 54 show a production step of a plasmid CHO-GMD in which the 5'-terminal of a clone 34-2 is introduced into the 5'-terminal of a CHO cell-derived G14D cDNA clone 22-8.

In addition, the following steps were carried out in order to prepare a plasmid in which the CHO cell-derived GMD cDNA fragments contained in the plasmids 22-8 and 34-2 are combined. The plasmid 22-8 (1 µg) was allowed to react with a restriction enzyme EcoRI (manufactured by Takara Shuzo) at 37° C. for 16 hours, the digest was subjected to agarose electrophoresis and then a DNA fragment of about 4 kbp was recovered using. Gene Clean II Kit (manufactured by BIO 101) in accordance with the manufacture's instructions. The plasmid 34-2 (2 µg) was allowed to react with a restriction enzyme EcoRI at 37° C. for 16 hours, the digest was subjected to agarose electrophoresis and then a DNA fragment of about 150 bp was recovered using Gene Clean II Kit (manufactured by BIO 101) in accordance with the manufacture's instructions. The recovered DNA fragments were respectively subjected to terminal dephosphorylation using Calf Intestine Alkaline Phosphatase (manufactured by Takara Shuzo) and then ligated using DNA Ligation Kit (manufactured by Takara Shuzo), and *E. coli* DH5α (manufactured by Toyobo) was transformed using the obtained recombinant plasmid DNA to obtain a plasmid CHO-GMD (cf. FIG. 54).

(2) Determination of 5'-Terminal Sequence of CHO Cell-Derived GMD cDNA

A 24 mer primer having the nucleotide sequence represented by SEQ ID NO:61 was prepared from 5'-terminal side non-coding region nucleotide sequences of CHO cell-derived human and mouse GMD cDNA, and a 32 mer primer having the nucleotide sequence represented by SEQ ID NO:62 from CHO cell-derived GMD cDNA sequence were prepared, and PCR was carried out by the following method to amplify cDNA. Then, 20 µl of a reaction solution [1× Ex Taq buffer (manufactured by Takara Shuzo), 0.2 mM dNTPs, 0.5 unit of Ex Taq polymerase (manufactured by Takara Shuzo) and 0.5 µM of the synthetic DNA primers of SEQ ID NO:61 and SEQ ID NO:62] containing 0.5 µl of the single-stranded cDNA prepared in Example 15-1(1) was prepared as the template, and the reaction was carried out therein using DNA Thermal Cycler 480 (manufactured by Perkin Elmer) by heating at 94° C. for 5 minutes, subsequent 20 cycles of heating at 94° C. for 1 minute, 55° C. for 1 minute and 72° C. for 2 minutes as one cycle and further 18 cycles of heating at 94° C. for 1 minute and 68° C. for 2 minutes as one cycle. After fractionation of the PCR reaction solution by agarose electrophoresis, a DNA fragment of about 300 bp was recovered using Gene Clean II Kit (manufactured by BIO 101) in accordance with the manufacturers instructions. The recovered DNA fragment was ligated to a pT7Blue(R) vector (manufactured by Novagen) using DNA Ligation Kit (manufactured by Takara Shuzo), and *E. coli* DH5α (manufactured by Toyobo) was transformed using the obtained recombinant plasmid DNA samples to thereby obtain a plasmid 5'GMD. Using DNA Sequencer 377 (manufactured by Parkin Elmer), the nucleotide sequence of 28 bases in downstream of the initiation methionine of CHO cell-derived GMD cDNA contained in the plasmid was determined.

(3) Determination of 3'-Terminal Sequence of CHO Cell-Derived GAMD cDNA

In order to obtain 3'-terminal cDNA sequence of CHO cell-derived GMD, RACE method was carried out by the following method. A single-stranded cDNA for 3' RACE was prepared from the CHO cell-derived RNA obtained in Example 15-1(1) using SMART™ RACE cDNA Amplification Kit (manufactured by CLONTECH) in accordance with the manufacture's instructions. In the case, PowerScript™ Reverse Transcriptase (manufactured by CLONTECH) was used as the reverse transcriptase. The single-stranded cDNA after the preparation was diluted 10 folds with the Tricin-EDTA buffer attached to the kit and used as the template of PCR.

Next, 20 µl of a reaction solution (ExTaq buffer (manufactured by Takara Shuzo), 0.2 mM dNTPs, 0.5 unit of EX Taq polymerase (manufactured by Takara Shuzo), 0.5 µM of the 25 mer synthetic DNA primer shown in SEQ ID NO:63 [generated on the base of the CHO cell-derived GMD cDNA sequence determined in the item (1) and 1× concentration of Universal Primer Mix (attached to SMART™ RACE cDNA Amplification Kit; manufactured by CLONTECH] containing 1 µl of the cDNA for 3' RACE as the template was prepared, and PCR was carried out using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle.

After completion of the reaction, 1 µl of the PCR reaction solution was diluted 20 folds with Tricin-EDTA buffer (manufactured by CLONTECH). Then, 20 µl of a reaction solution [ExTaq buffer (manufactured by Takara Shuzo), 0.2 mM dNTPs, 0.5 unit of EX Taq polymerase (manufactured by Takara Shuzo), 0.5 µM of the 25 mer synthetic DNA primer shown in SEQ ID NO:64 [generated on the base of the CHO cell-derived GMD cDNA sequence determined in the item (1)] and 0.5 µM of Nested Universal Primer (attached to SMART™ RACE cDNA Amplification Kit; manufactured by CLONTECH) containing 1 µl of the 20 folds-diluted aqueous solution as the template) was prepared, and the reaction was carried out using DNA Thermal Cycler 480 (manufactured by Perkin Elmer) by heating at 94° C. for 5 minutes and subsequent 30 cycles at 94° C. for 1 minute and 68° C. for 2 minutes as one cycle.

After completion of the reaction, the PCR reaction solution was fractionated by agarose electrophoresis and then a DNA fragment of about 700 bp was recovered using Gene Clean II Kit (manufactured by BIO 101) in accordance with the manufacture's instructions. The recovered DNA fragment was ligated to a pT7Blue(R) vector (manufactured by Novagen) using DNA Ligation Kit (manufactured by Takara Shuzo), and *E. coli* DH5α (manufactured by Toyobo) was transformed using the obtained recombinant plasmid DNA, thereby obtaining a plasmid 3'GMD Using DNA Sequencer 377 (manufactured by Parkin Elmer), the nucleotide sequence of 27 bases in upstream of the termination codon of CHO cell-derived GMD cDNA contained in the plasmid was determined.

The full length cDNA sequence of the CHO-derived GMD gene determined by the items (1), (2) and (3) and the corresponding amino acid sequence are shown in SEQ ID NOs:65 and 71, respectively.

2. Determination of Genomic Sequence Containing CHO/DG44-Derived Cell GMD Gene

A 25 mer primer having the nucleotide sequence represented by SEQ ID NO:66 was prepared from the mouse GMD cDNA sequence determined in Example 17-1. Next, a CHO cell-derived genome DNA was obtained by the following method. A CHO/DG44 cell-derived KC861 was suspended in IMDM-dFBS(10)-HT(1) medium [IMDM-dFBS(10) medium comprising 1× concentration of HT supplement (manufactured by Invitrogen)] to give a density of 3×10⁵ cells/ml, and the suspension was dispensed at 2 ml/well into a 6 well flat bottom plate for adhesion cell use (manufactured by Greiner). After culturing them at 37° C. in a 5% $CO_2$ incubator until the cells became confluent on the plate, genome DNA was prepared from the cells on the plate by a known method [*Nucleic Acids Research*, 3, 2303 (1976)] and dissolved overnight in 150 µl of TE-RNase buffer (pH 8.0) (10 mmol/l Tris-HCl, 1 mmol/l EDTA, 200 µg/ml RNase A).

A reaction solution (20 µl) [1× Ex Taq buffer (manufactured by Takara Shuzo), 0.2 mM dNTPs, 0.5 unit of EX Taq polymerase (manufactured by Takara Shuzo) and 0.5 µM of synthetic DNA primers of SEQ ID NO:59 and SEQ ID No:66] containing 100 ng of the obtained CHO/DG44 cell-derived genome DNA was prepared, and PCR was carried out using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle. After completion of the reaction, the PCR reaction solution was fractionated by agarose electrophoresis and then a DNA fragment of about 100 bp was recovered using Gene Clean II Kit (manufactured by BIO 101) in accordance with the manufacture's instructions. The recovered DNA fragment was ligated to a pT7Blue(R) vector (manufactured by Novagen) using DNA Ligation Kit (manufactured by Takara Shuzo), and *E. coli* DH5α (manufactured by Toyobo) was transformed using the obtained recombinant plasmid DNA, thereby obtaining a plasmid ex3. Using DNA Sequencer 377 (manufactured by Parkin Elmer), the nucleotide sequence of CHO cell-derived genome DNA contained in the plasmid was determined. The result is shown in SEQ ID NO:67.

Next, a 25 mer primer having the nucleotide sequence represented by SEQ ID NO:68 and a 25 mer primer having the nucleotide sequence represented by SEQ ID NO:69 were generated on the base of the CHO cell-derived GMD cDNA sequence determined in Example 17-1. Next, 20 µl of a reaction solution [1× Ex Taq buffer (manufactured by Takara Shuzo), 0.2 mM dNTPs, 0.5 unit of EX Taq polymerase (manufactured by Takara Shuzo) and 0.5 µM of the synthetic DNA primers of SEQ ID NO:68 and SEQ ID NO:69] containing 100 ng of the CHO/DG44-derived genome DNA was prepared, and PCR was carried out using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle.

After completion of the reaction, the PCR reaction solution was fractionated by agarose electrophoresis and then a DNA fragment of about 200 bp was recovered using Gene Clean II Kit (manufactured by BIO 101) in accordance with the manufacture's instructions. The recovered DNA fragment was ligated to a pT7Blue(R) vector (manufactured by Novagen) using DNA Ligation Kit (manufactured by Takara Shuzo), and *E. coli* DH5α (manufactured by Toyobo) was transformed using the obtained recombinant plasmid DNA, thereby obtaining a plasmid ex4. Using DNA Sequencer 377 (manufactured by Parkin Elmer), the nucleotide sequence of CHO cell-derived genome DNA contained in the plasmid was determined. The result is shown in SEQ ID NO:70.

EXAMPLE 18

Sugar Chain Analysis of Conventionally Available Antibodies

Sugar chains binding to a conventionally available anti-HER2/neu antibody Herceptin (manufactured by GENENTECH and Roche) produced by CHO cell as the host cell was analyzed in accordance with the method of Example 10(6) (FIG. 31). When calculated from each peak area of elution diagram, the content of α-1,6-fucose-free sugar chains of Herceptin was 16%, and the content of α-1,6-fucose-bound sugar chains was 84%. The same analysis was carried out on other commercially available antibodies, Rituxan (manufactured by GENENTECH, Roche and IDEC) and Zenapax (manufactured by Roche and PDL), and the α-1,6-fucose-free sugar chain content of was less than that in Herceptin.

FIG. 31 is a graph showing elution pattern of PA-treated sugar chains prepared from Herceptin, obtained by analyzing them by reverse phase HPLC. The relative fluorescence intensity and the elution time are plotted as the ordinate and the abscissa, respectively. The reverse phase HPLC analysis conditions, sugar chain structure analysis and calculation of the ratio of sugar chain group containing no α-1,6-fucose sugar chain were carried out by the same methods of Example 11(6).

While the invention has been described in detail and with reference to specific embodiments thereof, it will be apparent to one skill in the art that various changes and modifications can be made therein without departing from the spirit and scope thereof. All references cited herein are incorporated in their entirety.

We claim:

1. An isolated mammalian host cell in which the expression of the mRNA of α1,6-fucosyltransferase is inhibited by RNA interference, wherein when a gene encoding an antibody molecule is introduced into said host cell and expressed, said host cell produces an antibody composition comprising the encoded antibody molecule which includes an Fc region comprising complex N-glycoside-linked sugar chains bound to the Fc region, said N-glycoside-linked sugar chains having reduced levels of fucose bound to N-acetylglucosamine at the reducing end, thereby producing an antibody with increased antibody-dependent cellular cytotoxicity.

2. The isolated host cell of claim 1, wherein said host cell is a CHO cell.

3. The isolated host cell of claim 1, wherein said host cell is a NS0 cell.

4. The isolated host cell of claim 1, wherein said host cell is a SP2/0 cell.

5. The isolated host cell of claim 1, wherein said host cell is a YB2/0 cell.

6. The isolated host cell of claim 1, wherein said antibody molecule is an IgG antibody.

* * * * *